(12) United States Patent
Silver et al.

(10) Patent No.: US 10,175,256 B2
(45) Date of Patent: Jan. 8, 2019

(54) COMPOSITIONS AND METHODS UTILIZING LYSOPHOSPHATIDYLCHOLINE SCAFFOLDS

(71) Applicants: National University Of Singapore, Singapore (SG); David Lawrence Silver, Singapore (SG)

(72) Inventors: David Lawrence Silver, Singapore (SG); Nam Long Nguyen, Singapore (SG); Robert Zahler, Pennington, NJ (US)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 0 days.

(21) Appl. No.: 15/025,181

(22) PCT Filed: Sep. 26, 2014

(86) PCT No.: PCT/US2014/057871
§ 371 (c)(1),
(2) Date: Mar. 25, 2016

(87) PCT Pub. No.: WO2015/048554
PCT Pub. Date: Apr. 2, 2015

(65) Prior Publication Data
US 2017/0067919 A1 Mar. 9, 2017

Related U.S. Application Data

(60) Provisional application No. 61/882,693, filed on Sep. 26, 2013, provisional application No. 61/973,136, filed on Mar. 31, 2014, provisional application No. 61/992,822, filed on May 13, 2014.

(51) Int. Cl.
| | | |
|---|---|---|
| *G01N 33/92* | (2006.01) |
| *C12Q 1/6883* | (2018.01) |
| *G01N 33/50* | (2006.01) |
| *A61K 31/685* | (2006.01) |
| *A61K 49/00* | (2006.01) |
| *A23L 33/10* | (2016.01) |
| *A01K 67/027* | (2006.01) |

(52) U.S. Cl.
CPC ......... *G01N 33/92* (2013.01); *A01K 67/0276* (2013.01); *A23L 33/10* (2016.08); *A61K 31/685* (2013.01); *A61K 49/0008* (2013.01); *A61K 49/0052* (2013.01); *C12Q 1/6883* (2013.01); *G01N 33/502* (2013.01); *G01N 33/5088* (2013.01); *A01K 2227/105* (2013.01); *A01K 2267/03* (2013.01); *A23V 2002/00* (2013.01); *C12Q 2600/156* (2013.01); *C12Q 2600/158* (2013.01); *G01N 2333/705* (2013.01); *G01N 2405/04* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 4,874,795 A | 10/1989 | Yesair | |
| 2006/0222699 A1 | 10/2006 | Gilinski | |
| 2009/0131368 A1 | 5/2009 | Chen et al. | |
| 2011/0020242 A1 | 1/2011 | Zheng et al. | |
| 2011/0280852 A1 | 11/2011 | Miller | |
| 2016/0120893 A1* | 5/2016 | Gu | A01K 67/0276 514/50 |

FOREIGN PATENT DOCUMENTS

| | | |
|---|---|---|
| WO | 9728270 A1 | 8/1997 |
| WO | 0232396 | 4/2002 |
| WO | 2015048554 A1 | 4/2015 |

OTHER PUBLICATIONS

Angers et al. Mfsd2a encodes a novel major facilitator superfamily domain-containing protein highly induced in brown adipose tissue durng fasting and adaptive thermogenesis. Biochemical Journal, vol. 416, No. 3, pp. 347-355 Dec. 2008.*
Lagarde et al. Lysophosphatidylcholine as a preferred carrier form of docosahexaenoic acid to the brain. Journal of Molecular Neuroscience, vol. 16, pp. 201-204, 2001.*
Supporting Information for Reiling et al. Proceedings of the National Academy of Sciences, USA, vol. 108, No. 29, pp. 11756-11765, Jul. 2011, printed as pp. 1/10-10/10. (Year: 2011).*
Bernoud et al., "Preferential Transfer of 2-Docosahexaenoyl-1-Lysophosphatidylcholin e Through an In Vitro Blood-Brain Barrier Over Unesterified Docosahexaenoic Acid", Journal of Neurochemistry,vol. 72, No. 1, Jan. 18, 1999, pp. 338-345.
Cho et al., "Studies on the mechanism of hemolysis by acyl carnitines, lysolecithins and acyl cholines", Biochimica et Biophysica Acta, vol. 225, No. 2, Feb. 2, 1971.
Corr et al., "Potential Arrhythmogenic Electrophysiological Derangements in Canine Purkinje Fibers Induced by Lysophosphoglycerides Institutes of Health Grants HL 17646, SCOR in Ischemk Heart Disease, HL-21654, and a Missouri Heart Association Grant-in-Aid. Address for", Circulation Research, The American Heart Association, Jun. 1, 1979, 12 pages.
EP14847279.8 , "Extended European Search Report", dated Jul. 5, 2017, 25 pages.

(Continued)

*Primary Examiner* — Jennifer Dunston
(74) *Attorney, Agent, or Firm* — Kilpatrick Townsend & Stockton LLP

(57) ABSTRACT

The invention relates to compositions and methods for utilizing lysophosphatidylcholine scaffolds. The compositions and methods can be used for LPC-mediated delivery of fatty acids and other molecules; to screen and identify fatty acid formulations for parenteral nutrition; and for live animal organ imaging, among other uses. The invention also provides compositions and methods for utilizing mutations and polymorphisms in human Mfsd2a as markers for neurological deficits.

6 Claims, 33 Drawing Sheets

Specification includes a Sequence Listing.

(56) References Cited

OTHER PUBLICATIONS

Lagarde et al., "Lysophosphatidylcholine as a Preferred Carrier Form of Docosahexaenoic Acid to the Brain", Journal of Molecular Neuroscie, vol. 16, No. 2/03,, Apr. 1, 2001, pp. 201-204.

Lema et al., "Surface properties after a simulated PLA2 hydrolysis of pulmonary surfactant's main component, DPPC", Biochimica et Biophysica Acta (BBA)/Lipids and Lipid Metabolism, Jan. 1, 1997, pp. 86-92.

SG11201602331Q, "Written Opinion", dated Jul. 10, 2017, 14 pages.

Thiès et al., "Unsaturated Fatty Acids Esterified in 2-Acyl-1-Lysophosphatidylcholine Bound to Albumin Are More Efficiently Taken up by the Young Rat Brain than the Unesterified Form", Journal of Neurochemistry, vol. 59, No. 3, Sep. 1, 1992, pp. 1110-1116.

Zaki et al., "Diencephalic-mesencephalic junction dysplasia: a novel recessive brain malformation.", Brain, vol. 135, No. 8, Jul. 20, 2012, pp. 2416-2427.

Bassik et al., "Knocking out the door to tunicamycin entry", Proceedings of the National Academy of Sciences, vol. 108, No. 29, 2011, pp. 11731-11732.

EP14847279.8, "Extended European Search Report", dated Mar. 2, 2017, 9 pages.

Leon et al., "Isolation and Identification of Molecular Species of 1-5,14, 15 Phosphatidylcholine and Lysophosphatidylcholine from Jojoba Seed Meal (*Simmondsia chinensis*)", Journal of Agricultural and Food Chemistry,vol. 52, No. 5, 2004, pp. 1207-1211.

PCT/US2014/057871, "International Preliminary Report on Patentability", dated Apr. 7, 2016, 9 pages.

Reiling et al., "A haploid genetic screen identifies the major facilitator domain containing 2A (MFSD2A) transporter as a key mediator in the response to tunicamycin", Proceedings of the National Academy of Sciences, vol. 108, No. 29, 2011, pp. 11756-11765.

Berger et al., "Major Facilitator Superfamily Domain-Containing Protein 2a (MFSD2A) Has Roles in Body Growth, Motor Function, and Lipid Metabolism", PLoS ONE, Nov. 29, 2012 (Nov. 23, 2012), vol. 7, e50629, pp. 1-13.

Nguyen et al., "Mfsd2a is a transporter for the essential omega-3 fatty acid docosahexaenoic acid", Nature, May 14, 2014 (May 14, 2014), vol. 509, pp. 503-506.

Ben-Zvi et al., "MSFD2A is critical for the formation and function of the blood brain barrier", Nature, May 22, 2014 (May 22, 2014), vol. 509, pp. 507-511.

International Application No. PCT/US2014/057871, International Search Report and Written Opinion, dated Jan. 22, 2015.

European Patent Application No. 14847279.8, Examination Report dated Apr. 23, 2018.

Ohira, et al., "Synaptosomal-associated protein 25 mutation induces immaturity of the dentate granule cells of adult mice", Molecular Brain, Biomed Central Ltd., London UK, vol. 6, No. 1, Mar. 2013, p. 12. XP021142907.

McNamara, et al., "Deciphering the role of docosahexaenoic acid in brain maturation and pathology with magnetic resonance imaging" Prostaglandins Leukotrienes and Essential Fatty Acids', vol. 88, No. 1, Jan. 2013, pp. 33-42. XP055458226.

\* cited by examiner

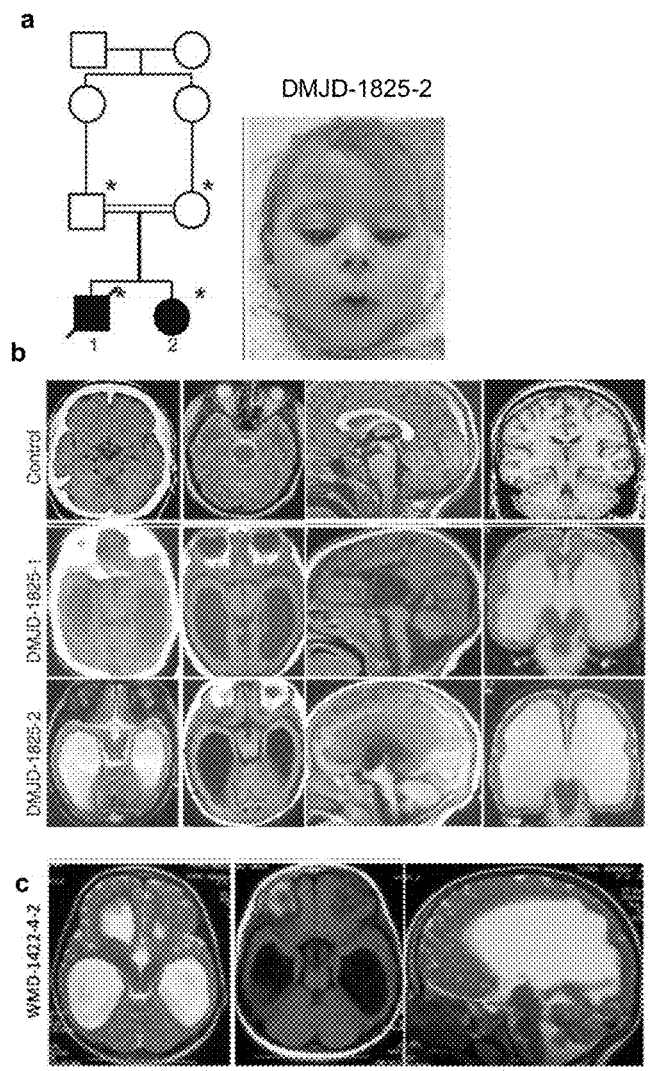

--PRIOR ART--
**Humans with *Mfsd2a* homozygous mutations exhibit severe microcephaly.** a, A pedigree from a consanguineous Egyptian family for the Thr159Met mutation. Black objects in the pedigree indicate affected children. The picture to the right of the pedigree is of the affected girl shown as #2 on the pedigree. b, brain structural images using MRI showing severe microcephaly and hydrocephalus in affected children. Note the small cortex and lack of brain folds. These data are from Zaki M S et al. Brain 2012;135:2416-2427, in which other clinical data can be found. c, Brain MRI image of an unrelated child from a Libyan family having a homozygous Ser166Leu mutation. Note the similarity in phenotype between these two unrelated patients.

Fig. 22

--PRIOR ART--

SEQUENCE LISTING

<160> NUMBER OF SEQ ID NOS: 30

<210> SEQ ID NO 1
<211> LENGTH: 1593
<212> TYPE: DNA
<213> ORGANISM: Homo sapiens

<400> SEQUENCE: 1

```
atggccaaag gagaaggcgc cgagagcggc tccgcggcgg ggctgctacc caccagcatc      60
ctccaaagca ctgaacgccc ggcccaggtg aagaaagaac cgaaaaagaa gaaacaacag     120
ttgtctgttt gcaacaagct ttgctatgca cttgggggag cccctacca ggtgacgggc      180
tgtgccctgg gtttcttcct tcagatctac ctattggatg tggctcaggt gggccctttc    240
tctgcctcca tcatcctgtt tgtgggccga gcctgggatg ccatcacaga ccccctggtg   300
ggcctctgca tcagcaaatc ccctggacc tgcctgggtc gccttatgcc ctggatcatc     360
ttctccacgc ccctggccgt cattgcctac ttcctcatct ggttcgtgcc cgacttccca    420
cacggccaga cctattggta cctgcttttc tattgcctct ttgaaacaat ggtcacgtgt    480
ttccatgttc cctactcggc tctcaccatg ttcatcagca ccgagcagac tgagcgggat    540
tctgccaccg cctatcggat gactgtggaa gtgctgggca cagtgctggg cacggcgatc    600
cagggacaaa tcgtgggcca agcagacacg ccttgtttcc aggacctcaa tagctctaca    660
gtagcttcac aaagtgccaa ccatacacat ggcaccacct cacacaggga aacgcaaaag    720
gcatacctgc tggcagcggg ggtcattgtc tgtatctata taatctgtgc tgtcatcctg    780
atcctgggcg tgcgggagca gagagaaccc tatgaagccc agcagtctga gccaatcgcc    840
tacttccggg gcctacggct ggtcatgagc cacggcccat acatcaaact tattactggc    900
ttcctcttca cctccttggc tttcatgctg gtggagggga ctttgtctt gttttgcacc    960
tacaccttgg gcttccgcaa tgaattccag aatctactcc tggccatcat gctctcggcc   1020
actttaacca ttcccatctg gcagtggttc ttgacccggt ttggcaagaa gacagctgta   1080
tatgttggga tctcatcagc agtgccattt ctcatcttgg tggccctcat ggagagtaac   1140
ctcatcatta catatgcggt agctgtggca gctggcatca gtgtggcagc tgccttctta   1200
ctaccctggt ccatgctgcc tgatgtcatt gacgacttcc atctgaagca gccccacttc   1260
catgaaccg agcccatctt cttctccttc tatgtcttct tcaccaagtt tgcctctgga   1320
gtgtcactgg gcatttctac cctcagtctg gactttgcag ggtaccagac ccgtggctgc   1380
tcgcagccgg aacgtgtcaa gtttacactg aacatgctcg tgaccatggc tcccatagtt   1440
ctcatcctgc tgggcctgct gctcttcaaa atgtacccca ttgatgagga gaggcggcgg   1500
```
cagaataaga aggccctgca ggcactgagg gacgaggcca gcagctctgg ctgctcagaa    1560
acagactcca cagagctggc tagcatcctc tag    1593

<210> SEQ ID NO 2
<211> LENGTH: 530
<212> TYPE: PRT
<213> ORGANISM: Homo sapiens

<400> SEQUENCE: 2

Met Ala Lys Gly Glu Gly Ala Glu Ser Gly Ser Ala Ala Gly Leu Leu
1               5                   10                  15

Pro Thr Ser Ile Leu Gln Ser Thr Glu Arg Pro Ala Gln Val Lys Lys
            20                  25                  30

Glu Pro Lys Lys Lys Lys Gln Gln Leu Ser Val Cys Asn Lys Leu Cys
        35                  40                  45

Tyr Ala Leu Gly Gly Ala Pro Tyr Gln Val Thr Gly Cys Ala Leu Gly
    50                  55                  60

Phe Phe Leu Gln Ile Tyr Leu Leu Asp Val Ala Gln Val Gly Pro Phe
65                  70                  75                  80

Ser Ala Ser Ile Ile Leu Phe Val Gly Arg Ala Trp Asp Ala Ile Thr
                85                  90                  95

Asp Pro Leu Val Gly Leu Cys Ile Ser Lys Ser Pro Trp Thr Cys Leu
            100                 105                 110

Gly Arg Leu Met Pro Trp Ile Ile Phe Ser Thr Pro Leu Ala Val Ile
        115                 120                 125

Ala Tyr Phe Leu Ile Trp Phe Val Pro Asp Phe Pro His Gly Gln Thr
    130                 135                 140

Tyr Trp Tyr Leu Leu Phe Tyr Cys Leu Phe Glu Thr Met Val Thr Cys
145                 150                 155                 160

Phe His Val Pro Tyr Ser Ala Leu Thr Met Phe Ile Ser Thr Glu Gln
                165                 170                 175

Thr Glu Arg Asp Ser Ala Thr Ala Tyr Arg Met Thr Val Glu Val Leu
            180                 185                 190

Gly Thr Val Leu Gly Thr Ala Ile Gln Gly Gln Ile Val Gly Gln Ala
        195                 200                 205

Asp Thr Pro Cys Phe Gln Asp Leu Asn Ser Ser Thr Val Ala Ser Gln
    210                 215                 220

Ser Ala Asn His Thr His Gly Thr Thr Ser His Arg Glu Thr Gln Lys
225                 230                 235                 240

Ala Tyr Leu Leu Ala Ala Gly Val Ile Val Cys Ile Tyr Ile Cys Cys
                245                 250                 255

Ala Val Ile Leu Ile Leu Gly Val Arg Glu Gln Arg Glu Pro Tyr Glu
            260                 265                 270

Ala Gln Gln Ser Glu Pro Ile Ala Tyr Phe Arg Gly Leu Arg Leu Val
        275                 280                 285

Met Ser His Gly Pro Tyr Ile Lys Leu Ile Thr Gly Phe Leu Phe Thr
    290                 295                 300

Ser Leu Ala Phe Met Leu Val Glu Gly Asn Phe Val Leu Phe Cys Thr
305                 310                 315                 320

Tyr Thr Leu Gly Phe Arg Asn Glu Phe Gln Asn Leu Leu Leu Ala Ile
                325                 330                 335

Met Leu Ser Ala Thr Leu Thr Ile Pro Ile Trp Gln Trp Phe Leu Thr
            340                 345                 350

```
Arg Phe Gly Lys Lys Thr Ala Val Tyr Val Gly Ile Ser Ser Ala Val
            355                 360                 365

Pro Phe Leu Ile Leu Val Ala Leu Met Glu Ser Asn Leu Ile Ile Thr
370                 375                 380

Tyr Ala Val Ala Val Ala Ala Gly Ile Ser Val Ala Ala Ala Phe Leu
385                 390                 395                 400

Leu Pro Trp Ser Met Leu Pro Asp Val Ile Asp Asp Phe His Leu Lys
                405                 410                 415

Gln Pro His Phe His Gly Thr Glu Pro Ile Phe Phe Ser Phe Tyr Val
            420                 425                 430

Phe Phe Thr Lys Phe Ala Ser Gly Val Ser Leu Gly Ile Ser Thr Leu
            435                 440                 445

Ser Leu Asp Phe Ala Gly Tyr Gln Thr Arg Gly Cys Ser Gln Pro Glu
450                 455                 460

Arg Val Lys Phe Thr Leu Asn Met Leu Val Thr Met Ala Pro Ile Val
465                 470                 475                 480

Leu Ile Leu Leu Gly Leu Leu Leu Phe Lys Met Tyr Pro Ile Asp Glu
                485                 490                 495

Glu Arg Arg Arg Gln Asn Lys Lys Ala Leu Gln Ala Leu Arg Asp Glu
                500                 505                 510

Ala Ser Ser Ser Gly Cys Ser Glu Thr Asp Ser Thr Glu Leu Ala Ser
            515                 520                 525

Ile Leu
    530

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3 tttttggat cccaccatgg ccaaaggaga aggcgccgag                          40

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tttttttcta gactagagga tgctagccag ctctgtggag tc                      42

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctttgaaaca atggtcatgt gtttccatgt tcc                                33

<210> SEQ ID NO 6
<211> LENGTH: 33
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 6
ggaacatgga aacacatgac cattgtttca aag                                33

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccatgttccc tacttggctc tcaccatgtt c                                  31

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gaacatggtg agagccaagt agggaacatg g                                  31

<210> SEQ ID NO 9
<211> LENGTH: 7
<212> TYPE: PRT
<213> ORGANISM: Homo sapiens

<400> SEQUENCE: 9

Thr Met Val Thr Cys Phe His
1               5

<210> SEQ ID NO 10
<211> LENGTH: 7
<212> TYPE: PRT
<213> ORGANISM: Pan troglodytes

<400> SEQUENCE: 10

Thr Met Val Thr Cys Phe His
1               5

<210> SEQ ID NO 11
<211> LENGTH: 7
<212> TYPE: PRT
<213> ORGANISM: Mus musculus

<400> SEQUENCE: 11

Thr Leu Val Thr Cys Phe His
1               5

<210> SEQ ID NO 12
<211> LENGTH: 7
<212> TYPE: PRT
<213> ORGANISM: Rattus norvegicus

<400> SEQUENCE: 12

Thr Leu Val Thr Cys Phe His
1               5
```

```
<210> SEQ ID NO 13
<211> LENGTH: 7
<212> TYPE: PRT
<213> ORGANISM: Gallus gallus

<400> SEQUENCE: 13

Thr Leu Val Thr Cys Phe His
1               5

<210> SEQ ID NO 14
<211> LENGTH: 7
<212> TYPE: PRT
<213> ORGANISM: Xenopus tropicalis

<400> SEQUENCE: 14

Thr Leu Val Thr Cys Phe His
1               5

<210> SEQ ID NO 15
<211> LENGTH: 7
<212> TYPE: PRT
<213> ORGANISM: Danio rerio

<400> SEQUENCE: 15

Thr Leu Gln Thr Cys Phe His
1               5

<210> SEQ ID NO 16
<211> LENGTH: 7
<212> TYPE: PRT
<213> ORGANISM: Danio rerio

<400> SEQUENCE: 16

Thr Leu Gln Thr Cys Phe His
1               5

<210> SEQ ID NO 17
<211> LENGTH: 7
<212> TYPE: PRT
<213> ORGANISM: Homo sapiens

<400> SEQUENCE: 17

Val Pro Tyr Ser Ala Leu Thr
1               5

<210> SEQ ID NO 18
<211> LENGTH: 7
<212> TYPE: PRT
<213> ORGANISM: Pan troglodytes

<400> SEQUENCE: 18

Val Pro Tyr Ser Ala Leu Thr
1               5

<210> SEQ ID NO 19
<211> LENGTH: 7
<212> TYPE: PRT
<213> ORGANISM: Mus musculus

<400> SEQUENCE: 19

Val Pro Tyr Ser Ala Leu Thr
1               5

<210> SEQ ID NO 20
```

```
<211> LENGTH: 7
<212> TYPE: PRT
<213> ORGANISM: Rattus norvegicus

<400> SEQUENCE: 20

Val Pro Tyr Ser Ala Leu Thr
1               5

<210> SEQ ID NO 21
<211> LENGTH: 7
<212> TYPE: PRT
<213> ORGANISM: Gallus gallus

<400> SEQUENCE: 21

Val Pro Tyr Ser Ala Leu Thr
1               5

<210> SEQ ID NO 22
<211> LENGTH: 7
<212> TYPE: PRT
<213> ORGANISM: Xenopus tropicalis

<400> SEQUENCE: 22

Val Pro Tyr Ser Ala Leu Thr
1               5

<210> SEQ ID NO 23
<211> LENGTH: 7
<212> TYPE: PRT
<213> ORGANISM: Danio rerio

<400> SEQUENCE: 23

Val Pro Tyr Ser Ala Leu Thr
1               5

<210> SEQ ID NO 24
<211> LENGTH: 7
<212> TYPE: PRT
<213> ORGANISM: Danio rerio

<400> SEQUENCE: 24

Val Pro Tyr Ser Ala Leu Thr
1               5

<210> SEQ ID NO 25
<211> LENGTH: 14
<212> TYPE: DNA
<213> ORGANISM: Homo sapiens

<400> SEQUENCE: 25
tactyggctc tcac                                                     14

<210> SEQ ID NO 26
<211> LENGTH: 14
<212> TYPE: DNA
<213> ORGANISM: Homo sapiens

<400> SEQUENCE: 26
tacttggctc tcac                                                     14

<210> SEQ ID NO 27
<211> LENGTH: 14
<212> TYPE: DNA
<213> ORGANISM: Homo sapiens
```

```
<400> SEQUENCE: 27
tactcggctc tcac                                                      14

<210> SEQ ID NO 28
<211> LENGTH: 14
<212> TYPE: DNA
<213> ORGANISM: Homo sapiens

<400> SEQUENCE: 28
gtcayggtga gtgt                                                      14

<210> SEQ ID NO 29
<211> LENGTH: 14
<212> TYPE: DNA
<213> ORGANISM: Homo sapiens

<400> SEQUENCE: 29
gtcatggtga gtgt                                                      14

<210> SEQ ID NO 30
<211> LENGTH: 14
<212> TYPE: DNA
<213> ORGANISM: Homo sapiens

<400> SEQUENCE: 30
gtcacggtga gtgt                                                      14
```

COMPOSITIONS AND METHODS UTILIZING LYSOPHOSPHATIDYLCHOLINE SCAFFOLDS

This application is the U.S. national stage of PCT/US2014/057871, filed Sep. 26, 2014, which claims the benefit of priority to U.S. Provisional Application No. 61/882,693, filed Sep. 26, 2013, U.S. Provisional Application No. 61/973,136, filed Mar. 31, 2014, and U.S. Provisional Application No. 61/992,822, filed May 13, 2014, all of which are incorporated by reference herein in their entirety for all purposes.

SEQUENCE LISTING

The instant application contains a Sequence Listing which has been submitted electronically in ASCII format and is hereby incorporated by reference in its entirety. Said ASCII copy, created on May 21, 2018, is named 097520-1005812_SL.txt and is 11,466 bytes in size.

FIELD

The invention relates to compositions and methods for utilizing scaffolds, such as lysophosphatidylcholine scaffolds. The compositions and methods can be used for LPC-mediated delivery of fatty acids and other molecules; to screen and identify fatty acid formulations for parenteral nutrition; and for live animal organ imaging. The invention also relates to compositions and methods for utilizing mutations and polymorphisms in human Mfsd2a as markers for neurological deficits.

BACKGROUND

The bloodstream contains numerous species of lipids circulating on lipoproteins, albumin and other lipid-binding proteins. The diversity of lipids in blood is complex, with the majority of species belonging to the phospholipids, fatty acids, and sphingolipid classes. Many members of these classes have structural roles, such as phosphatidylcholines and signaling roles, such as sphingosine-1-phosphate. One lipid species of which relatively little is known about their functions in blood are the lysophosphatidylcholines (LPCs). LPCs are structurally composed of three major lipid components: a glycerol, phosphocholine, and a fatty acid esterified to either the sn-1 or sn-2 hydroxyls of glycerol. Within cellular membranes, the majority of LPCs are synthesized through the hydrolysis of the fatty acid moiety in the sn-2 position of phosphatidylcholine lipids via phospholipase $A_2$ enzymes. The newly generated LPCs are precursors for the re-synthesis of phosphatidylcholines through acylation reactions via lysophosphatidylcholine acyltransferase (LPCAT) enzymes that constitute the Lands Cycle of phospholipid remodeling. The Lands Cycle has been proposed to be important for regulating membrane properties, such as maintaining high levels of saturated fatty acids in phospholipids in the nuclear envelop. In addition, the Lands Cycle might also serves to keep LPCs, which are toxic to cells, at extremely low levels within cellular membranes. Interestingly, the levels of LPCs in blood are quite high, reaching about 100 µM in human and rodents (Croset, M., Brossard, N., Polette, A. & Lagarde, M. Characterization of plasma unsaturated lysophosphatidylcholines in human and rat. *The Biochemical Journal* 345 Pt 1, 61-67 (2000); Quehenberger, O. et al. Lipidomics reveals a remarkable diversity of lipids in human plasma. *Journal of lipid research* 51, 3299-3305, doi:10.1194/jlr.M009449 (2010)). A minor amount of the total blood LPCs are generated on lipoproteins in circulation by the action of lecithin-cholesterol acyltransferase on high density lipoproteins and through lipoprotein-associated phospholipase $A_2$ on low density lipoproteins. The majority of LPCs in human and rodent blood are synthesized through the action of phospholipase $A_2$ in the liver, where they are secreted on albumin. The most abundant of blood LPCs in human and rodents are LPC-palmitate, -stearate, and -oleate. The other classes of non-membrane localized lyso-lipids, such as lyso-PE, lyso-PI, and lyso-PS are found at extremely low levels in blood and primarily circulate on lipoproteins. The physiological function of blood LPCs has remained enigmatic, but some reports suggest a largely signaling role in inflammation, angiogenesis, cell proliferation and migration. Provided herein are new uses for LPCs in diverse areas including nutrition.

With respect to nutrition, the majority of low birth weight and extremely low birth weight preterm newborns remain in the neonatal intensive care unit (NICU) for a period equivalent to the third trimester. During this time, preterm infants that are unable to obtain adequate nutrition via the GI tract require parenteral nutritional (PN) support. Poor nutrition in preterm infants has been shown to have major negative outcomes later in life on physical and intellectual development, and increased risk for cardiovascular and metabolic disorder (Isaacs E B, et al. (2008) The effect of early human diet on caudate volumes and IQ. *Pediatric research* 63(3): 308-314; Lapillonne A & Griffin I J (2013) Feeding preterm infants today for later metabolic and cardiovascular outcomes. *The Journal of pediatrics* 162(3 Suppl):S7-16.).

Although international guidelines on pediatric PN have recently been refined and have become the standard of care worldwide (Nutritional needs of the preterm infant: scientific basis and practical guidelines. Cincinnati: Digital Educational Publishing Inc., OH.; Koletzko B, Goulet O, Hunt J, Krohn K, & Shamir R (2005) 1. Guidelines on Paediatric Parenteral Nutrition of the European Society of Paediatric Gastroenterology, Hepatology and Nutrition (ESPGHAN) and the European Society for Clinical Nutrition and Metabolism (ESPEN), Supported by the European Society of Paediatric Research (ESPR). *Journal of pediatric gastroenterology and nutrition* 41 Suppl 2:S1-87), it is becoming widely accepted that nutritional intake in preterm infants using PN in NICUs is inadequate (Martin C R, et al. (2009) Nutritional practices and growth velocity in the first month of life in extremely premature infants. *Pediatrics* 124(2):649-657; Olsen I E, Richardson D K, Schmid C H, Ausman L M, & Dwyer J T (2002) Intersite differences in weight growth velocity of extremely premature infants. *Pediatrics* 110(6): 1125-1132). Importantly, the optimal composition of nutrients in PN remains unknown (Beardsall K, et al. (2008) Early insulin therapy in very-low-birth-weight infants. *The New England journal of medicine* 359(18):1873-1884; Clark R H, Chace D H, & Spitzer A R (2007) Effects of two different doses of amino acid supplementation on growth and blood amino acid levels in premature neonates admitted to the neonatal intensive care unit: a randomized, controlled trial. *Pediatrics* 120(6):1286-1296). The standard of care is a formulation of amino acids, glucose, and lipids. The lipids are typically derived from soybean oil (up to 20%) and, in some newer formulations, contain omega-3 oils (e.g. SUM-FLipid, from F). Soybean oil provides fatty acids for energy and the omega-3 and omega-6 fatty acid precursors are synthesized into docosahexaenoic acid (DHA) and arachidonic acid (ARA), which are essential for brain development. Conversion of precursor fatty acids into DHA and ARA rely on the newborn liver, which often has poor function and cannot provide adequate amounts of these essential fatty acids. Provided herein are solutions to these and other nutritional problems.

Furthermore, the role of mutations in the Mfsd2a protein as the basis of neurological diseases and deficits has also been elucidated. Disclosed herein are solutions to these medical challenges as well.

SUMMARY

Disclosed herein are compositions and methods for utilizing scaffolds such as lysophosphatidylcholine scaffolds for transport through the Mfsd2a protein. The compositions and methods can be used for LPC-mediated delivery of fatty acids and other molecules; to screen and identify fatty acid formulations for parenteral nutrition; and for live animal organ imaging, among other uses. Also disclosed herein are compositions and methods for utilizing mutations and polymorphisms in human Mfsd2a as markers for neurological deficits.

In a first aspect, provided herein is a method for screening one or more compound to determine transport via the Mfsd2a protein, the method comprising: (a) contacting a biological mixture to be tested with a genetically modified mouse that comprises in its genome a homozygous disruption of the Mfsd2a gene (KO mouse) and a wild type mouse; (b) measuring the amount of one or more compound in a tissue or fluid of the KO mouse and the wild type mouse; and (c) comparing the amount of said one or more compound in the tissue or fluid of the KO mouse and the wild-type mouse, wherein higher amounts of said one or more compound in the wild-type mouse as compared to the KO mouse is an indication of transport of the compound via Mfsd2a protein.

In some embodiments, the KO mouse does not express functional Mfsd2a protein. In some embodiments, the biological mixture is derived from milk, fish oil extracts, or LPC formulations. In some embodiments, the tissue or fluid is brain, liver, heart, or breast milk. In some embodiments, the method of contacting is by oral or i.v. administration.

In a second aspect, provided herein is a method for screening one or more compound to determine transport via the Mfsd2a protein, the method comprising: (a) contacting a biological mixture to be tested with a cell line comprising a human wild type Mfsd2a cDNA or a mutant human Mfsd2a cDNA or a mock transfected cell; (b) measuring the amount of said one or more compound in cells comprising the human wild type Mfsd2a cDNA and a cell comprising mutant human Mfsd2a cDNA or a mock transfected cell; and (c) comparing the amount of said one or more compound in the cells comprising wild type Mfsd2a cDNA and cells comprising mutant human Mfsd2a cDNA or mock transfected cells, wherein higher amounts of said one or more compound in the cells comprising wild-type Mfsd2a cDNA as compared to cells comprising mutant human Mfsd2a cDNA or mock transfected cells is an indication of transport of the compound via Mfsd2a protein.

In some embodiments, the cell is HEK 293. In some embodiments, the mutant human Mfsd2a cDNA comprises a mutation at a position corresponding to D93 or D97 in the human Mfsd2a protein sequence.

In a third aspect, provided herein is a nutritional supplement comprising one or more LPC components selected from the group consisting of: LPC-16:0, LPC-18:0, LPC-18:1, LPC-18:2 n-6, LPC-20:4 n-6, LPC-22:6 n-3, LPC-20:5 n-3.

In a fourth aspect, provided herein is a nutritional supplement comprising LPC-16:0, LPC-18:0, LPC-18:1, LPC-18:2 n-6, LPC-20:4 n-6, LPC-22:6 n-3, LPC-20:5 n-3 at the concentrations of 37, 14, 10, 20, 4, 25, and 0.5 mM respectively.

In a fifth aspect, provided herein is a nutritional supplement comprising one or more PC components selected from the group consisting of: PC-16:0, PC-18:0, PC-18:1, PC-18:2 n-6, PC-20:4 n-6, PC-22:6 n-3, PC-20:5 n-3.

In a sixth aspect, provided herein is a nutritional supplement comprising PC-16:0, PC-18:0, PC-18:1, PC-18:2 n-6, PC-20:4 n-6, PC-22:6 n-3, PC-20:5 n-3 at the concentrations of 37, 14, 10, 20, 4, 25, and 0.5 mM respectively.

In some embodiments, the nutritional supplement further comprises human albumin. In some embodiments, the nutritional supplement further comprises an additional lipid formula selected from the group consisting of Intralipid™, SMOFKabiven™, Omegaven™, Lipofundin™, ClinOleic™, and Liposyn™.

In a seventh aspect, provided herein is a method of screening for compounds that modulate transport through the Mfsd2a protein comprising: (a) contacting cell lines comprising a human wild type Mfsd2a cDNA or a mutant human Mfsd2a cDNA or a mock transfected cell with LPC-palmitate, -oleate, -stearate, -linoleate, -linolenate, -arachidonate, -docosahexaenoate or a derivative; (b) measuring the uptake of the LPC-palmitate, -oleate, -stearate, -linoleate, -linolenate, -arachidonate, -docosahexaenoate or a derivative in the presence and absence of a test compound in the cells comprising the human wild type Mfsd2a cDNA and the cells comprising mutant human Mfsd2a cDNA or mock transfected cells; wherein an increased or decreased level of uptake of LPC-palmitate, -oleate, -stearate, -linoleate, -linolenate, -arachidonate, -docosahexaenoate or a derivative into cells comprising the human wild type Mfsd2a cDNA in the presence of the test compound as compared to in the absence of the test compound identities the compound as a modulator of transport through the Mfsd2a protein.

In some embodiments, the cell is HEK 293. In some embodiments, the mutant human Mfsd2a cDNA comprises a mutation at a position corresponding to D93 or D97 in the human Mfsd2a protein sequence. In some embodiments, the test compound is directly transported through the Mfsd2a protein.

In an eighth aspect, provided herein is a method of imaging an organ comprising administering to a subject a labeled scaffold or conjugate and determining the uptake or interaction of said labeled scaffold or conjugate with the Mfsd2a protein in an organ of interest.

In some embodiments, the scaffold is LPC. In some embodiments, the label is fluorescent. In some embodiments, the label is fluorinated. In some embodiments, the organ is the brain or eye. In some embodiments, the labeled scaffold is Top-Fluor-LPC or NBD-LPC.

In a ninth aspect, provided herein is a method of transporting compounds through the Mfsd2a protein comprising providing a subject a scaffold or conjugate under conditions sufficient to allow uptake of the scaffold or conjugate.

In some embodiments, the scaffold is LPC. In some embodiments, the compound is conjugated to LPC via the omega carbon of LPC. In some embodiments, the scaffold or conjugate crosses or accumulates in the BBB. In some embodiments, the scaffold or conjugate accumulates in the brain or eye.

In a tenth aspect, provided herein is a composition comprising a scaffold conjugated to a compound.

In some embodiments, the scaffold is LPC. In some embodiments, the compound is conjugated to LPC via the omega carbon of LPC. In some embodiments, the compound is a pharmaceutical agent. In some embodiments, the compound is an imaging agent.

In an eleventh aspect, provided herein is a method of evaluating increased susceptibility for neurological deficits in a subject comprising: (a) providing a biological sample from the subject, wherein the sample comprises all, or a portion of, an Mfsd2a gene; and (b) detecting the presence of a mutation or polymorphism in the Mfsd2a gene or the portion thereof in the sample; and (c) evaluating that the subject has an increased susceptibility to neurological deficits based on the presence of the mutation or polymorphism in the Mfsd2a gene or the portion thereof.

In some embodiments, the mutation is Thr159Met or Ser166Leu. In some embodiments, the polymorphism is one or more of the single nucleotide polymorphisms listed in Table 4, 7, or 8. In some embodiments, the mutation results in loss of function. In some embodiments, the mutation is a hypomorphic allele of Mfsd2a.

In some embodiments, the neurological deficit is a deficit in memory and learning or anxiety.

In some embodiments, the subject is a woman prior to conception or during pregnancy.

In some embodiments, the method further comprises administering a high DHA diet or i.v. or enteral treatment with LPCs, if the mutation or polymorphism in the Mfsd2a gene or the portion thereof is present. In some embodiments, the LPC comprises LPC-DHA.

In some embodiments, the subject is a child or adult diagnosed with problems with cognitive function. In some embodiments, the cognitive function is a learning disability or anxiety.

In some embodiments, the detecting comprises contacting the sample with an oligonucleotide probe that preferentially hybridizes to the Mfsd2a gene or the portion thereof. In some embodiments, the detecting comprises amplifying by PCR the Mfsd2a gene or the portion thereof. In some embodiments, the detecting comprises sequencing the Mfsd2a gene, the portion thereof, or the corresponding Mfsd2a cDNA or a portion thereof.

In a twelveth aspect, provided herein is a method for evaluating the transport function of a Mfsd2a protein from a subject comprising: (a) expressing a test Mfsd2a cDNA in a first cell and a wild type Mfsd2a cDNA in a second cell; (b) contacting the first cell expressing the test Mfsd2a cDNA and the second cell expressing the wild type Mfsd2a cDNA with LPC-DHA or LPC-omega 3 fatty acids; and (c) measuring the uptake of LPC-DHA or LPC-omega 3 fatty acids into the first cell expressing the test Mfsd2a cDNA and the second cell expressing the wild type Mfsd2a cDNA, wherein a decreased level of uptake of LPC-DHA or LPC-omega 3 fatty acids into the first cell expressing the test Mfsd2a cDNA as compared to the second cell expressing the wild type Mfsd2a cDNA indicates that the test Mfsd2a cDNA encodes a protein deficient for transport.

In some embodiments, the test Mfsd2a cDNA encodes a Thr159Met or Ser166Leu mutation. In some embodiments, the test Mfsd2a cDNA encodes one or more of the polymorphisms listed in Table 4, 6, or 7.

BRIEF DESCRIPTION OF THE DRAWINGS

FIG. 2 $b$, $d$, $f$, total DHA levels in brain, liver, and heart phospholipids (WT, n=5; KO, n=4). FIG. 2 $c$, $e$, $g$, total AA levels in brain, liver, and heart. *P<0.0001, P<0.01, *P<0.05. DHA and AA levels are expressed as mean±SEM of percentage of total level of phospholipids. See Table 2.

FIG. 22. Humans with Mfsd2a homozygous mutations exhibit severe microcephaly. a, A pedigree from a consanguineous Egyptian family for the Thr159Met mutation. Black objects in the pedigree indicate affected children. The picture to the right of the pedigree is of the affected girl shown as #2 on the pedigree. b, brain structural images using MRI showing severe microcephaly and hydrocephalus in affected children. Note the small cortex and lack of brain folds. These data are from Zaki M S et al. Brain 2012; 135:2416-2427, in which other clinical data can be found. c, Brain MRI image of an unrelated child from a Libyan family having a homozygous Ser166Leu mutation. Note the similarity in phenotype between these two unrelated patients.

FIG. 23 discloses SEQ ID NOS 9-24, respectively, in order of appearance. (E) Location of mutations relative to predicted protein. TM: transmembrane domains, orange: Major facilitator superfamily domain, general substrate transporter domain.

FIG. 27 discloses SEQ ID NOS 25, 28, 26, 29, 27 and 30, respectively, in order of appearance.

DETAILED DESCRIPTION

Introduction

Figure 1:
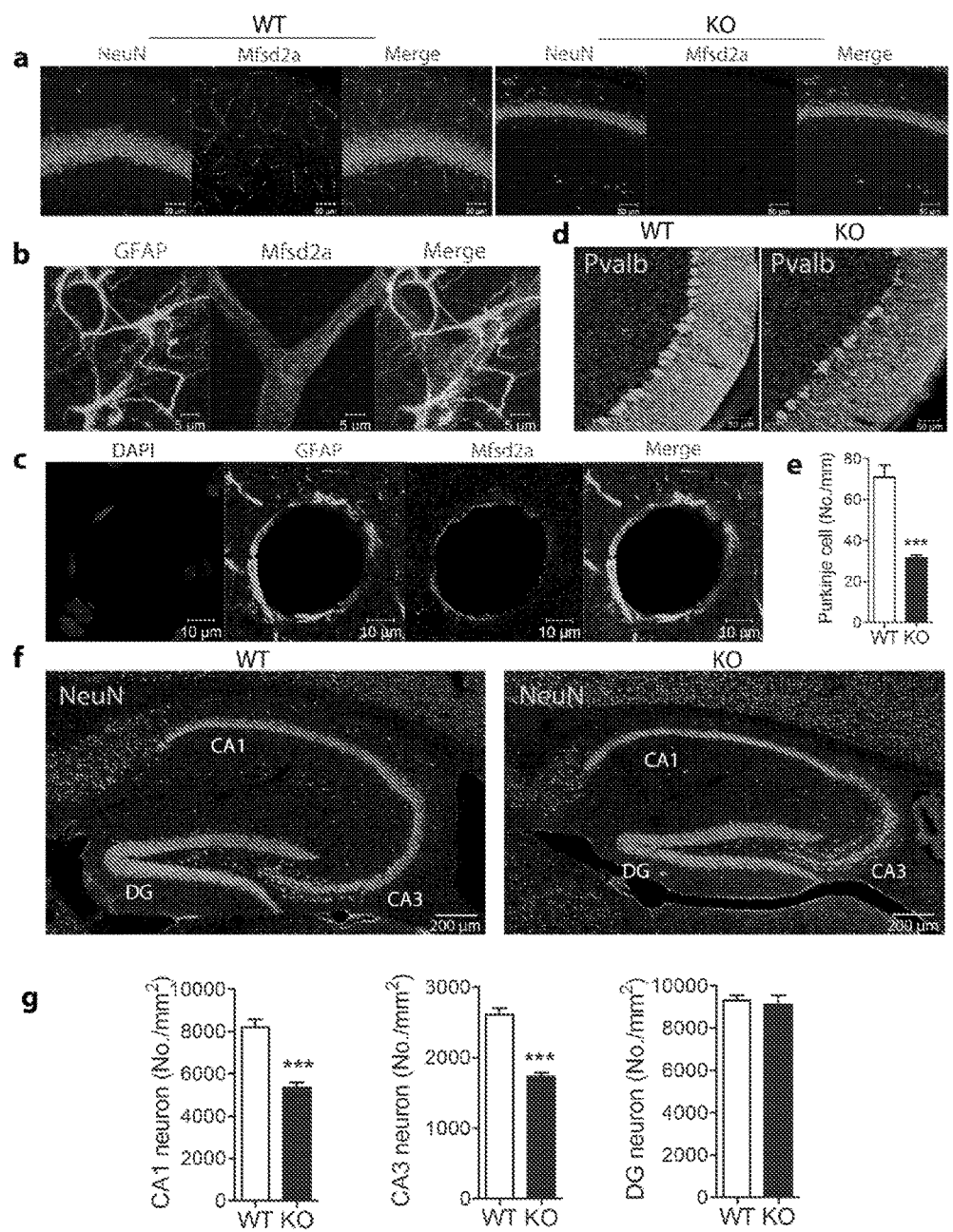
FIG. 1. Localization of Mfsd2a in the blood-brain barrier and neuronal deficits in KO mice. a, Mfsd2a is highly enriched in brain micro-vessels, shown here in CA1 region with NeuN staining of mature neurons. b, c, Mfsd2a is expressed in endothelial cells of blood brain barrier in close contact with endfeet of astrocytes as shown by GFAP staining. d, Loss of Purkinje cells detected by parvalbumin (Pvalb) staining in cerebellum of KO mice. e, quantification of Purkinje cells in the cerebellum of WT and KO mice. *P<0.001. f, NeuN staining in hippocampus of sagittal brain sections of 8 weeks old WT and KO mice indicate decreased mature neurons in specific hippocampal regions of KO mice. g, quantification of neuron numbers in CA1, CA3, and dentate gyrus (DG) regions from mice examined in (f) above. *P<0.001. Data are expressed as mean±SEM.

Docosahexaenoic acid (DHA) is an omega-3 fatty acid essential for normal brain growth and cognitive function (Kidd, P. M. Omega-3 DHA and EPA for cognition, behavior, and mood: clinical findings and structural-functional synergies with cell membrane phospholipids. *Alternative medicine review: a journal of clinical therapeutic* 12, 207-227 (2007); Horrocks, L. A. & Yeo, Y. K. Health benefits of docosahexaenoic acid (DHA). *Pharmacological research: the official journal of the Italian Pharmacological Society* 40, 211-225, doi:10.1006/phrs.1999.0495 (1999); Mozaffarian, D. & Wu, J. H. Omega-3 fatty acids and cardiovascular disease: effects on risk factors, molecular pathways, and clinical events. *Journal of the American College of Cardiology* 58, 2047-2067, doi:10.1016/j.jacc.2011.06.063 (2011); Connor, W. E. Importance of n-3 fatty acids in health and disease. *The American journal of clinical nutrition* 71, 171S-175S (2000)). In line with its importance in the brain, DHA is highly enriched in brain phospholipids (Breckenridge, W. C., Gombos, G. & Morgan, I. G. The lipid composition of adult rat brain synaptosomal plasma membranes. *Biochim Biophys Acta* 266, 695-707 (1972); Innis, S. M. Dietary (n-3) fatty acids and brain development. *The Journal of nutrition* 137, 855-859 (2007); Salem, N., Jr., Litman, B., Kim, H. Y. & Gawrisch, K. Mechanisms of action of docosahexaenoic acid in the nervous system. *Lipids* 36, 945-959 (2001)). Despite being an abundant fatty acid in brain phospholipids, DHA cannot be de novo synthesized in brain and must be imported across the blood-brain barrier, but mechanisms for DHA uptake in brain have remained enigmatic. Here we identify a member of the Major Facilitator Superfamily, the previously orphaned transporter Mfsd2a that we show to be exclusively expressed in endothelium of the blood-brain barrier of micro-vessels, as the major transporter for DHA uptake into brain. Lipidomic analysis indicates that Mfsd2a-deficient mice (KO) have dramatically reduced levels of DHA in brain accompanied with neuronal cell loss in hippocampus and cerebellum, and neurological and severe behavioral disorders, and importantly reduced brain size. Surprisingly, cell-based studies indicated that Mfsd2a transported DHA in the form of lysophosphatidylcholine (LPC), but not unesterified fatty acid, in a sodium-dependent manner. Notably, Mfsd2a transported common plasma LPCs carrying long chain fatty acids such as LPC-oleate and LPC-palmitate, but not LPCs having less than a 14-carbon acyl chain. Moreover, we determined that the phosphor-zwitterionic headgroup of LPC is critical for transport. Importantly, KO mice had dramatically reduced uptake of labeled LPC-DHA, and other LPCs from plasma into brain demonstrating that Mfsd2a is required for brain uptake of DHA. Our findings reveal an unexpected essential physiological role of plasma-derived LPCs in brain growth and function.

Based on the the findings disclosed herein, compositions and methods are provided for LPC-mediated delivery of DHA and omega-3 fatty acids across the blood-brain, blood-eye, and placental endothelial barrier; LPC-DHA, LPCs and omega-3 fatty acid formulations for parenteral nutrition; systems to screen for optimized formulations of LPC-nutritional conjugates and other conjugates; and methods for use of LPC-conjugates and other conjugates for live animal imaging of the brain and eye, and for identifying propensity for displaying neurological deficits.

Terms Used

It is to be understood that this invention is not limited to particular methods, reagents, compounds, compositions or biological systems, which can, of course, vary. It is also to be understood that the terminology used herein is for the purpose of describing particular aspects only, and is not intended to be limiting. As used in this specification and the appended claims, the singular forms "a", "an" and "the" include plural references unless the content clearly dictates otherwise.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

"Vertebrate," "mammal," "subject," "mammalian subject," or "patient" are used interchangeably and refer to mammals such as human patients and non-human primates, as well as experimental animals such as rabbits, rats, and mice, and other animals. Animals include all vertebrates, e.g., mammals and non-mammals, such as mice, sheep, dogs, cows, avian species, ducks, geese, pigs, chickens, amphibians, and reptiles.

The Major Facilitator Superfamily (MFS)

The Major Facilitator Superfamily (MFS) is the largest secondary transporter family in both prokaryotes and eukaryotes. The vast majority of characterized MFS proteins transport hydrophilic compounds and none has yet been identified that transports biological lipids, and specifically phospholipids (Law, C. J., Maloney, P. C. & Wang, D. N. Ins and outs of major facilitator superfamily antiporters. *Annu Rev Microbiol* 62, 289-305, doi:10.1146/annurev.micro.61.080706.093329 (2008)), which is a function co-opted by the ATP Binding Cassette transport family of proteins. Mfsd2a is an orphan transporter classified as a member of the MFS 3 (Law, C. J., Maloney, P. C. & Wang, D. N. Ins and outs of major facilitator superfamily antiporters. *Annu Rev Microbiol* 62, 289-305, doi:10.1146/annurev.micro.61.080706.093329 (2008)). In bacteria, the Mfsd2a has remote homology to the sodium/disaccharide symporter, melB, a transporter for the bacterial disaccharide melibiose. Comprehensive sequence analysis indicates strong phylogenetic conservation of Mfsd2a from fish to man (Berger, J. H., Charron, M. J. & Silver, D. L. Major facilitator superfamily domain-containing protein 2a (MFSD2A) has roles in body growth, motor function, and lipid metabolism. *PLoS One* 7, e50629, doi:10.1371/journal.pone.0050629 (2012)). Fish Mfsd2a is expressed in brain (www.fishbase.org). Using an unbiased screen in cell culture models, human Mfsd2a was identified as a receptor for the syncytiotrophblast fusion factor syncytin-2, a retrovirus-derived protein found in primate genomes, while mouse Mfsd2a does not bind to syncytins or mediate cell fusion. Thus, it was suggested that the fusion function of human Mfsd2a is likely a "secondary" function and that its primary function is in transport (Esnault, C. et al. A placenta-specific receptor for the fusogenic, endogenous retrovirus-derived, human syncytin-2. *Proceedings of the National Academy of Sciences of the United States of America* 105, 17532-17537, doi:10.1073/pnas.0807413105 (2008)). In separate studies, Mfsd2a was described as a fasting-induced gene in mouse liver, but is highly and constitutively expressed in brain (Angers, M., Uldry, M., Kong, D., Gimble, J. M. & Jetten, A. M. Mfsd2a encodes a novel major facilitator superfamily domain-containing protein highly induced in brown adipose tissue during fasting and adaptive thermogenesis. *The Biochemical Journal* 416, 347-355, doi:10.1042/BJ20080165 (2008)). We found that basal Mfsd2a levels in mouse liver are exceedingly low, and fasting-induced expression of Mfsd2a in liver was regulated by the master regulator of fatty acid metabolism PPARα (Angers, M., Uldry, M., Kong, D., Gimble, J. M. & Jetten, A. M. Mfsd2a encodes a novel major facilitator superfamily domain-containing protein highly induced in brown adipose tissue during fasting and adaptive thermogenesis. *The Biochemical Journal* 416, 347-355, doi: 10.1042/BJ20080165 (2008)), suggesting that Mfsd2a might be involved in fatty acid transport.

The MFS family of proteins is vast, with members found from *E. coli* to human. The majority of characterized MFS members known to date transport hydrophilic molecules. It has been shown that despite high overall structural similarity in the MFS family, MFS proteins achieve ligand specificity by changes in relatively few amino acid residues (Law, C. J., Maloney, P. C. & Wang, D. N. Ins and outs of major facilitator superfamily antiporters. *Annu Rev Microbiol* 62, 289-305, doi:10.1146/annurev.micro.61.080706.093329 (2008)). The overall mechanism of transport of the MFS family has been first inferred from the X-ray structure of glycerol-3-phosphate transporter GlpT from *E. coli*, and confirmed by structures of other MFS family members (Huang, Y., Lemieux, M. J., Song, J., Auer, M. & Wang, D. N. Structure and mechanism of the glycerol-3-phosphate transporter from *Escherichia coli*. *Science* 301, 616-620, doi:10.1126/science.1087619 (2003); Shi, Y. Common folds and transport mechanisms of secondary active transporters. *Annual Review of Biophysics* 42, 51-72, doi:10.1146/annurev-biophys-083012-130429 (2013)). The model has been described as a "rocker-switch" model in which an outward open conformation binds to ligands causing a conformation switch to the inside-open conformation (Shi, Y. Common folds and transport mechanisms of secondary active transporters. *Annual Review of Biophysics* 42, 51-72, doi: 10.1146/annurev-biophys-083012-130429 (2013)). The energy to drive this conformational change is provided by the binding of cations, such as sodium, that flow down their concentration gradients. In the case of Mfsd2a, it utilizes sodium to drive the transport of LPC. Indeed, Mfsd2a contains a conserved sodium-binding site that we have shown is essential for sodium-dependent transport of LPC. The minimal ligand structure of the lysolipid that is required for transport by Mfsd2a is a phosphate-based zwitterion headgroup and a minimum of an alkyl side-chain having 14 carbons. The use of the zwitterionic headgroup of LPC as an important ligand structural feature is congruous with the use of hydrophilic ligands for most MFS family members. The tolerance of Mfsd2a for the alkyl side-chain is a new attribute for an MFS protein. In vivo, Mfsd2a transports LPC ligands bound to albumin, but our study shows that Mfsd2a can also transport LPC ligands dissolved in ethanol or in the form of micelles. Thus, binding of LPC to albumin is not required for transport. We propose the following simple model for Mfsd2a transport of LPCs: 1) LPC first absorbs onto the outer leaflet of the plasma membrane, followed by lateral diffusion and 2) binding to Mfsd2a. 3) The phosphocholine headgroup is co-transported with sodium through the transporter while the alkyl side chain hangs off the transporter into the surrounding hydrophobic environment of the membrane. This configuration ultimately would allow the movement of the alkyl-side chain and entire LPC molecule across the membrane to the inner leaflet.

A representative cDNA sequence encoding a human Mfsd2a protein is shown below:

(SEQ ID NO: 1)
ATGGCCAAAGGAGAAGGCGCCGAGAGCGGCTCCGCGGCGGGGCTGCTAC

CCACCAGCATCCTCCAAAGCACTGAACGCCCGGCCCAGGTGAAGAAAGA

ACCGAAAAAGAAGAAACAACAGTTGTCTGTTTGCAACAAGCTTTGCTAT

GCACTTGGGGGAGCCCCCTACCAGGTGACGGGCTGTGCCCTGGGTTTCT

TCCTTCAGATCTACCTATTGGATGTGGCTCAGGTGGGCCCTTTCTCTGC

CTCCATCATCCTGTTTGTGGGCCGAGCCTGGGATGCCATCACAGACCCC

CTGGTGGGCCTCTGCATCAGCAAATCCCCCTGGACCTGCCTGGGTCGCC

TTATGCCCTGGATCATCTTCTCCACGCCCCTGGCCGTCATTGCCTACTT

CCTCATCTGGTTCGTGCCCGACTTCCCACACGGCCAGACCTATTGGTAC

CTGCTTTTCTATTGCCTCTTTGAAACAATGGTCACGTGTTTCCATGTTC

CCTACTCGGCTCTCACCATGTTCATCAGCACCGAGCAGACTGAGCGGGA

TTCTGCCACCGCCTATCGGATGACTGTGGAAGTGCTGGGCACAGTGCTG

GGCACGGCGATCCAGGGACAAATCGTGGGCCAAGCAGACACGCCTTGTT

TCCAGGACCTCAATAGCTCTACAGTAGCTTCACAAAGTGCCAACCATAC

ACATGGCACCACCTCACACAGGGAAACGCAAAAGGCATACCTGCTGGCA

GCGGGGGTCATTGTCTGTATCTATATAATCTGTGCTGTCATCCTGATCC

TGGGCGTGCGGGAGCAGAGAGAACCCTATGAAGCCCAGCAGTCTGAGCC

AATCGCCTACTTCCGGGGCCTACGGCTGGTCATGAGCCACGGCCCATAC

ATCAAACTTATTACTGGCTTCCTCTTCACCTCCTTGGCTTTCATGCTGG

TGGAGGGGAACTTTGTCTTGTTTTGCACCTACACCTTGGGCTTCCGCAA

TGAATTCCAGAATCTACTCCTGGCCATCATGCTCTCGGCCACTTTAACC

ATTCCCATCTGGCAGTGGTTCTTGACCCGGTTTGGCAAGAAGACAGCTG

TATATGTTGGGATCTCATCAGCAGTGCCATTTCTCATCTTGGTGGCCCT

CATGGAGAGTAACCTCATCATTACATATGCGGTAGCTGTGGCAGCTGGC

ATCAGTGTGGCAGCTGCCTTCTTACTACCCTGGTCCATGCTGCCTGATG

TCATTGACGACTTCCATCTGAAGCAGCCCACTTCCATGGAACCGAGCC

CATCTTCTTCTCCTTCTATGTCTTCTTCACCAAGTTTGCCTCTGGAGTG

TCACTGGGCATTTCTACCCTCAGTCTGGACTTTGCAGGGTACCAGACCC

GTGGCTGCTCGCAGCCGGAACGTGTCAAGTTTACACTGAACATGCTCGT

GACCATGGCTCCCATAGTTCTCATCCTGCTGGGCCTGCTGCTCTTCAAA

ATGTACCCCATTGATGAGGAGAGGCGGCGGCAGAATAAGAAGGCCCTGC

AGGCACTGAGGGACGAGGCCAGCAGCTCTGGCTGCTCAGAAACAGACTC

CACAGAGCTGGCTAGCATCCTCTAG

A representative human Mfsd2a protein sequence is shown below:

(SEQ ID NO: 2)
MAKGEGAESGSAAGLLPTSILQSTERPAQVKKEPKKKQQLSVCNKLCY

ALGGAPYQVTGCALGFFLQIYLLDVAQVGPFSASIILFVGRAWDAITDP

-continued
LVGLCISKSPWTCLGRLMPWIIFSTPLAVIAYFLIWFVPDFPHGQTYWY

LLFYCLFETMVTCFHVPYSALTMFISTEQTERDSATAYRMTVEVLGTVL

GTAIQGQIVGQADTPCFQDLNSSTVASQSANHTHGTTSHRETQKAYLLA

AGVIVCIYIICAVILILGVREQREPYEAQQSEPIAYFRGLRLVMSHGPY

IKLITGFLFTSLAFMLVEGNFVLFCTYTLGFRNEFQNLLLAIMLSATLT

IPIWQWFLTRFGKKTAVYVGISSAVPFLILVALMESNLIITYAVAVAAG

ISVAAAFLLPWSMLPDVIDDFHLKQPHFHGTEPIFFSFYVFFTKFASGV

SLGISTLSLDFAGYQTRGCSQPERVKFTLNMLVTMAPIVLILLGLLLFK

MYPIDEERRRQNKKALQALRDEASSSGCSETDSTELASIL

In some embodiments, variants of the above sequences may be used in the practice of the invention, including sequences at least 80%, 81%, 82%, 83%, 84%, 85%, 86%, 87%, 88%, 89%, 90%, 91%, 92%, 93%, 94%, 95%, 96%, 97%, 98%, or 99% identical to the nucleic acid and amino acid sequences set forth above.

Functionally active variants comprise naturally occurring functionally active variants such as allelic variants and species variants and non-naturally occurring functionally active variants that can be produced by, for example, mutagenesis techniques or by direct synthesis.

A functionally active variant differs by about, for example, 1, 2, 3, 4, 5, 6, 7, 8, 9, or 10 amino acid residues from the sequence shown above, and yet retains a biological activity. Where this comparison requires alignment the sequences are aligned for maximum homology. Guidance concerning how to make phenotypically silent amino acid substitutions is provided in Bowie et al., *Science,* 247: 1306-1310 (1990), which teaches that there are two main strategies for studying the tolerance of an amino acid sequence to change. The first strategy exploits the tolerance of amino acid substitutions by natural selection during the process of evolution. By comparing amino acid sequences in different species, the amino acid positions which have been conserved between species can be identified. These conserved amino acids are likely to be important for protein function. In contrast, the amino acid positions in which substitutions have been tolerated by natural selection indicate positions which are not critical for protein function. Thus, positions tolerating amino acid substitution can be modified while still maintaining specific immunogenic activity of the modified peptide.

The second strategy uses genetic engineering to introduce amino acid changes at specific positions of a cloned gene to identify regions critical for protein function. For example, site-directed mutagenesis or alanine-scanning mutagenesis can be used (Cunningham et al., *Science,* 244: 1081-1085 (1989)). The resulting variant peptides can then be tested for specific biological activity.

According to Bowie et al., these two strategies have revealed that proteins are surprisingly tolerant of amino acid substitutions. The authors further indicate which amino acid changes are likely to be permissive at certain amino acid positions in the protein. For example, the most buried or interior (within the tertiary structure of the protein) amino acid residues require nonpolar side chains, whereas few features of surface or exterior side chains are generally conserved.

Methods of introducing a mutation into amino acids of a protein are well known to those skilled in the art. See, e. g., Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989)).

Mutations can also be introduced using commercially available kits such as "QuikChange Site-Directed Mutagenesis Kit" (Stratagene) or directly by peptide synthesis. The generation of a functionally active variant to a peptide by replacing an amino acid which does not significantly influence the function of said peptide can be accomplished by one skilled in the art.

A type of amino acid substitution that may be made in one of the peptides according to the invention is a conservative amino acid substitution. A "conservative amino acid substitution" is one in which an amino acid residue is substituted by another amino acid residue having a side chain R group with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See e.g. Pearson, *Methods Mol. Biol.* 243:307-31 (1994).

Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., *Science* 256:1443-45 (1992). A "moderately conservative" replacement is any change having a non-negative value in the PAM250 log-likelihood matrix.

Furthermore, NCBI BLAST searches can be run by one of skill in the art to identify proteins that have 80% or more sequence identity to the sequences above.

Once coding sequences for the desired proteins have been prepared, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, Sambrook et al., supra; *DNA Cloning*, supra; B. Perbal, supra. The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence can or can not contain a signal peptide or leader sequence. Leader sequences can be removed by the host in post-translational processing. See, e.g., U.S. Pat. Nos. 4,431,739; 4,425,437; 4,338,397.

Other regulatory sequences can also be desirable which allow for regulation of expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements can also be present in the vector, for example, enhancer sequences.

The control sequences and other regulatory sequences can be ligated to the coding sequence prior to insertion into a vector, such as the cloning vectors described above. Alternatively, the coding sequence can be cloned directly into an expression vector which already contains the control sequences and an appropriate restriction site.

In some cases it can be necessary to modify the coding sequence so that it can be attached to the control sequences with the appropriate orientation; i.e., to maintain the proper reading frame. It can also be desirable to produce mutants or analogs of the protein. Mutants or analogs can be prepared by the deletion of a portion of the sequence encoding the protein, by insertion of a sequence, and/or by substitution of one or more nucleotides within the sequence. Techniques for modifying nucleotide sequences, such as site-directed mutagenesis, are described in, e.g., Sambrook et al., supra; *DNA Cloning*, supra; *Nucleic Acid Hybridization*, supra.

The expression vector is then used to transform an appropriate host cell. A number of mammalian cell lines are known in the art and include immortalized cell lines available from the AMERICAN TYPE CULTURE COLLECTION (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, Human Embryonic Kidney (HEK293) cells, as well as others.

Expression vectors can be introduced into suitable host cells by any manner known in the art, such as, for example, calcium phosphate transfection, electroporation, lipofection, transduction by retrovirus vectors, lentiviral vectors, adenoviral vectors, or other viral vector systems, etc.

Lipid Analysis

In some embodiments, the analysis of the lipid composition of an individual is performed. As used herein, the term "lipid" is intended broadly and encompasses a diverse range of molecules that are relatively water-insoluble or non-polar compounds of biological origin, including waxes, triglycerides, free fatty acids, diacylglyercols, fatty-acid derived phospholipids, sphingolipids, glycolipids and terpenoids, such as retinoids, cholesterol, cholesterol esters, and steroids. Some lipids are linear aliphatic molecules, while others have ring structures. Some are aromatic, while others are not.

As used herein, the term lipid "class" refers to a collection of lipid molecules that share structural and/or biochemical properties. Suitable lipid classes include polar and non-polar classes of lipids. Exemplary non-polar lipid classes include without limitation the free fatty acids, monoacylglycerides, diacylglycerides, triacylglycerides, sterols and/or cholesterol esters. Exemplary polar classes include without limitation the phospholipid classes such as phosphatidic acid, lysophosphatidylcholine, sphingomyelin, phosphatidylinositol, phosphatidylglycerol, phosphatidylcholine, phosphatidylserine, phosphatidylethanolamine, lysophosphatidylethalolamine, cardiolipin and/or lysocardiolipin.

The term "lipidomics" as used herein refers to the evaluation of lipid metabolites in biological samples. Lipid profiling generally involves an evaluation of lipid metabolites in one or more lipid classes (e.g., fatty acids, triglycerides, diglycerides, cholesterol esters, and the phospholipid classes including phosphatidylcholine, phosphatidylethanolamine, lysophosphatidylcholine, sphingomyelin, phosphatidylcholine, phosphatidylserine, phosphatidylethanolamine and cardiolipin).

The term "lipid profile" as used herein refers to the evaluation of one or more lipid metabolites within a biological sample. In particular embodiments, two or more, three or more, four or more, five or more, six or more, seven or more, eight or more, nine or more, ten or more, twelve or more, fifteen or more, twenty or more, fifty or more, 100 or more, or an even greater number of lipid metabolites are evaluated. In embodiments wherein two or more lipid metabolites are assessed, the two or more lipids can belong to the same class or can be belong to two or more, three or more, four or more, five or more, six or more, seven or more or a greater number of different lipid classes.

The lipid profile can be quantitative, semi-quantitative and/or qualitative. For example, the lipid profile can evaluate the presence or absence of a lipid, can evaluate the presence of a lipid(s) above or below a particular threshold, and/or can evaluate the relative or absolute amount of a lipid(s). In particular embodiments, a ratio among two, three, four or more lipids is determined. Changes or perturbations in lipid ratios can be advantageous in indicating where there are metabolic blocks (or releases of such blocks) or other alterations in metabolic pathways associated with disease, response to treatment, development of side effects, and the like. Methods of evaluating ratios of lipid precursors and products to evaluate enzyme activities and flow through metabolic pathways are known in the art (see, e.g., Attie et al., (2002) *J. Lipid Res.* 43:1899-1907 and Pan et al., (1995) *J. Clin. Invest.* 96:2802-2808).

The lipid profile can be determined using any suitable biological sample. The biological sample can be taken from a subject (e.g., a patient) and can be a centrally and/or peripherally derived biological sample, including without limitation body fluids, tissue, cellular, sub-cellular and/or extracellular biological samples. Illustrative tissues and cells include, but are not limited to, skeletal muscle tissue and cells, skin tissue and cells, neural tissue and cells including brain tissue and cells, spinal cord tissue and cells, eye tissue and cells (e.g., retinal cells), cardiac muscle tissue and cells, lung tissue and cells, pancreatic tissue and cells, liver tissue and cells, tissue and cells of the gastrointestinal system, adipose tissue and cells, and the like. Sub-cellular samples include one or more fractions and/or organelles of the foregoing cell types including but not limited to cytoplasm, nuclei, mitochondria, Golgi apparatus, endoplasmic reticulum, ribosomes, lysosomes, plasma membranes, endosomal traction, and the like. Examples of body fluids include but are not limited to blood, plasma, serum, saliva, urine, lymph, semen, tears, breast milk and cerebrospinal fluid.

The lipid profile of the biological sample can be determined using any suitable method. The different classes of lipids and methods of detecting and optionally quantifying the same are well known in the art (e.g., thin layer chromatography, gas chromatography, liquid chromatography, mass and NMR spectrometry, and any combination thereof (e.g., GC/MS), and the like). One suitable method of detecting, and optionally quantifying, lipids in a biological sample employs stable isotope tracers to label the lipids. Methods of obtaining lipid profiles from biological samples have been described, see, e.g., U.S. Patent Publication No. 2004/0143461 A1 (S. M. Watkins) and Watkins et al. (2002) *J. Lipid Res.* 43(11):1809-17.

The lipidomics analysis of the invention can generate high-density data sets that can be evaluated using informatics approaches. High data density informatics analytical methods are known and software is available to those in the art, e.g., cluster analysis (Pirouette, Informetrix), class prediction (SIMCA-P, Umetrics), principal components analysis of a computationally modeled dataset (SIMCA-P, Umetrics), 2D cluster analysis (GeneLinker Platinum, Improved Outcomes Software), and metabolic pathway analysis (biotech.icmb.utexas.edu). The choice of software packages offers specific tools for questions of interest (Kennedy et al., Solving Data Mining Problems Through Pattern Recognition. Indianapolis: Prentice Hall PTR, 1997; Golub et al., (2999) *Science* 286:531-7; Eriksson et al., Multi and Megavariate Analysis Principles and Applications: Umetrics, Umea, 2001). In general, any suitable mathematic analyses can be used to evaluate one, two or more lipid metabolites in a lipid profile. For example, methods such as multivariate analysis of variance, multivariate regression, and/or multiple regression can be used to determine relationships between dependent variables (e.g., clinical measures) and independent variables (e.g., levels of lipid metabolites). Clustering, including both hierarchical and non-hierarchical methods, as well as non-metric Dimensional Scaling can be used to determine associations among variables and among changes in those variables.

In addition, principal component analysis is a common way of reducing the dimension of studies, and can be used to interpret the variance-covariance structure of a data set. Principal components may be used in such applications as multiple regression and cluster analysis. Factor analysis is used to describe the covariance by constructing "hidden" variables from the observed variables. Factor analysis may be considered an extension of principal component analysis, where principal component analysis is used as parameter estimation along with the maximum likelihood method. Furthermore, simple hypothesis such as equality of two vectors of means can be tested using Hotelling's T squared statistic.

Sequencing of Mutations

In some embodiments, nucleic acids from patient samples are sequenced to determine mutations in the Mfsd2a gene. Any technique for sequencing nucleic acid known to those skilled in the art can be used. DNA sequencing techniques include classic dideoxy sequencing reactions (Sanger method) using labeled terminators or primers and gel separation in slab or capillary electrophoresis. In one embodiment, next generation (NextGen) sequencing platforms are advantageously used in the practice of the invention. NextGen sequencing refers to any of a number of post-classic Sanger type sequencing methods which are capable of high throughput sequence determination. NextGen sequencing platforms can include: sequencing by synthesis using reversibly terminated labeled nucleotides, pyrosequencing, 454 sequencing, allele-specific hybridization to a library of labeled oligonucleotide probes, sequencing by synthesis using allele-specific hybridization to a library of labeled clones that is followed by ligation, real time monitoring of the incorporation of labeled nucleotides during a polymerization step, polony sequencing, single molecule real time sequencing, and SOLiD sequencing. Examples of specific sequencing platforms include: 454 sequencing (Roche) (Margulies, M et al. 2005, Nature, 437, 376-380); pyrosequencing, which makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed. Another example of a DNA sequencing technique that can be used is SOLiD technology (Applied Biosystems). SOLEXA (Illumina) sequencing is based on the amplification of DNA on a solid surface using fold-back PCR and anchored primers. Another example of a sequencing technology that can be used includes the single molecule, real-time (SMRT™) technology of Pacific Biosciences. A further example of a sequencing technique that can be used is nanopore sequencing (Soni G V and Meller A. (2007) Clin Chem 53: 1996-2001). Another example of a sequencing technique that can be used involves using a chemical-sensitive field effect transistor (chemFET) array to sequence DNA (for example, as described in US Patent Application Publication No. 20090026082).

Scaffolds and Conjugates

In some embodiments, the present disclosure provides scaffolds for delivery of compounds or moieties via the Mfsd2a protein. As used herein a "scaffold" refers to any molecule that interacts with or allows transport via the Mfsd2a protein. An interaction includes transport, binding, blocking, activation, or inhibition of the Mfsd2a protein. In some embodiments, the scaffolds are lysophosphatidylcholine (LPC) scaffolds. Such scaffolds may be used for LPC-mediated delivery of fatty acids and other molecules. In some embodiments, a scaffold minimally includes a zwitterionic head head group and an acyl or alkyl chain. In some embodiments, a scaffold minimally includes the phosphocholine head group, the phosphate group, and an acyl or alkyl chain length of at least 14 carbons.

In some embodiments, a scaffold can be a naturally occurring molecule or modification thereof. In some embodiments, a scaffold can be a synthetic entity not normally found in nature, so long as it interacts with or is transported via the Mfsd2a protein.

In some embodiments, a compound or moiety may be attached to a scaffold to form a "conjugate" to be transported via the Mfsd2a protein. In one embodiment, the omega-carbon of the acyl chain of the LPC may be modified for the attachment of compounds or moieties for transport. However, any position may be used for attachment provided that the attachment does not interfere with transport via the Mfsd2a protein. Moreover, any method, covalent or non-covalent, known in the art for conjugation may be used to attach a compound or moiety of interest to a scaffold.

Examples of compounds or moieties that may be attached for transport may include, but are not limited to, fatty acids, a non-fatty acid, a drug, and labels, among others.

In one embodiment, the compound or moiety to be transported may comprise an agent for imaging as discussed below. In such embodiments, the label can be on the scaffold or be on a compound or moiety that is attached to the scaffold for transport.

Imaging Agents

In some embodiments, the present disclosure provides LPC-conjugates for live animal imaging. Examples of suitable labels for such applications include, but are not limited to, those disclosed below.

The label may be fluorescent molecules such as: xanthenes such as rhodamines, rhodols and fluoresceins, and their derivatives; bimanes; coumarins and their derivatives such as umbelliferone and aminomethyl coumarins; aromatic amines such as dansyl; squarate dyes; benzofurans; fluorescent cyanines; carbazoles; dicyanomethylene pyranes, polymethine, oxabenzanthrane, xanthene, pyrylium, carbostyl, perylene, acridone, quinacridone, rubrene, anthracene, coronene, phenanthrecene, pyrene, butadiene, stilbene, lanthanide metal chelate complexes, rare-earth metal chelate complexes, and derivatives of such dyes. Fluorescent dyes are discussed, for example, in U.S. Pat. No. 4,452,720, U.S. Pat. No. 5,227,487, and U.S. Pat. No. 5,543,295.

In the case of fluorescein dyes, typical fluorescein dyes include, but are not limited to, 5-carboxyfluorescein, fluorescein-5-isothiocyanate and 6-carboxyfluorescein; examples of other fluorescein dyes can be found, for example, in U.S. Pat. No. 6,008,379, U.S. Pat. No. 5,750,409, U.S. Pat. No. 5,066,580, and U.S. Pat. No. 4,439,356. Further examples of rhodamine dyes include tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED™), and other rhodamine dyes. Other rhodamine dyes can be found, for example, in U.S. Pat. No. 6,080,852, U.S. Pat. No. 6,025,505, U.S. Pat. No. 5,936,087, U.S. Pat. No. 5,750,409. Furthermore, a cyanine dye, such as, for example, Cy3, Cy3B, Cy3.5, Cy5, Cy5.5, Cy 7, may also be used.

In some embodiments, the label is a positron-emitting isotope (e.g., $^{18}F$) for positron emission tomography (PET), gamma-ray isotope (e.g., $^{99m}Tc$) for single photon emission computed tomography (SPECT), a paramagnetic molecule or nanoparticle (e.g., $Gd^{3+}$ chelate or coated magnetite nanoparticle) for magnetic resonance imaging (MRI), a near-infrared fluorophore for near-infra red (near-IR) imaging, a luciferase (firefly, bacterial, or coelenterate) or other luminescent molecule for bioluminescence imaging.

In some embodiments, the label is a radioactive moiety, for example a radioactive isotope such as $^{211}At$, $^{131}I$, $^{125}I$, $^{90}Y$, $^{186}Re$, $^{188}Re$, $^{153}Sm$, $^{212}Bi$, $^{32}P$, $^{18}F$, radioactive isotopes of Lu, and others.

Some of the above compounds or their derivatives will produce phosphorescence in addition to fluorescence, or will only phosphoresce. Some phosphorescent compounds include porphyrins, phthalocyanines, polyaromatic compounds such as pyrenes, anthracenes and acenaphthenes, and so forth. The labels may also include a fluorescence quencher, such as, for example, a (4-dimethylamino-phenylazo)benzoic acid (DABCYL) group.

Examples of other labels include: indocarbocyanine dye, IRDYE 800CW, ALEXA647, a MRI contrast agent, and Gd complex of [4,7,10-tris(carboxymethyl)-1,4,7,10-tetraazacyclododec-1-yl]acetyl.

Nutritional Compostions

The nutritional composition of the present invention can be produced by conventional formulation techniques and food production techniques.

The nutritional composition can be useful as a pharmaceutical product, food or drink, and the like for increasing energy consumption.

The nutritional composition can be directly administered into the bowels and stomach of patients showing insufficient oral ingestion, by using an administration tube, or when oral ingestion is possible, it can be given as a food or drink.

The nutritional composition can be formulated as a liquid preparation such as an elixir, suspension, syrup, emulsion, ampoule; or a solid preparation such as gel, gum, drop, powder, granule, pill, tablet (including sugar-coated tablet, film-coated tablet), capsule, package agent, powder, and the like.

When the nutritional composition can be provided as food and drink, such products can include liquid products such as drinks, milk products such as milk, milk beverage, yogurt, jelly products such as jelly drinks, jelly, gum products, powder products, granular products, sheet products, capsule products, tablet products, solid products such as snack bar, cookie, and the like.

Examples of materials which can be used for forming the nutritional composition as a food or drinks include a sweetener, colorant, preservative, thickening stabilizer, antioxidant, color former, fungicide, gum base, bittering agent, enzyme, gloss agent, acidulant, seasoning, emulsifier, enhancement agent, agent for production, flavor, spice, and the like.

When the nutritional composition is provided as food and drink, it can be packaged as a single serving. Single serving packaging can be used when the amount of food and drink to be ingested per meal is determined in advance. Examples thereof include a single serving package such as pack, bag, bottle, box in case of drinks, gum, jelly, yogurt, cookie and the like. The single serving package can be a pack, bag, and the like, in case of foods in the form of granule, powder, slurry, and the like. Particularly, when the food or drink are specified for health, nutritional, special-use, or invalid uses, the composition can be packaged as a single serving unit amount, such as when the composition is to be suspended or dissolved in a bottle to give a drink etc., for a single consumption and the like.

The amount of the nutritional composition to be ingested per day can be individually determined depending on the age, sex, body weight, meal condition, and the like, and can be about 50 kcal-2000 kcal for an adult per day. This amount can be ingested in about 1 to 3 portions a day. When the nutritional composition is formulated in a single serving food or drink in a package form of one ingestion amount unit, the amount to be ingested one time as determined above can be individually packed.

The following examples of specific aspects for carrying out the present invention are offered for illustrative purposes only, and are not intended to limit the scope of the present invention in any way.

EXAMPLES

Methods and Materials
Chemicals

Non-radiolabeled lysophosphatidylcholines, lysophosphatidylethanolamine, lysophosphatidylserine, and other lysophospholipids were purchased from Avanti Polar Lipids. Radiolabeled 1-palmitoyl 2-lysophosphocholine (LPC-[$^3$H] palmitate), 1-oleoyl 2-lysophosphocholine (LPC-[$^{14}$C] oleate), 1-docosahexaenoyl 2-lysophosphocholine (LPC-[$^{14}$C]DHA), and [1-$^{14}$C]docosahexaenoic acid ([$^{14}$C]DHA) were purchased from Americans Radiochemicals. Lysophospholipids either in chloroform (non-labeled) or ethanol/toluene (radiolabeled) were completely dried under the nitrogen gas and were solubilized in 12% fatty acid-free BSA (Sigma), which was dissolved in 150 mM NaCl. To prepare LPC-[$^{14}$C]-oleate/LPC-oleate mixture, 25 µCi LPC-[$^{14}$C]-oleate (specific activity 55 mCi/mmol) were dried and dissolved in 3 ml 20 mM non-labeled LPC-18:0/BSA. LPC-[$^3$H]-palmitate)/LPC-palmitate were prepared by dissolved 25 µCi LPC-[$^3$H]-palmitate (specific activity 60Ci/ mmol) in 4 ml 10 mM LPC-palmitate. 1-docosahexaenoyl LPC was prepared from hydrolysis of 1,2-didocosahaxaenoyl PC with honey bee venom PLA2 (Sigma) in borax buffer (pH 8.5) containing 5 mM CaCl2 and purified by TLC methods. To prepare LPC-[$^{14}$C]-DHA/LPC-DHA mixture, 10 µCi LPC-[$^{14}$C]-DHA was mixed with non-labeled LPC-DHA/BSA to a final concentration of 10 mM. To prepare [$^{14}$C]-DHA/DHA mixture, 50 µCi [$^{14}$C]-DHA was mixed with non-labeled DHA/BSA to a final concentration of 12.2 mM.

Animals

Mfsd2a knockout mice were generated as previously described (Berger, J. H., Charron, M. J. & Silver, D. L. Major facilitator superfamily domain-containing protein 2a (MFSD2A) has roles in body growth, motor function, and lipid metabolism. *PLoS One* 7, e50629, doi:10.1371/journal.pone.0050629 (2012)). Mice were maintained on a high energy diet 5LJ5 (PicoLab) containing a total 11% fat. Pups were weaned at 3 weeks old and maintained in the high energy diet. Experimental protocols were approved by the SingHealth Institutional Animal Care and Use Committee.

Lipidomic Analysis

For tissue lipid analysis, brain, liver, and heart of female WT and KO mice with age of 7-8 weeks born to HET mothers, and brains from e18.5 embryos were collected and immediately frozen with liquid nitrogen until extraction. Lipid extraction was followed by chloroform/methanol method. For cell-based free fatty acid transport, lipids from HEK293 cells expressing mouse Mfsd2a and mock controls after overnight treatment with 100 µM docosahexaenoic, arachidonic, eicosapentaenoic, alpha-linolenic, linoleic, oleic, palmitic acids in BSA complex were extracted using HIP buffer (hexane:iso-propanol 3:2, per volume) and dried under N2 gas. Phospholipid species were measured by high performance liquid chromatography (HPLC) 1100 system (Agilent) coupled with an Triple Quadrupole/Ion Trap mass spectrometer (4000Qtrap, Applied Biosystem). Levels of individual phospholipid species were analyzed as described previously and quantified using spiked internal standards that includes PC-14:0/14:0, PE-14:0/14:0, PS-14:0/14:0 (Avanti Polar Lipids, Alabaster, Ala., USA), and dioctanoyl PI (Echelon Biosciences, Inc., Salt Lake City, Utah, USA).

In Vitro Transport of Radiolabeled and Fluorescent LPCs

Radiolabeled LPC palmitate (LPC-[$^3$H]palmitate), oleate (LPC-[$^{14}$C]oleate), and docosahexaenoate (LPC-[$^{14}$C] DHA) or TopFluor-LPC, TopFluor-LPE, and NBD-LPCs were dissolved in 12% BSA, which was diluted in 150 mM NaCl. Uptake assays of radiolabeled LPCs or fluorescent LPCs were tested using HEK293 cells overexpressing Mfsd2a and mutants constructs. Briefly, HEK293 cells at 90-95% confluency were transfected using LIPO-FECTAMINE 2000 (Invitrogen) with pcDNA3.1Mfsd2a (WT), pcDNA3.1Mfsd2aD92A (D92A), pcDNA3.1Mfsd2aD96A (D96A), or pcDNA3.1 (mock) plasmids. Uptake assays were performed after 24 hours of transfections. Prior to ligand incubation, HEK293 transfected cells were washed with serum-free DMEM before assays. For concentration and time dependent assays, radiolabeled LPCs were diluted in pre-warmed DMEM media. For sodium dependent assay, radiolabeled LPCs were diluted in transport buffer (5 mM KCl, 10 mM Hepes, pH 7.4) with 150 mM NaCl or 150 mM choline chloride. For sodium concentration dependent assays, any reductions in the concentration of NaCl were replaced by choline chloride in order to maintain a constant cation molarity of 150 mM. All assays were performed in 12 well-plates with triplicates and at 37° C.

For Albumin-Free Ligand Transport Assays

To prepare LPC-palmitate dissolved in ethanol, 0.75 μCi LPC-[$^3$H]palmitate were diluted in LPC-palmitate in chloroform. Mixture was dried and dissolved in 50 μl ethanol before adding 6 ml of transport buffer with 150 mM sodium as described above to have 50 μM LPC-palmitate. To prepare LPC-palmitate micelles, 0.75 μCi LPC-[$^3$H]palmitate were diluted in LPC-palmitate in chloroform. Mixture was dried and dissolved in 6 ml of transport buffer with 150 mM sodium to have 100 μM LPC-palmitate and sonicated on ice for 5 mins. Activated charcoal was added and spun to remove the monomers of LPC-palmitate. Transport assays were similar performed with HEK293 cells overexpressing with pcDNA3.1Mfsd2a or pcDNA3.1 plasmid as control for 30 mins at 37° C.

Competition Transport Assay

Briefly, 24 h post transfection of HEK293 cells with pcDNA3.1Mfsd2a (WT), pcDNA3.1Mfsd2aD92A (D92A), pcDNA3.1Mfsd2aD96A, or pcDNA3.1 (mock) plasmids were washed once with serum-free DMEM medium before addition of a mixture of 25 μM radiolabeled LPC-palmitate and 250 μM cold competitors, which were dissolved in 12% BSA. Total BSA concentration was kept constant in samples with or without cold competitors. Assays were performed at 37° C. for 30 mins. Competition assays with other LPC analogs such as foscholine detergents, and PAF were performed under the same conditions except for 15 mins. The reduced reaction time was necessary in order to limit potential negative effects of detergents and bioactive lipids on cell survival. All assays were performed in 12 well-plates with triplicates and at 37° C.

In Vivo Transport of Radiolabeled, Fluorescent LPCs, and Unesterified DHA

Male and female mice of age of 6-8 weeks were IV injected with 75 μl of 20 mM radiolabeled LPC-[$^{14}$H]oleate, 100 μl of 10 mM LPC-[$^{14}$C]DHA/BSA complex or 82 μl of 12.2 mM [$^{14}$C]DHA/BSA complex in a total volume of 150 μl of phosphate-buffered saline. At 2 hours post injection, mice were anesthetized and perfused for 5 mins with PBS containing 0.5% BSA in order to remove blood and lipid tracer bound to the brain vasculature. Tissues were harvested for lipid extraction. For lipid extraction, tissues were weighed and similar amounts of tissues were homogenized in chloroform/methanol. Lipids from the organic phase were mixed with scintillant and scintillation counted. Similar experiments were also performed with an injection of 300 μg NBD-LPC/BSA or 300 μg TopFluor-LPC/BSA complex per mouse. In this experiment, mice were perfused for 5 mins with PBS followed 15 mins perfusion with 4% paraformaldehyde (PFA) for tissue fixation. Brain sections of WT and KO with a thickness of 40 μm were prepared and scanned using green fluorescence mode in Typhoon FLA 9000 scanner (Agilent). NBD-LPC accumulation was expressed as fluorescence of each section per its area. Dietary DHA transport from mother to fetus was also measured using [$^{14}$C]DHA/BSA complex. Pregnant females at e18.5 was gavaged with bolus of [$^{14}$C]DHA/BSA complex (200 μl of 10 mM [$^{14}$C]DHA/BSA/mouse). Brain of fetuses were collected 20 hours post-gavage and weighed. Lipid extraction and radioactivity were performed as described above.

TLC Analysis of Phospholipids

HEK293 cells overexpressing with pcDNA3.1Mfsd2a (WT), pcDNA3.1Mfsd2aD92A (D92A), pcDNA3.1Mfsd2aD96A, or pcDNA3.1 (mock) plasmids or human Mfsd2a (in Sport6 plasmid) were washed once with serum-free DMEM medium before incubation with 50 μM radiolabeled LPC [$^{14}$C]oleate, LPC [$^{14}$C]DHA or with 50 μM TopFluor-LPC and NBD-LPC. Lipids were extracted twice with HIP buffer for 30 mins. Lipids were dried with nitrogen stream and reconstituted in chloroform and spotted on TLC plates (Milipore). Solvent for phospholipid separation was chloroform/methanol/ammonia solution (25%) (50:25:6, per volume). TLC plates of radiolabeled phospholipids were dried for 30 mins and exposed overnight to Phosphorscreens and scanned with Typhoon FLA 9000 scanner (Agilent). TLC plates of fluorescent phospholipids were scanned with Typhoon FLA 9000 scanner and quantified using Imagequant software.

Histological Studies

Adult male WT and KO mice aged 7.5-8 weeks old born to HET parents, were deeply anaesthetized and perfused transcardially with 50 ml of saline, followed by 100 ml of 4% PFA in 0.1M PB (pH 7.4) for 30 minutes. For embryos, brains were fixed in 4% PFA then 30% sucrose both overnight. Sagittal sections at 40 μm thickness were sectioned in a cryostat, and serial sections were transferred to different wells of a 24-well tissue culture dish for immunostaining. Sections of embryos were embedded on slides. The brain sections were processed for immunocytochemistry procedure using antibodies against NeuN (1:1000, Chemicon, CA, USA), Mfsd2a (1:500), GFAP (1:1000, Chemicon, CA, USA), parvalbumin (1:500, Swant, Switzerland), Glut1 (1:500, Abcam), PDGFR-beta (1:150 eBioscience) and incubated for 5 min in 4',6-diaminodino-2-phenylindole (DAPI, 1:5000) before washing and mounting. The images were acquired on Zeiss LSM 710 inverted fluorescence confocal microscope (Carl Zeiss, Pte. Ltd., Singapore). The same localization procedures were performed on hippocampal sections from Cynomolgus Macaque. NeuN immunostained neuronal profile in the hippocampus and parvalbumin stained Purkinje cells in cerebellum were counted and indicated as density (number of immunopositive neurons per square millimeter (No./mm2) and number of immunopositive cells per millimeter (No./mm) in mean±SEM. Statistical significance was assessed using the Student's t-test.

Behavior Studies

Y maze spontaneous alternation test: Mice were placed in the center of a Y-shaped maze with three arms at a 120° angle from each other. The animal is allowed to freely explore all three arms. If the mouse has an intact spatial working memory, it would have a reduced tendency to enter the recently visited arm. The Topscan program (Cleversys Inc., Reston, Va.) was used to score the number of arm entries, and determine the number of alternations. A mouse is considered as having entered an arm when all four limbs are within the arm.

Novel object recognition test: The novel object recognition test was carried out as previously described. In brief, mice were trained with identical 'familiar' objects for 5 minutes and then assessed for short term (STM) and long term (LTM), which took place 20 minutes and 24 hours after training, respectively. The bouts of exploration for each object were scored using the Annostar program (Cleversys Inc., Reston, Va.). Preference score was calculated as (Time spent with novel object−Time spent with familiar object)/(Total time spent with both objects). Preferences for familiar object and novel object were defined as negative scores and scores approaching zero showed no preference for either object.

Anxiety tests: All behavioral apparatus were cleaned between each animal with surface disinfectant and 70% ethanol. In the zero maze, mice were placed in the closed arm and allowed 10 minutes for exploration. Behaviors, such as the time spent in, number of entries into, number of transitions between and latency to enter the open arms, were scored using the Annostar behavior scoring program (Cleversys Inc., Reston, Va.). In addition, exploratory behaviors, such as head dips and stretch attends, were recorded. At the start of the light/dark box test, mice were placed into the dark box measuring 20×40×16 cm, and allowed to move freely between the dark and light boxes for 10 minutes. Behavioral measures, such as time spent and horizontal activity in the light box, latency to enter the light box and the number of transitions between the two boxes, were recorded using the Versamax program (AccuScan Instruments Inc., Columbus, Ohio).

Open field activity: Mice were placed into the chamber for 60 minutes and the total distance traveled, number of rears, and time spent in the corners and center were recorded using the Versamax program (AccuScan Instruments, Columbus, Ohio).

Statistical Analysis

Statistical differences of DHA and AA levels, and histological analyses between genotypes were calculated using an unpaired Student's t-test. Statistical analysis of LPC-[$^{14}$C] DHA, LPC-[$^{3}$H]palmitate, LPC-[$^{14}$C]oleate signals expressed as DPM between mock vs. WT and mutants were calculated using 2way-ANOVA; a p<0.05 was considered to be significant.

For the behavioral tests, genotype was the between subject factors. A one-way ANOVA was used to analyze the zero maze, light/dark box, open field and Y maze. A two-way ANOVA was used to analyze novel object test, with test day as the between subjects factor. Bonferroni corrected pairwise comparisons were used as post-hoc tests. Data was expressed as mean±SEM and p<0.05 was considered statistically significant.

Example 1: Immunolocalization of Mfsd2a

Figure 5:
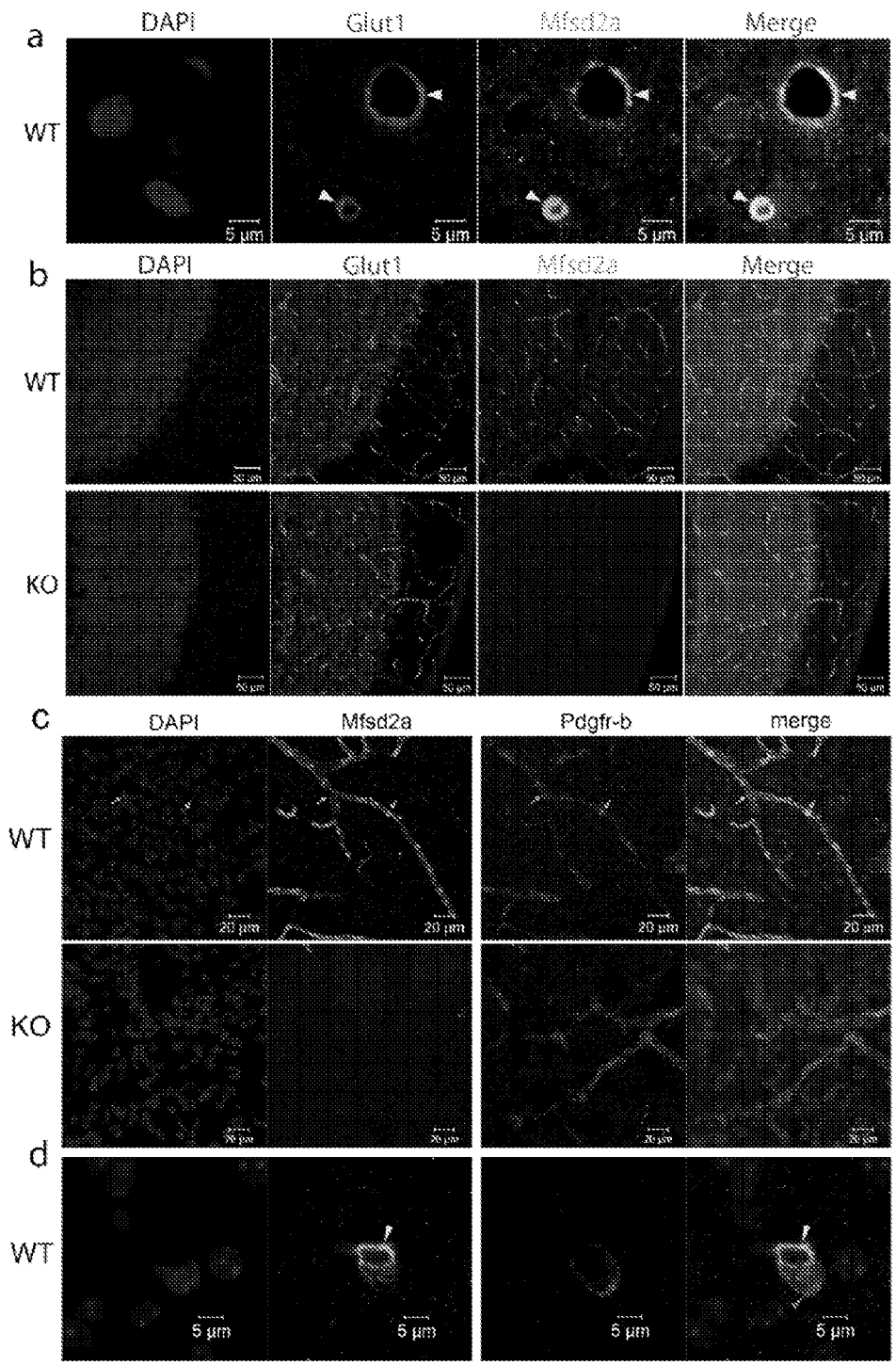
FIG. 5. Mfsd2a is highly expressed in endothelium of micro-vessels in brain. a, Expression of Mfsd2a in endothelium is co-localized with glucose transporter Slc2a1 (Glut1). Arrowhead show endothelial cells in blood brain vessels. Scale bars: 5 μm. b, Mfsd2a is highly expressed in micro-vessels in brain, shown here are sections in dentate gyrus regions. Scale bars: 50 μm. c, Mfsd2a and the pericyte marker Pdgfr-b co-localize in brain microvasculature, but as shown in panel d Mfsd2a is not expressed in pericytes. Arrowhead in panel d indicates endothelial cell and pericyte, respectively. (Scale bars in c: 20 μm; in d: 5 μm).
Figure 6:
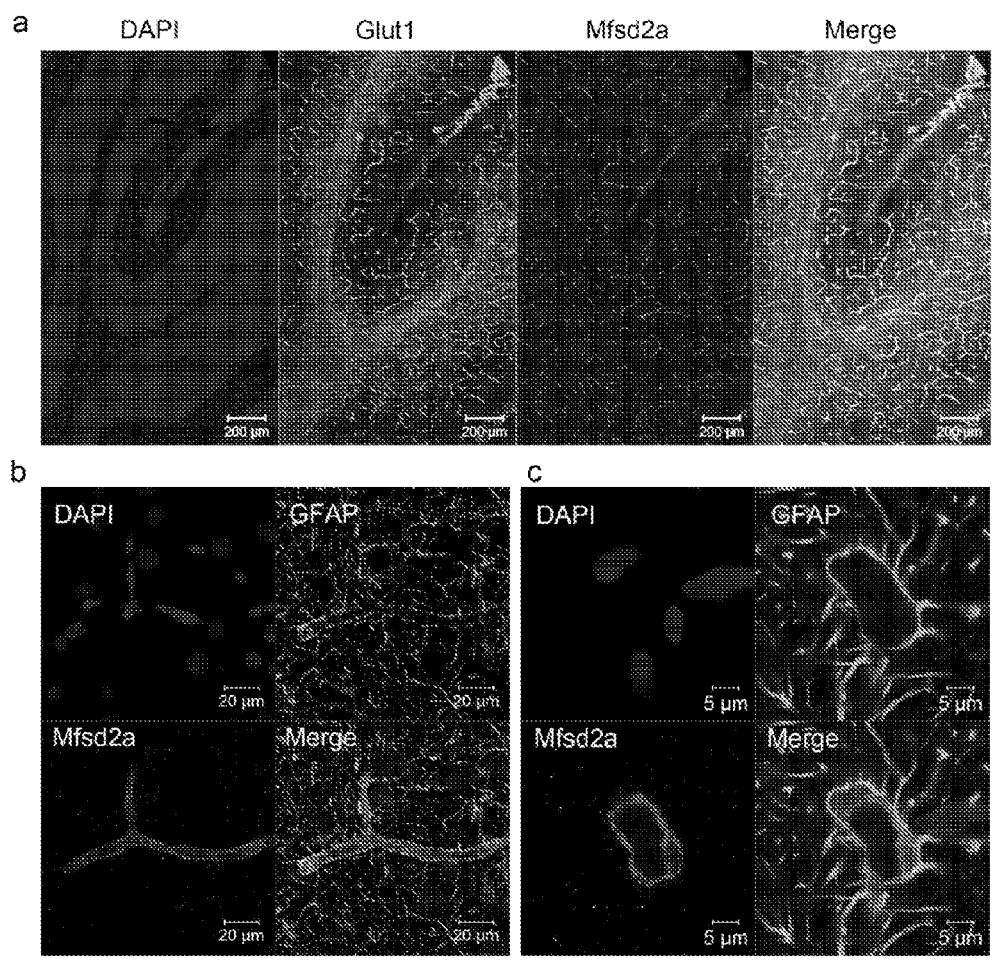
FIG. 6. Similar expression pattern of Mfsd2a is found in endothelium of micro-vessels in brain of monkey. a, Mfsd2a is highly expressed in micro-vessels and is co-localized with glucose transporter Slc2a1 (Glut1) in brain, shown here are sections in cerebellum of P4 monkey. Scale bars: 200 μm. b, c, Expression of Mfsd2a in endothelium in of brain microvessels. Shown is hippocampal region. GFAP is astrocytes marker.
Figure 7:
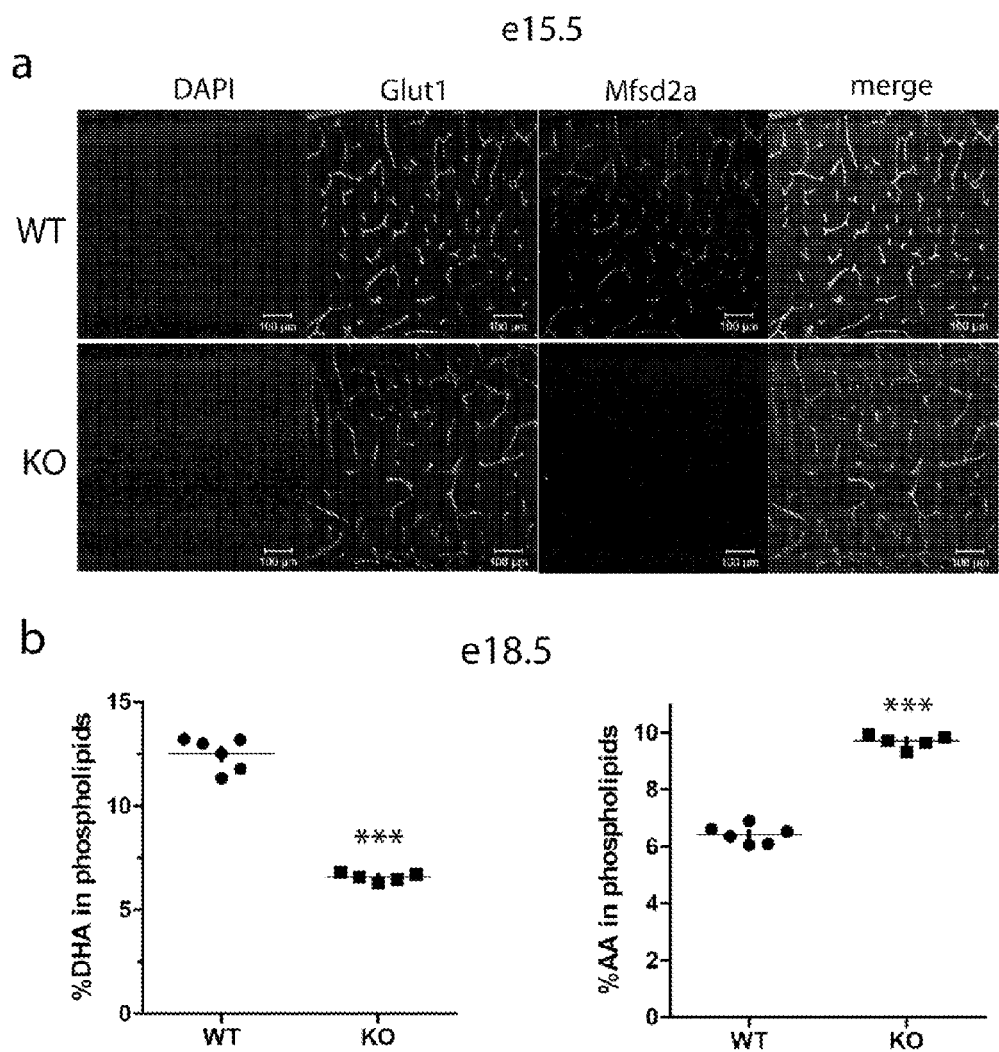
FIG. 7. Localization of Mfsd2a at the BBB of e15.5 fetus and lipid analysis. a, Mfsd2a is highly expressed in microvessels and is co-localized with glucose transporter Slc2a1 (Glut1) in fetal brain. Scale bars: 100 μm. b, mass spectrometry measurement of phospholipids in the e18.5 fetal brain of WT (n=6) and KO (n=5) showed that KO fetal brains had significantly reduced DHA levels, while AA levels were increased. ***P<0.001. See source file for full dataset.

Immunolocalization of Mfsd2a indicates that it is highly enriched in brain micro-vessels where it is exclusively found in endothelium constituting the BBB (FIG. 1a, b, c, and FIG. 5a, b), but not expressed in pericytes which enwrap the endothelium (Armulik, A. et al. Pericytes regulate the blood-brain barrier. Nature 468, 557-561, doi:10.1038/nature09522 (2010); Bell, R. D. et al. Pericytes control key neurovascular functions and neuronal phenotype in the adult brain and during brain aging. Neuron 68, 409-427, doi: 10.1016/j.neuron.2010.09.043 (2010)) (FIG. 5c, d), confirming a previous report indicating that mRNA of Mfsd2a is one of the highest enriched transcripts found in the BBB (Daneman, R et al. The mouse blood-brain barrier transcriptome: a new resource for understanding the development and function of brain endothelial cells. PLoS One 5, e13741, doi:10.1371/journal.pone.0013741 (2010)). This localization pattern in BBB was also noted in the cerebellum and hippocampus of monkey (FIG. 6). Mfsd2a was found to be expressed in the BBB at e15.5 (FIG. 7a). The localization of Mfsd2a to the endothelium of the BBB suggests a transport function in the BBB.

Example 2: Phenotypic Differences in Mfsd2a Knock Out Mice

Figure 8:
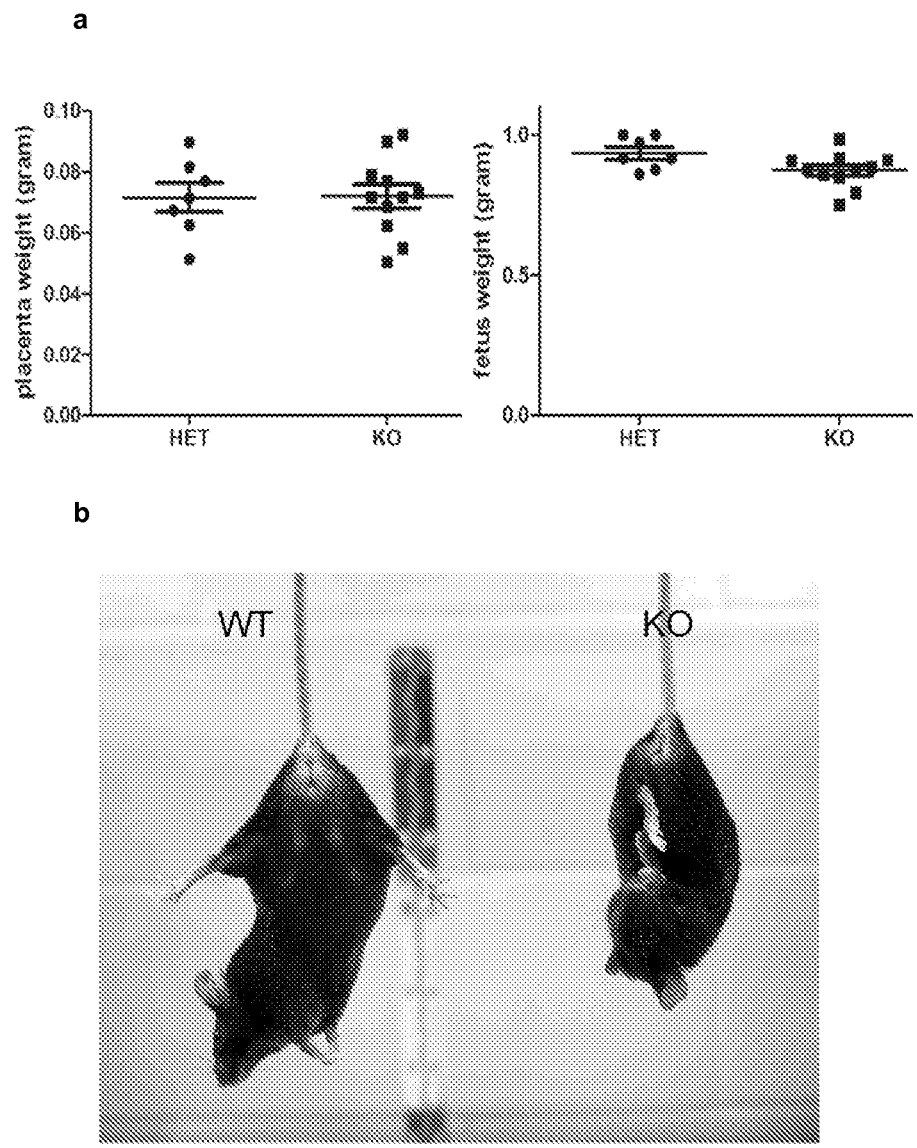
FIG. 8. shows a, placental and fetal weights. Placentas and fetuses of two HET pregnant mice (E18.5) crossed with a KO male were collected and weighed. There was no significant differences in placental and fetal weight between HET (n=7) and KO (n=11). b, tail suspension was used to test for the presence of the paw clasping phenotype of 10 weeks old WT and KO mice.
Figure 9:
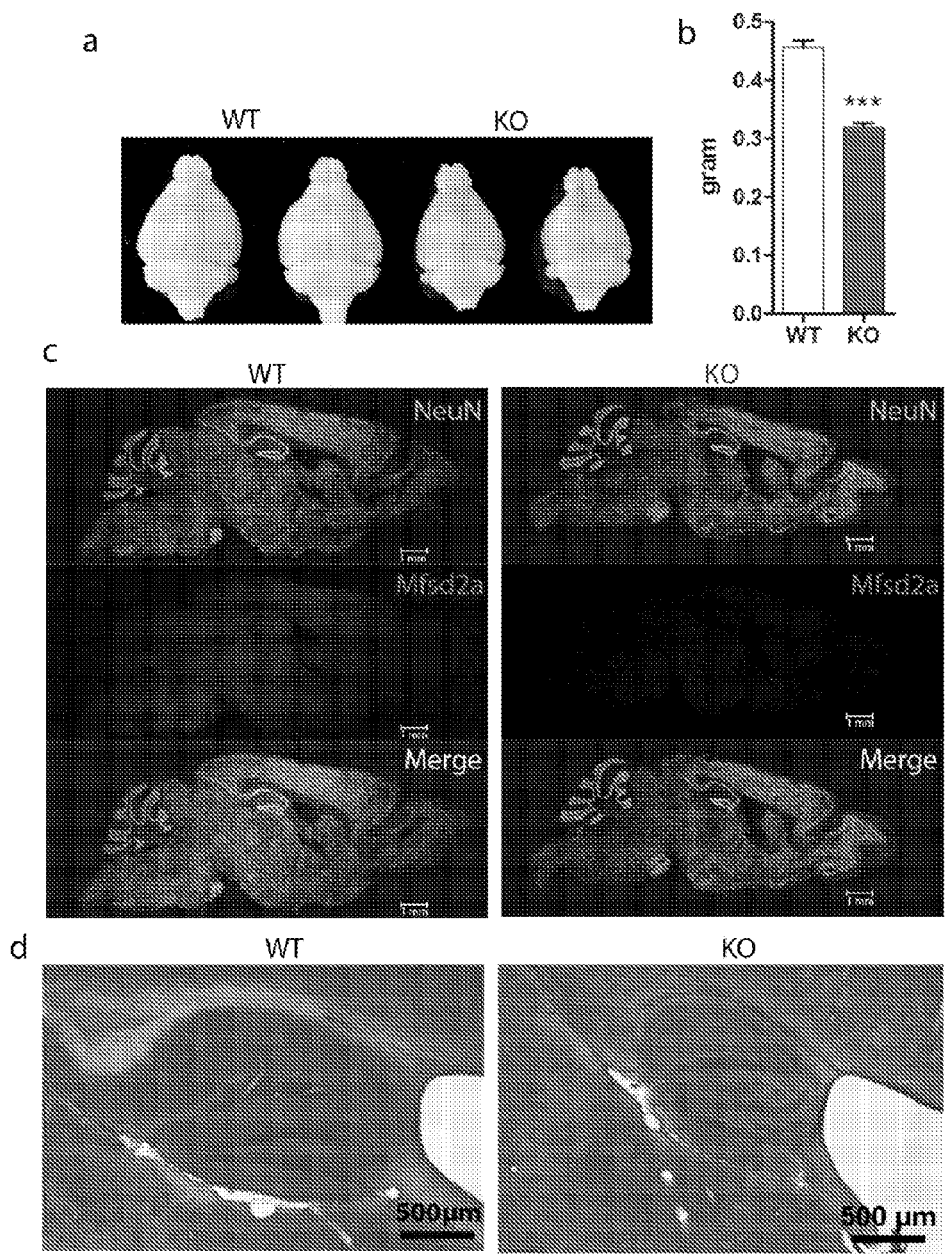
FIG. 9. shows a, A representative image of brains of two 8 weeks old WT and KO littermates. b, brain weight of KO (n=4) mice is significantly lower than WT (n=4) littermates. ***P<0.001. Data were expressed as mean±SEM. c, Gross morphology of brains and sagittal sections of brains. Sagittal brain sections of 8 weeks old WT and KO mice was stained with NeuN to visualize neuronal cells and Mfsd2a polyclonal antibody to visualize expression of Mfsd2a. Mfsd2a is shown to widely expressed in brain. Scale bars: 1 mm. d, H&E staining of hippocampus region of 8 weeks old WT and KO mice indicating a smaller hippocampus in KO mice. Scale bars: 500 μm.
Figure 10:
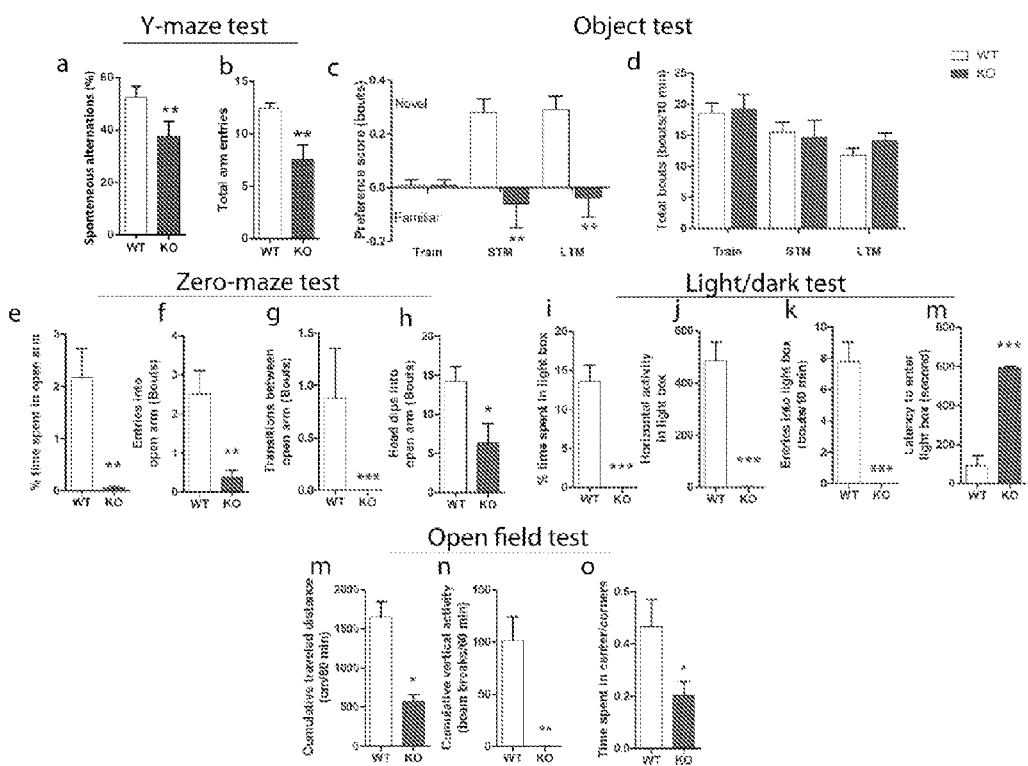
FIG. 10. Mfsd2a KO mice exhibit deficits in learning, memory, and severe anxiety. a, b, The Y-maze test and c, d, novel object recognition test was used to assess spatial learning, short term memory (STM) and long term memory (LTM) of the WT and KO mice, respectively. KO mice exhibited significantly decreased total arm entries in an Y maze test for spatial working memory. KO mice showed significantly reduced preferences for novel objects in novel object recognition tests, indicative of defects in short term memory and long term memory, respectively. "Train" indicates the training period. e-h, Zero-maze test, i-m, light/dark box tests were used to assess anxiety of the WT and KO mice, respectively. KO mice showed decreased transitions and head dips into open arms during Zero-maze test for anxiety behaviors. KO mice showed decreased entry into light box and increased latency to enter light box during light/dark box test for anxiety. m-o, Open field test for activity. KO mice showed reduced travel distance in the open field test for locomotor activity. During the open field test, KO mice had no vertical activity indicative of motoric dysfunction, and decreased time spent in the center, indicative of reduced exploration compared to WT mice. The increased time spent in the corners of the open field suggests that KO mice were more anxious than WT mice, and are congruent with our results from the Zero-maze and light/dark box tests. WT mice (n=11-13) and KO mice (n=8-10). *P<0.001, P<0.01, *P<0.05. Data were expressed as mean±SEM.
Figure 11A:
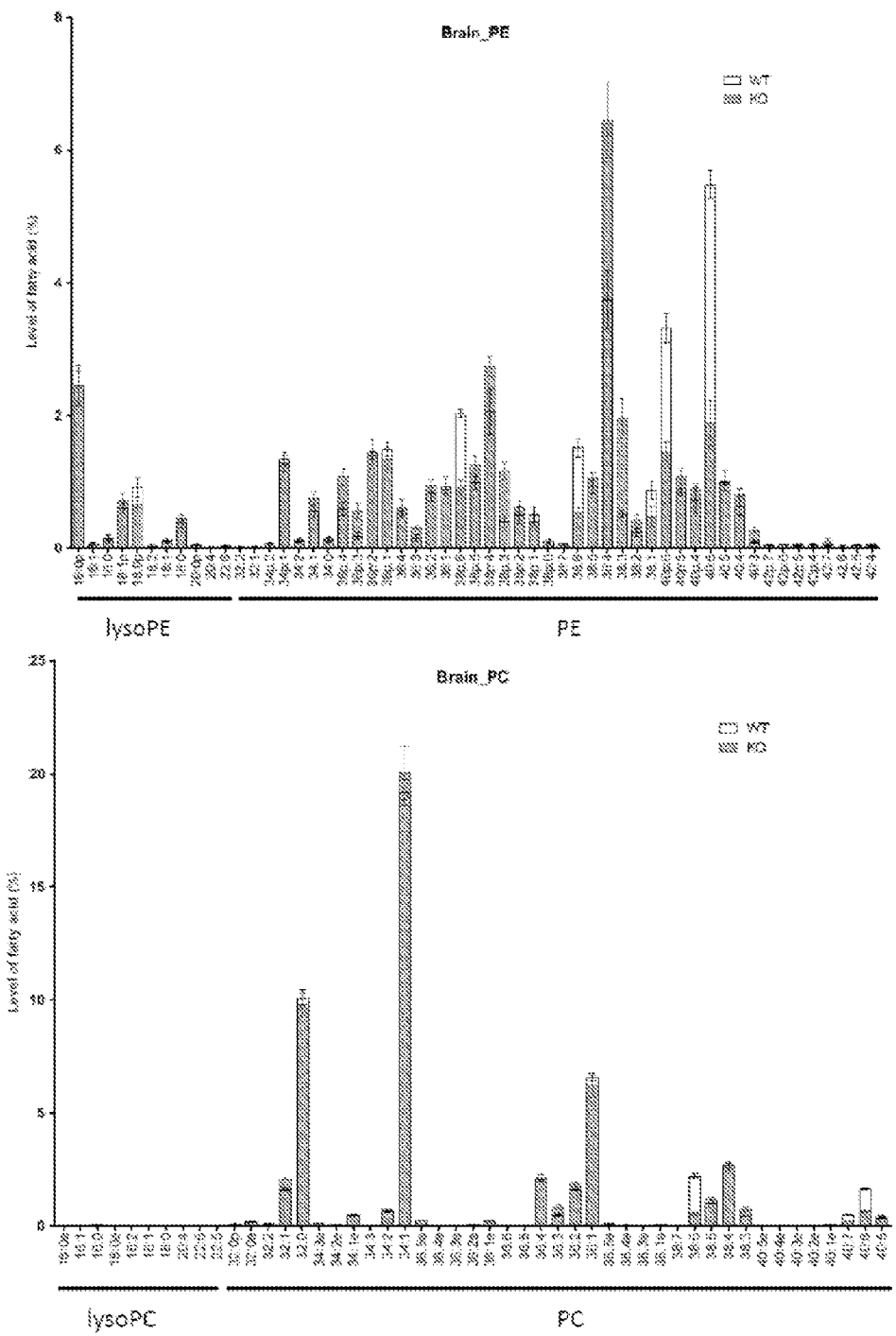
FIG. 11a-e. Individual phospholipid species analyzed by mass spectrometry. Comprehensive lipidomic analysis of brain, liver, and heart phospholipids of Mfsd2a knockout (KO, n=4, hatched bars) and wild type (WT, n=5, blank bars) littermates. LysoPC: lysophosphatidyl choline, PC: phosphatidyl choline, lysoPE: lysophosphatidyl ethanolamine, PE: phosphatidyl ethanolamine, lysoPI: lysophosphatidyl inositol, PI: phosphatidyl inositol, PS: phosphatidyl serine, p: plasmalogen, e: esther. Fatty acid levels were calculated as percent of total phospholipids in corresponding organs and expressed as mean±SEM. The superimposed graphs were used to present the differences of the same fatty acid species of WT with KO mice.
Figure 11B:
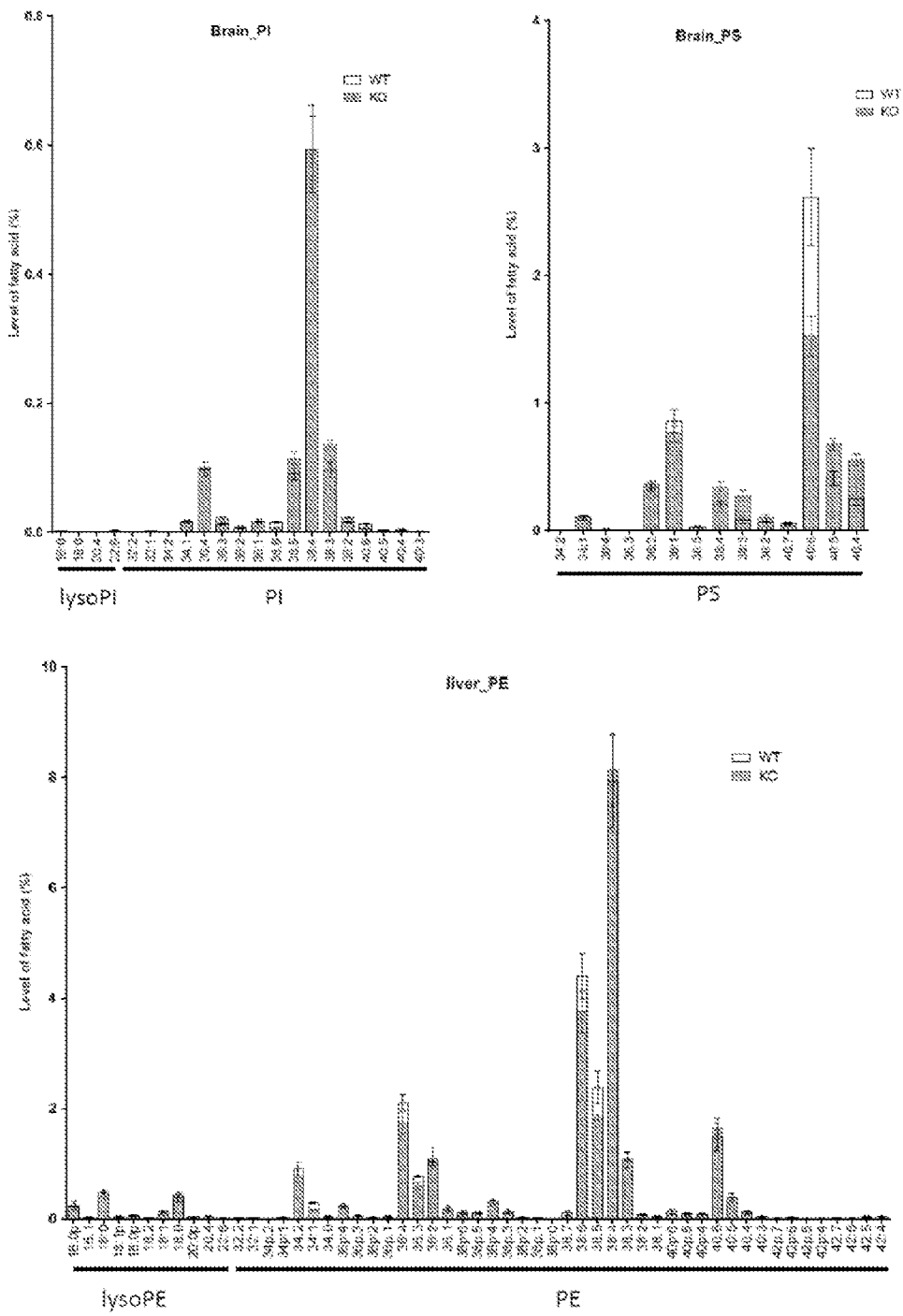
Figure 11C:
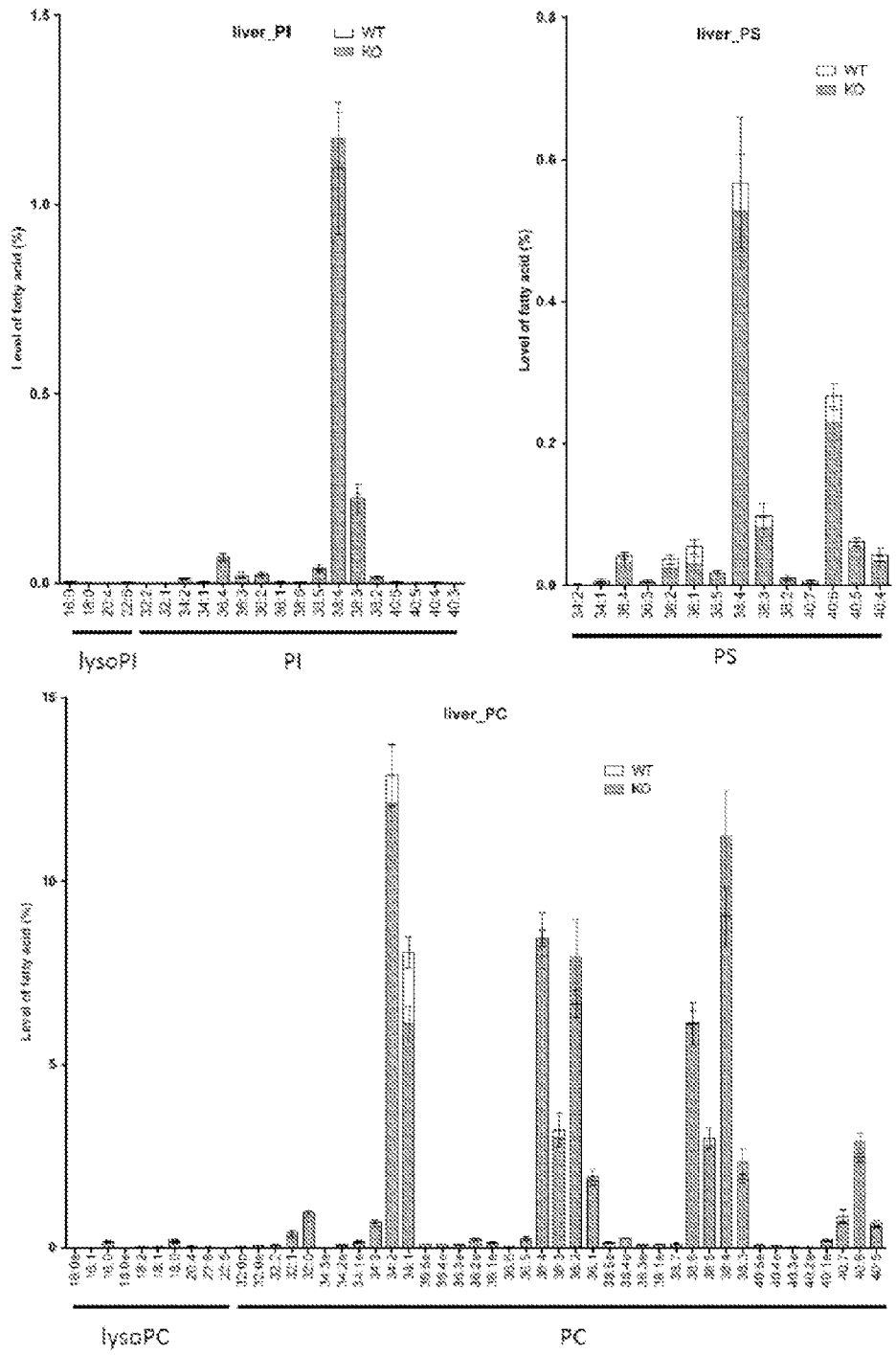
Figure 11D:
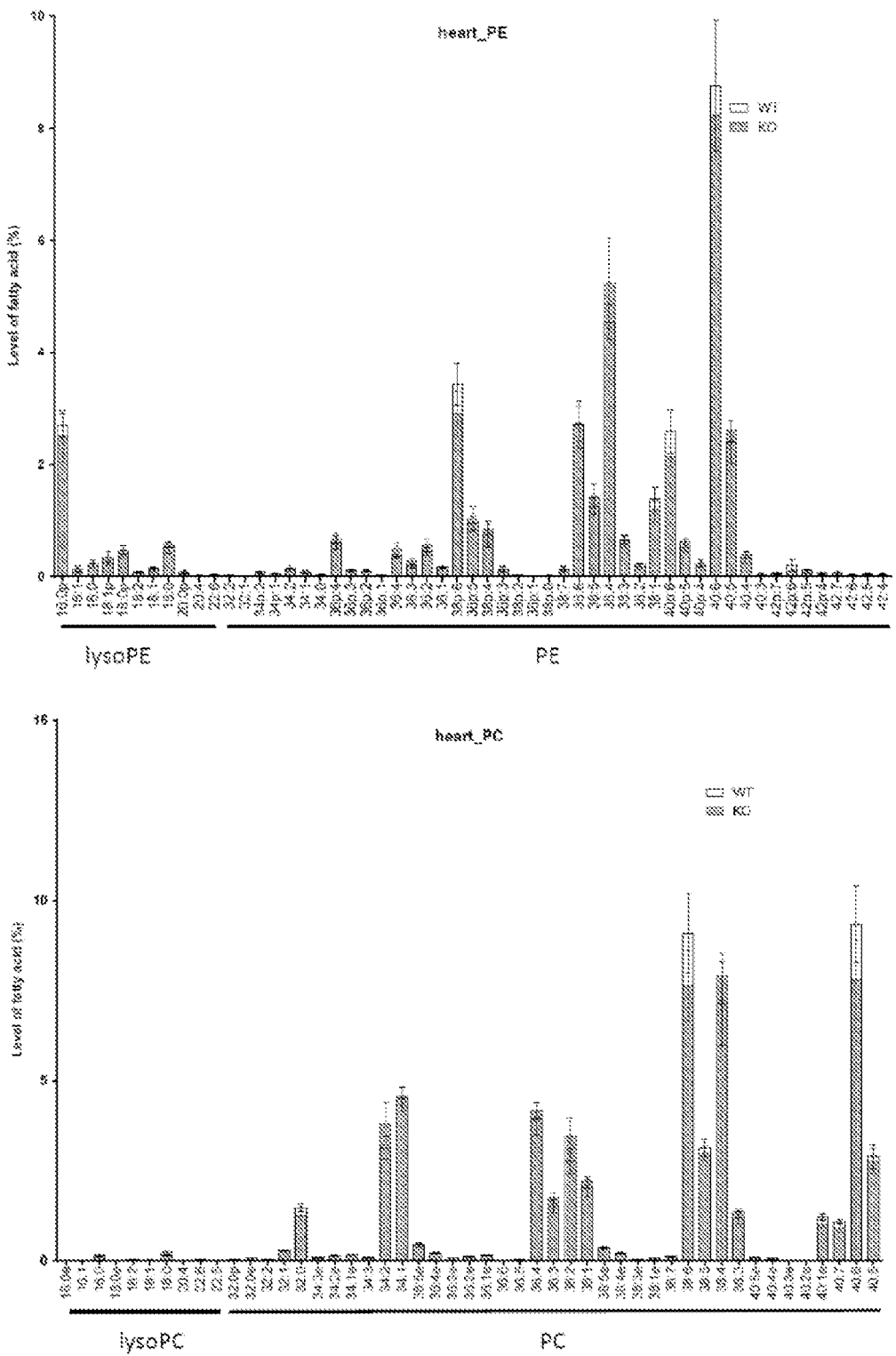
Figure 11E:
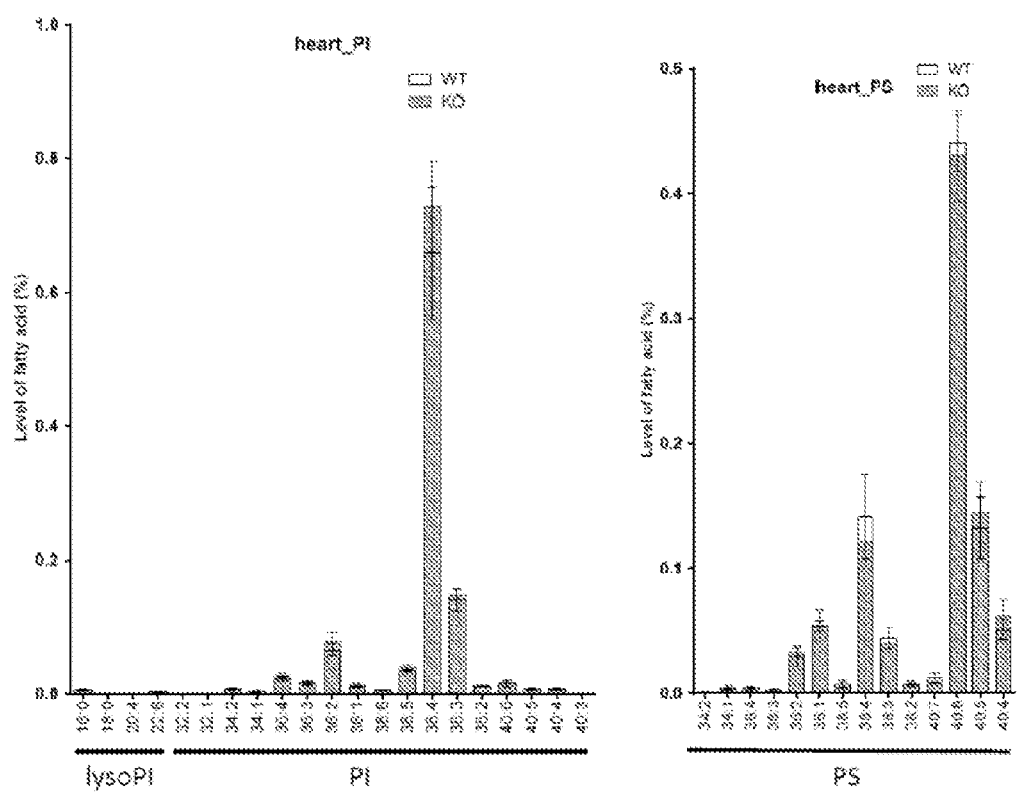

Male and female Mfsd2a gene deficient (KO) mice were born at Mendelian ratios, but had significantly increased postnatal mortality early in life (Berger, J. H., Charron, M. J. & Silver, D. L. Major facilitator superfamily domain-containing protein 2a (MFSD2A) has roles in body growth, motor function, and lipid metabolism. PLoS One 7, e50629, doi:10.1371/journal.pone.0050629 (2012)). Physiological and biochemical measurements of tissue and systemic health were reported to be unremarkable in an independently generated Mfsd2a KO mouse model (Tang, T. et al. A mouse knockout library for secreted and transmembrane proteins. Nature Biotechnology 28, 749-755, doi:10.1038/nbt.1644 (2010)). Consistently, fetal and placental weights of KO mice at E18.5 were similar to WT littermates (FIG. 8a). In addition, KO mice after weaning exhibited motor dysfunction, (Berger, J. H., Charron, M. J. & Silver, D. L. Major facilitator superfamily domain-containing protein 2a (MFSD2A) has roles in body growth, motor function, and lipid metabolism. PLoS One 7, e50629, doi:10.1371/journal.pone.0050629 (2012)), with front paw clasping during tail suspension (FIG. 8b). Brain size and weight of KO mice was significantly smaller than WT littermates (FIG. 9a, b). However, there were no visible differences in gross anatomy of WT and KO brains (FIG. 9c, d). Interestingly, cerebellum of KO mice exhibited a significant loss of Purkinje cells (FIG. 1d, e). Furthermore, there was a significant decrease in neuronal cell density in the hippocampus, particularly in the CA1 and CA3 regions, but normal cell density in the dentate gyrus (DG) of KO mice (FIG. 1f, g). These data suggested that KO mice might have deficits in learning and memory. Indeed, behavioral tests indicated that KO mice had severe deficits in learning, short and long term memory as well as severe anxiety (FIG. 10).

Example 3: Lipidomic Analysis in Wild-Type and Mfsd2a Knock Out Mice

Figure 2:
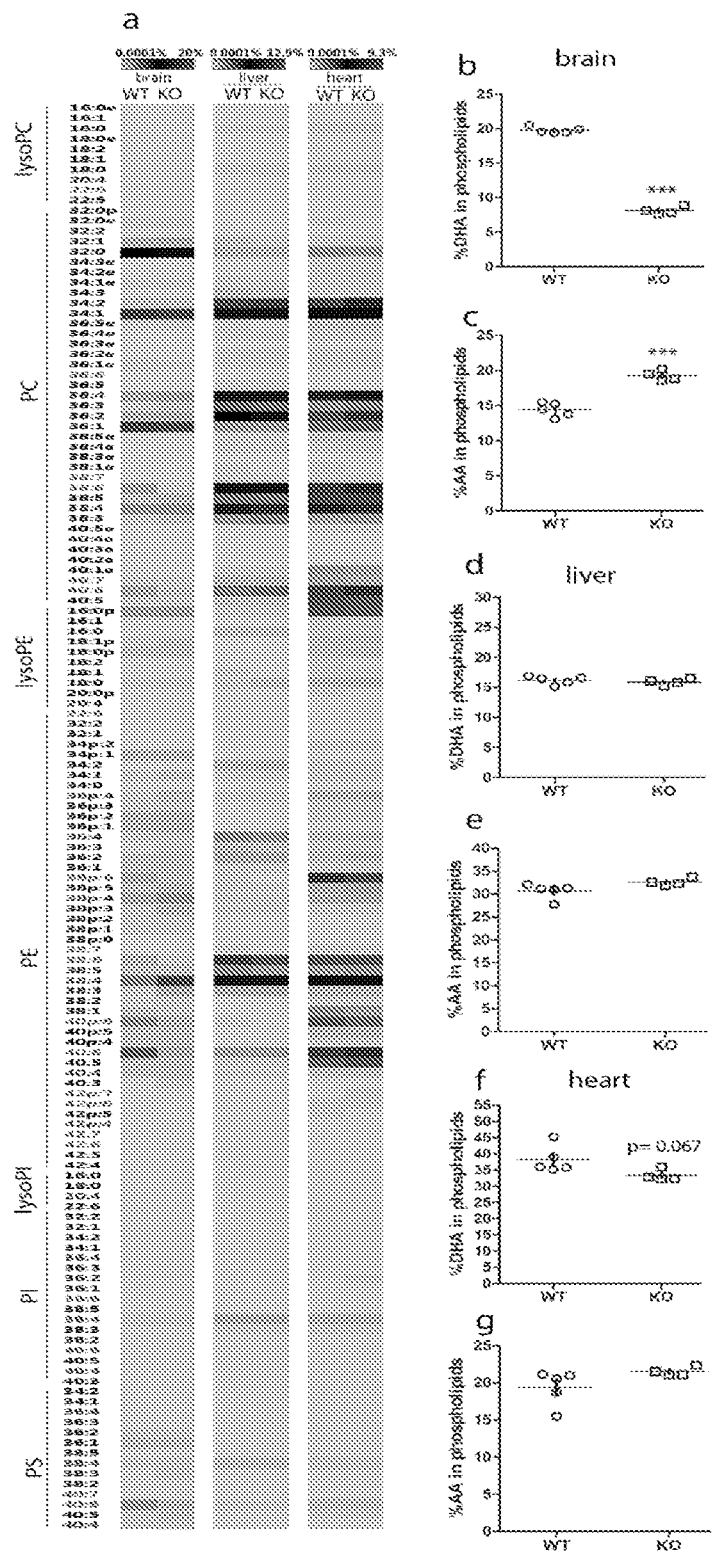
FIG. 2$a$-$g$. Brains of Mfsd2a KO mice are DHA deficient. Comprehensive lipidomic analysis of brain, liver, and heart phospholipids of adult MFSD2A knockout (KO) and wild type (WT) mice. a, heatmap representation of percentage of individual phospholipid species measured from brain, liver, and heart. LysoPC: lysophosphatidyl choline, PC: phosphatidyl choline, lysoPE: lysophosphatidyl ethanolamine, PE: phosphatidyl ethanolamine, lysoPI: lysophosphatidyl inositol, PI: phosphatidyl inositol, PS: phosphatidyl serine, p: plasmalogen, e: esther.

Deficiency of omega-3 fatty acid has been linked with cognitive dysfunction and anxiety in rodent models (Lafourcade, M. et al. Nutritional omega-3 deficiency abolishes endocannabinoid-mediated neuronal functions. Nature Neuroscience 14, 345-350, doi:10.1038/nn.2736 (2011); Carrie, I., Clement, M., de Javel, D., Frances, H. & Bourre, J. M. Phospholipid supplementation reverses behavioral and biochemical alterations induced by n-3 polyunsaturated fatty acid deficiency in mice. Journal of Lipid Research 41, 473-480 (2000)) These KO phenotypes suggested to us that Mfsd2a KO mice might have reductions in brain levels of omega-3 fatty acids and alterations in other lipid species. We performed a comprehensive lipidomic analysis of brain, liver, and heart by mass spectrometry on WT and KO mice. Strikingly, we found that DHA, but not other omega-3 fatty acid species, in major phospholipid species of PE, PC, PI, and PS of brain of KO mice were significantly decreased compared to WT mice (FIG. 2a and detailed in FIG. 11). DHA is found mainly as phospholipid species 38:6 and 40:6 in PE, PC, PI and PS (Kim, H. Y. Novel metabolism of docosahexaenoic acid in neural cells. The Journal of Biological Chemistry 282, 18661-18665, doi:10.1074/jbc.R700015200 (2007)) (FIG. 2a and FIG. 11). The total level of DHA-containing species was not significantly different in the liver and heart of KO mice compared to WT mice (FIG. 2d, f and FIG. 11). However, the total level of DHA in brain of KO mice was reduced by approximately 58.8% with minor changes in other fatty acid species (FIG. 2b and FIG. 11). Brains of KO mice had a 33.8% increase in arachidonic acid in phospholipids (FIG. 2c, and FIG. 11), which is commonly increased in rodent models of DHA deficiency (Simopoulos, A. P. The importance of the omega-6/omega-3 fatty acid ratio in cardiovascular disease and other chronic diseases. Exp Biol Med (Maywood) 233, 674-688, doi:10.3181/0711-MR-311 (2008)). It is noteworthy that KO mice were grown on DHA sufficient diet underscoring a physiological role of Mfsd2a in maintaining brain DHA levels. Despite the lack of anatomical changes in the developing brains of KO embryos, biochemical changes in brain phospholipids were apparent at e18.5 with significantly reduced levels of DHA in phospholipids (FIG. 7c), indicating that Mfsd2a plays an essential role in maintaining DHA levels during embryogenesis.

Example 4: Transport of LPCs by Mfsd2a

Figure 3:
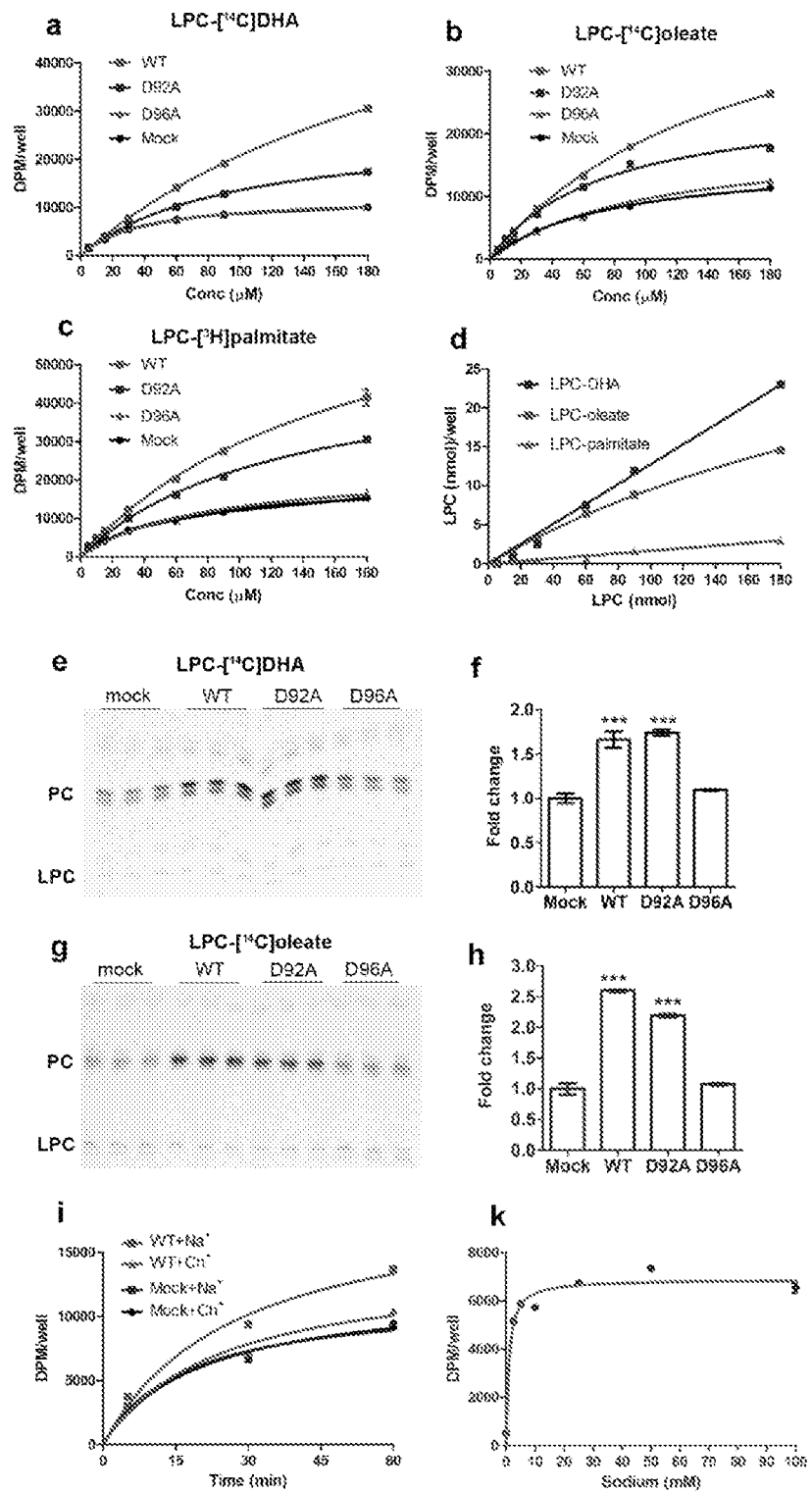
FIG. 3. Cell-based transport assays of radiolabeled LPCs. a, b, c, concentration-dependent transport of LPC-[$^{14}$C] DHA, LPC-[$^{14}$C]oleate, LPC-[$^{3}$H]palmitate after 30 mins. Mouse Mfsd2a (WT) and mutant constructs D92A, D96A were tested for uptake of radiolabeled LPCs at indicated concentrations. d, Comparison transport preference of LPC-[$^{14}$C]DHA, LPC-[$^{14}$C]oleate, LPC-[$^{3}$H]palmitate. e, biological incorporation of radiolabeled LPC-[$^{14}$C]DHA. f, quantification of PC bands from TLC plates shown in e. g, LPC-[$^{14}$C]oleate bio-incorporation into phosphatidylcholine. h, f, quantification of PC bands from TLC plates shown in g. i, transport activity of mouse Mfsd2a is dependent on sodium (Ch$^+$ indicates choline). k, dose-response curve for sodium concentration dependency of transport of 50 μM LPC-[$^{14}$C]oleate by Mfsd2a. For a-d, f, h, i,k data in triplicates are expressed as mean±SEM. ***P<0.0001.
Figure 12:
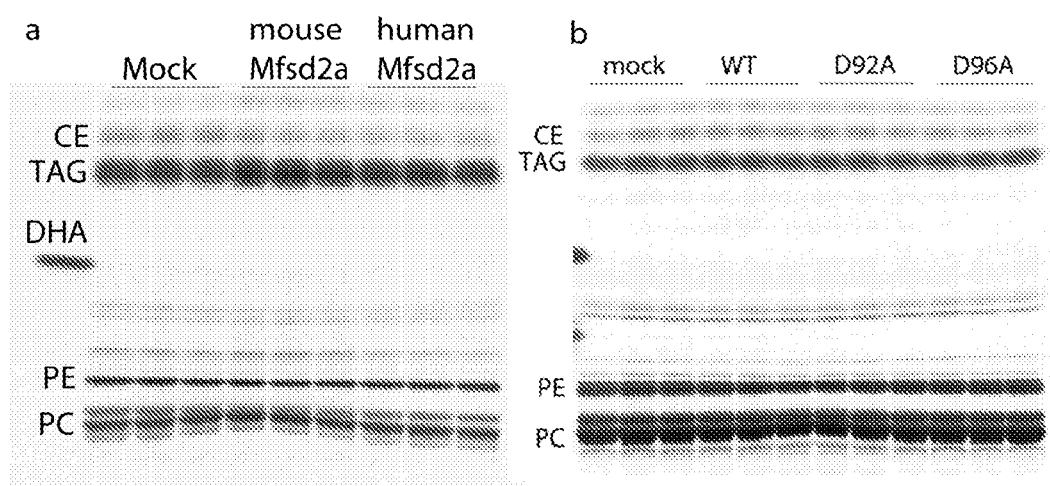
FIG. 12. Mfsd2a does not transport unesterified fatty acids. a, Thin layer chromatography (TLC) analysis of phospholipids and neutral lipids of HEK293 cells transfected with mouse Mfsd2a and human Mfsd2a after overnight incubation with 100 μM [$^{14}$C]-DHA. Std: free [$^{14}$C]-DHA. b, TLC analysis of phospholipids and neutral lipids of HEK293 cells transfected with mouse Mfsd2a and mutants after overnight incubation with 100 μM [$^{14}$C]-oleate. TLC protocol used was described in Methods. PC: phosphatidylcholine, PE: phosphatidylethanolamine, TAG: triglyceride, CE: cholesteryl ester.
Figure 13:
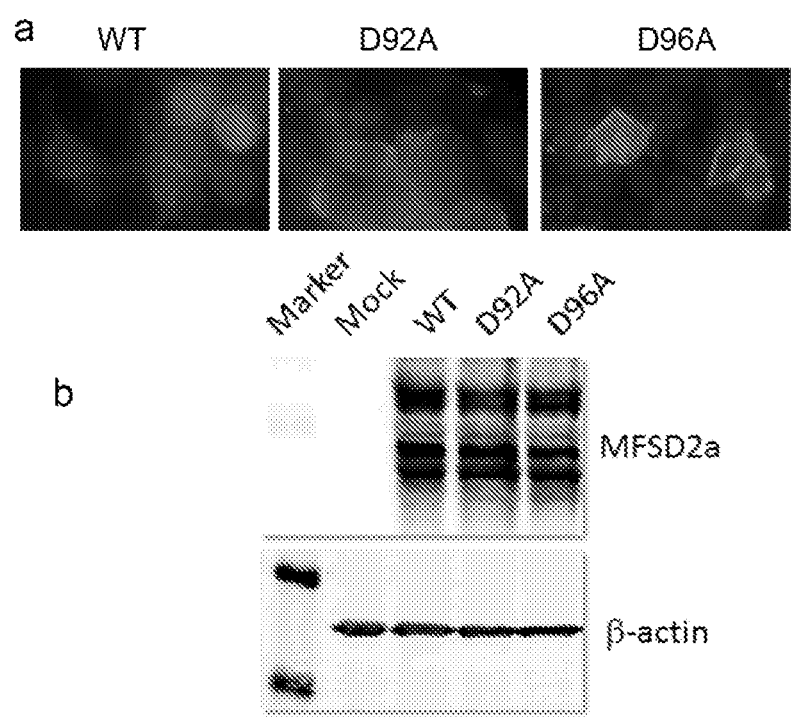
FIG. 13. Expression and localization of mouse Mfsd2a and mutants in HEK293 cells 24 hrs post transfection. a, localization of Mfsd2a, D92A, and D96A at plasma membrane. b, Western blot analysis of expression of Mfsd2a, D92A, and D96A in HEK293 cells post 24 hrs transfection.
Figure 14:
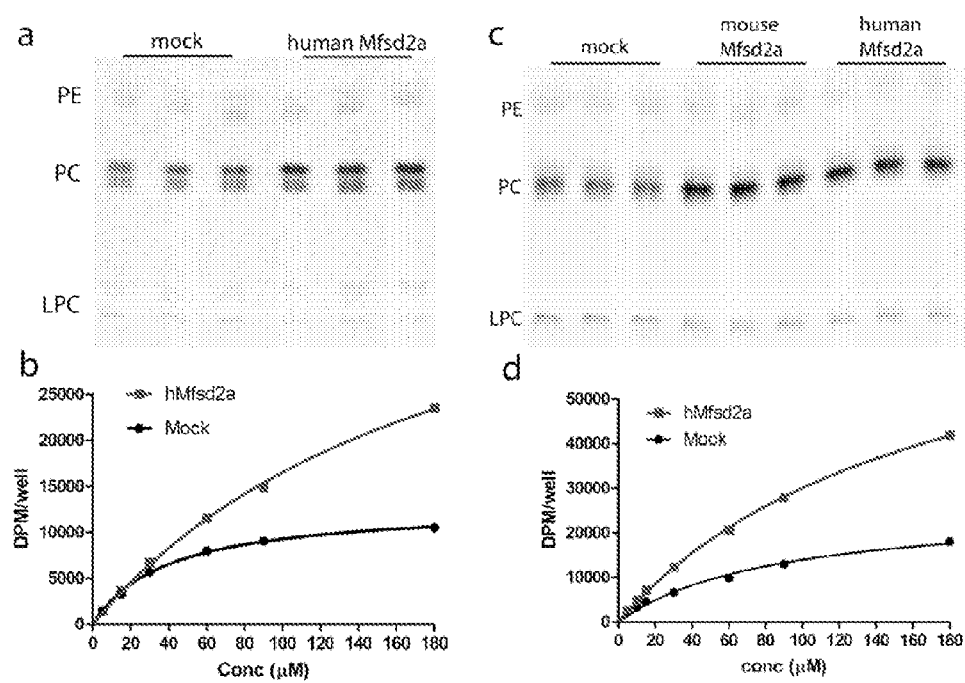
FIG. 14. LPC transport activity of human Mfsd2a. a, biological incorporation of radiolabeled LPC-[$^{14}$C]DHA and c, LPC-[$^{14}$C]oleate into phosphatidylcholine (PC). Cells expressing human Mfsd2a were incubated with LPC-[$^{14}$C] DHA or 50 μM LPC-[$^{14}$C]oleate. Lipids were extracted from cells after 30 mins incubation with LPC-[$^{14}$C]DHA and 120 mins incubation LPC-[$^{14}$C]oleate and analyzed using TLC method for resolving phosphatidylcholine (PC) and lysophosphatidylcholine (LPC). b, Dose-dependent transport of LPC-[$^{14}$C]DHA and d, LPC-[$^3$H]oleate by human Mfsd2a (hMfsd2a) and empty plasmid (mock) expressing HEK293.
Figure 15:
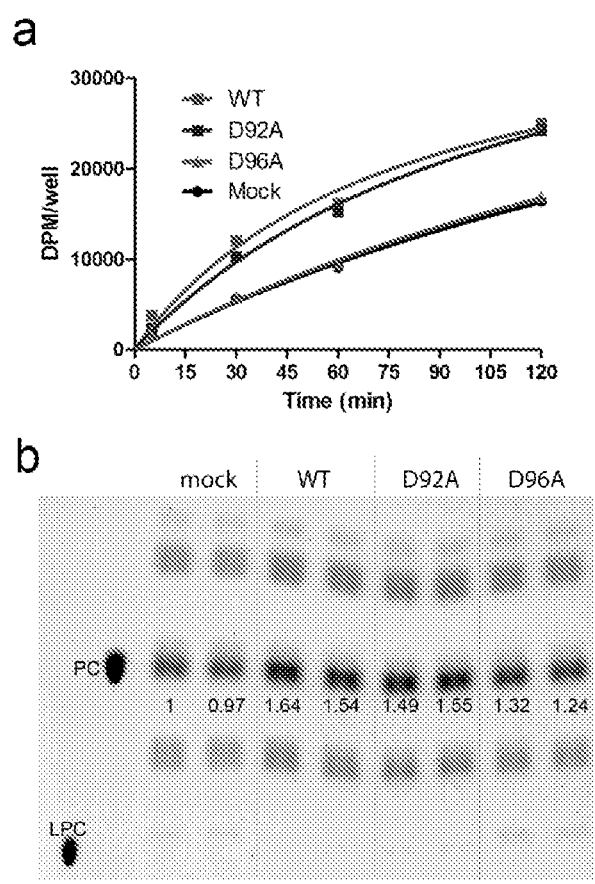
FIG. 15. Time-dependent and mass transport of LPC. a, Time-dependency of transport of 50 μM LPC-[$^{14}$C]oleate. b, Increased net uptake of LPC ligand in cells expressing Mfsd2a. Thin layer chromatography (TLC) analysis of phospholipids of HEK293 cells transfected with mouse Mfsd2a and mutants after 1 hour post incubation with 100 μM unlabeled LPC-oleate. Shown numbers are fold changes of PC levels relative to mock. Standard PC: phosphatidylcholine, LPC: lysophosphatidylcholine.

The brain selectively accumulates a high amount of plasma-derived DHA. In plasma, the exchangeable pool of plasma DHA is found in albumin as either unesterified fatty acid or as LPC[17]. Using cell based assays, we found that Mfsd2a did not transport unesterified DHA, or other unesterified fatty acids (FIG. 12, Table 1), thus ruling out Mfsd2a as a fatty acid transporter. We next tested whether Mfsd2a can transport DHA in LPC form. Remarkably, cells expressing Mfsd2a exhibited an enhanced concentration-dependent uptake of LPC-[$^{14}$C]DHA relative to control cells (FIG. 3a), indicating that Mfsd2a is indeed a LPC-DHA transporter. Alanine mutagenesis of the phylogenetically conserved residues aspartate 92 (D92A) and 96 (D96A) critical for sodium binding in MFS proteins (Granell, M., Leon, X., Leblanc, G., Padros, E. & Lorenz-Fonfria, V. A. Structural insights into the activation mechanism of melibiose permease by sodium binding. *Proceedings of the National Academy of Sciences of the United States of America* 107, 22078-22083, doi:10.1073/pnas.1008649107 (2010)) resulted in reduced and absence of transport, respectively (FIG. 3a). D92A and D96A mutants had similar expression as wild-type (FIG. 13). We next examined transport specificity of Mfsd2a for the most common LPCs found in plasma, LPC-oleate and LPC-palmitate. Cells expressing wild-type Mfsd2a showed concentration-dependent uptake of LPC-[$^{14}$C]oleate and LPC-[$^3$H]palmitate (FIG. 3b, c). Human Mfsd2a also transported LPCs in a similar manner (FIG. 14). A comparison of Mfsd2a-mediated uptake of LPC-oleate, LPC-palmitate, and LPC-DHA, indicated that Mfsd2a had highest capacity to transport LPC-DHA, followed by LPC-oleate, and LPC-palmitate (FIG. 3d). Moreover, cells expressing wild-type and partially active D92A mutant exhibited saturation kinetics over time (FIG. 15a). Importantly, Mfsd2a-dependent transport of LPC-[$^{14}$C]DHA and LPC-[$^{14}$C]oleate resulted in the rapid conversion of transported LPCs into PCs (FIG. 3e, f, g, h). Moreover, expression of Mfsd2a resulted in increases in PC mass indicating Mfsd2a transport activity results in net uptake of LPC into cells (FIG. 15b).

Figure 16:
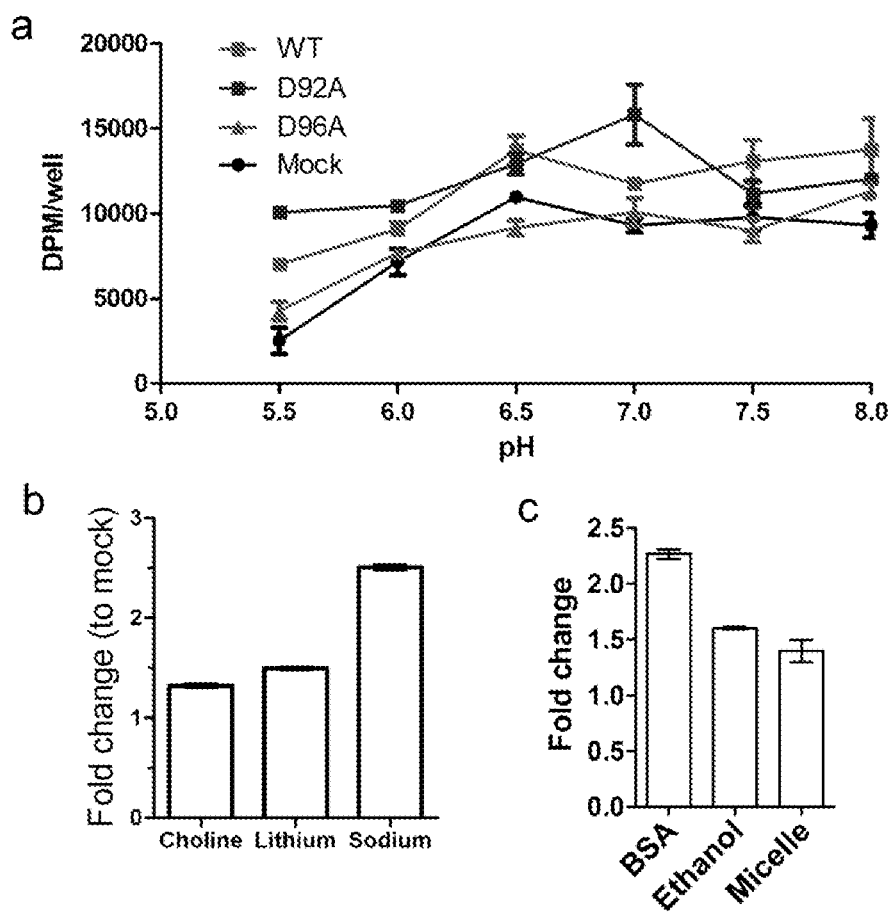
FIG. 16. Transport activity of Mfsd2a is not proton- and lithium-dependent. a, Transport activity of mouse Mfsd2a (WT), D92A, D96A, and mock expressing cells was not significantly different at indicated pHs. b, Activity of Mfsd2a is sodium—but not lithium—dependent. Data were expressed as fold change of Mfsd2a expressing cells to corresponding mock cells treated with the same conditions. c, Transport activity of Mfsd2a is not BSA-dependent as LPC-palmitate solubilized in either ethanol or micellular form was transported by Mfsd2a, albeit to a lower level than with BSA.

MFS family members are facilitative transporters that utilize the co-transport of cations such as $Na^+$, $H^+$, and $Li^+$ down their concentration gradients to drive solute transport. Given the requirement of the phylogenetically conserved cation binding site residue D96 for the transport of LPCs as described above, we tested if transport by Mfsd2a was dependent on sodium. In the absence of sodium, transport of LPC by cells expressing wild-type Mfsd2a was similar to mock-transfected cells, indicating that LPC transport was sodium-dependent (FIG. 3i). Consistent with the characteristics of other sodium-dependent MFS symporters, the transport is highly sensitive to low sodium concentrations indicating high affinity for sodium (FIG. 3k) (Paroder-Belenitsky, M. et al. Mechanism of anion selectivity and stoichiometry of the Na+/I− symporter (NIS). *Proceedings of the National Academy of Sciences of the United States of America* 108, 17933-17938, doi:10.1073/pnas.1108278108 (2011)). LPC transport was not dependent on pH or lithium (FIG. 16a, b). In addition, both LPC-[$^3$H]16:0 solubilized in ethanol or in micelles was transported by Mfsd2a, albeit with lesser capacity compared with BSA bound form, indicating that albumin is not essential for transport (FIG. 16c). Our findings reveal Mfsd2a as the first facilitative transporter identified for the transport of phospholipids.

Example 5: Ligand Specificity and Requirements for Transport by Mfsd2a

Figure 17:
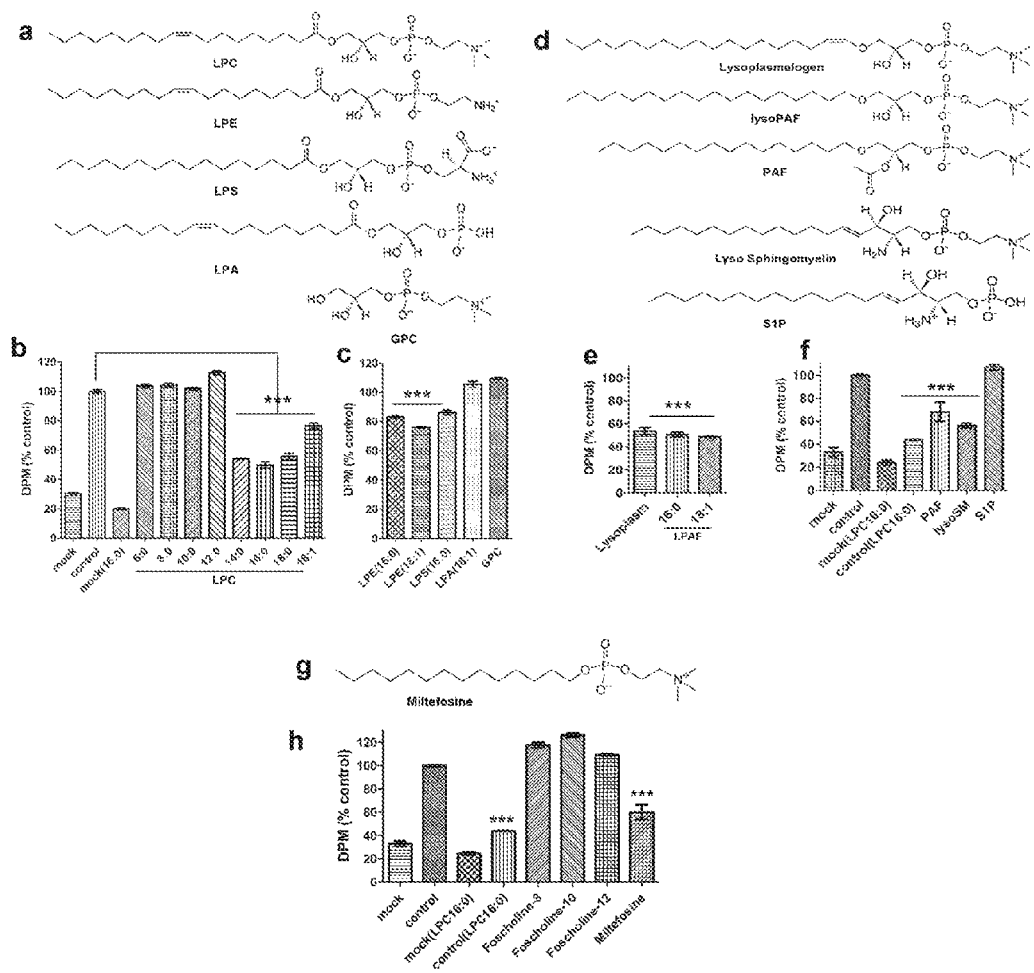
FIG. 17. Competition assay to determine the ligand structures of Mfsd2a. All competition assays were performed using 25 µM LPC-[$^3$H]palmitate as ligand with or without 10-fold molar excess (250 µM) of the indicated competitors. a, The structures of the lipid competitors used in b and c. b, Competition assays with indicated acyl chain LPCs. c, Competition assay with indicated headgroups. Assays were stopped after 30 mins of incubation. Competitive activity was expressed as percent to control (activity of Mfsd2a without competitor). LPC: lysophosphatidylcholine, LPE: lysophosphatidylethanolamine, LPS: lysophosphatidylserine, LPA: lysophosphatidic acid, 6:0: hexanoate, 8:0: docanoate, 10:0: octanoate, 12:0: laurate, 14:0: myristate, 16:0: palmitate, 18:0: stearate, 18:1: oleate. GPC: alpha-glycerylphosphocholine. d, representative structures of bioactive lipid competitors used in e and f. e, Competition assay with lysophospholipid forms of plasmalogens and platelet activating factor (PAF). This experiment was performed together with b, so that the control and mock shown in b can be used as reference. f, PAF and lysosphingomyelin (lys-oSM) also showed strong competition, whereas sphingosine 1-phosphate (S1P) did not compete for LPC-[$^3$H] 16:0 uptake. Competitive activity was expressed as percent to control (activity of Mfsd2a without competitor). g, representative structure of non-biological lysophospholipid analogs foscholine-16 (Miltefosine) having an alkyl chain of 16 carbons. h, competition assays of indicated foscholines with LPC-[$^3$H]palmitate. Assays were stopped after 15 mins of incubation. Competitive activity was expressed as percent to control (activity of Mfsd2a without competitor). Foscholine with alkyl chain length of 8 (Fos-8), 10 (Fos-10), and 12 (Fos-12) carbons did not compete, whereas foscholine with an alkyl chain length of 16 carbons (Miltefosine) showed strong competition with LPC-[$^3$H]16:0. Data are expressed as mean±SEM; ***P<0.001.
Figure 18:
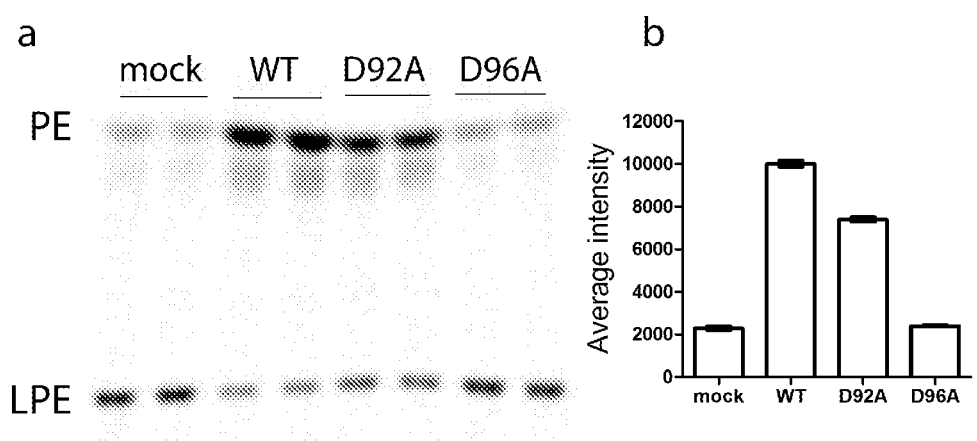
FIG. 18. Thin layer chromatography (TLC) analysis of phospholipids of HEK293 cells transfected with mouse Mfsd2a and mutants after 30 mins post incubation with 25 µM TopFluor-LPE. a, TLC analysis of phospholipids. b, quantification of intensity of PE band from TLC plate. PE: phosphatidylethanolamine, LPE: lysophosphatidylethanolamine.

We next sought to determine ligand specificity and the chemical features of the LPC ligands that are required for transport by Mfsd2a. To carry out this goal, we set up competition assays using cells expressing Mfsd2a or mock control cells, and treated them with 25 µM LPC-[$^3$H]palmitate in the presence or absence of 10-fold excess of unlabeled competitor. We found that a LPC with a minimum acyl chain length of 14 carbons can effectively compete for uptake (FIG. 17a, b, c). The lysophospholipids LPE and LPS showed weak competition, while LPA was non-competitive for the transport of LPC-[$^3$H]palmitate (FIG. 17c). We confirmed that Mfsd2a can directly transport LPE using fluorescent LPE (FIG. 18). These results indicate that the zwitterionic charge of the phosphatidylcholine headgroup is critical for ligand transport. Furthermore, short chain fatty acids and glycerophosphatidylcholine alone was not a competitor (FIG. 17b, c), supporting the conclusion that a long acyl chain of the LPC is a requisite for ligand transport. Lysoplasmalogen, lysoplatelet activating factor, and platelet activating factor were strong competitors, indicating that the carbonyl group of the acyl chain of LPC is not required for transport (FIG. 17d, e, f). Lysosphingomyelin also competed for LPC-[$^3$H]palmitate transport, indicating that the glycerol backbone is not required for ligand function (FIG. 17O. Similar to LPA, sphingosine-1-phosphate was not a competitor (FIG. 17O, further supporting the conclusion that the choline portion of the phosphocholine headgroup is essential for ligand transport. Using lysolipid-like detergents we confirmed that the acyl side chain of a minimal length of 14 carbons and the phosphocholine headgroup, but not the glycerol backbone and carbonyl group, are essential chemical features of the LPC ligand (FIG. 17g, h).

Example 6: Requirement for Mfsd2a for LPC-DHA Transport into the Brain

Figure 19:
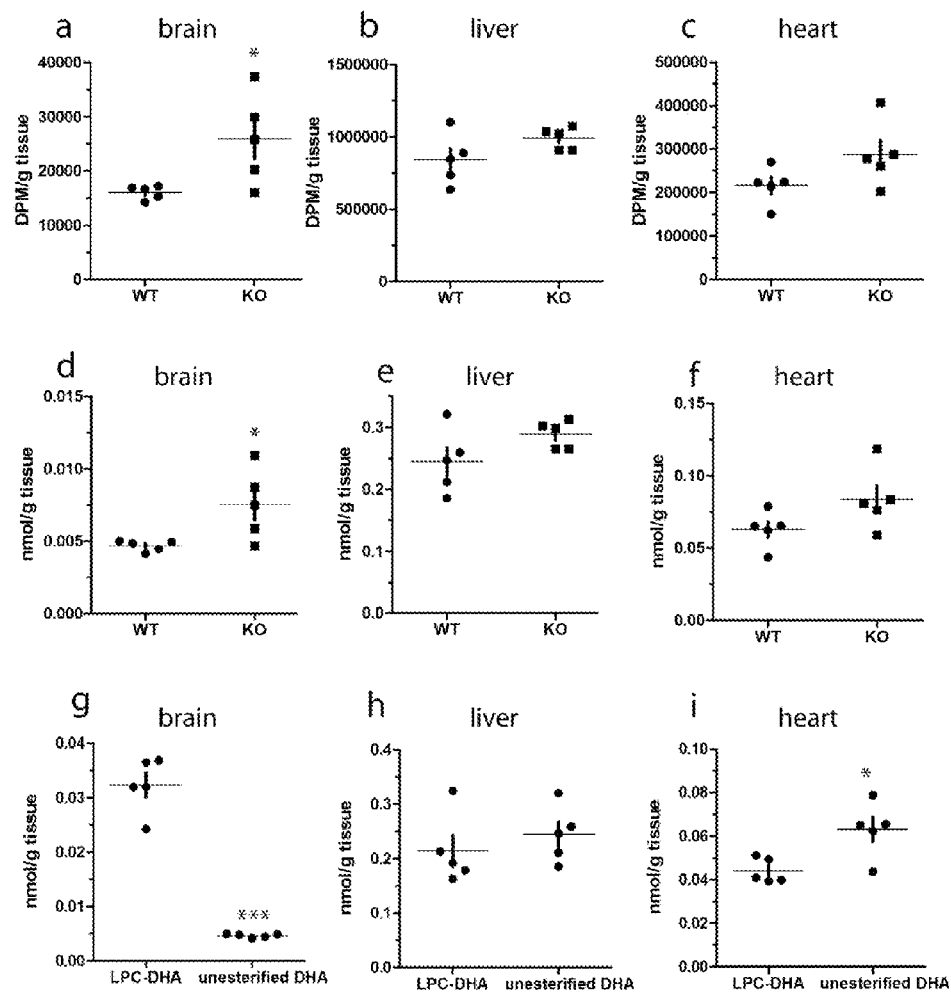
FIG. 19. Brain uptake of unesterified [$^{14}$C]DHA was not reduced in the Mfsd2a deficient mice. Male mice aged 7 weeks old were i.v. injected with 1 mmol of [$^{14}$C]DHA/BSA complex. Brain, liver, and heart were collected 2 hrs post-injection for lipid extraction and DPM quantified using scintillation counting. a-c, Uptake of unesterified [$^{14}$C]DHA in the WT and KO brain, heart, and liver were expressed as DPM/g. d-f, Level of uptake of DHA in "a-c" was converted into nmole/g. g-i, A comparison between the absolute amount of DHA uptake in the form of LPC-DHA (converted from FIG. 4 into nmole/g in 2 hrs) and unesterified DHA (taken from d-f above) in brain, heart, and liver of WT mice. The same amount of LPC-DHA and DHA were injected in mice. The amount of LPC-DHA uptake was far greater than unesterified DHA uptake by wild-type brain. Data are expressed as mean±SEM. (WT, n=5; KO, n=5). ***P<0.0001, *P<0.05.

We next sought to determine if Mfsd2a is required for LPC-DHA transport into brain. Mfsd2a KO and wild-type littermate mice were intravenously injected with LPC-[$^{14}$C]DHA. Remarkably, Mfsd2a KO mice had a reduction in brain uptake of LPC-[$^{14}$C]DHA by more than 90% compared with wild-type controls (FIG. 4a). In contrast, LPC-[$^{14}$C]DHA uptake in peripheral tissues of KO mice were not decreased compared with wild-type controls (FIG. 4a, b). Since unesterified DHA can be taken up by brain via diffusion (Rapoport, S. I., Chang, M. C. & Spector, A. A. Delivery and turnover of plasma-derived essential PUFAs in mammalian brain. *J Lipid Res* 42, 678-685 (2001)), we tested whether the diffusional pathway of DHA uptake is altered in Mfsd2a KO mice. Brain uptake of unesterified [$^{14}$C]DHA was significantly lower relative to LPC-[$^{14}$C]DHA uptake, but was not reduced in KO relative to wild-type mice (FIG. 19). Together, these findings represent a causal link to low brain DHA levels in Mfsd2a KO mice, and support the conclusion that Mfsd2a is a physiological transporter for LPC-DHA uptake in brain.

Figure 20:
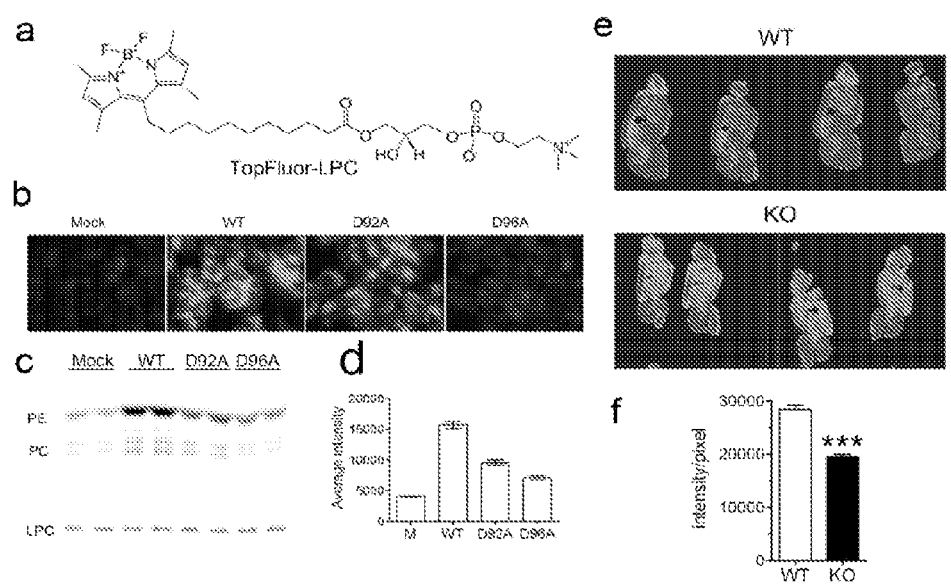
FIG. 20. Brain uptake of unesterified TopFluor-LPC was reduced in the Mfsd2a deficient mice. This experiment was carried out as described for NBD-LPC in FIG. 4. a, structure of TopFluor-LPC. b, HEK293 cells expressing wild-type Mfsd2a showed significantly enhanced uptake activity to TopFluor-LPC compared with mock (empty plasmid), D92A and D96A mutant. c, TLC analysis showed that TopFluor-LPC was bio-incorporated into PC. d, quantification of PC band from TLC plates shown in c. e, brain uptake of TopFluor-LPC was decreased in KO mice. Male mice (WT, n=3; KO, n=3) aged 7 weeks old were i.v. injected with 300 µg TopFluor-LPC/BSA complex. f, Fluorescence from 10 brain sections of WT and KO mice was quantified and expressed as fluorescence intensity per pixel. Data are expressed as mean±SEM. **P<0.001.
Figure 21:
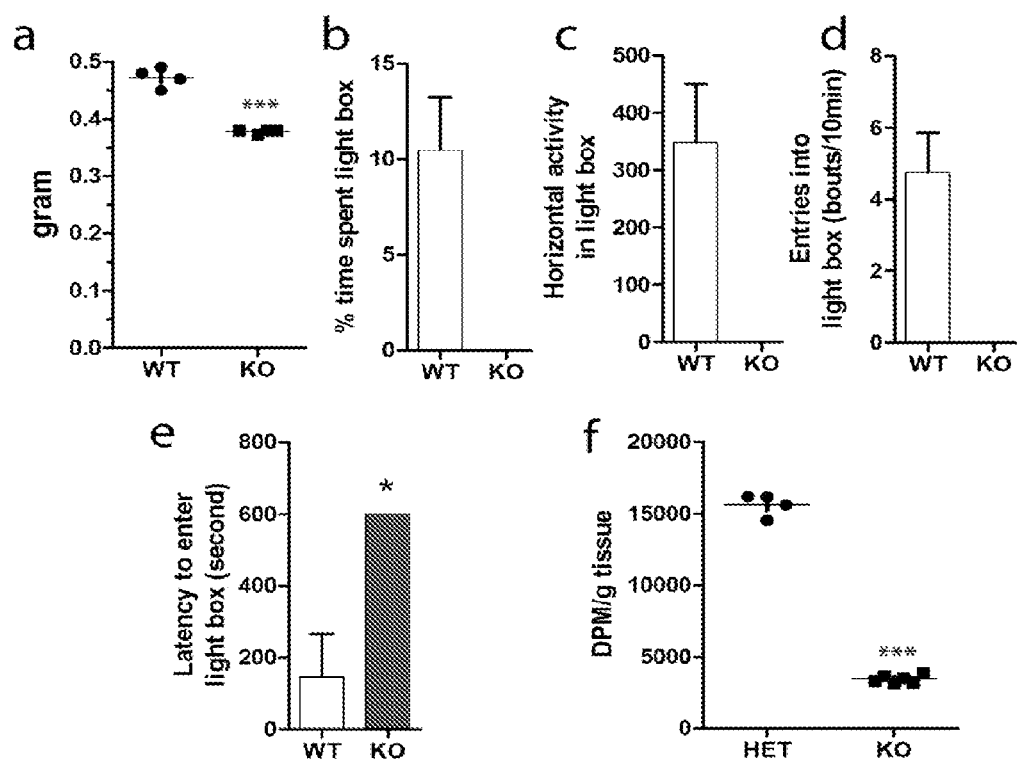
FIG. 21. Dietary DHA supplementation failed to rescue Mfsd2a knockout phenotypes. Heterozygous female mice were gavaged with 100 ul DHA oil (containing 26% DHA triglyceride and 6% EPA, total omega-3 is 35%) every 2 days for 2 weeks prior to conception in crosses with KO males. Heterozygous mice do not exhibit detectable phenotypes, have similar brain DHA as WT mice (not shown) and are thus similar to WT. The rationale for using HET and KO intercrosses was to increase the yield of KO mice in this rescue study. During gestation, pregnant mice were continued on gavages of DHA every 2 days. Gavages of mothers continued during breastfeeding and pups were weaned onto normal diet at 3 weeks of age and gavaged every 2 days with DHA for 8 weeks. a, brain weight of adult WT (n=4) and KO (n=4) mice aged 8 weeks after treatment with dietary DHA oil. KO mice brains were still significantly smaller. b-e, DHA-treated KO mice did not reduce the strong anxiety phenotype as determined using the light/dark box test. To investigate why dietary DHA failed to rescue KO phenotypes, we tested the hypothesis that uptake of maternally-derived DHA (in this case the DHA delivered to the mother via gavage), might not get into the brain of KO mice during brain development. To test this possibility, pregnant het mothers intercrossed to KO fathers at e17.5-e19.5, were gavaged with [$^{14}$C]DHA and uptake into fetal brains were quantified. The data show in f indicate that brains of KO mice exhibited an 80% reduction in the uptake of [$^{14}$C]DHA relative to het mice within the same mothers (n=4 WT, n=6 KO). Therefore, Mfsd2a expressed during fetal development is important for DHA transport into brain. Data are expressed as mean±SEM. *P<0.05. ***P<0.001.

Consistent with cell culture studies indicating that Mfsd2a can also transport common plasma LPCs, brain uptake of LPC-[$^{14}$C]oleate was markedly reduced in KO mice (FIG. 4b). In a separate approach to test the in vivo transport of LPCs by Mfsd2a, we examined the transport of NBD-LPC, a fluorescent LPC analog (FIG. 4c). We first validated in cells that NBD-LPC is transported by Mfsd2a. Similar to native LPCs, NBD-LPC was transported by Mfsd2a, but transport was reduced by D92 and absent in D96 mutants, respectively (FIG. 4d). Importantly, NBD-LPC was bio-incorporated into membrane phospholipids (FIG. 4e, f). Moreover, excess native LPC competed for NBD-LPC uptake (FIG. 4e, f). We next tested in vivo transport. Mfsd2a KO and wild-type mice were injected intravenously with the same dose of NBD-LPC and brain sections were examined for the accumulation of fluorescence. Consistent with the transport of native ligands, the fluorescence of sections of KO brains were significantly reduced compared with wild-type controls (FIG. 4g, h), indicating that brain uptake of NBD-LPC is dependent on Mfsd2a. Similar findings were obtained both in cell culture and in vivo using TopFluor-LPC, a structurally different fluorophore than NBD-LPC (FIG. 20).

Example 7: Studies on Rescue of Mfsd2a Knock Out Mice by Dietary DHA Treatment

We tested if KO mice can be rescued by dietary DHA treatment. Dietary DHA treatment of Mfsd2a heterozygous mice from pre-pregnancy through breastfeeding, and DHA treatment continued on the weaned pups until 8 weeks of age did not rescue KO phenotypes, such as brain size and anxiety (FIG. 21a-e). Importantly, brain uptake of dietary DHA by KO embryos at e18.5 was dramatically reduced compared to wild-type embryos (FIG. 21), consistent with reduced brain DHA levels in KO embryos (FIG. 7b), and indicating that a lack of rescue is likely caused by the essential role of Mfsd2a during embryogenesis for DHA transport into brain.

Taken together, the current study identifies the orphan transporter Mfsd2a as a sodium/LPC symporter, and represents the major mechanism by which DHA enters the brain, and indicates for the first time an important physiological role of plasma-derived LPCs for normal brain growth and function. Given these findings, we propose to rename Mfsd2a to Sodium/LPC Symporter 1 (NLS1).

Example 8: LPC Formulations for Parenteral Nutrition

The findings disclosed herein indicate that the major pathway by which omega-3 fatty acids are taken up by the brain is through their natural conjugation to LPC and transport into brain by Mfsd2a. Triglycerides containing omega-3 fatty acids and non-conjugated fatty acids are not transported by this major pathway and thus are taken up primarily by the liver and other organs. Moreover, Mfsd2a deficient mice exhibit small brains and neurological deficits, and are deficient in brain DHA. We can conclude that brain uptake of LPC-fatty acids such as LPC-DHA and other common LPC-fatty acids are essential for normal brain growth and function. Importantly, the standard of care for pediatric PN does not provide LPC-fatty acids and LPC-DHA, which are required for normal brain growth and function.

Thus, LPCs can be produced and tested to see if addition of LPCs as supplements to PN will result in improved outcomes in neonates in the NICU. LPC levels in normal human serum are approximately 100-200 μM (7-9 μmol/kg) and circulate on albumin (Barber M N, et al. (2012) Plasma lysophosphatidylcholine levels are reduced in obesity and type 2 diabetes. *PLoS One* 7(7):e41456; Croset M, Brossard N, Polette A, & Lagarde M (2000) Characterization of plasma unsaturated lysophosphatidylcholines in human and rat. *Biochem J* 345 Pt 1:61-67). The most abundant LPCs in human plasma are LPC-palmitate, LPC-stearate, and LPC-oleate. Our approach is to purify mixtures of LPCs from material that contains the LPCs listed above plus LPCs having omeg-3 and omeg-6 fatty acids (DHA, EPA, ARA). These latter polyunsaturated fatty acids have been linked to brain development and function in humans (Kidd P M (2007) Omega-3 DHA and EPA for cognition, behavior, and mood: clinical findings and structural-functional synergies with cell membrane phospholipids. *Alternative medicine review: a journal of clinical therapeutic* 12(3):207-227; Horrocks L A & Yeo Y K (1999) Health benefits of docosahexaenoic acid (DHA). *Pharmacological research: the official journal of the Italian Pharmacological Society* 40(3): 211-225; Mozaffarian D & Wu J H (2011) Omega-3 fatty acids and cardiovascular disease: effects on risk factors, molecular pathways, and clinical events. *Journal of the American College of Cardiology* 58(20):2047-2067; Connor W E (2000) Importance of n-3 fatty acids in health and disease. *The American journal of clinical nutrition* 71(1 Suppl):171S-175S)). One possible source of these LPCs is chicken eggs enriched in omega-3 and 6 fatty acids, which are currently available in the market. Thus, one can purify an LPC mixture, and then use this mixture in Parenteral Nutrition (PN) to test outcomes in clinical trials. The majority of outcomes from neonates can be measured within the first 9 months of life. These will include improved growth of body and head circumference while in the NICU and following release from the NICU, and monitoring of normal developmental milestones.

Based on the disclosures herein supplements for PN can be formulated, such as that shown below.

| | LPC | Example composition of an LPC formulation for parenteral nutrition. | |
| --- | --- | --- | --- |
| | | μM | % |
| Component 1 | LPC-16 | 37 | 33.4841629 |
| Component 2 | LPC-18 | 14 | 12.6696833 |
| Component 3 | LPC-18:1 | 10 | 9.04977376 |
| Component 4 | LPC-18:2 n-6 | 20 | 18.0995475 |
| Component 5 | LPC-20:4 n-6 | 4 | 3.6199095 |
| Component 6 | LPC-22.6 n-3 | 25 | 22.6244344 |
| Component 7 | LPC-20:5 n-3 | 0.5 | 0.45248869 |
| | Total | 110.5 | |

Figure 4:
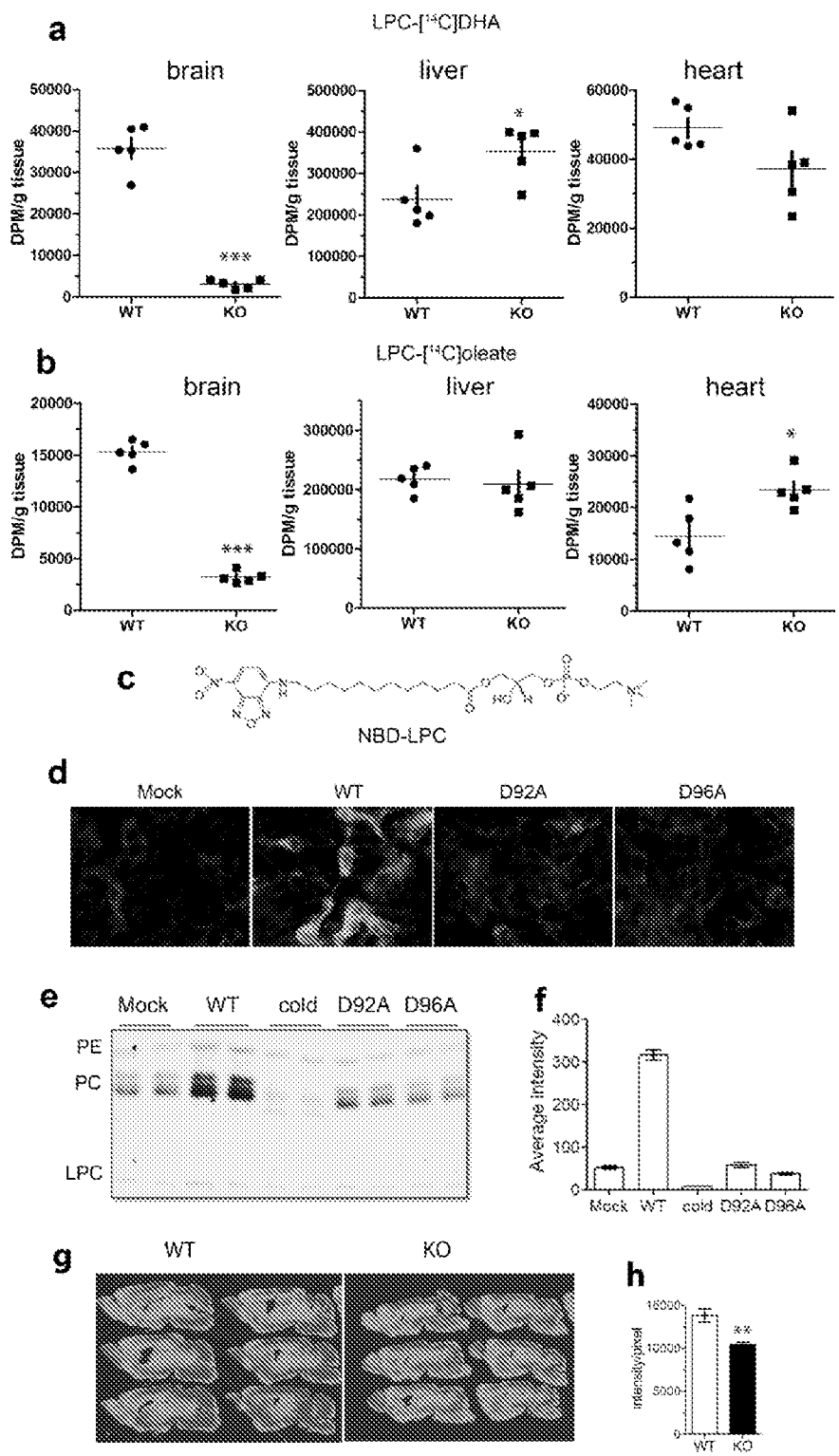
FIG. 4. Uptake of radiolabeled LPCs by brain was decreased in KO mice. a, Male mice aged 6-7 weeks old were i.v. injected with the same dose of LPC-[$^{14}$C]DHA and b, LPC-[$^{14}$C] oleate. Brain, liver, and heart were collected 2 hrs post-injection for lipid extraction and DPM quantified using scintillation counting. Uptake is expressed as mean±SEM. (WT, n=5; KO, n=5). ***P<0.0001, *P<0.05. c, structure of fluorescence NBD-LPC. d, HEK293 cells expressing wild-type Mfsd2a showed significantly enhanced uptake activity to NBD-LPC compared with mock (empty plasmid), D92A and D96A mutant. e, TLC analysis showed that NBD-LPC was bio-incorporated into PC. Transport of NBD-LPC was suppressed by 10-fold molar excess of LPC-18:0 (cold). Mutant D92A, D96A had similar transport activity for NBD-LPC as mock-transfected cells. f, quantification of PC band from TLC plates shown in e. g, brain uptake of NBD-LPC was decreased in KO mice. Male mice (WT, n=3; KO, n=3) aged 6 weeks old were i.v. injected with 300 μg NBD-LPC/BSA complex. h, fluorescence from fifteen brain sections of WT and KO mice was quantified and expressed as fluorescence intensity per pixel. Data are expressed as mean±SEM. **P<0.001.

Shown above are potential concentration ranges of each of the seven (7) component LPCs, 0.5 μM to 200 μM, to be used as a supplement in PN (based on the kinetic analysis of transport by Mfsd2a expressed in human cells as shown in FIG. 4, above). Such formulations can be solubilized with human albumin (derived from recombinant expression or any commercial source) as a carrier to generate a nutritional composition. Furthermore, the LPC mixtures or supplements can be be provided alone and in combination with current PN lipid formulas such as Intralipid™, SMOFKabiven™, Omegaven™ (Fresenius), Lipofundin (B. Braun), ClinOleic™ (Baxter) Liposyn™ (Hospira Inc).

LPCs can be isolated as a mixture as LPCs or as PCs from egg yolk, purified by reverse phase chromatography and solubilized on albumin. LPCs can be produced from PC starting material using specific phospholipases (as described herein) and can be scaled according to need. The ratios of each LPC component can be modified by addition of purified individual LPCs and ranges adjusted as suggested above.

In a further embodiment, also provided are supplements for enteral nutrition comprising PC forms of the above and other LPCs. In this embodiment, PCs are provided for oral administration. Upon consumption, the PCs would be converted into LPCs in the liver and then cross the BBB via the Mfsd2a protein as described.

Example 9: Functional Mfsd2a Mutations in Humans

As discussed herein, DHA is an omega-3 fatty acid essential for normal brain growth and cognitive function (Kidd, P. M. (2007). Omega-3 DHA and EPA for cognition, behavior, and mood: clinical findings and structural-functional synergies with cell membrane phospholipids. *Alternative medicine review: a journal of clinical therapeutic* 12, 207-227; Horrocks, L. A., and Yeo, Y. K. (1999). Health benefits of docosahexaenoic acid (DHA). *Pharmacological research: the official journal of the Italian Pharmacological Society* 40, 211-225; Mozaffarian, D., and Wu, J. H. (2011). Omega-3 fatty acids and cardiovascular disease: effects on risk factors, molecular pathways, and clinical events. *Journal of the American College of Cardiology* 58, 2047-2067; Connor, W. E. (2000). Importance of n-3 fatty acids in health and disease. *Am J Clin Nutr* 71, 171S-175S)). In line with its importance in the brain, DHA is highly enriched in brain phospholipids (Breckenridge, W. C., Gombos, G., and Morgan, I. G. (1972). The lipid composition of adult rat brain synaptosomal plasma membranes. *Biochim Biophys Acta* 266, 695-707; Innis, S. M. (2007). Dietary (n-3) fatty acids and brain development. *The Journal of Nutrition* 137, 855-859)). Despite being an abundant fatty acid in brain phospholipids, DHA cannot be de novo synthesized in brain and must be imported across the blood-brain barrier (BBB), but mechanisms for DHA uptake in brain have remained enigmatic. As shown herein, we have identified a member of the Major Facilitator Superfamily, the previously orphaned transporter Mfsd2a, that we showed to be expressed in endothelium of the blood-brain barrier of micro-vessels, as the major transporter for DHA uptake into fetal and adult brain (Nguyen et al. *Nature* 2014; 509:503-6). Lipidomic analysis indicated that Mfsd2a deficient mice (KO) have dramatically reduced levels of DHA in brain accompanied with neuronal cell loss in hippocampus and cerebellum, and neurological and severe behavioral disorders, and importantly reduced brain size. Surprisingly, cell-based studies indicated that Mfsd2a transported DHA in the form of lysophosphatidylcholine (LPC), but not unesterified fatty acid, in a sodium-dependent manner. Notably, Mfsd2a transported common plasma LPCs carrying long chain fatty acids such LPC-oleate and LPC-palmitate. Importantly, KO mice had dramatically reduced uptake of LPC-DHA, and other LPCs from plasma into brain demonstrating that Mfsd2a is required for brain uptake of DHA. Moreover, our findings reveal an unexpected essential physiological role of plasma-derived LPCs in brain growth and function.

In line with these findings in mice, children with rare inactivating mutations in Mfsd2a (Zaki, M. S., Saleem, S. N., Dobyns, W. B., Barkovich, A. J., Bartsch, H., Dale, A. M., Ashtari, M., Akizu, N., Gleeson, J. G., and Grijalvo-Perez, A. M. (2012). Diencephalic-mesencephalic junction dysplasia: a novel recessive brain malformation. *Brain: a journal of neurology* 135, 2416-2427) (FIG. 22) exhibit severe microcephaly, hydrocephalus, are paraplegic, and non-verbal, clearly demonstrating that Mfsd2a is essential for normal brain growth and function in humans. Importantly, both Thr159Met and Ser166Leu mutations can be shown to result in inactive transport, linking the phenotype of the affected children to inactive Mfsd2a.

These findings raise the likelihood that hypomorphic alleles of Mfsd2a result in neurological deficits such as deficits in memory and learning, and behavioral disorders such as anxiety. Single nucleotide polymorphisms in codons of human Mfsd2a have been identified in NHLBI Exome Sequencing Project (Table 4). More than 12,000 combined European American and African Americans have been genotyped. The mutations shown in Table 4 might be functional mutations resulting in inactivation of Mfsd2a transport activity and can be used for genetic screening in these populations.

TABLE 4

Single nucleotide polymorphisms in codons of human Mfsd2a

NHLBI Exome Sequencing Project. Genotype of ~12,000 exoms from European Americans and African Americans.

see the internet at evs.gs.washington.edu/EVS/

| Human 2A | SNP | Origin | Freq | Info Source | Mouse 2A |
|---|---|---|---|---|---|
| | R114H | EA | 1 in 8000 | Sanger | R113H |
| | Y147C | AA | 1 in 4000 | Sanger | Y151C |
| | L168F | AA | 1 in 4000 | Sanger | L173F |
| | | EA | 1 in 8000 | Sanger | |
| (Same as S186G) | S173G | AA | 0 | Sanger | S177G |
| | | EA | 1 in 4000 | Sanger | |
| | S223L | AA | 1 in 4000 | Sanger | S227L |
| | V264M | EA | 1 in 4000 | Sanger | V268M |
| | Q274R | AA | 1 in 4000 | Sanger | Q278R |
| Y | A281T | AA | 1 in 4000 | Sanger | |
| | R283W | AA | 1 in 4000 | Sanger | Not in Mouse |
| (Same as G890C) | G284A | AA | 1 in 4000 | Sanger | G288A |
| (Same as C895) | R286W | EA | 1 in 8000 | Sanger | R290W |
| (Same as M350V) | M337V | EA | 1 in 8000 | Sanger | M341V |
| (Same as T371A) | T358A | EA | 1 in 8000 | Sanger | T362A |
| (Same as V387M) | V374M | AA | 1 in 4000 | Sanger | V378M |

TABLE 4-continued

Single nucleotide polymorphisms in codons of human Mfsd2a

NHLBI Exome Sequencing Project. Genotype of ~12,000 exoms from European Americans and African Americans.

see the internet at evs.gs.washington.edu/EVS/

| Human 2A | SNP | Origin | Freq | Info Source | Mouse 2A |
|---|---|---|---|---|---|
| | K503 | EA | 1 in 8000 | Sanger | K507 |
| G28A | L181F | EA | 1 in 8000 | Sanger | L172F |
| | | AA | 1 in 4000 | Sanger | |
| (Dup) A556G | S186G | EA | 1 in 8000 | Sanger | S177G |
| | | AA | 1 in 4000 | Sanger | |
| C668T | T223M | EA | 1 in 8000 | Sanger | Not Conserved |
| | | AA | 1 in 4000 | Sanger | |
| C707T | S236L | EA | 1 in 8000 | Sanger | |
| | | AA | 1 in 4000 | Sanger | |
| G829A | V277M | EA | 1 in 8000 | Sanger | |
| | | AA | 1 in 4000 | Sanger | |
| A860G | Q287R | EA | 1 in 8000 | Sanger | Q228R |
| | | AA | 1 in 4000 | Sanger | |
| G877A | A293T | EA | 1 in 8000 | Sanger | Not Conserved |
| | | AA | 1 in 4000 | Sanger | |
| C886T | R296W | EA | 1 in 8000 | Sanger | Not Conserved |
| | | AA | 1 in 4000 | Sanger | |
| (Dup) G890C | G297A | EA | 1 in 8000 | Sanger | G288A |
| | | AA | 1 in 4000 | Sanger | |
| (Dup) C895T | R299W | EA | 1 in 8000 | Sanger | R290W |
| | | AA | 1 in 4000 | Sanger | |
| A926G | K309R | EA | 1 in 8000 | Sanger | K300R |
| | | AA | 1 in 4000 | Sanger | |
| (Dup) A1048G | M350V | EA | 1 in 8000 | Sanger | M341V |
| | | AA | 1 in 4000 | Sanger | |
| (Dup) A111G | T371A | EA | 1 in 8000 | Sanger | T362A |
| | | AA | 1 in 4000 | Sanger | |
| (Dup) G1159A | V387M | EA | 1 in 8000 | Sanger | V378M |
| | | AA | 1 in 4000 | Sanger | |
| C1196T | A399V | EA | 1 in 8000 | Sanger | Not Conserved |
| | | AA | 1 in 4000 | Sanger | |
| C1537T | R513W | EA | 1 in 8000 | Sanger | R504W |
| | | AA | 1 in 4000 | Sanger | | homozygous mutations chr.1: 40431005 C > T T159M    Egyptian family
Chr1: 40431162 C > T S166L    Libyan family

Example 10: Inactivating Mutations in MFSD2A Result in a Lethal Microcephaly Syndrome In this example, we expanded on the results described in Example 9. We performed exome sequencing in a cohort of 3396 patients with mostly recessive neurodevelopmental disease. Patient and knockout mouse sera were assessed for lysophosphatidylcholine (LPC)-lipids. Cells were transfected with cDNA constructs encoding wild-type or mutant MFSD2A, and lipid uptake monitored.

We identified two families with documented consanguinity displaying non-synonymous homozygous mutations in highly conserved residues. Patients displayed a lethal form of microcephaly with massive hydrocephalus, intractable seizures and cerebral palsy. Sera from patients displayed elevated LPC lipids, suggesting a defect in cellular uptake. Mutant MFSD2A lacked in vitro LPC lipid uptake in transfected cells.

Thus, MFSD2A mutations produce a characteristic lethal microcephaly syndrome linked to inadequate uptake of essential LPC lipids.

Methods

Study Oversight

The study was conducted in compliance with the provisions of the Declaration of Helsinki. The institutional review board of the University of California San Diego and the Ethics Committees of National Research Center, Egypt and Tripoli Children's Hospital approved the study protocol. The recruitment was part of a larger study of neurodevelopmental diseases consisting of 3396 families on whom exome sequencing has been performed in order to identify the genetic basis of disease. Written informed consent was obtained from all study participants or designates.

Study Participants

We identified two families with a similar presentation of microcephaly, spastic quadriparesis with poor head control and truncal hypotonia, developmental delay, intellectual disability, and ventriculomegaly as well as hypoplasia of the corpus callosum and the brainstem (Table 5).

TABLE 5

Clinical characteristics of affected members of families 1422 and 1825.

| | Patient ID | | |
|---|---|---|---|
| | 1422-IV-2 | 1825-IV-1 | 1825-IV-2 |
| Country of origin | Libya | Egypt | Egypt |
| Gender | F | M | F |
| Parental consanguinity | + | + | + |
| Mutation cDNA | c.497C > T | c.476C > T | c.476C > T |
| Mutation protein | p.S166L | p.T159M | p.T159M |
| Evaluation | | | |
| Weight at birth (kg) | 3.8 | 2 | 3.4 |
| Length at birth (cm) | n/a | 48 | 47 |
| HC at birth (SD) | n/a | −1.5 | −0.6 |
| HC at latest examination (SD) | −3.5 | −5.3 | −6.2 |
| Speech | Non-verbal | Non-verbal | Non-verbal |
| Gait | Non-ambulatory | Non-ambulatory | Non-ambulatory |
| Head lag | No independent head support | No independent head support | Minimal head support |
| External dysmorphisms | Not obvious apart from squint | Bilateral talipes equinovarus | Bilateral talipes equinovarus |
| Neurological findings | | | |
| Hypotonia | + | + | + |
| Ataxia | − | − | − |
| Spastic quadriparesis | + | + | + |
| Hyperreflexia | + | + | + |
| Intellectual disability | + | + | + |
| Autistic features | − | + | + |
| Other | Recurrent pulmonary insufficiency | Recurrent dysphagia | Recurrent dysphagia |
| Seizures | | | |
| Seizures | + (Clonic) | + (Tonic) | + (Tonic) |
| Seizure onset | 2 years | 7 days | 30 days |
| MRI findings | | | |
| Ventricles | Hugely dilated | Hugely dilated | Hugely dilated |
| Cerebellum | Atrophy/hypoplasia | Atrophy/hypoplasia | Atrophy/hypoplasia |
| Cerebral cortex | Effacement, thin corpus callosum | Effacement, thin corpus callosum | Effacement, thin corpus callosum |
| Brainstem | Hypoplastic | Hypoplastic | Hypoplastic |

Abbreviations.
HC head circumference,
MRI Magnetic resonance imaging,
SD Standard deviation,
n/a not available.

Each living affected member was evaluated, including general and neurological evaluation, anthropomorphic measurements, and review of brain imaging studies. At the time of ascertainment, there was one living and one deceased in each family. Blood sampling was obtained and an aliquot used for DNA extraction, and frozen for subsequent lipidomic evaluation. Complete metabolic screening from blood for known lysosomal, peroxisomal and mitochondrial diseases was negative. All affected members succumbed from complications of neurological disease within the first few years of life, attributed to failure-to-thrive, and cardiopulmonary failure, consistent with a lethal condition.

Genotyping and Genetic Mapping

DNA samples from six (6) individuals including both sets of parents and one affected member in each family were available for genetic studies. These samples were part of a larger effort involving 3396 patients who underwent genetic investigation, including 1349 Egyptian patients and 93 Libyan patients used as ethnically matched individuals for comparison of sequence analysis. One individual from each family underwent comparative genomic hybridization (CGH) analysis and karyotype, which did not detect structural chromosomal abnormalities.

Targeted Sequence Capture and Sequencing

We performed whole exome sequencing (WES) on the affected member from each family. In family 1825 we additionally performed WES of both parents, to increase the specificity of results. Genomic DNA was subject to Agilent Human All Exon 50 Mb kit library preparation, then paired-end sequencing (2×150 bp) on the Illumina HISEQ 2000 instrument. For each patient sample, >90% of the exome was covered at >30×. GATK was used for variant identification (DePristo M A, Banks E, Poplin R, et al. A framework for variation discovery and genotyping using next-generation DNA sequencing data. *Nat Genet* 2011; 43:491-8). We tested for segregating rare structural variants using XHMM (Fromer M, Moran J L, Chambert K, et al. Discovery and statistical genotyping of copy-number variation from whole-exome sequencing depth. *American Journal of Human Genetics* 2012; 91:597-607). We then filtered for homozygous variants using custom Python scripts, to remove alleles with over 0.1% frequency in the population, not occurring in homozygous intervals, or without high scores for likely damage to protein function. Novel mutations were identified in the MFSD2A gene in families 1422 and 1825. No other members of the cohort displayed putative deleterious variants.

Functional Analysis of mfsd2a

We examined the effects of MFSD2A mutations in transport assays (Nguyen L N, Ma D, Shui G, et al. Mfsd2a is a transporter for the essential omega-3 fatty acid docosahexaenoic acid. *Nature* 2014; 509:503-6)_ENREF_5 and the effects of the mutations introduced into the wild-type (WT) human MFSD2A in rescuing the MO phenotype. Serum from patients was subjected to lipidomic analysis (Shui G, Stebbins J W, Lam B D, et al. Comparative plasma lipidome between human and cynomolgus monkey: are plasma polar lipids good biomarkers for diabetic monkeys? *PloS One* 2011; 6:e19731). Detailed methodology of the functional analysis is provided below.

Human Subjects.

Patients were enrolled according to standard local practice in approved human subjects protocols at the University of California.

Whole Exome Sequencing.

For each sample DNA was extracted from peripheral blood leukocytes by salt extraction. Exon capture was performed with the Agilent SureSelect Human All Exome 50 Mb Kit and paired-end sequencing was done with Illumina HISEQ 2000 instruments resulting in ~94% recovery at >10× coverage. Sequences were aligned to the human genome (hg19) with Burrows-Wheeler Aligner (BWA) and variants delineated using the Genome Analysis Toolkit (GATK) software and SAMTools algorithms for both SNPs and insertion/deletion polymorphisms. Variants were subsequently filtered for the following criteria: occurring in coding regions and/or splice sites, non-synonymous, found in less than 0.1% frequency in control populations (our in house exome dataset of 5000 individuals, dbSNP and Exome variant server), homozygous in consanguineous families, within linkage intervals or blocks of homozygosity. The remaining variants were ranked by the type of mutation (nonsense/splice/indel>missense), amino acid conservation across species, and damage prediction programs (PolyPhen and Grantham score). Variants were analyzed using an automated prioritization workflow taking into account familial inheritance patterns and severity of variant (nonsense/splice/indel>missense). A list of all possible deleterious variants passing this threshold of likely null allele, GERP score >4, or Phastcon score >0.8 were tested for segregation by Sanger sequencing in the whole family to exclude exome sequencing error or variants not passing segregation analysis (i.e.: according to a recessive inheritance model). Only those in which a single deleterious variant segregated were marked as potentially causative. HomozygosityMapper was used to construct autozygosity maps from exome sequence (Seelow D, Schuelke M, Hildebrandt F, Nurnberg P. HomozygosityMapper—an interactive approach to homozygosity mapping. *Nucleic Acids Research* 2009; 37:W593-9).

Sanger Sequencing.

Primers were designed using the Primer3 program and tested for specificity using NIH BLAST software. PCR products were treated with Exonuclease I (Fermentas) and Shrimp Alkaline Phosphatase (USB Corporation) and sequenced using Big Dye terminator cycle sequencing Kit v.3.1 on an ABI 3100 DNA analyzer (Applied Biosystems). Sequence data was analyzed by Sequencher 4.9 (Gene Codes).

Mutagenesis of Human MFSD2A.

The human MFSD2A from Sport6 (OpenBiosystems) was PCR using primers hMfsd2aBamHI and hMfsd2aXbaI (Table 8) and cloned into pcDNA3.1 into BamHI and XbaI sites. For mutagenesis of MFSD2A p.T159M and p.S166L by PCR, specific primers were used (Table 6). The mutated PCR products of p.T159M and p.S166L were subsequently cloned into pcDNA3.1 and sequenced.

TABLE 6

Primers used in this study

| Primers | |
|---|---|
| hMfsd2aBamHI | 5'-tttttttGGATCCcaccatggccaaaggagaagg cgccgag-3' (SEQ ID NO: 3) |
| hMfsd2aXbaI | 5'-tttttttTCTAGA ctagaggatgctagccagct ctgtggagtc-3' (SEQ ID NO: 4) |
| T159M-F | 5'-CTTTGAAACAATGGTCAtGTGTTTCCATGTTC C-3'( SEQ ID NO: 5) |
| T159M-R | 5'-GGAACATGGAAACACaTGACCATTGTTTCAAA G-3' (SEQ ID NO: 6) |
| S166L-F | 5'-CCATGTTCCCTACTtGGCTCTCACCATGTTC-3' (SEQ ID NO: 7) |
| S166L-R | 5'-GAACATGGTGAGAGCCaAGTAGGGAACATGG-3' (SEQ ID NO: 8) |

PNGase F Treatment.

PNGaseF treatment of MFSD2A, p.T159M, p.S166L expressed in HEK293 cells was performed as previous described with the exception that incubation time was 3 h (Daneman R, Zhou L, Agalliu D, Cahoy J D, Kaushal A, Barres B A. The mouse blood-brain barrier transcriptome: a new resource for understanding the development and function of brain endothelial cells. *PloS One* 2010; 5:e13741).

Modeling of MFSD2A.

The 3D structure of MFSD2A was modeled using i-Tasser program. The best fit model for MFSD2A is the bacterial melibiose permease (MelB) for which atomic structure was recently solved (Ethayathulla A S, Yousef M S, Amin A, Leblanc G, Kaback H R, Guan L. Structure-based mechanism for Na(+)/melibiose symport by MelB. *Nat Commun* 2014; 5:3009). The transmembrane domains and residues of modelled MFSD2A were subsequently viewed using PyMol.

Transport Assay.

Transport assay using HEK293 cells was performed as previously described (Nguyen L N, Ma D, Shui G, et al. Mfsd2a is a transporter for the essential omega-3 fatty acid docosahexaenoic acid. *Nature* 2014; 509:503-6). Briefly, WT MFSD2A, p.T159M and p.S166L plasmids were transfected into HEK293 cells. Uptake assay was performed after 24 h of transfection with a range of LPC [$^{14}$C]-oleate. Experiments were repeated twice with triplicates in 12 well plates. Uptake activity was expressed as DPM/well. Radiolabeled 1-oleoyl 2-lysophosphocholine (LPC [$^{14}$C]-oleate was purchased from ARC and non-radiolabeled LPC-oleate was obtained from Avanti Polar Lipids, Inc.

TLC Analysis of Phospholiopids.

HEK293 cells overexpressing pcDNA3.1hMfsd2a (WT), pcDNA3.1Mfsd2aT159M (p.T159M), pcDNA3.1Mfsd2aS166L (p.S166L), or pcDNA3.1 (mock) plasmids were washed once with serum-free DMEM medium before incubation with 100 µM radiolabeled LPC

[$^{14}$C]oleate and incubated for 30 min. Wells were washed three times with DMEM containing 0.5% BSA. Lipids were extracted twice with HIP (Hexanes/Isopropanol, ratio 3:2) buffer for 30 min, dried with nitrogen stream, reconstituted in chloroform and spotted on TLC plates (Milipore). Solvent for phospholipid separation was chloroform/methanol/ammonia solution (25%) (50:25:6, per volume). TLC plates of radiolabeled phospholipids were dried for 30 min and exposed overnight to Phosphorscreens and scanned with Typhoon FLA 9000 scanner (Agilent). Phospholipid bands were quantified using Imagequant software and expressed as fold change to mock.

Lipidomic Analysis of Plasma Samples.

For human plasma samples, single plasma sample of the father, mother and affected from family 1825, and duplicated plasma samples from the father, mother and affected from family 1422 were used for LPC analysis. Lysophospholipids were extracted using a methanol-based protocol described previously (Zhao Z, Xu Y. An extremely simple method for extraction of lysophospholipids and phospholipids from blood samples. *J Lipid Res* 2010; 51:652-9). Briefly, plasma samples (24) were re-suspended in 200$\mu$ of methanol containing 100 pmol/mL of LPC 20:0 as an internal standard (Avanti Polar Lipids, USA), followed by 30 s vortexing and 30 min sonication on ice. Samples were centrifuged at 14,000 rpm for 10 min at 4° C. to remove debris. The supernatants were diluted 5× with methanol (total volume 25 $\mu$L) prior to injection in LC-MS/MS. For mouse plasma samples, lysophospholipids were extracted using activated charcoal. Briefly, plasma (150 $\mu$L) from 5 WT and 5 KO littermates aged 3.5 months of were first diluted with 650 $\mu$L PBS and then with 800 $\mu$L activated charcoal solution (1 g/50 ml PBS). Samples were rotated for 1 hr at 25° C. followed by a centrifugation for 5 min at 10,000 rpm to collect the charcoal pellets. The pellets were washed three times with PBS and then resuspended in 500 $\mu$L PBS. An equal amount of choloform/methanol (2:1) was added to the samples and rigorously vortexed for 30 min at 25° C. Organic phase was separated by centrifugation, and lipid extraction was performed twice with choloform/methanol (2:1) and dried with N2 gas. Prior to lipidomic analysis, dried lipid extracts were re-suspended in 150 $\mu$L of chloroform/methanol 1/1, and further diluted with 200 $\mu$L of methanol containing 0.91 nmol/mL of LPC 20:0 as an internal standard. These solutions were used for injection into LC/MSMS.

Mass Spectrometry Analysis.

Samples were randomized for injection into LC/MSMS. Each sample was analyzed in technical triplicates. Each sample analysis was followed by a blank injection to avoid carry-over. Stability of signal throughout the analysis was monitored by regular injection of a QC sample. Chromatographic analysis was undertaken on a 1290 Liquid Chromatography System (Agilent Technologies, USA) using a Kinetex HILIC stationary phase (150×2.1 mm, 2.6 $\mu$m, 100 Å, Phenomenex, USA). For the gradient elution, solvents used were A: 95% Acetonitrile/5% 10 mM ammonium formate/0.1% formic acid, and B: 50% Acetonitrile/50% 10 mM ammonium formate/0.1% formic acid. The gradient went from 0.1% to 75% B in 6 min, to 90% B in 1 min, to 0.1% B in 0.1 min, kept at 0.1% B for 3 min (total runtime 10.1 min). Under these conditions, LPC species elute at about 4.9 min. The flow rate was 0.5 mL/min. LPC species were quantified using Multiple Reaction Monitoring (MRM) on a 6460 triple quadruple mass spectrometer (Agilent Technologies, USA). The source conditions were as follows: gas temperature 300° C., gas flow 5 L/min, sheath gas flow 11 L/min, and capillary voltage 3500V. MRM transitions were from precursor ions to the choline head fragment (m/z 184) with a collision energy of 29V. 36 transitions were monitored simultaneously with a dwell time of 20 ms. Quantification data were extracted using MassHunter Quantitative Analysis (QQQ) software (Agilent Technologies, USA). The data was manually curated to ensure correct peak integration. Areas under curve (AUC) of the extracted ion chromatogram peaks for each MRM transition were extracted to excel. AUC of lipid species were normalized to the AUC of the internal standard. Total and individual LPC species from human and mouse samples were calculated and expressed as $\mu$M.

Blood LPC [$^{14}$C]-Oleate Analysis.

Mfsd2a KO and WT mice were injected intravenously with 100 $\mu$M radioactive labeled LPC [$^{14}$C]-oleate. 10 $\mu$l of blood samples were collected after 2 min (initial dose) and after 2 hr from tail vein, and radioactivity was quantified by scintillation counting. The amount of plasma LPC [$^{14}$C]-oleate in the KO mice was expressed as ratio to the WT at each time point.

Statistical Analysis

We performed all in vitro experiments in quadruplicate. Data are expressed as means and standard errors. We used the Student t-test to perform between group comparisons (two-tailed). For multiple comparisons, we performed Tukey's test in conjunction with analysis of variance using GraphPad Prism software. Kaplan-Meier curves were calculated for survival after MO injection as of 1, 2, and 3 days post fertilization, irrespective of the mRNA injected, including no injection. Survival curves were compared using Log-rank (Mantel-Cox) test using GraphPad Prism software. A p-value <0.05 was considered indicative of statistical significance. All p-values were tested as two-sided.

Results

Study Population

The 3396 patients recruited to study represented many individually rare forms of neurodevelopmental disorders, mostly discernable based upon a static vs. progressive neurological course, the presence of epilepsy, autism or intellectual disability, gross dysmorphic features, or striking findings on diagnostic studies such as brain MRI, EEG or blood chemistry analysis. While the two families displayed, in retrospect, many similar features including microcephaly, mixed hypotonic/spastic quadriparesis, absent head control, epileptic seizures, and hugely dilated ventricles, it would have been difficult to discern their clinical presentation from the rest of the cohort, given the absence of unusual or pathognomonic clinical finding upon routine testing.

Figure 23:
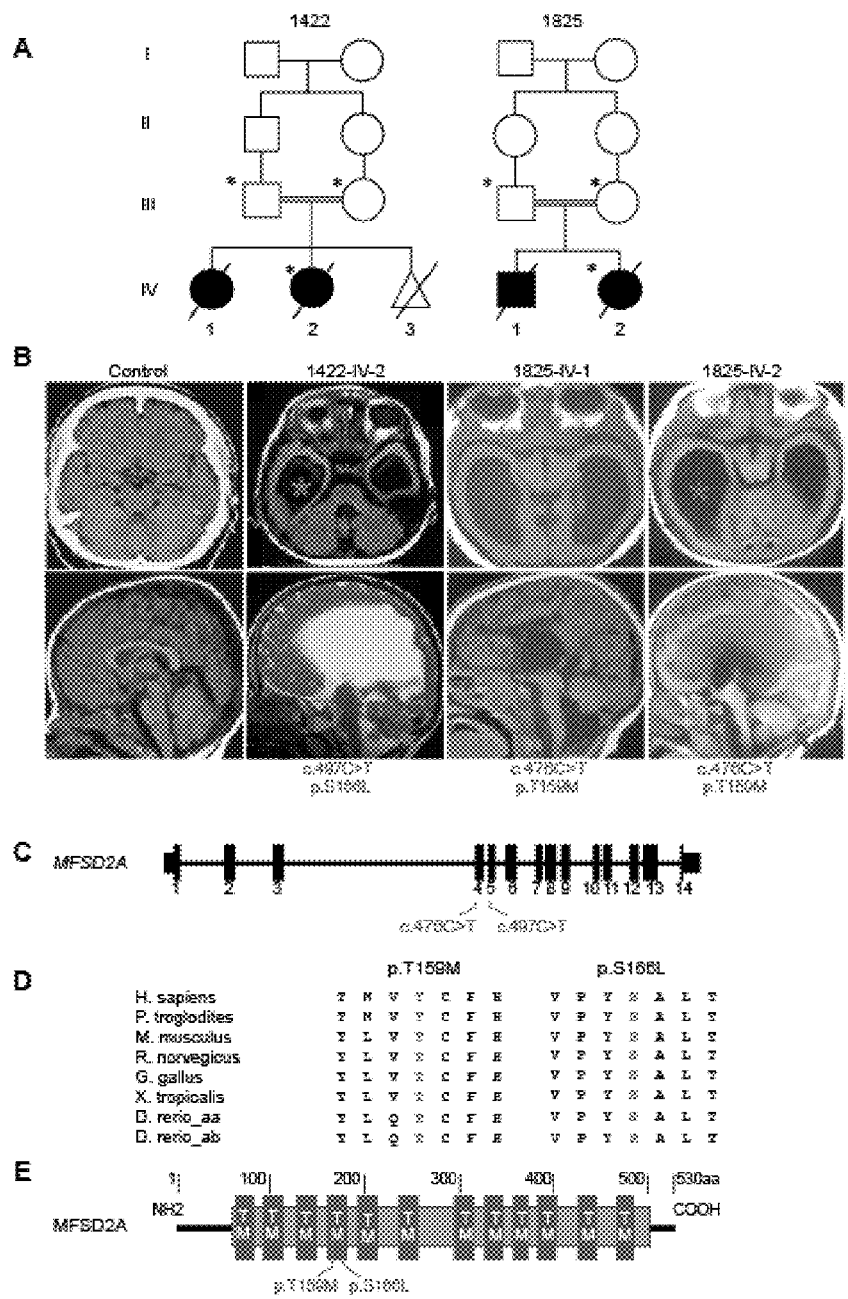
FIG. 23. MFSD2A mutations cause severe microcephaly and ventriculomegaly. (A) Consanguineous families 1422 and 1825 designated by number in each generation. Circles: females, squares: males, slashes: deceased, asterisk: sampled. (B) Upper: axial MRI, lower: parasagittal MRI. Images show hugely enlarged lateral ventricles (asterisks) as well as hypoplasia of the corpus callosum and the brain stem (arrow heads) and cerebellum (arrows) in all affected children. (C) Exonic structure of MFSD2A gene with location of the patient mutations (D) Alignment of amino acid sequences of human, mouse, fish, and bacterial orthologs of MFSD2A showing the conservation of residues T159 and S166.

The two families, one from Libya and the other from Egypt, were brought to medical attention due to absent milestones within the first 3 months of life. Consistent with recessive mode of inheritance, both families demonstrated first-cousin parental consanguinity, each with two affected members (FIG. 23A), and no environmental risk factors for developmental delay (Engle P L, Black M M, Behrman J R, et al. Strategies to avoid the loss of developmental potential in more than 200 million children in the developing world. *Lancet* 2007; 369:229-42). The clinical characteristics of the affected members show normal appearance and growth parameters at birth, except for microcephaly, but constitutive growth retardation, seizures, and absent head growth became apparent within the first months. There was mixed hypotonic/spastic quadriparesis, difficulty maintaining head control, gastroesophageal reflux and aspiration pneumonias. Seizure onset was between 7 days and 2 years of age, and consisted of clonic or tonic spasms lasting 3-10 minutes, precipitated by illness. Routine blood chemistries were entirely normal including full chemistry, complete blood count, erythrocyte sedimentation rate, standard lipid profile, lactate/pyruvate, detailed karyotype, and clinical tandem mass spectrometry for metabolic intermediates. Brain imaging studies showed gross hydrocephalus, with hugely dilated lateral ventricles, effacement of the cortical surface, cerebellar and brainstem hypoplasia/atrophy (FIG. 23B). Obstructive hydrocephalus was excluded based upon a patent Aqueduct of Sylvius, and the presumptive diagnosis that the condition represented a heretofore-unknown form of disease of the deep white matter.

Whole-Exome Sequencing

Figure 26:
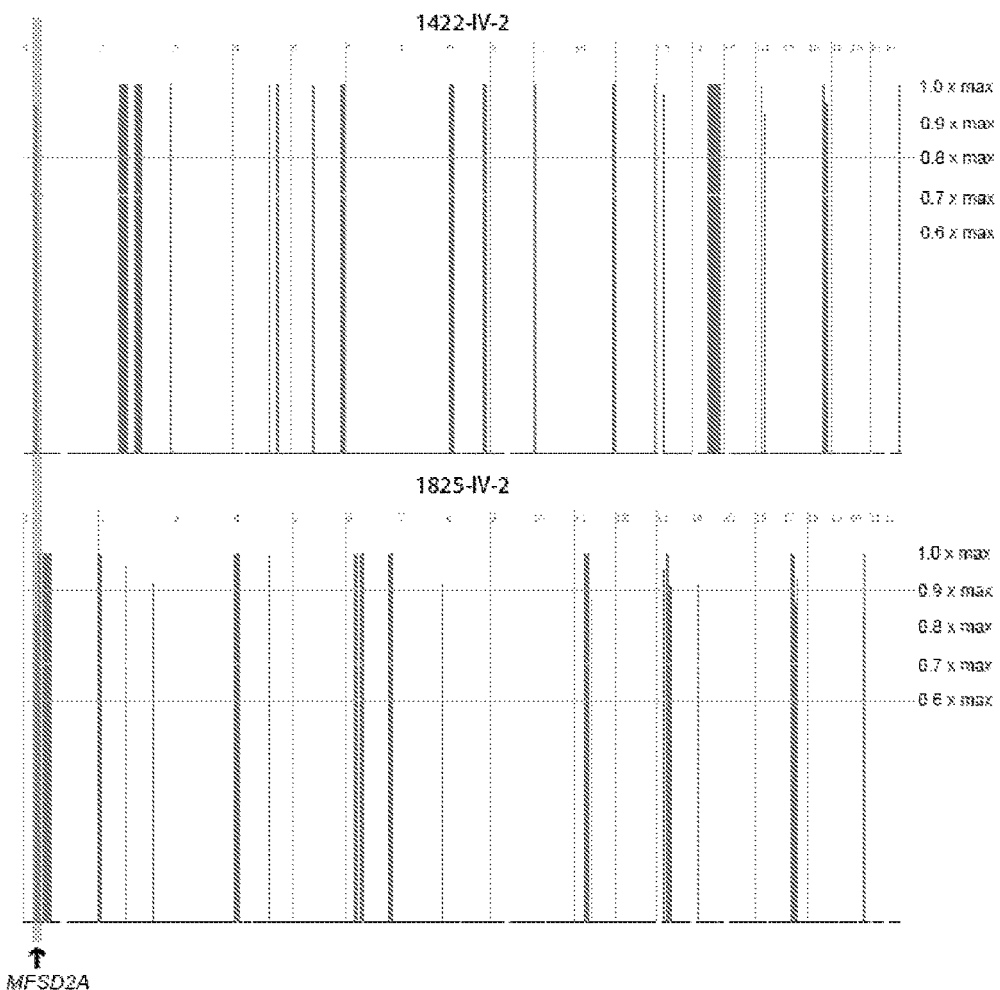
FIG. 26. Homozygosity map of affected individuals. Homozygosity plots showing homozygous blocks in affected individuals from families 1422 and 1825, with homozygous MFSD2A mutations homozygous block comprising MFSD2A overlaps in all the affected. Arrow: location of MFSD2A.
Figure 27:
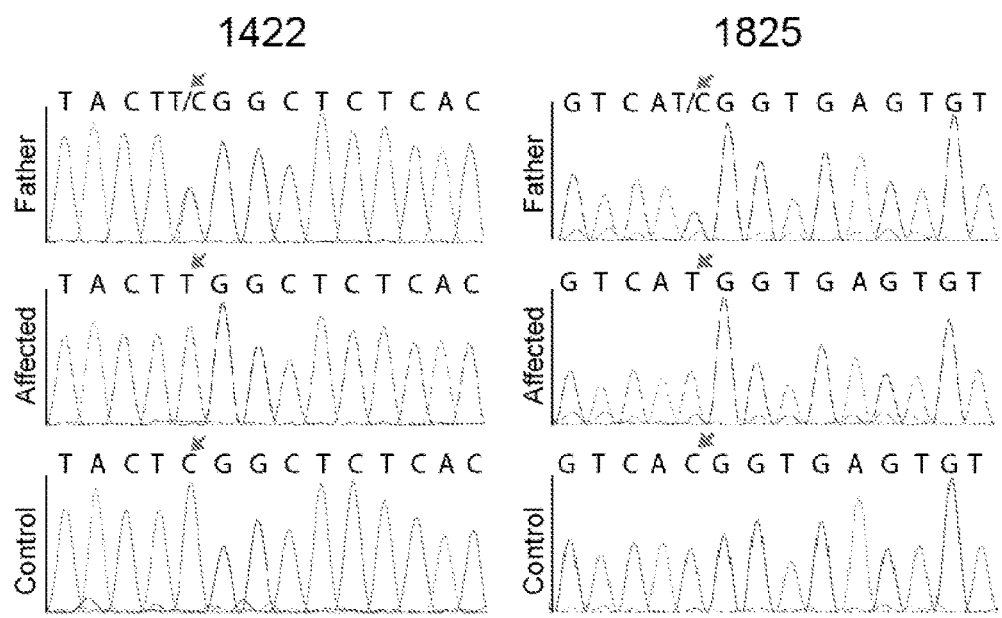
FIG. 27. Chromatograms from Sanger sequencing of father (heterozygous), affected (homozygous) and an unaffected sibling or non-related control (reference normal homozygous) showing the mutations (arrow).
Figure 28:
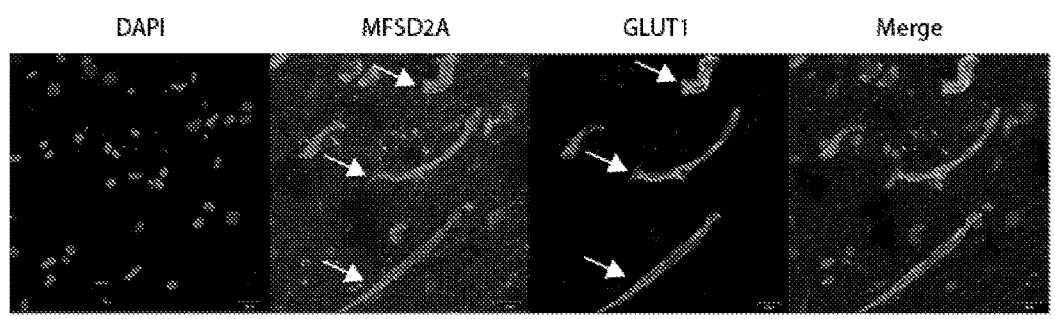
FIG. 28. MFSD2A is expressed in endothelial cells of microvessels in human fetal brain. MFSD2A is highly expressed in endothelium and co-localizes with glucose transporter GLUT1 in the human fetal brain. Arrows show endothelial cells in blood brain vessels. Scale bar 20 µm.
Figure 29:
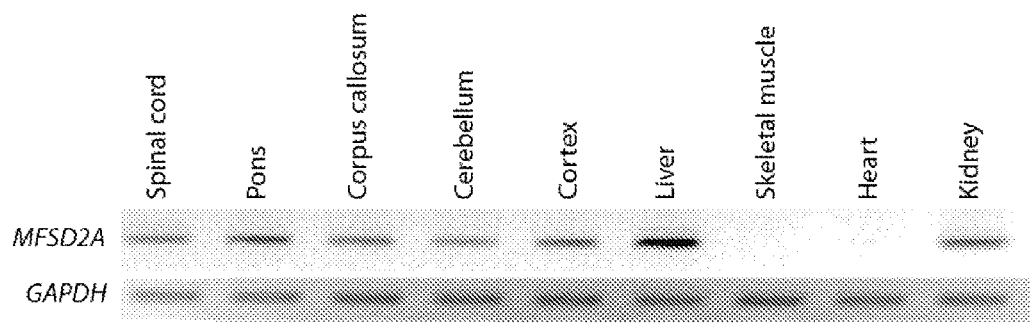
FIG. 29. Expression of MFSD2A in human tissues. RT-PCR across human adult tissues shows expression in all tissues tested but skeletal muscle and heart. GAPDH was used as loading control.

We filtered data from WES in the affected members by removing common variants (>0.1% allele frequency in our in-house exome database of 5000 individuals, or the NHLBI database of 4000 individuals), and variants not heterozygous in parents (Tennessen J A, Bigham A W, O'Connor T D, et al. Evolution and functional impact of rare coding variation from deep sequencing of human exomes. *Science* 2012; 337:64-9). We identified rare protein-altering variants in each family member. Among these variants, in family 1825, only 4 were consistent with the mode of inheritance (Table 7), and of these only 1 passed segregation analysis, which was a chr1:40431005C>T variant in the MFSD2A gene, leading to a c.476C>T nucleotide and p.T159M protein change. After this identification, we searched the database and found that family 1422 harbored a chr1:40431162C>T variant in the same gene, leading to a c.497C>T nucleotide and p.S166L protein change (FIG. 23C). Comparing the phenotype of the two families showed that they matched precisely. Both variants showed high damage prediction using standard programs (Table 7, Table 8), occurred in blocks of homozygosity (FIG. 26) and were in amino acid residues perfectly conserved throughout vertebrate evolution, located in the 4th transmembrane domain of the protein (FIG. 23D,E). Both mutations were in constitutively spliced exons and segregated in the respective family according to a strict recessive mode of inheritance (FIG. 27). These variants were not present in our in-house dataset of approximately 10,000 chromosomes or in publicly available databases.

TABLE 7

Genetic variants from family 1825 from exome sequencing

| chr | position | dbSNP | ref | mut | gene | functionGVS | cDNA Position |
|---|---|---|---|---|---|---|---|
| 11 | 2182393 | rs3842740 | C | CGCAA | INS | utr-5 | |
| 1 | 40431005 | | C | T | MFSD2A | missense | c.476C > T |
| 2 | 95815141 | | GT | G | ZNF514 | frameshift | c.1462GT > G |
| 1 | 32381592 | | T | TAA | PTP4A2 | intron | |

| chr | AA Change | Score PhastCons | Vert PhastCons | Cons Score GERP | Distance To Splice | accession |
|---|---|---|---|---|---|---|
| 11 | | 0.006 | 0.006 | 2.730 | 2 | NM_001185098.1 |
| 1 | p.T159M | 1.000 | 1.000 | 5.750 | 2 | NM_032793.3 |
| 2 | p.H362Sfs*57 | 0.939 | 0.376 | 2.740 | 871 | NM_032788.1 |
| 1 | | 0.943 | 0.993 | 5.320 | 2 | NM_080391.3 |

TABLE 8

Genetic variants from family 1825 from exome sequencing

| chr | position | dbSNP | ref | mut | gene | functionGVS | cDNA Position |
|---|---|---|---|---|---|---|---|
| 2 | 131704214 | | T | G | intron | ARGEF4 | |
| 5 | 127710395 | | A | T | missense | FBN2 | c.2021T > A |
| 14 | 81259453 | | T | G | missense | CEP128 | c.1211a > C |
| 5 | 169661114 | | A | G | intron | C5ORF58 | |
| 12 | 86374869 | | C | T | missense | IMMT | c.1489G > A |
| 14 | 71570306 | | C | G | missense | PCNX | c.6015C > G |
| 1 | 40431162 | | C | T | missense | MFSD2A | c.497C > T |
| 5 | 115336146 | | G | A | missense | AQPEP | c.1532G > A |

TABLE 8-continued

Genetic variants from family 1825 from exome sequencing

| chr | AA_Change | Score PhastCons | Vert PhastCons | Cons Score GERP | Distance To Splice | accession |
|---|---|---|---|---|---|---|
| 2 | | 0.454 | 0.569 | 1.590 | 4 | NM_0.2995.1 |
| 5 | p.I647N | 1.000 | 1.000 | 4.180 | 49 | NM_001999.3 |
| 14 | p.N404T | 0.962 | 0.589 | -0.935 | 2 | NM_152446.3 |
| 5 | | 0.001 | 0.001 | -0.058 | 3 | NM_001102609.1 |
| 12 | p.V497I | 1.000 | 1.000 | 4.820 | 45 | NM_006839.2 |
| 14 | p.S2005R | 1.000 | 1.000 | 4.320 | 81 | NM_014982.2 |
| 1 | p.S166L | 1.000 | 1.000 | 5.310 | 20 | NM_032793.3 |
| 5 | p.R511G | 0.749 | 1.000 | 2.770 | 17 | NM_173800.4 |

Effect of Mutation on mfsd2a Function

Figure 24:
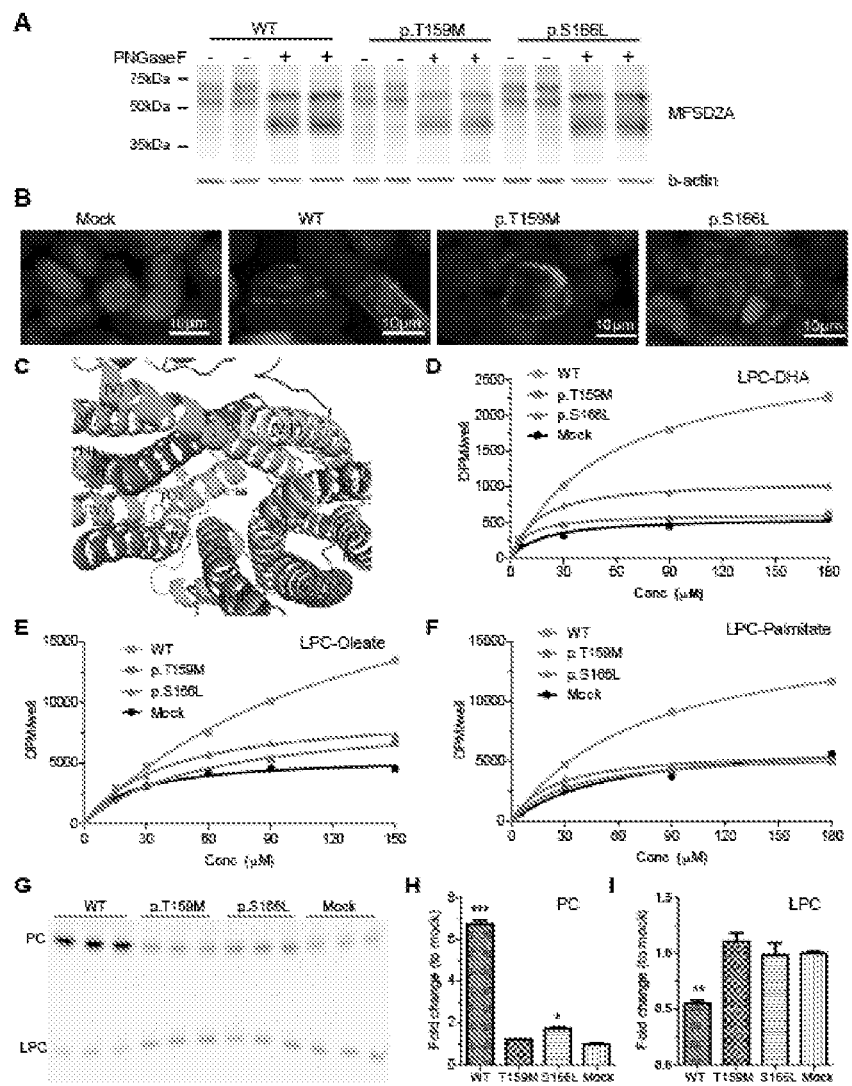
FIG. 24. MFSD2A p.T159M and p.S166L mutations display impaired LPC transport. (A) Western blot of MFSD2A (WT), mutant p.T159M, and p.S166L proteins expressed in HEK293 cells. Mutant proteins show posttranslational modification and stability indistinguishable from wild-type. (B) Mutant proteins show membrane localization in transfected HEK293 cells indistinguishable from wild-type. (C) View of the internal cavity of human MFSD2A generated from a threading model using an atomic resolution structure of MelB as the template. Transmembrane domain II contains the conserved sodium binding residues D93 and D97. Transmembrane domain IV contains the T159 and S166 residues. Concentration-dependent transport of LPC-[$^{14}$C]DHA (D) LPC-[$^{14}$C]oleate (E) and LPC [$^{14}$C]palmitate (F) after 30 min. Mutant constructs p.T159M and p.S166L show defective transport across a range of concentrations. (G) Mutants and mock showed reduced biological incorporation of radiolabeled LPC-[$^{14}$C]oleate into phosphatidylcholine (PC) compared to WT. The greater amount of LPC seen in mock, p.T159M, and p.S166L expressing cells reflects defective LPC uptake. Quantification of radiolabeled PC (H) and LPC (I) bands from TLC plates shown in (G). Experiments were performed twice with triplicates. Data are expressed as mean±SEM. *P<0.001, P<0.01, *P<0.05.

As discussed herein, MFSD2A encodes a 12-pass transmembrane protein recently implicated in the formation and function of the BBB and required for DHA transport in mice (Nguyen L N, Ma D, Shui G, et al. Mfsd2a is a transporter for the essential omega-3 fatty acid docosahexaenoic acid. Nature 2014; 509:503-6; Ben-Zvi A, Lacoste B, Kur E, et al. Mfsd2a is critical for the formation and function of the blood-brain barrier. Nature 2014; 509:507-11) _ENREF_8_ENREF_8. MFSD2A expression in HEK293 cells resolves on SDS-PAGE as two isoforms, ~55 kDa and ~70 kDa, due to glycosylation at residues N217 and N227 (Berger J H, Charron M J, Silver D L. Major facilitator superfamily domain-containing protein 2a (MFSD2A) has roles in body growth, motor function, and lipid metabolism. PloS One 2012; 7:e50629). The p.T159M and p.S166L mutations were introduced into the MFSD2A human protein, expressed in HEK293 cells and examined by Western blot and immunofluorescence. Both were expressed at similar levels and showed post-translational modifications identical to WT, resolving to lower molecular weight entities following glycohydrolase PNGase F treatment (FIG. 24A). Furthermore, both mutant proteins were stably expressed and partially localized to the plasma membrane in a fashion similar to WT (FIG. 24B). To provide a molecular basis for the inactivating mutations, we took advantage of the structural information of MelB, the E. coli sodium-melibiose transporter part of the MFS family and sharing high sequence similarity with Mfsd2a. Both p.T159 and p.S166 reside on transmembrane domain 4, which communicates sodium and ligand binding, respectively (Ethayathulla A S, Yousef M S, Amin A, Leblanc G, Kaback H R, Guan L. Structure-based mechanism for Na(+)/melibiose symport by MelB. Nat Commun 2014; 5:3009; Cordat E, Leblanc G, Mus-Veteau I. Evidence for a role of helix IV in connecting cation- and sugar-binding sites of Escherichia coli melibiose permease. Biochemistry 2000; 39:4493-9). The human residue p.T159 is conserved to residue p.T221 of MelB and p.T159M mutation is predicted to disrupt sodium binding interaction while p.S166 is not conserved in MelB (p.W228) and p.S166L mutation is predicted to interfere with LPC binding (FIG. 24C).

To test for functional impairment, we used a cell-based assay with a range of concentrations of LPC-[$^{14}$C]DHA, LPC-[$^{14}$C]oleate and LPC-[$^{14}$C]palmitate (FIG. 24D-F) following transfection into HEK293 cells. Both p.T159M and p.S166L mutants were largely inactive, exhibiting transport activity similar to background in mock transfected cells for all LPC-lipids tested, indicating that the mutations impair MFSD2A function as a LPC transporter. LPCs taken up by HEK293 cells are esterified into phosphatidylcholine (PC) by cellular lysophosphatidylcholine acyltransferases (LPCATs) enzymes, and provides further biochemical evidence for cellular uptake. Thus, MFSD2A and mutant constructs were assessed for conversion of LPC to PC (FIG. 24G-I). Cells expressing WT MFSD2A showed significantly greater conversion of exogenous LPC into membrane PC compared to cells expressing p.T159M and p.S166L mutants, consistent with loss of transport function in mutants (FIG. 24F,G).

Effect of mfsd2a Mutations on Plasma Lpc Levels

Figure 25:
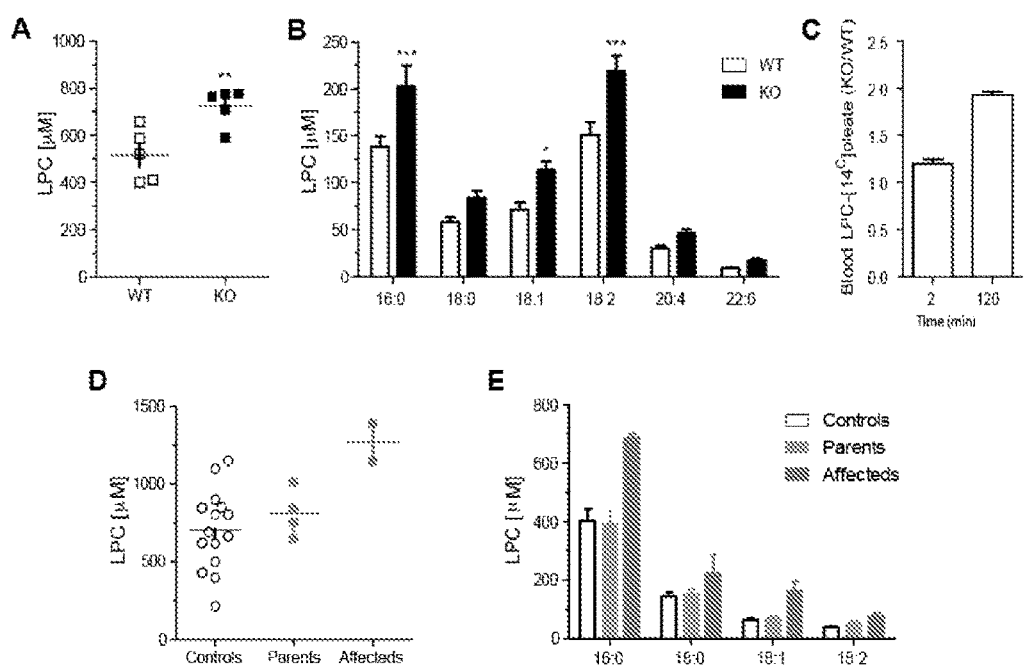
FIG. 25. Total plasma LPC and individual LPC species by lipodimic mass spectrometry. Concentration of total plasma LPC (A) and common C16-22 chain length LPC species (B) from WT (n=5) and Mfsd2a KO (n=5) mice, with 3 technical replicates. (C) Quantification of injected LPC [$^{14}$C]oleate over time in the plasma of Mfsd2a KO mice (n=4) relative to WT (n=3) littermates. Total plasma LPC (D) and common LPC species (E) concentrations from controls, unaffected parents and affected individuals from families 1422 and 1825. Analysis was performed once with 3 technical replicates from two independent plasma samples collected on different days. *P<0.05, P<0.01, *P<0.001.

We hypothesized that plasma lipid uptake by MFSD2A at the BBB affects plasma LPC levels, such that MSFD2A deficiency should result in increased plasma LPC levels. Indeed, we found Msfd2a KO mice showed total plasma LPC levels increased by 40% compared with controls (FIG. 25A). Msfd2a KO mice had also increased levels of individual LPC compared with controls (FIG. 25B). Other less abundant plasma LPC species such as LPC-DHA showed a trend toward increased levels in Msfd2a KO mice (FIG. 25B). Consistent with increased plasma LPC steady-state levels in Msfd2a KO mice, and with the finding that brain uptake of LPCs in Msfd2a KO mice were reduced between 85-90% depending on the LPC species_ENREF_5, tracer studies of intravenous-injected LPC-[$^{14}$C]oleate showed increased levels of plasma LPC-[$^{14}$C]oleate in Msfd2a KO mice at 2 hrs post-injection (FIG. 25C). Given these results, we tested whether patients have increased plasma levels of LPCs relative to heterozygous parents and healthy age-matched controls. Lipidomic analysis indicated that total plasma LPCs were increased in the probands relative to their heterozygous parents and controls (FIG. 25D). Similar to the findings in Msfd2a KO mice, the common plasma LPC species containing 16:0, 18:0, 18:1 and 18:2 length fatty acids were increased in the sera from MSFD2A mutant patients, suggesting a defect in LPC uptake (FIG. 25E).

Example 11: Modeling Human MFSD2A Mutations

We took advantage of the detailed structural information of MelB to provide a molecular basis for the inactivating mutations p.T159M and p.S166L. The overall mechanism of transport of the MFS family has been first inferred from the X-ray structure of glycerol-3-phosphate transporter GlpT from E. coli, and confirmed by structures of other MFS family members and more recently including MelB, a close ortholog of MFSD2A (Ethayathulla A S, Yousef M S, Amin A, Leblanc G, Kaback H R, Guan L. Structure-based mechanism for Na(+)/melibiose symport by MelB. Nat Commun 2014; 5:3009; Huang Y, Lemieux M J, Song J, Auer M, Wang D N. Structure and mechanism of the glycerol-3-phosphate transporter from Escherichia coli. Science 2003; 301:616-20; Shi Y. Common folds and transport mechanisms of secondary active transporters. Annu Rev Biophys 2013; 42:51-72). The model has been described as a "rocker-switch, alternating access" model in which an outward open conformation binds to ligands causing a conformation switch to the inside-open conformation (Shi Y. Common folds and transport mechanisms of secondary active transporters. Annu Rev Biophys 2013; 42:51-72). The energy to drive this conformational change is provided by the binding of cations that flow down their concentration gradients. In the case of MFSD2A, it utilizes sodium to drive the transport of LPC. Indeed, MFSD2A contains a conserved sodium-binding site that has been shown to be essential for sodium-dependent transport of LPC (Nguyen L N, Ma D, Shui G, et al. Mfsd2a is a transporter for the essential omega-3 fatty acid docosahexaenoic acid. Nature 2014; 509:503-6).

A molecular explanation for loss of function of p.T159M in the affected children can be inferred from the atomic resolution structure of MelB. Sequence alignment of human MFSD2A and MelB indicated conservation of T159 with T121 in MelB. T121 in MelB faces the sodium-binding site and forms hydrogen bonds with the sodium binding residue D59, which is equivalent to D97 in human MFSD2A (FIG. 24C). Both T121 and D59 are required for MelB transport (Ethayathulla A S, Yousef M S, Amin A, Leblanc G, Kaback H R, Guan L. Structure-based mechanism for Na(+)/melibiose symport by MelB. Nat Commun 2014; 5:3009). Threading the human MFSD2A sequence on the MelB model revealed that T159 in human is also in close proximity to the sodium-binding residue D97, which is equivalent to D96 in mouse MFSD2A and essential for function (Nguyen L N, Ma D, Shui G, et al. Mfsd2a is a transporter for the essential omega-3 fatty acid docosahexaenoic acid. Nature 2014; 509:503-6). Similar to p.T159M, p.T121A in MelB is non-functional. Therefore, the p.T159M mutation is predicted to disrupt sodium binding and prevent ligand transport. The p.S166L mutation is also non-functional, and the affected child is a clinical phenocopy of the children having the p.T159M mutation. Interestingly, p.T159M and p.S166L both reside on transmembrane domain 4 (TMD4), which has been proposed to communicate ligand and sodium binding (Ethayathulla A S, Yousef M S, Amin A, Leblanc G, Kaback H R, Guan L. Structure-based mechanism for Na(+)/melibiose symport by MelB. Nat Commun 2014; 5:3009; Cordat E, Leblanc G, Mus-Veteau I. Evidence for a role of helix IV in connecting cation- and sugar-binding sites of Escherichia coli melibiose permease. Biochemistry 2000; 39:4493-9). The S166 residue is conserved in all sequenced vertebrates, but not conserved in MelB. Moreover, the S166 residue faces the transport cavity (FIG. 24C), suggesting a role in ligand binding. Indeed, S166 corresponding residue in MelB, W128, is critical for melibiose transport (Ethayathulla A S, Yousef M S, Amin A, Leblanc G, Kaback H R, Guan L. Structure-based mechanism for Na(+)/melibiose symport by MelB. Nat Commun 2014; 5:3009; Cordat E, Leblanc G, Mus-Veteau I. Evidence for a role of helix IV in connecting cation- and sugar-binding sites of Escherichia coli melibiose permease. Biochemistry 2000; 39:4493-9). Therefore, S166 residue is predicted to play a role in substrate binding by potentially forming a hydrogen bond with the phosphorylcholine headgroup of LPC.

The studies disclosed in Examples 9, 10, and 11 establish an association between omega-3 fatty acid transport and brain growth in humans. The two consanguineous families that we identified harboring inactivating mutations in MFSD2A exhibited a lethal microcephaly syndrome presenting in the first three (3) months of life with massive hydrocephalus, spastic quadriparesis and epilepsy. Lipid analysis pointed to elevated serum LPC levels, likely as a result of failed cellular uptake due to the lack of MFSD2A activity. The severity of the overall phenotype of the patients was greater than would have been predicted from the knockout mouse, which survived, exhibiting microcephaly, ataxia, memory and learning deficits, and anxiety (Nguyen L N, Ma D, Shui G, et al. Mfsd2a is a transporter for the essential omega-3 fatty acid docosahexaenoic acid. Nature 2014; 509:503-6)_ENREF_5.

While specific aspects of the invention have been described and illustrated, such aspects should be considered illustrative of the invention only and not as limiting the invention as construed in accordance with the accompanying claims.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

TABLE 1

Mass spectrometry analysis of free fatty acid uptake in HEK239 cells. Mfsd2a expressing HEK293 cells were incubated with 100 uM of indicated fatty acid/BSA complex overnight. Lipids extraction and phospholipid analysis by MS were performed as described in Methods section. Amount of each lipid species was normalized to internal standard and expressed as mol percent in total phospholipid analysed.

|  | Mfsd2a | Mfsd2a | Mfsd2a | Mfsd2a | mock | mock | mock |
| --- | --- | --- | --- | --- | --- | --- | --- |
|  | Docosahexaenoic acid | | | | | | |
| LysoPC16:0e | 0.005111 | 0.004575 | 0.004499 | 0.004664 | 0.005025 | 0.003881 | 0.00548 |
| LysoPC16:1 | 0.008945 | 0.007244 | 0.00707 | 0.006958 | 0.007425 | 0.006576 | 0.006821 |
| LysoPC16:0 | 0.037257 | 0.034809 | 0.030814 | 0.026837 | 0.031153 | 0.028458 | 0.030548 |
| LysoPC18:0e | 0.002316 | 0.001944 | 0.002079 | 0.002217 | 0.002177 | 0.002156 | 0.002215 |
| LysoPC18:2 | 0.001278 | 0.000877 | 0.001437 | 0.000994 | 0.001507 | 0.001078 | 0.000583 |
| LysoPC18:1 | 0.015653 | 0.015021 | 0.0138 | 0.013074 | 0.015186 | 0.013421 | 0.015624 |

TABLE 1-continued

Mass spectrometry analysis of free fatty acid uptake in HEK239 cells. Mfsd2a expressing HEK293 cells were incubated with 100 uM of indicated fatty acid/BSA complex overnight. Lipids extraction and phospholipid analysis by MS were performed as described in Methods section. Amount of each lipid species was normalized to internal standard and expressed as mol percent in total phospholipid analysed.

| | | | | | | | |
|---|---|---|---|---|---|---|---|
| LysoPC18:0 | 0.009464 | 0.008616 | 0.009301 | 0.008257 | 0.008486 | 0.008947 | 0.009444 |
| LysoPC20:4 | 0.000998 | 0.000496 | 0.000492 | 0.00065 | 0.000391 | 0.000539 | 0.0007 |
| LysoPC22:6 | 0.004592 | 0.004194 | 0.004121 | 0.003173 | 0.003071 | 0.003449 | 0.003556 |
| LysoPC22:5 | 0.001118 | 0.000991 | 0.001248 | 0.001682 | 0.000782 | 0.001078 | 0.001574 |
| PC32:1e | 1.144616 | 1.168701 | 1.212525 | 1.200386 | 1.260457 | 1.206188 | 1.296724 |
| PC32:0e | 1.066749 | 1.097978 | 1.130972 | 1.118729 | 1.158401 | 1.067023 | 1.166719 |
| PC32:2 | 0.939045 | 0.947497 | 0.994785 | 0.981755 | 1.021564 | 0.986229 | 1.069012 |
| PC32:1 | 7.392288 | 7.412563 | 7.732107 | 7.619429 | 8.198692 | 7.713966 | 8.428326 |
| PC32:0 | 3.735936 | 3.830171 | 3.931765 | 3.812257 | 3.978504 | 3.811843 | 4.086111 |
| PC34:3e | 0.134811 | 0.133401 | 0.145564 | 0.136974 | 0.13935 | 0.138411 | 0.151866 |
| PC34:2e | 0.787223 | 0.777609 | 0.819806 | 0.80789 | 0.857928 | 0.801035 | 0.871673 |
| PC34:1e | 2.925273 | 2.952596 | 3.037816 | 2.981085 | 3.137045 | 2.945268 | 3.167684 |
| PC34:3 | 0.36526 | 0.361697 | 0.369089 | 0.360727 | 0.379639 | 0.362573 | 0.397301 |
| PC34:2 | 4.167404 | 4.107877 | 4.251816 | 4.14263 | 4.382763 | 4.142509 | 4.523405 |
| PC34:1 | 19.48388 | 19.14666 | 19.70234 | 18.93842 | 20.83676 | 20.00276 | 21.38624 |
| PC36:5e | 0.804434 | 0.786759 | 0.796289 | 0.780404 | 0.795399 | 0.773008 | 0.822411 |
| PC36:4e | 0.375562 | 0.350717 | 0.368748 | 0.346544 | 0.36021 | 0.355081 | 0.368677 |
| PC36:3e | 0.387821 | 0.388195 | 0.398012 | 0.376401 | 0.404427 | 0.374539 | 0.407212 |
| PC36:2e | 0.927625 | 0.891528 | 0.923667 | 0.876511 | 0.94558 | 0.890237 | 0.96734 |
| PC36:1e | 1.036799 | 1.017762 | 1.033199 | 0.976747 | 1.079235 | 1.026869 | 1.089474 |
| PC36:6 | 0.260438 | 0.245452 | 0.258801 | 0.246347 | 0.258992 | 0.246261 | 0.272893 |
| PC36:5 | 0.766059 | 0.752179 | 0.768311 | 0.713885 | 0.781107 | 0.742771 | 0.846896 |
| PC36:4 | 0.563763 | 0.53921 | 0.549928 | 0.498695 | 0.555557 | 0.525885 | 0.598546 |
| PC36:3 | 0.763783 | 0.730181 | 0.753225 | 0.719123 | 0.766424 | 0.708384 | 0.784983 |
| PC36:2 | 4.068132 | 3.91622 | 4.005492 | 3.800444 | 4.136724 | 3.890427 | 4.210811 |
| PC36:1 | 3.275119 | 3.185238 | 3.256615 | 3.047909 | 3.402234 | 3.248499 | 3.522894 |
| PC38:5e | 0.574944 | 0.567728 | 0.565845 | 0.530005 | 0.561363 | 0.525508 | 0.579891 |
| PC38:4e | 0.280683 | 0.271378 | 0.279406 | 0.265385 | 0.280654 | 0.259466 | 0.285136 |
| PC38:3e | 0.215035 | 0.205116 | 0.203675 | 0.19038 | 0.204558 | 0.198992 | 0.206375 |
| PC38:1e | 0.250495 | 0.251209 | 0.253394 | 0.243824 | 0.254135 | 0.241626 | 0.264965 |
| PC38:7 | 0.423361 | 0.416255 | 0.424856 | 0.394827 | 0.422404 | 0.395775 | 0.45181 |
| PC38:6 | 3.235945 | 3.15306 | 3.099558 | 2.826258 | 3.093722 | 2.96106 | 3.302818 |
| PC38:5 | 1.120537 | 1.075522 | 1.080346 | 0.963826 | 1.083367 | 1.046919 | 1.159199 |
| PC38:4 | 0.461057 | 0.450339 | 0.456049 | 0.412451 | 0.468072 | 0.45641 | 0.4953 |
| PC38:3 | 0.405511 | 0.396811 | 0.404742 | 0.365812 | 0.413304 | 0.394535 | 0.425692 |
| PC40:5e | 0.186483 | 0.176712 | 0.184582 | 0.171495 | 0.17536 | 0.173876 | 0.183639 |
| PC40:4e | 0.084017 | 0.079797 | 0.084578 | 0.078675 | 0.085084 | 0.082303 | 0.088205 |
| PC40:3e | 0.080982 | 0.079987 | 0.082612 | 0.079363 | 0.082404 | 0.08807 | 0.084999 |
| PC40:2e | 0.129061 | 0.130008 | 0.132066 | 0.127034 | 0.135442 | 0.127308 | 0.135893 |
| PC40:1e | 0.205451 | 0.200121 | 0.205868 | 0.188354 | 0.203609 | 0.201687 | 0.21168 |
| PC40:7 | 1.359651 | 1.298523 | 1.338315 | 1.211701 | 1.313439 | 1.270004 | 1.386095 |
| PC40:6 | 1.008647 | 0.986956 | 0.998717 | 0.893217 | 0.997724 | 0.965263 | 1.0598 |
| PC40:5 | 0.237557 | 0.225627 | 0.23052 | 0.206245 | 0.239787 | 0.229391 | 0.245551 |
| Total PC + lysoPC | 65.71817 | 64.78422 | 66.54087 | 63.70064 | 68.92662 | 65.64753 | 71.08079 |
| % DHA in PC + lysoPC | 0.416721 | 0.383914 | 0.392328 | 0.341554 | 0.42366 | 0.32335 | 0.432031 |
| Lyso PE16:0p | 3.181686 | 3.1158 | 3.231435 | 3.696993 | 2.842916 | 2.772201 | 2.420066 |
| LysoPE16:1 | 0.116606 | 0.1154 | 0.213062 | 0.190566 | 0.23691 | 0.249 | 0.069944 |
| LysoPE16:0 | 0.08329 | 0.038467 | 0.07102 | 0.05717 | 0.063176 | 0.083 | 0.069944 |
| Lyso PE18:1p | 0.16658 | 0.3462 | 0.195307 | 0.190566 | 0.284292 | 0.1162 | 0.097922 |
| Lyso PE18:0p | 0.399793 | 0.8078 | 0.497144 | 0.552643 | 0.379055 | 0.5478 | 0.58753 |
| LysoPE18:2 | 0 | 0.038467 | 0.017755 | 0.019056 | 0.015794 | 0.0166 | 0.027978 |
| LysoPE18:1 | 0.16658 | 0.269267 | 0.106531 | 0.190566 | 0.189528 | 0.0996 | 0.111911 |
| LysoPE18:0 | 0.16658 | 0.2308 | 0.230817 | 0.133396 | 0.252703 | 0.249 | 0.153877 |
| Lyso PE20:0p | 0.199896 | 0.2885 | 0.213062 | 0.190566 | 0.173734 | 0.2656 | 0.195844 |
| LysoPE20:4 | 0.049974 | 0.038467 | 0 | 0.019056 | 0.031588 | 0 | 0.027978 |
| 1ysoPE22:6 | 0.033316 | 0.038467 | 0.017755 | 0.038114 | 0.015794 | 0 | 0.027978 |
| PE32:2 | 0.066632 | 0.038467 | 0.142041 | 0.11434 | 0.105293 | 0.077467 | 0.111911 |
| PE32:1 | 0.244318 | 0.487244 | 0.272245 | 0.190566 | 0.252703 | 0.332 | 0.27045 |
| PE34p:2 | 0.133264 | 0.153867 | 0.118367 | 0.11434 | 0.14741 | 0.121733 | 0.130562 |
| PE34p:1 | 0.821796 | 0.641111 | 0.568164 | 0.990946 | 0.705464 | 0.575467 | 0.550227 |
| PE34:2 | 0.788481 | 0.577 | 0.935104 | 0.940129 | 0.663347 | 0.586534 | 0.63416 |
| PE34:1 | 1.354854 | 1.538667 | 1.432248 | 1.854848 | 1.147696 | 1.427601 | 1.137757 |
| PE34:0 | 0.222107 | 0.205156 | 0.248572 | 0.266793 | 0.189528 | 0.110667 | 0.139888 |
| PE36p:4 | 0.655216 | 0.512589 | 0.544491 | 0.68604 | 0.431702 | 0.475867 | 0.47562 |
| PE36p:3 | 0.544163 | 0.243622 | 0.43796 | 0.34302 | 0.357997 | 0.5644 | 0.27045 |
| PE36p:2 | 0.31095 | 0.269267 | 0.224898 | 0.393838 | 0.294821 | 0.2988 | 0.186517 |
| PE36p:1 | 0.344266 | 0.487244 | 0.355103 | 0.34302 | 0.231645 | 0.498 | 0.223821 |
| PE36:4 | 0.199896 | 0.333378 | 0.272245 | 0.266793 | 0.136881 | 0.243467 | 0.205169 |
| PE36:3 | 0.222107 | 0.384667 | 0.284082 | 0.431951 | 0.326409 | 0.354133 | 0.279776 |
| PE36:2 | 1.810173 | 2.166956 | 1.597962 | 2.045415 | 1.747867 | 1.903467 | 1.314949 |
| PE36:1 | 1.8657 | 2.0772 | 1.68082 | 1.905666 | 1.621515 | 1.593601 | 1.352252 |
| PE38p:6 | 3.320502 | 3.167089 | 2.994699 | 3.519131 | 3.116678 | 3.242535 | 2.611246 |
| PE38p:5 | 1.021693 | 1.154 | 0.958777 | 1.283148 | 0.800228 | 0.996 | 0.783374 |

TABLE 1-continued

Mass spectrometry analysis of free fatty acid uptake in HEK239 cells. Mfsd2a expressing HEK293 cells were incubated with 100 uM of indicated fatty acid/BSA complex overnight. Lipids extraction and phospholipid analysis by MS were performed as described in Methods section. Amount of each lipid species was normalized to internal standard and expressed as mol percent in total phospholipid analysed.

| | | | | | | | |
|---|---|---|---|---|---|---|---|
| PE38p:4 | 0.510846 | 0.487244 | 0.651021 | 0.647926 | 0.410644 | 0.520133 | 0.401013 |
| PE38p:3 | 0.477531 | 0.487244 | 0.426123 | 0.368429 | 0.31588 | 0.320933 | 0.335732 |
| PE38p:2 | 0.14437 | 0.179511 | 0.165715 | 0.241384 | 0.15794 | 0.210267 | 0.214495 |
| PE38p:1 | 0.14437 | 0.1154 | 0.213062 | 0.152454 | 0.105293 | 0.121733 | 0.177192 |
| PE38p:0 | 0.055527 | 0.038467 | 0.118367 | 0.050818 | 0.094764 | 0.044267 | 0.074607 |
| PE38:7 | 0.31095 | 0.320556 | 0.295919 | 0.215976 | 0.15794 | 0.2324 | 0.251799 |
| PE38:6 | 0.6219 | 0.512889 | 0.674695 | 0.660631 | 0.558054 | 0.741467 | 0.606182 |
| PE38:5 | 0.699638 | 0.756511 | 0.899594 | 0.91472 | 0.684406 | 0.8632 | 0.512923 |
| PE38:4 | 0.899534 | 0.859089 | 0.946941 | 1.041764 | 0.779169 | 1.073467 | 0.7927 |
| PE38:3 | 0.744059 | 0.602644 | 0.627348 | 0.711449 | 0.536995 | 0.608667 | 0.494272 |
| PE38:2 | 0.388688 | 0.3462 | 0.213062 | 0.317611 | 0.31588 | 0.3652 | 0.289102 |
| PE38:1 | 0.93285 | 1.102711 | 0.864083 | 1.02906 | 0.663347 | 0.830001 | 0.58753 |
| PE40p:6 | 1.69912 | 1.820756 | 1.574289 | 1.664282 | 1.368811 | 1.637867 | 1.277645 |
| PE40p:5 | 0.344266 | 0.538533 | 0.355103 | 0.279498 | 0.357997 | 0.320933 | 0.373035 |
| PE40p:4 | 0.188791 | 0.217978 | 0.082858 | 0.139749 | 0.126352 | 0.143867 | 0.149214 |
| PE40:6 | 1.166063 | 1.205289 | 1.337553 | 1.232331 | 1.010814 | 1.117734 | 1.035173 |
| PE40:5 | 0.233213 | 0.359022 | 0.390613 | 0.34302 | 0.252703 | 0.332 | 0.307754 |
| PE40:4 | 0.099948 | 0.179511 | 0.177551 | 0.139749 | 0.126352 | 0.088533 | 0.167866 |
| PE40:3 | 0.14437 | 0.038467 | 0.118367 | 0.165158 | 0.15794 | 0.121733 | 0.083933 |
| PE42p:7 | 0.344266 | 0.089756 | 0.142041 | 0.304906 | 0.14741 | 0.210267 | 0.223821 |
| PE42p:6 | 0.233213 | 0.282089 | 0.177551 | 0.177862 | 0.252703 | 0.2656 | 0.242473 |
| PE42p:5 | 0.077738 | 0.1154 | 0.165715 | 0.11434 | 0.263233 | 0.110667 | 0.130562 |
| PE42p:4 | 0.111053 | 0.076933 | 0.047347 | 0.076226 | 0.063176 | 0.0996 | 0.065281 |
| PE42:7 | 0.066632 | 0.1154 | 0.059184 | 0.050818 | 0.126352 | 0.088533 | 0.083933 |
| PE42:6 | 0.033316 | 0.1154 | 0.047347 | 0.11434 | 0.063176 | 0.0664 | 0.055955 |
| PE42:5 | 0.033316 | 0.1154 | 0.118367 | 0.012704 | 0.084235 | 0.110667 | 0.027978 |
| PE42:4 | 0.122159 | 0.1154 | 0.082858 | 0.11434 | 0.052647 | 0.0996 | 0.074607 |
| Total PE + lysoPE | 29.12936 | 30.61306 | 28.58577 | 32.00884 | 25.79683 | 28.26981 | 23.34734 |
| % DHA in PE + lysoPE | 26.87762 | 25.04712 | 25.61077 | 24.92558 | 26.42857 | 26.89372 | 27.48152 |
| LPI16:0 | 0.003896 | 0.00362 | 0.004663 | 0.002596 | 0.003621 | 0.004425 | 0.003813 |
| LPI18:0 | 0.033949 | 0.028209 | 0.031355 | 0.025138 | 0.035401 | 0.037213 | 0.03756 |
| LPI20:4 | 0.002783 | 0.001509 | 0.002251 | 0.002323 | 0.003017 | 0.002816 | 0.002288 |
| LPI22:6 | 0.010018 | 0.012521 | 0.011577 | 0.010383 | 0.014885 | 0.013075 | 0.014109 |
| PI 32:2 | 0.001484 | 0.001961 | 0.000965 | 0.000273 | 0.000402 | 0.001207 | 0.001716 |
| PI 32:1 | 0.014099 | 0.011163 | 0.011577 | 0.009973 | 0.009655 | 0.011265 | 0.010486 |
| PI 34:2 | 0.035804 | 0.028662 | 0.029747 | 0.025548 | 0.024741 | 0.035202 | 0.036607 |
| PI 34:1 | 0.095353 | 0.070146 | 0.085864 | 0.075142 | 0.077641 | 0.088909 | 0.084081 |
| PI 36:4 | 0.045079 | 0.034696 | 0.042128 | 0.03115 | 0.034597 | 0.043248 | 0.032222 |
| PI 36:3 | 0.06697 | 0.057927 | 0.066569 | 0.057791 | 0.066779 | 0.071007 | 0.069401 |
| PI 36:2 | 0.197199 | 0.157942 | 0.183466 | 0.153836 | 0.175799 | 0.223078 | 0.18761 |
| PI 36:1 | 0.162137 | 0.13803 | 0.147126 | 0.122413 | 0.127323 | 0.176008 | 0.13861 |
| PI 38:6 | 0.059178 | 0.051139 | 0.05676 | 0.046588 | 0.055314 | 0.066782 | 0.056054 |
| PI 38:5 | 0.14878 | 0.113893 | 0.124133 | 0.106975 | 0.12672 | 0.147042 | 0.116303 |
| PI 38:4 | 0.466932 | 0.387841 | 0.430285 | 0.360545 | 0.432055 | 0.532852 | 0.46445 |
| PI 38:3 | 0.746869 | 0.653793 | 0.701866 | 0.602776 | 0.67061 | 0.821505 | 0.700107 |
| PI 38:2 | 0.210555 | 0.174988 | 0.197133 | 0.174076 | 0.199131 | 0.237158 | 0.204388 |
| PI 40:6 | 0.177163 | 0.145572 | 0.177999 | 0.136485 | 0.148645 | 0.187876 | 0.168354 |
| PI 40:5 | 0.035433 | 0.031679 | 0.032963 | 0.024865 | 0.029166 | 0.037213 | 0.035272 |
| PI 40:4 | 0.017253 | 0.012068 | 0.015436 | 0.013116 | 0.014482 | 0.023535 | 0.012774 |
| PI 40:3 | 0.019108 | 0.015236 | 0.021386 | 0.014755 | 0.019913 | 0.022529 | 0.018494 |
| Total PI + lysoPI | 2.550039 | 2.132596 | 2.375248 | 1.996731 | 2.269897 | 2.783944 | 2.3947 |
| % DHA in PI and lysoPI | 0.236341 | 0.196711 | 0.234759 | 0.183073 | 0.203959 | 0.254658 | 0.224408 |
| PS:34:2 | 0.017048 | 0.011383 | 0.014841 | 0.010975 | 0.02271 | 0.023712 | 0.015531 |
| PS:34:1 | 0.294405 | 0.278316 | 0.290467 | 0.285351 | 0.383638 | 0.369623 | 0.362387 |
| PS:36:4 | 0.003278 | 0.002277 | 0.00477 | 0.00334 | 0.002433 | 0.004882 | 0.002219 |
| PS:36:3 | 0.009835 | 0.014798 | 0.006891 | 0.010021 | 0.006489 | 0.011158 | 0.014791 |
| PS:36:2 | 0.20392 | 0.162209 | 0.165905 | 0.183235 | 0.240078 | 0.239209 | 0.240359 |
| PS:36:1 | 1.157949 | 1.048382 | 1.065398 | 0.965326 | 1.302585 | 1.428977 | 1.38077 |
| PS:38:5 | 0.020326 | 0.026181 | 0.024912 | 0.015747 | 0.034065 | 0.03208 | 0.026624 |
| PS:38:4 | 0.043931 | 0.039841 | 0.041344 | 0.031971 | 0.043798 | 0.054397 | 0.044374 |
| PS:38:3 | 0.093108 | 0.080251 | 0.086398 | 0.069668 | 0.092462 | 0.106005 | 0.093185 |
| PS:38:2 | 0.121303 | 0.127491 | 0.137283 | 0.116431 | 0.141938 | 0.166679 | 0.159007 |
| PS:40:7 | 0.026883 | 0.025612 | 0.030213 | 0.028153 | 0.026765 | 0.025106 | 0.031801 |
| PS:40:6 | 0.466852 | 0.503701 | 0.454782 | 0.425164 | 0.522332 | 0.615109 | 0.621235 |
| PS:40:5 | 0.102943 | 0.101309 | 0.125622 | 0.107842 | 0.139505 | 0.1611 | 0.133861 |
| PS:40:4 | 0.040653 | 0.048378 | 0.049295 | 0.04056 | 0.047853 | 0.060674 | 0.05103 |
| PS(sum) | 2.602435 | 2.470129 | 2.498119 | 2.293784 | 3.006652 | 3.298711 | 3.177175 |
| % DHA in PS | 0.493735 | 0.529313 | 0.484995 | 0.453317 | 0.549097 | 0.640215 | 0.653037 |

TABLE 1-continued

Mass spectrometry analysis of free fatty acid uptake in HEK239 cells. Mfsd2a expressing HEK293 cells were incubated with 100 uM of indicated fatty acid/BSA complex overnight. Lipids extraction and phospholipid analysis by MS were performed as described in Methods section. Amount of each lipid species was normalized to internal standard and expressed as mol percent in total phospholipid analysed.

| | Eicosapentaenoic | | | | | | |
|---|---|---|---|---|---|---|---|
| LysoPC16:0e | 0.005369 | 0.005332 | 0.003584 | 0.004376 | 0.00417 | 0.00451 | 0.003651 |
| LysoPC16:1 | 0.007044 | 0.005803 | 0.006296 | 0.00575 | 0.005898 | 0.006502 | 0.006931 |
| LysoPC16:0 | 0.026944 | 0.025336 | 0.024555 | 0.023307 | 0.025082 | 0.02349 | 0.024816 |
| LysoPC18:0e | 0.002414 | 0.001699 | 0.001986 | 0.001832 | 0.001609 | 0.002109 | 0.001671 |
| LysoPC18:2 | 0.000936 | 0.001604 | 0.001162 | 0.000763 | 0.001132 | 0.001464 | 0.001114 |
| LysoPC18:1 | 0.016255 | 0.015145 | 0.012059 | 0.014605 | 0.016861 | 0.014703 | 0.014667 |
| LysoPC18:0 | 0.006896 | 0.007974 | 0.005812 | 0.007684 | 0.006911 | 0.007615 | 0.006374 |
| LysoPC20:4 | 0.00064 | 0.000283 | 0.000533 | 0.00056 | 0.000477 | 0.000703 | 0.000371 |
| LysoPC22:6 | 0.001182 | 0.000991 | 0.000533 | 0.001069 | 0.001013 | 0.001113 | 0.000805 |
| LysoPC22:5 | 0.001379 | 0.001982 | 0.001453 | 0.002036 | 0.002036 | 0.001757 | 0.002475 |
| PC32:1e | 1.541288 | 1.518207 | 1.436763 | 1.618619 | 1.375843 | 1.456238 | 1.576664 |
| PC32:0e | 1.444545 | 1.42257 | 1.351331 | 1.470634 | 1.258593 | 1.315593 | 1.424796 |
| PC32:2 | 1.248892 | 1.209923 | 1.1269 | 1.258072 | 1.098744 | 1.151108 | 1.258695 |
| PC32:1 | 8.269611 | 7.97915 | 7.562841 | 8.313646 | 7.472139 | 7.764104 | 8.475815 |
| PC32:0 | 3.381525 | 3.335356 | 3.165519 | 3.47499 | 3.028189 | 3.209406 | 3.407493 |
| PC34:3e | 0.168069 | 0.175515 | 0.158661 | 0.176991 | 0.158121 | 0.160327 | 0.176065 |
| PC34:2e | 1.063336 | 1.048562 | 0.971145 | 1.076145 | 0.97929 | 1.043442 | 1.083187 |
| PC34:1e | 4.022275 | 3.943762 | 3.63448 | 4.11858 | 3.552121 | 3.738069 | 4.017625 |
| PC34:3 | 0.481203 | 0.468937 | 0.434526 | 0.487565 | 0.422291 | 0.459014 | 0.483328 |
| PC34:2 | 5.399189 | 5.201149 | 4.847975 | 5.425556 | 4.772465 | 5.01131 | 5.392294 |
| PC34:1 | 20.11807 | 19.03623 | 17.84374 | 19.65751 | 18.12785 | 19.18995 | 20.28387 |
| PC36:5e | 1.086488 | 1.036248 | 0.992164 | 1.069376 | 0.937704 | 0.965827 | 1.008862 |
| PC36:4e | 0.499675 | 0.475354 | 0.450072 | 0.467413 | 0.415619 | 0.443549 | 0.469156 |
| PC36:3e | 0.521201 | 0.515647 | 0.481359 | 0.528225 | 0.462149 | 0.487775 | 0.522254 |
| PC36:2e | 1.206973 | 1.171423 | 1.096727 | 1.228048 | 1.072947 | 1.141325 | 1.186907 |
| PC36:1e | 1.230322 | 1.156844 | 1.085879 | 1.21904 | 1.066095 | 1.117074 | 1.200398 |
| PC36:6 | 0.16531 | 0.146829 | 0.145536 | 0.157653 | 0.135302 | 0.144862 | 0.154838 |
| PC36:5 | 0.585384 | 0.567028 | 0.543884 | 0.565832 | 0.53555 | 0.566679 | 0.590019 |
| PC36:4 | 0.442141 | 0.432702 | 0.405709 | 0.42314 | 0.404358 | 0.422461 | 0.457274 |
| PC36:3 | 0.85192 | 0.848041 | 0.774029 | 0.870656 | 0.768382 | 0.830161 | 0.875436 |
| PC36:2 | 5.382392 | 5.200961 | 4.841727 | 5.421485 | 4.78164 | 5.043411 | 5.408508 |
| PC36:1 | 2.961008 | 2.787579 | 2.587976 | 2.897759 | 2.6451 | 2.801765 | 3.024915 |
| PC38:5e | 1.003635 | 0.951463 | 0.916853 | 0.97854 | 0.83785 | 0.871634 | 0.93955 |
| PC38:4e | 0.419138 | 0.398637 | 0.371226 | 0.419069 | 0.363309 | 0.380871 | 0.417481 |
| PC38:3e | 0.273531 | 0.288138 | 0.257122 | 0.282941 | 0.250765 | 0.259381 | 0.282137 |
| PC38:1e | 0.305647 | 0.302481 | 0.27199 | 0.311337 | 0.278648 | 0.287382 | 0.314875 |
| PC38:7 | 0.204274 | 0.191415 | 0.176629 | 0.194293 | 0.173552 | 0.182469 | 0.192093 |
| PC38:6 | 0.969007 | 0.911972 | 0.886342 | 0.928516 | 0.836718 | 0.898053 | 0.944129 |
| PC38:5 | 1.054125 | 1.017234 | 0.96049 | 1.019098 | 0.918937 | 0.989316 | 1.040548 |
| PC38:4 | 0.493961 | 0.484743 | 0.454383 | 0.481408 | 0.443382 | 0.467273 | 0.500161 |
| PC38:3 | 0.424014 | 0.421708 | 0.391034 | 0.437745 | 0.397864 | 0.426913 | 0.459688 |
| PC40:5e | 0.348108 | 0.342632 | 0.313593 | 0.35846 | 0.286631 | 0.314972 | 0.330532 |
| PC40:4e | 0.1328 | 0.130284 | 0.121708 | 0.132667 | 0.123148 | 0.125883 | 0.130022 |
| PC40:3e | 0.110979 | 0.10512 | 0.098945 | 0.107681 | 0.101939 | 0.104209 | 0.113251 |
| PC40:2e | 0.158267 | 0.162682 | 0.151009 | 0.164014 | 0.145729 | 0.155582 | 0.165111 |
| PC40:1e | 0.212056 | 0.198304 | 0.184717 | 0.208033 | 0.185527 | 0.195825 | 0.205585 |
| PC40:7 | 0.415936 | 0.386653 | 0.357084 | 0.387925 | 0.348693 | 0.378177 | 0.400277 |
| PC40:6 | 0.616565 | 0.604867 | 0.555992 | 0.597281 | 0.533405 | 0.55883 | 0.588039 |
| PC40:5 | 0.290081 | 0.288326 | 0.269762 | 0.275715 | 0.267149 | 0.273323 | 0.291915 |
| Total PC + lysoPC | 69.572 | 66.93142 | 62.7358 | 69.27365 | 62.02882 | 65.39751 | 69.85667 |
| % DHA in PC + lysoPC | 0.157699 | 0.141429 | 0.142985 | 0.140962 | 0.138497 | 0.146872 | 0.152799 |
| Lyso PE16:0p | 2.495149 | 3.134147 | 3.765612 | 2.379353 | 3.984046 | 3.089787 | 2.343478 |
| LysoPE16:1 | 0.109163 | 0.048466 | 0.23173 | 0.183027 | 0.064259 | 0.125747 | 0.185011 |
| LysoPE16:0 | 0.093568 | 0.096932 | 0.096554 | 0.076261 | 0.064259 | 0.179639 | 0.107923 |
| Lyso PE18:1p | 0.296299 | 0.193865 | 0.289662 | 0.183027 | 0.192776 | 0.23353 | 0.185011 |
| Lyso PE18:0p | 0.483435 | 0.743148 | 0.482771 | 0.47282 | 0.771106 | 0.395205 | 0.462528 |
| LysoPE18:2 | 0 | 0.064621 | 0.019311 | 0.015252 | 0.042839 | 0.035928 | 0 |
| LysoPE18:1 | 0.093568 | 0.17771 | 0.096554 | 0.152522 | 0.128518 | 0.08982 | 0.06167 |
| LysoPE18:0 | 0.109163 | 0.306952 | 0.193108 | 0.213532 | 0.235616 | 0.251494 | 0.123341 |
| Lyso PE20:0p | 0.171542 | 0.258486 | 0.308973 | 0.289793 | 0.449812 | 0.197603 | 0.169594 |
| LysoPE20:4 | 0 | 0.016155 | 0.038622 | 0 | 0 | 0.035928 | 0.015417 |
| LysoPE22:6 | 0.015595 | 0 | 0.019311 | 0.015252 | 0 | 0.071855 | 0 |
| PE32:2 | 0.083172 | 0.150784 | 0.077243 | 0.101682 | 0.128518 | 0.119759 | 0.113062 |
| PE32:1 | 0.280704 | 0.301567 | 0.399091 | 0.254205 | 0.342713 | 0.239518 | 0.298074 |
| PE34p:2 | 0.14555 | 0.118473 | 0.257477 | 0.193195 | 0.171357 | 0.095807 | 0.071949 |
| PE34p:1 | 0.738148 | 0.603135 | 0.823929 | 0.6711 | 0.942463 | 0.658675 | 0.668096 |
| PE34:2 | 0.904491 | 0.753919 | 1.004163 | 0.83379 | 0.956742 | 0.85029 | 0.698932 |
| PE34:1 | 1.330746 | 1.389364 | 1.840966 | 1.413377 | 1.842086 | 1.724532 | 1.367029 |
| PE34:0 | 0.280704 | 0.215405 | 0.360469 | 0.142354 | 0.299875 | 0.227542 | 0.164455 |
| PE36p:4 | 0.654977 | 0.786229 | 0.785307 | 0.579586 | 0.685427 | 0.874242 | 0.657818 |
| PE36p:3 | 0.447048 | 0.463122 | 0.553577 | 0.355886 | 0.471231 | 0.514965 | 0.411136 |
| PE36p:2 | 0.249515 | 0.312337 | 0.411964 | 0.345718 | 0.314154 | 0.287422 | 0.308352 |

TABLE 1-continued

Mass spectrometry analysis of free fatty acid uptake in HEK239 cells. Mfsd2a expressing HEK293 cells were incubated with 100 uM of indicated fatty acid/BSA complex overnight. Lipids extraction and phospholipid analysis by MS were performed as described in Methods section. Amount of each lipid species was normalized to internal standard and expressed as mol percent in total phospholipid analysed.

| | | | | | | | |
|---|---|---|---|---|---|---|---|
| PE36p:1 | 0.395065 | 0.247716 | 0.360469 | 0.366054 | 0.55691 | 0.467061 | 0.390579 |
| PE36:4 | 0.187136 | 0.183095 | 0.167361 | 0.193195 | 0.271315 | 0.251494 | 0.236403 |
| PE36:3 | 0.280704 | 0.344648 | 0.437712 | 0.305045 | 0.428392 | 0.431133 | 0.298074 |
| PE36:2 | 1.829776 | 1.841715 | 2.394543 | 1.759094 | 2.15624 | 1.856267 | 1.983733 |
| PE36:1 | 1.445107 | 1.497067 | 1.931083 | 1.382872 | 1.756407 | 1.485014 | 1.55204 |
| PE38p:6 | 1.860965 | 1.712472 | 2.124191 | 1.677749 | 2.084841 | 2.02393 | 1.695938 |
| PE38p:5 | 1.725811 | 1.669391 | 1.85384 | 1.738758 | 2.113401 | 1.82034 | 1.644546 |
| PE38p:4 | 0.571805 | 0.721608 | 0.772433 | 0.61009 | 1.013861 | 0.886218 | 0.678375 |
| PE38p:3 | 0.343083 | 0.430811 | 0.334721 | 0.366054 | 0.399832 | 0.455085 | 0.339187 |
| PE38p:2 | 0.17674 | 0.215405 | 0.205982 | 0.183027 | 0.314154 | 0.155687 | 0.19529 |
| PE38p:1 | 0.093568 | 0.247716 | 0.283226 | 0.172859 | 0.185637 | 0.191615 | 0.19529 |
| PE38p:0 | 0.072775 | 0.01077 | 0.051496 | 0.030505 | 0.042839 | 0.035928 | 0.041114 |
| PE38:7 | 0.187136 | 0.118473 | 0.180234 | 0.101682 | 0.128518 | 0.215567 | 0.143898 |
| PE38:6 | 0.571805 | 0.624675 | 0.746685 | 0.488073 | 0.756826 | 0.742507 | 0.616704 |
| PE38:5 | 0.852509 | 0.786229 | 1.248767 | 0.803286 | 1.213778 | 0.898194 | 0.945614 |
| PE38:4 | 0.883699 | 0.958554 | 1.042785 | 0.884631 | 1.07098 | 0.838315 | 0.668096 |
| PE38:3 | 0.582201 | 0.764689 | 0.836802 | 0.508409 | 0.671147 | 0.862266 | 0.760602 |
| PE38:2 | 0.291101 | 0.323108 | 0.334721 | 0.437232 | 0.414112 | 0.359278 | 0.236403 |
| PE38:1 | 0.509426 | 0.538513 | 0.502082 | 0.4474 | 0.585469 | 0.6467 | 0.472807 |
| PE40p:6 | 1.122817 | 0.872375 | 1.145776 | 0.935472 | 0.942463 | 1.185616 | 0.966171 |
| PE40p:5 | 0.64458 | 0.678527 | 0.746685 | 0.630427 | 1.013861 | 0.538916 | 0.441972 |
| PE40p:4 | 0.187136 | 0.269257 | 0.334721 | 0.2237 | 0.242756 | 0.215567 | 0.246682 |
| PE40:6 | 0.395065 | 0.592364 | 0.592199 | 0.477904 | 0.628308 | 0.514965 | 0.58587 |
| PE40:5 | 0.187136 | 0.226176 | 0.308973 | 0.305045 | 0.456951 | 0.407181 | 0.328909 |
| PE40:4 | 0.155947 | 0.161554 | 0.205982 | 0.122018 | 0.171357 | 0.167663 | 0.113062 |
| PE40:3 | 0.114361 | 0.096932 | 0.128739 | 0.193195 | 0.199916 | 0.119759 | 0.164455 |
| PE42p:7 | 0.103964 | 0.161554 | 0.257477 | 0.11185 | 0.214196 | 0.203591 | 0.123341 |
| PE42p:6 | 0.239118 | 0.323108 | 0.167361 | 0.183027 | 0.328434 | 0.239518 | 0.205568 |
| PE42p:5 | 0.083172 | 0.129243 | 0.141612 | 0.152522 | 0.314154 | 0.179639 | 0.102784 |
| PE42p:4 | 0.093568 | 0.140013 | 0.128739 | 0.050841 | 0.099958 | 0.155687 | 0.06167 |
| PE42:7 | 0.041586 | 0.075392 | 0.051496 | 0.040673 | 0.085678 | 0.047904 | 0.020557 |
| PE42:6 | 0.083172 | 0.096932 | 0.038622 | 0.061009 | 0.099958 | 0.107783 | 0.051392 |
| PE42:5 | 0.041586 | 0.032311 | 0.141612 | 0.050841 | 0.099958 | 0.035928 | 0.030835 |
| PE42:4 | 0.103964 | 0.096932 | 0.025748 | 0.050841 | 0.142797 | 0.107783 | 0.102784 |
| Total PE + lysoPE | 25.2114 | 27.09798 | 32.07529 | 24.75442 | 32.95049 | 28.89789 | 24.86861 |
| % DHA in PE + lysoPE | 18.3299 | 16.89189 | 16.59643 | 16.53317 | 15.99133 | 18.52466 | 17.73094 |
| LPI16:0 | 0.00427 | 0.002996 | 0.00331 | 0.004891 | 0.004685 | 0.004731 | 0.003589 |
| LPI18:0 | 0.029157 | 0.030812 | 0.031146 | 0.035707 | 0.036312 | 0.040308 | 0.038455 |
| LPI20:4 | 0.002209 | 0.001997 | 0.000752 | 0.002935 | 0.002845 | 0.001892 | 0.003589 |
| LPI22:6 | 0.008099 | 0.009843 | 0.010833 | 0.009294 | 0.007865 | 0.013058 | 0.009058 |
| PI 32:2 | 0.001031 | 0.000999 | 0.002106 | 0.00163 | 0.000502 | 0.002082 | 0.000855 |
| PI 32:1 | 0.012811 | 0.012696 | 0.013993 | 0.016141 | 0.011212 | 0.014193 | 0.009742 |
| PI 34:2 | 0.041673 | 0.043793 | 0.039722 | 0.053315 | 0.040161 | 0.040876 | 0.042899 |
| PI 34:1 | 0.092035 | 0.101707 | 0.095244 | 0.107772 | 0.085844 | 0.098405 | 0.0899 |
| PI 36:4 | 0.048005 | 0.047501 | 0.043334 | 0.048913 | 0.037484 | 0.039551 | 0.040164 |
| PI 36:3 | 0.085408 | 0.10941 | 0.100058 | 0.105 | 0.076306 | 0.095756 | 0.090413 |
| PI 36:2 | 0.239584 | 0.255481 | 0.239538 | 0.292175 | 0.205825 | 0.246012 | 0.225605 |
| PI 36:1 | 0.143279 | 0.165613 | 0.162952 | 0.17674 | 0.13136 | 0.152906 | 0.158436 |
| PI 38:6 | 0.022383 | 0.026675 | 0.023322 | 0.026087 | 0.016734 | 0.021952 | 0.02256 |
| PI 38:5 | 0.134297 | 0.149352 | 0.15242 | 0.16712 | 0.119814 | 0.147229 | 0.126304 |
| PI 38:4 | 0.509504 | 0.550761 | 0.514887 | 0.57473 | 0.432902 | 0.50546 | 0.496843 |
| PI 38:3 | 0.798713 | 0.900674 | 0.847412 | 0.976633 | 0.717042 | 0.849877 | 0.853025 |
| PI 38:2 | 0.232222 | 0.273597 | 0.254434 | 0.293153 | 0.202813 | 0.242795 | 0.255002 |
| PI 40:6 | 0.025622 | 0.030099 | 0.026482 | 0.025435 | 0.021419 | 0.027818 | 0.025466 |
| PI 40:5 | 0.037403 | 0.042937 | 0.040926 | 0.043859 | 0.03079 | 0.03728 | 0.040677 |
| PI 40:4 | 0.018701 | 0.018544 | 0.021366 | 0.028696 | 0.013722 | 0.020816 | 0.019142 |
| PI 40:3 | 0.022383 | 0.023251 | 0.023021 | 0.028696 | 0.017403 | 0.022898 | 0.021877 |
| Total PI + lysoPI | 2.50879 | 2.798737 | 2.647261 | 3.018921 | 2.21304 | 2.625896 | 2.573602 |
| % DHA in PI and lysoPI | 0.048005 | 0.056774 | 0.049804 | 0.051522 | 0.038153 | 0.04977 | 0.048026 |
| PS:34:2 | 0.029978 | 0.033342 | 0.033664 | 0.034486 | 0.032908 | 0.033228 | 0.023445 |
| PS:34:1 | 0.426406 | 0.540329 | 0.386178 | 0.484286 | 0.450205 | 0.503171 | 0.420925 |
| PS:36:4 | 0.001551 | 0.004903 | 0.004809 | 0.003941 | 0.006301 | 0.006781 | 0.003817 |
| PS:36:3 | 0.010337 | 0.012748 | 0.014428 | 0.015765 | 0.011203 | 0.0217 | 0.012541 |
| PS:36:2 | 0.260495 | 0.331454 | 0.260177 | 0.311362 | 0.270963 | 0.328892 | 0.276437 |
| PS:36:1 | 1.18515 | 1.310616 | 1.094091 | 1.232637 | 1.198679 | 1.276236 | 1.160816 |
| PS:38:5 | 0.031011 | 0.041677 | 0.035107 | 0.032516 | 0.032908 | 0.04001 | 0.030533 |
| PS:38:4 | 0.049618 | 0.057367 | 0.042802 | 0.055178 | 0.058814 | 0.063744 | 0.052343 |
| PS:38:3 | 0.09045 | 0.117186 | 0.099069 | 0.117253 | 0.094522 | 0.117994 | 0.106867 |
| PS:38:2 | 0.157124 | 0.202501 | 0.144757 | 0.180807 | 0.202347 | 0.196657 | 0.163027 |
| PS:40:7 | 0.014472 | 0.025496 | 0.012023 | 0.018228 | 0.014703 | 0.017631 | 0.023445 |

TABLE 1-continued

Mass spectrometry analysis of free fatty acid uptake in HEK239 cells. Mfsd2a expressing HEK293 cells were incubated with 100 uM of indicated fatty acid/BSA complex overnight. Lipids extraction and phospholipid analysis by MS were performed as described in Methods section. Amount of each lipid species was normalized to internal standard and expressed as mol percent in total phospholipid analysed.

| | | | | | | | |
|---|---|---|---|---|---|---|---|
| PS:40:6 | 0.191754 | 0.192694 | 0.174093 | 0.199528 | 0.169439 | 0.208185 | 0.172296 |
| PS:40:5 | 0.197956 | 0.213778 | 0.183711 | 0.198542 | 0.179942 | 0.189198 | 0.191379 |
| PS:40:4 | 0.061506 | 0.087767 | 0.056748 | 0.06848 | 0.08472 | 0.075272 | 0.063248 |
| PS(sum) | 2.707808 | 3.171858 | 2.541657 | 2.953009 | 2.807652 | 3.078699 | 2.701118 |
| % DHA in PS | 0.206225 | 0.218191 | 0.186116 | 0.217756 | 0.184143 | 0.225816 | 0.195741 |
| | | | | Arachidonic | | | |
| LysoPC16:0e | 0.008218 | 0.00827 | 0.009441 | 0.010261 | 0.008219 | 0.011981 | 0.009457 |
| LysoPC16:1 | 0.006514 | 0.005638 | 0.007023 | 0.005461 | 0.005685 | 0.005799 | 0.006002 |
| LysoPC16:0 | 0.024153 | 0.024104 | 0.028554 | 0.021723 | 0.023219 | 0.025173 | 0.028069 |
| LysoPC18:0e | 0.001403 | 0.001832 | 0.001957 | 0.00156 | 0.00137 | 0.002231 | 0.001637 |
| LysoPC18:2 | 0.000802 | 0.001222 | 0.001957 | 0.00132 | 0.00089 | 0.001529 | 0.001455 |
| LysoPC18:1 | 0.011575 | 0.010948 | 0.015889 | 0.012662 | 0.013082 | 0.014976 | 0.015823 |
| LysoPC18:0 | 0.006865 | 0.00639 | 0.005642 | 0.008281 | 0.006849 | 0.006628 | 0.006426 |
| LysoPC20:4 | 0.003808 | 0.002725 | 0.005124 | 0.00288 | 0.002671 | 0.003059 | 0.004001 |
| LysoPC22:6 | 0.000551 | 0.000893 | 0.000461 | 0.00072 | 0.000548 | 0.000319 | 0.000546 |
| LysoPC22:5 | 0.000802 | 0.000799 | 0.001382 | 0.0003 | 0.001507 | 0.001083 | 0.000727 |
| PC32:1e | 1.003081 | 0.986295 | 1.14327 | 1.080914 | 0.969122 | 1.062549 | 1.091461 |
| PC32:0e | 1.020168 | 0.987657 | 1.168543 | 1.095736 | 0.96878 | 1.049102 | 1.089036 |
| PC32:2 | 0.951669 | 0.912902 | 1.075511 | 0.997984 | 0.919944 | 0.990281 | 1.048964 |
| PC32:1 | 6.268327 | 6.009815 | 7.055585 | 6.660707 | 6.097545 | 6.776659 | 7.012778 |
| PC32:0 | 3.966623 | 3.827008 | 4.4949 | 4.26911 | 3.73546 | 4.15352 | 4.312921 |
| PC34:3e | 0.142961 | 0.133865 | 0.154977 | 0.154819 | 0.135755 | 0.145365 | 0.158227 |
| PC34:2e | 0.732492 | 0.712316 | 0.815067 | 0.774456 | 0.680968 | 0.778255 | 0.80053 |
| PC34:1e | 2.769621 | 2.728462 | 3.185197 | 2.987411 | 2.661131 | 2.981676 | 3.048926 |
| PC34:3 | 0.505699 | 0.483492 | 0.566195 | 0.529146 | 0.476376 | 0.52111 | 0.542578 |
| PC34:2 | 3.604285 | 3.479777 | 4.06123 | 3.823615 | 3.398264 | 3.77032 | 3.974037 |
| PC34:1 | 14.51831 | 13.96577 | 16.01867 | 15.35909 | 14.33519 | 15.78261 | 16.25516 |
| PC36:5e | 0.658932 | 0.623794 | 0.738903 | 0.675204 | 0.624393 | 0.687633 | 0.713293 |
| PC36:4e | 1.464985 | 1.399729 | 1.630364 | 1.569075 | 1.344333 | 1.490105 | 1.545833 |
| PC36:3e | 0.456142 | 0.446936 | 0.514267 | 0.491461 | 0.444047 | 0.480196 | 0.497838 |
| PC36:2e | 0.779645 | 0.763813 | 0.873788 | 0.837224 | 0.76364 | 0.831787 | 0.86085 |
| PC36:1e | 0.803296 | 0.769499 | 0.8678 | 0.88505 | 0.781928 | 0.866456 | 0.884978 |
| PC36:6 | 0.062987 | 0.058827 | 0.071328 | 0.071949 | 0.061782 | 0.064493 | 0.067777 |
| PC36:5 | 0.371007 | 0.347935 | 0.414384 | 0.382908 | 0.340004 | 0.379122 | 0.379623 |
| PC36:4 | 3.354041 | 3.190528 | 3.756228 | 3.533479 | 3.368332 | 3.561544 | 3.712266 |
| PC36:3 | 1.050183 | 1.020454 | 1.174645 | 1.110918 | 1.01515 | 1.106841 | 1.140748 |
| PC36:2 | 3.127349 | 3.105623 | 3.514494 | 3.439867 | 3.003053 | 3.394957 | 3.521666 |
| PC36:1 | 1.987771 | 1.931429 | 2.226667 | 2.140046 | 2.035232 | 2.257909 | 2.301805 |
| PC38:5e | 1.04407 | 0.987375 | 1.140391 | 1.096936 | 0.958437 | 1.084982 | 1.109588 |
| PC38:4e | 1.102146 | 1.046391 | 1.213044 | 1.189948 | 1.01378 | 1.142083 | 1.152085 |
| PC38:3e | 0.31263 | 0.284128 | 0.339717 | 0.32266 | 0.287196 | 0.31584 | 0.321364 |
| PC38:1e | 0.208303 | 0.196498 | 0.23045 | 0.224428 | 0.204318 | 0.222031 | 0.225579 |
| PC38:7 | 0.121414 | 0.111499 | 0.128322 | 0.120015 | 0.113015 | 0.12083 | 0.125672 |
| PC38:6 | 0.451131 | 0.431947 | 0.509719 | 0.48036 | 0.456513 | 0.483446 | 0.495716 |
| PC38:5 | 1.983011 | 1.876079 | 2.223098 | 2.068457 | 1.94345 | 2.098141 | 2.165827 |
| PC38:4 | 2.652166 | 2.532951 | 3.013007 | 2.774264 | 2.629144 | 2.853454 | 2.909674 |
| PC38:3 | 0.614085 | 0.599314 | 0.698086 | 0.664943 | 0.594117 | 0.664882 | 0.685346 |
| PC40:5e | 0.418009 | 0.404366 | 0.466254 | 0.452336 | 0.389663 | 0.431444 | 0.435033 |
| PC40:4e | 0.307569 | 0.287887 | 0.349158 | 0.332561 | 0.290346 | 0.313099 | 0.335004 |
| PC40:3e | 0.104427 | 0.104686 | 0.116175 | 0.116955 | 0.103494 | 0.114775 | 0.116336 |
| PC40:2e | 0.116704 | 0.112768 | 0.129761 | 0.128056 | 0.114248 | 0.124335 | 0.131067 |
| PC40:1e | 0.165961 | 0.161399 | 0.185028 | 0.186023 | 0.163084 | 0.1822 | 0.18575 |
| PC40:7 | 0.223336 | 0.217266 | 0.25296 | 0.247051 | 0.218975 | 0.242679 | 0.250495 |
| PC40:6 | 0.416105 | 0.390458 | 0.456698 | 0.440995 | 0.400827 | 0.437944 | 0.456554 |
| PC40:5 | 0.821887 | 0.777768 | 0.910632 | 0.851266 | 0.754941 | 0.836057 | 0.868792 |
| Total PC + lysoPC | 60.72722 | 58.47153 | 67.96195 | 64.63258 | 58.86001 | 64.8735 | 67.00532 |
| % DHA in PC + lysoPC | 0.081658 | 0.079642 | 0.097533 | 0.091943 | 0.091131 | 0.092884 | 0.094949 |
| Lyso PE16:0p | 2.789602 | 2.681287 | 2.306933 | 2.640386 | 3.43917 | 2.895063 | 2.927626 |
| LysoPE16:1 | 0.201879 | 0.230423 | 0.199934 | 0.167113 | 0.269739 | 0.116468 | 0.148862 |
| LysoPE16:0 | 0.146821 | 0.08379 | 0.107657 | 0.133691 | 0.089913 | 0.083192 | 0.082701 |
| Lyso PE18:1p | 0.183526 | 0.293266 | 0.153795 | 0.133691 | 0.179826 | 0.149745 | 0.082701 |
| Lyso PE18:0p | 0.587285 | 0.586531 | 0.322971 | 0.534762 | 0.651869 | 0.415957 | 0.215023 |
| LysoPE18:2 | 0.055058 | 0 | 0 | 0 | 0 | 0.016638 | 0.01654 |
| LysoPE18:1 | 0.238584 | 0.146633 | 0.107657 | 0.050134 | 0.292217 | 0.116468 | 0.148862 |

TABLE 1-continued

Mass spectrometry analysis of free fatty acid uptake in HEK239 cells. Mfsd2a expressing HEK293 cells were incubated with 100 uM of indicated fatty acid/BSA complex overnight. Lipids extraction and phospholipid analysis by MS were performed as described in Methods section. Amount of each lipid species was normalized to internal standard and expressed as mol percent in total phospholipid analysed.

| | | | | | | | |
|---|---|---|---|---|---|---|---|
| LysoPE18:0 | 0.256937 | 0.230423 | 0.246073 | 0.116979 | 0.179826 | 0.216298 | 0.165402 |
| Lyso PE20:0p | 0.330348 | 0.272318 | 0.184555 | 0.217247 | 0.292217 | 0.183021 | 0.115782 |
| LysoPE20:4 | 0.018352 | 0.020947 | 0.046139 | 0.066845 | 0.022478 | 0.016638 | 0.01654 |
| LysoPE22:6 | 0 | 0.020947 | 0.030759 | 0 | 0 | 0.066553 | 0 |
| PE32:2 | 0.110116 | 0.05586 | 0.092277 | 0.100268 | 0.059942 | 0.055461 | 0.066161 |
| PE32:1 | 0.318113 | 0.474811 | 0.23582 | 0.278522 | 0.254753 | 0.221844 | 0.264644 |
| PE34p:2 | 0.146821 | 0.181546 | 0.143542 | 0.155972 | 0.224782 | 0.177475 | 0.198483 |
| PE34p:1 | 0.636225 | 0.796007 | 0.451134 | 0.51248 | 0.614405 | 0.366042 | 0.496208 |
| PE34:2 | 0.819751 | 1.200993 | 0.584423 | 0.791002 | 0.974057 | 0.698808 | 0.639557 |
| PE34:1 | 1.590563 | 1.396503 | 1.189352 | 1.258918 | 1.768288 | 1.120311 | 1.069604 |
| PE34:0 | 0.146821 | 0.2793 | 0.174302 | 0.155972 | 0.119884 | 0.144199 | 0.187456 |
| PE36p:4 | 1.810794 | 2.401986 | 1.507197 | 1.79368 | 2.532548 | 1.885673 | 1.852509 |
| PE36p:3 | 0.587285 | 0.656356 | 0.369109 | 0.456776 | 0.479536 | 0.45478 | 0.41902 |
| PE36p:2 | 0.318113 | 0.19551 | 0.174302 | 0.25624 | 0.404608 | 0.366042 | 0.275671 |
| PE36p:1 | 0.367053 | 0.418765 | 0.246073 | 0.289663 | 0.344666 | 0.321673 | 0.374913 |
| PE36:4 | 0.575049 | 0.963587 | 0.553664 | 0.63503 | 0.62939 | 0.565702 | 0.694691 |
| PE36:3 | 0.575049 | 0.404986 | 0.307591 | 0.37879 | 0.449565 | 0.321673 | 0.308751 |
| PE36:2 | 1.908675 | 2.206475 | 1.599474 | 1.91623 | 2.157911 | 1.730383 | 1.797375 |
| PE36:1 | 1.712913 | 1.745629 | 1.435425 | 1.626567 | 1.543506 | 1.563999 | 1.488623 |
| PE38p:6 | 0.67293 | 0.935657 | 0.625435 | 0.924692 | 0.749274 | 0.643347 | 0.66161 |
| PE38p:5 | 1.333625 | 1.480294 | 1.035557 | 1.303482 | 1.258781 | 1.26451 | 1.179872 |
| PE38p:4 | 2.385843 | 2.611462 | 1.773775 | 1.92737 | 2.502577 | 2.063148 | 1.830456 |
| PE38p:3 | 0.758576 | 0.782042 | 0.615182 | 0.646171 | 0.569448 | 0.654439 | 0.595449 |
| PE38p:2 | 0.159056 | 0.237406 | 0.194808 | 0.233958 | 0.299709 | 0.277305 | 0.198483 |
| PE38p:1 | 0.207997 | 0.19551 | 0.13329 | 0.167113 | 0.16484 | 0.122014 | 0.165402 |
| PE38p:0 | 0.085646 | 0.069825 | 0.010253 | 0.044564 | 0.044957 | 0.022184 | 0.077188 |
| PE38:7 | 0.110116 | 0.069825 | 0.10253 | 0.100268 | 0.119884 | 0.110922 | 0.022053 |
| PE38:6 | 0.159056 | 0.251371 | 0.174302 | 0.155972 | 0.224782 | 0.210752 | 0.20951 |
| PE38:5 | 1.517152 | 1.745629 | 1.537955 | 1.292341 | 1.648404 | 1.508538 | 1.400409 |
| PE38:4 | 3.19336 | 3.211958 | 2.727308 | 2.807499 | 3.491619 | 2.795233 | 2.701576 |
| PE38:3 | 1.19904 | 0.935657 | 0.830496 | 0.868988 | 1.258781 | 0.898468 | 0.782906 |
| PE38:2 | 0.367053 | 0.404986 | 0.287085 | 0.267381 | 0.359652 | 0.232936 | 0.319778 |
| PE38:1 | 0.391523 | 0.321196 | 0.307591 | 0.311944 | 0.224782 | 0.288397 | 0.275671 |
| PE40p:6 | 0.550579 | 0.544637 | 0.410122 | 0.523621 | 0.689332 | 0.587886 | 0.540315 |
| PE40p:5 | 0.880927 | 0.754112 | 0.594676 | 0.746438 | 1.004028 | 0.831915 | 0.694691 |
| PE40p:4 | 0.697401 | 0.754112 | 0.451134 | 0.612748 | 0.76426 | 0.499149 | 0.441074 |
| PE40:6 | 0.501639 | 0.628427 | 0.389615 | 0.490198 | 0.689332 | 0.587886 | 0.38594 |
| PE40:5 | 0.550579 | 0.656356 | 0.451134 | 0.467916 | 0.644376 | 0.521333 | 0.551342 |
| PE40:4 | 0.391523 | 0.698252 | 0.57417 | 0.389931 | 0.524492 | 0.476965 | 0.341832 |
| PE40:3 | 0.220232 | 0.181546 | 0.13329 | 0.211676 | 0.254753 | 0.221844 | 0.220537 |
| PE42p:7 | 0.146821 | 0.167581 | 0.10253 | 0.178254 | 0.269739 | 0.122014 | 0.121295 |
| PE42p:6 | 0.134586 | 0.251371 | 0.123037 | 0.111409 | 0.284724 | 0.166383 | 0.187456 |
| PE42p:5 | 0.171291 | 0.05586 | 0.123037 | 0.144831 | 0.089913 | 0.066553 | 0.088215 |
| PE42p:4 | 0.146821 | 0.11172 | 0.051265 | 0.066845 | 0.194811 | 0.09983 | 0.187456 |
| PE42:7 | 0.061175 | 0.08379 | 0.030759 | 0.055704 | 0.059942 | 0.077646 | 0.033081 |
| PE42:6 | 0.097881 | 0.209475 | 0.061518 | 0.055704 | 0.074927 | 0.088738 | 0.077188 |
| PE42:5 | 0.171291 | 0.13965 | 0.112783 | 0.089127 | 0.059942 | 0.110922 | 0.132322 |
| PE42:4 | 0.122351 | 0.13965 | 0.092277 | 0.144831 | 0.16484 | 0.166383 | 0.099242 |
| Total PE + lysoPE | 33.42628 | 36.08565 | 26.56049 | 29.71827 | 36.36229 | 29.6217 | 28.2673 |
| % DHA in PE + lysoPE | 7.28404 | 8.765479 | 7.720518 | 8.734769 | 8.695651 | 8.987081 | 7.918861 |
| LPI 16:0 | 0.003583 | 0.003359 | 0.003156 | 0.002319 | 0.003611 | 0.003895 | 0.00338 |
| LPI18:0 | 0.025081 | 0.030534 | 0.026671 | 0.030307 | 0.033066 | 0.034207 | 0.022277 |
| LPI20:4 | 0.003732 | 0.003817 | 0.003788 | 0.005134 | 0.005321 | 0.004234 | 0.002458 |
| LPI22:6 | 0.006121 | 0.006107 | 0.008996 | 0.009274 | 0.010642 | 0.008298 | 0.00845 |
| PI 32:2 | 0.001344 | 0.001985 | 0.00142 | 0.001656 | 0.00228 | 0.000847 | 0.001383 |
| PI 32:1 | 0.005375 | 0.006259 | 0.008364 | 0.00679 | 0.005321 | 0.004911 | 0.00507 |
| PI 34:2 | 0.020005 | 0.019084 | 0.02099 | 0.019873 | 0.016533 | 0.018797 | 0.01859 |
| PI 34:1 | 0.041802 | 0.045953 | 0.049555 | 0.049849 | 0.039717 | 0.041658 | 0.045015 |
| PI 36:4 | 0.119435 | 0.116944 | 0.126886 | 0.123876 | 0.097868 | 0.107533 | 0.105394 |
| PI 36:3 | 0.047774 | 0.050075 | 0.05571 | 0.054155 | 0.038387 | 0.047924 | 0.04394 |
| PI 36:2 | 0.120779 | 0.115112 | 0.110473 | 0.118743 | 0.090267 | 0.118879 | 0.104626 |
| PI 36:1 | 0.077484 | 0.092059 | 0.080645 | 0.078002 | 0.072594 | 0.086534 | 0.074974 |
| PI 38:6 | 0.006569 | 0.006259 | 0.009469 | 0.008115 | 0.007031 | 0.006096 | 0.006299 |
| PI 38:5 | 0.140635 | 0.153432 | 0.158134 | 0.144578 | 0.114591 | 0.136321 | 0.116302 |
| PI 38:4 | 1.34902 | 1.345618 | 1.259545 | 1.390464 | 1.090613 | 1.282266 | 1.093576 |
| PI 38:3 | 0.53925 | 0.559987 | 0.519537 | 0.554132 | 0.444873 | 0.538342 | 0.449844 |
| PI 38:2 | 0.092114 | 0.098624 | 0.093902 | 0.100194 | 0.079055 | 0.09805 | 0.087418 |
| PI 40:6 | 0.007315 | 0.007633 | 0.006628 | 0.006956 | 0.005701 | 0.007112 | 0.004916 |
| PI 40:5 | 0.012093 | 0.011755 | 0.015624 | 0.013249 | 0.011402 | 0.009653 | 0.010908 |

TABLE 1-continued

Mass spectrometry analysis of free fatty acid uptake in HEK239 cells. Mfsd2a expressing HEK293 cells were incubated with 100 uM of indicated fatty acid/BSA complex overnight. Lipids extraction and phospholipid analysis by MS were performed as described in Methods section. Amount of each lipid species was normalized to internal standard and expressed as mol percent in total phospholipid analysed.

| | | | | | | | |
|---|---|---|---|---|---|---|---|
| PI 40:4 | 0.039115 | 0.047327 | 0.039928 | 0.04339 | 0.035157 | 0.035562 | 0.032263 |
| PI 40:3 | 0.01478 | 0.014656 | 0.013257 | 0.015071 | 0.012352 | 0.012531 | 0.010601 |
| Total PI + lysoPI | 2.673406 | 2.736578 | 2.612676 | 2.776125 | 2.216384 | 2.60365 | 2.247684 |
| % DHA in PI and lysoPI | 0.013884 | 0.013893 | 0.016097 | 0.015071 | 0.012732 | 0.013209 | 0.011215 |
| PS:34:2 | 0.02243 | 0.022242 | 0.016511 | 0.016897 | 0.012837 | 0.017916 | 0.021765 |
| PS:34:1 | 0.379227 | 0.347246 | 0.341225 | 0.361174 | 0.286467 | 0.365115 | 0.293832 |
| PS:36:4 | 0.013041 | 0.016341 | 0.022515 | 0.016369 | 0.012837 | 0.017298 | 0.012437 |
| PS:36:3 | 0.0193 | 0.014071 | 0.012508 | 0.015313 | 0.006756 | 0.012356 | 0.010364 |
| PS:36:2 | 0.247254 | 0.216518 | 0.240158 | 0.232334 | 0.164854 | 0.22673 | 0.195888 |
| PS:36:1 | 1.232619 | 0.992262 | 1.036683 | 1.073489 | 0.937774 | 1.071251 | 0.934873 |
| PS:38:5 | 0.022952 | 0.018157 | 0.026017 | 0.022177 | 0.017566 | 0.014827 | 0.019692 |
| PS:38:4 | 0.271771 | 0.246023 | 0.253667 | 0.222301 | 0.258091 | 0.255148 | 0.22439 |
| PS:38:3 | 0.135103 | 0.118472 | 0.140593 | 0.119863 | 0.114857 | 0.142092 | 0.109345 |
| PS:38:2 | 0.166923 | 0.137083 | 0.130586 | 0.151017 | 0.13918 | 0.160626 | 0.125928 |
| PS:40:7 | 0.010433 | 0.007263 | 0.005504 | 0.006336 | 0.008108 | 0.008649 | 0.006219 |
| PS:40:6 | 0.112673 | 0.101223 | 0.112574 | 0.108775 | 0.105398 | 0.10626 | 0.082916 |
| PS:40:5 | 0.142927 | 0.134359 | 0.164608 | 0.149433 | 0.13918 | 0.14271 | 0.128519 |
| PS:40:4 | 0.396441 | 0.33499 | 0.361738 | 0.377543 | 0.357408 | 0.360173 | 0.313525 |
| PS(sum) | 3.173094 | 2.706251 | 2.864887 | 2.873021 | 2.561313 | 2.901152 | 2.479695 |
| % DHA in PS | 0.123105 | 0.108486 | 0.118078 | 0.115111 | 0.113506 | 0.114909 | 0.089134 |
| Alpha-linolenic | | | | | | | |
| LysoPC16:0e | 0.004349 | 0.003802 | 0.005532 | 0.004823 | 0.005097 | 0.005159 | 0.004145 |
| LysoPC16:1 | 0.008052 | 0.007381 | 0.008361 | 0.004823 | 0.007834 | 0.006826 | 0.006714 |
| LysoPC16:0 | 0.02586 | 0.025331 | 0.028414 | 0.022926 | 0.027276 | 0.025239 | 0.027768 |
| LysoPC18:0e | 0.001528 | 0.001007 | 0.001383 | 0.001468 | 0.002076 | 0.00246 | 0.002321 |
| LysoPC18:2 | 0.001411 | 0.001398 | 0.00176 | 0.002027 | 0.001133 | 0.001349 | 0.001658 |
| LysoPC18:1 | 0.014106 | 0.012134 | 0.015904 | 0.014189 | 0.014346 | 0.016112 | 0.01492 |
| LysoPC18:0 | 0.008875 | 0.009786 | 0.00943 | 0.009646 | 0.009721 | 0.008413 | 0.010278 |
| LysoPC20:4 | 0.002351 | 0.001062 | 0.001509 | 0.001258 | 0.001416 | 0.001111 | 0.001409 |
| LysoPC22:6 | 0.000882 | 0.000783 | 0.000377 | 0.000839 | 0.001227 | 0.000794 | 0.000995 |
| LysoPC22:5 | 0.002116 | 0.001678 | 0.002263 | 0.003215 | 0.001982 | 0.002699 | 0.003481 |
| PC32:1e | 1.103585 | 1.081518 | 1.220183 | 1.14273 | 1.132379 | 1.177201 | 1.1816 |
| PC32:0e | 1.063737 | 1.056522 | 1.168698 | 1.119932 | 1.076694 | 1.112039 | 1.119681 |
| PC32:2 | 0.94478 | 0.942058 | 1.055606 | 1.024245 | 0.999302 | 1.043861 | 1.037702 |
| PC32:1 | 5.986406 | 5.837882 | 6.601875 | 6.301266 | 6.39608 | 6.61763 | 6.505223 |
| PC32:0 | 3.981592 | 3.915855 | 4.424027 | 4.234114 | 4.245618 | 4.395694 | 4.343364 |
| PC34:3e | 0.575684 | 0.574058 | 0.640015 | 0.579501 | 0.592522 | 0.616935 | 0.615294 |
| PC34:2e | 0.767696 | 0.778832 | 0.850042 | 0.818823 | 0.813938 | 0.857106 | 0.84606 |
| PC34:1e | 2.556929 | 2.522424 | 2.787813 | 2.686354 | 2.695039 | 2.784741 | 2.704624 |
| PC34:3 | 4.027083 | 4.016172 | 4.479222 | 4.271299 | 4.445422 | 4.627055 | 4.824458 |
| PC34:2 | 3.664276 | 3.5615 | 3.972792 | 3.838787 | 3.76909 | 4.004564 | 3.966711 |
| PC34:1 | 12.61985 | 12.10611 | 13.56723 | 12.84856 | 13.58392 | 14.09181 | 13.96907 |
| PC36:5e | 0.90546 | 0.875571 | 0.990165 | 0.896686 | 0.923137 | 0.941317 | 0.922071 |
| PC36:4e | 0.591964 | 0.572828 | 0.64869 | 0.601099 | 0.607811 | 0.636143 | 0.618858 |
| PC36:3e | 0.531604 | 0.508858 | 0.588969 | 0.544764 | 0.570531 | 0.580346 | 0.569373 |
| PC36:2e | 0.778451 | 0.749698 | 0.840424 | 0.80051 | 0.824415 | 0.854408 | 0.847552 |
| PC36:1e | 0.793674 | 0.765635 | 0.854631 | 0.799182 | 0.848199 | 0.886552 | 0.847055 |
| PC36:6 | 0.684473 | 0.665261 | 0.732235 | 0.698323 | 0.697756 | 0.728528 | 0.752975 |
| PC36:5 | 1.581823 | 1.483683 | 1.69562 | 1.557056 | 1.636277 | 1.717863 | 1.697757 |
| PC36:4 | 2.158564 | 2.118861 | 2.362729 | 2.177656 | 2.264663 | 2.445121 | 2.432745 |
| PC36:3 | 1.665868 | 1.627226 | 1.824554 | 1.676158 | 1.792099 | 1.916365 | 1.906972 |
| PC36:2 | 2.593486 | 2.560951 | 2.818176 | 2.701801 | 2.743833 | 2.959591 | 2.844129 |
| PC36:1 | 1.880861 | 1.820033 | 2.020122 | 1.909538 | 2.104971 | 2.173521 | 2.117928 |
| PC38:5e | 0.617589 | 0.591169 | 0.665223 | 0.614449 | 0.623667 | 0.648683 | 0.625987 |
| PC38:4e | 0.288812 | 0.281549 | 0.308409 | 0.282097 | 0.302396 | 0.316603 | 0.303047 |
| PC38:3e | 0.192482 | 0.185202 | 0.201792 | 0.198503 | 0.194424 | 0.205407 | 0.196035 |
| PC38:1e | 0.320784 | 0.313143 | 0.344807 | 0.328647 | 0.333258 | 0.345414 | 0.348139 |
| PC38:7 | 0.269005 | 0.272043 | 0.293762 | 0.276855 | 0.293996 | 0.290173 | 0.298653 |
| PC38:6 | 1.357074 | 1.307317 | 1.470946 | 1.38756 | 1.452801 | 1.495789 | 1.470472 |
| PC38:5 | 1.873103 | 1.737609 | 1.962791 | 1.818814 | 1.965382 | 2.024466 | 2.004617 |
| PC38:4 | 0.897526 | 0.869531 | 0.96898 | 0.89382 | 0.969006 | 1.014415 | 1.024606 |
| PC38:3 | 0.362278 | 0.351168 | 0.383342 | 0.366601 | 0.398003 | 0.409385 | 0.398619 |
| PC40:5e | 0.226159 | 0.210477 | 0.236744 | 0.220589 | 0.224343 | 0.247393 | 0.224798 |
| PC40:4e | 0.09533 | 0.098864 | 0.11108 | 0.102117 | 0.101459 | 0.110879 | 0.102038 |
| PC40:3e | 0.088395 | 0.081361 | 0.088072 | 0.086391 | 0.095041 | 0.097783 | 0.09607 |
| PC40:2e | 0.181433 | 0.178212 | 0.197329 | 0.188228 | 0.197067 | 0.211439 | 0.199019 |
| PC40:1e | 0.356695 | 0.341382 | 0.385668 | 0.367929 | 0.386677 | 0.385257 | 0.381378 |
| PC40:7 | 0.266184 | 0.257057 | 0.297093 | 0.276785 | 0.287106 | 0.30946 | 0.302549 |

TABLE 1-continued

Mass spectrometry analysis of free fatty acid uptake in HEK239 cells. Mfsd2a expressing HEK293 cells were incubated with 100 uM of indicated fatty acid/BSA complex overnight. Lipids extraction and phospholipid analysis by MS were performed as described in Methods section. Amount of each lipid species was normalized to internal standard and expressed as mol percent in total phospholipid analysed.

| | | | | | | | |
|---|---|---|---|---|---|---|---|
| PC40:6 | 0.479178 | 0.471672 | 0.521831 | 0.491993 | 0.515507 | 0.535027 | 0.516572 |
| PC40:5 | 0.34829 | 0.331037 | 0.371273 | 0.344234 | 0.370916 | 0.39748 | 0.38975 |
| Total PC + lysoPC | 59.74769 | 58.08469 | 65.02789 | 61.54381 | 63.54685 | 66.28361 | 65.62724 |
| % DHA in PC + lysoPC | 0.23528 | 0.219443 | 0.242248 | 0.219062 | 0.247 | 0.24317 | 0.24286 |
| Lyso PE16:0p | 3.295863 | 3.843986 | 2.808645 | 2.876305 | 3.1478 | 2.170805 | 2.853376 |
| LysoPE16:1 | 0.197357 | 0.242778 | 0.185001 | 0.190484 | 0.078206 | 0.198852 | 0.118187 |
| LysoPE16:0 | 0.13815 | 0.242778 | 0.235455 | 0.076193 | 0.039103 | 0.16571 | 0.033768 |
| Lyso PE18:1p | 0.315771 | 0.222547 | 0.117727 | 0.209532 | 0.234619 | 0.215423 | 0.168839 |
| Lyso PE18:0p | 0.532864 | 0.465325 | 0.370001 | 0.571451 | 0.410583 | 0.381134 | 0.472749 |
| LysoPE18:2 | 0 | 0 | 0.016818 | 0.019048 | 0.078206 | 0 | 0 |
| LysoPE18:1 | 0.157886 | 0.121389 | 0.151364 | 0.11429 | 0.097758 | 0.132568 | 0.101303 |
| LysoPE18:0 | 0.394714 | 0.283241 | 0.218637 | 0.342871 | 0.215067 | 0.281708 | 0.202607 |
| Lyso PE20:0p | 0.41445 | 0.283241 | 0.319546 | 0.190484 | 0.117309 | 0.298279 | 0.21949 |
| LysoPE20:4 | 0.019736 | 0.020231 | 0.050455 | 0.038097 | 0.019551 | 0.016571 | 0 |
| LysoPE22:6 | 0.019736 | 0.020231 | 0 | 0 | 0.039103 | 0.033142 | 0 |
| PE32:2 | 0.065786 | 0.202315 | 0.067273 | 0.101591 | 0.091241 | 0.066284 | 0.033768 |
| PE32:1 | 0.513129 | 0.418118 | 0.201837 | 0.292075 | 0.247653 | 0.37561 | 0.24763 |
| PE34p:2 | 0.223671 | 0.161852 | 0.123333 | 0.228581 | 0.156413 | 0.254089 | 0.157583 |
| PE34p:1 | 0.855214 | 0.647408 | 0.549396 | 0.69844 | 0.586546 | 0.618652 | 0.652844 |
| PE34:2 | 0.749957 | 0.944137 | 0.661517 | 0.93972 | 0.651718 | 0.883788 | 0.686611 |
| PE34:1 | 1.565699 | 1.685959 | 1.367883 | 1.447677 | 1.264334 | 1.159972 | 1.474526 |
| PE34:0 | 0.171043 | 0.202315 | 0.257879 | 0.139688 | 0.195515 | 0.198852 | 0.146327 |
| PE36p:4 | 0.907842 | 0.836236 | 0.706366 | 0.927021 | 0.821165 | 0.629699 | 0.664099 |
| PE36p:3 | 0.565757 | 0.768797 | 0.448486 | 0.647645 | 0.482271 | 0.508178 | 0.393957 |
| PE36p:2 | 0.486814 | 0.431605 | 0.190607 | 0.406365 | 0.391031 | 0.320373 | 0.281398 |
| PE36p:1 | 0.513129 | 0.431605 | 0.370001 | 0.380968 | 0.456203 | 0.276184 | 0.438981 |
| PE36:4 | 0.986786 | 1.092501 | 0.784851 | 1.231796 | 0.690822 | 0.773315 | 0.844194 |
| PE36:3 | 1.157828 | 0.890186 | 0.953033 | 1.231796 | 0.92544 | 1.060546 | 0.799171 |
| PE36:2 | 2.328813 | 2.657071 | 1.883642 | 2.158817 | 2.215842 | 1.800718 | 2.048578 |
| PE36:1 | 1.973571 | 1.996175 | 1.737883 | 2.006429 | 1.720536 | 1.579772 | 1.575829 |
| PE38p:6 | 1.170985 | 1.73991 | 1.110003 | 1.587365 | 1.394677 | 1.17102 | 1.035545 |
| PE38p:5 | 2.315656 | 2.791948 | 1.995763 | 2.336601 | 2.163705 | 1.999571 | 2.059834 |
| PE38p:4 | 0.868371 | 0.836236 | 0.874548 | 0.774634 | 0.860268 | 0.58551 | 0.832938 |
| PE38p:3 | 0.526286 | 0.552994 | 0.482123 | 0.368268 | 0.377996 | 0.441894 | 0.405213 |
| PE38p:2 | 0.302614 | 0.17534 | 0.257879 | 0.266678 | 0.273722 | 0.16571 | 0.135071 |
| PE38p:1 | 0.236828 | 0.17534 | 0.134546 | 0.139688 | 0.156413 | 0.198852 | 0.202607 |
| PE38p:0 | 0.105257 | 0.148364 | 0.100909 | 0.11429 | 0.065172 | 0.154663 | 0.067535 |
| PE38:7 | 0.105257 | 0.121389 | 0.112121 | 0.165086 | 0.052138 | 0.143616 | 0.225118 |
| PE38:6 | 1.092042 | 1.402718 | 1.065154 | 0.965118 | 0.847234 | 0.927978 | 0.754147 |
| PE38:5 | 2.013042 | 1.901761 | 1.704247 | 1.688957 | 1.498952 | 1.358824 | 1.508294 |
| PE38:4 | 1.394657 | 1.483644 | 1.323034 | 1.447677 | 1.003646 | 1.193114 | 1.170616 |
| PE38:3 | 0.802586 | 0.944137 | 0.650493 | 0.812731 | 0.729924 | 0.596557 | 0.619076 |
| PE38:2 | 0.421028 | 0.458581 | 0.291516 | 0.507957 | 0.443169 | 0.419799 | 0.438981 |
| PE38:1 | 0.407871 | 0.40463 | 0.347577 | 0.279376 | 0.443169 | 0.187805 | 0.270142 |
| PE40p:6 | 1.065728 | 0.80926 | 0.583032 | 0.812731 | 0.873303 | 0.629699 | 0.697867 |
| PE40p:5 | 0.565757 | 0.741822 | 0.62788 | 0.634946 | 0.703856 | 0.651794 | 0.675355 |
| PE40p:4 | 0.249985 | 0.310216 | 0.291516 | 0.317473 | 0.404065 | 0.276184 | 0.405213 |
| PE40:6 | 0.697328 | 0.606945 | 0.392425 | 0.495258 | 0.755993 | 0.563415 | 0.585308 |
| PE40:5 | 0.394714 | 0.499044 | 0.526971 | 0.419064 | 0.364962 | 0.408752 | 0.55154 |
| PE40:4 | 0.223671 | 0.161852 | 0.179395 | 0.215882 | 0.234619 | 0.220947 | 0.157583 |
| PE40:3 | 0.144728 | 0.283241 | 0.168182 | 0.190484 | 0.234619 | 0.231995 | 0.213862 |
| PE42p:7 | 0.171043 | 0.35068 | 0.145758 | 0.330172 | 0.286756 | 0.231995 | 0.112559 |
| PE42p:6 | 0.131571 | 0.269753 | 0.269092 | 0.304774 | 0.325859 | 0.276184 | 0.315166 |
| PE42p:5 | 0.105257 | 0.161852 | 0.067273 | 0.215882 | 0.182481 | 0.055237 | 0.135071 |
| PE42p:4 | 0.105257 | 0.121389 | 0.033637 | 0.126989 | 0.20855 | 0.176758 | 0.135071 |
| PE42:7 | 0.026314 | 0.067438 | 0.123333 | 0.11429 | 0.078206 | 0.044189 | 0.033768 |
| PE42:6 | 0.131571 | 0.17534 | 0.15697 | 0.139688 | 0.182481 | 0.110473 | 0.123815 |
| PE42:5 | 0.118414 | 0.121389 | 0.145758 | 0.165086 | 0.182481 | 0.143616 | 0.135071 |
| PE42:4 | 0.1842 | 0.188827 | 0.134546 | 0.215882 | 0.234619 | 0.121521 | 0.135071 |
| Total PE + lysoPE | 34.1954 | 36.63252 | 28.63584 | 33.09974 | 30.33749 | 27.71228 | 28.3593 |
| % DHA in PE + lysoPE | 13.48595 | 15.18777 | 13.82146 | 14.8475 | 15.93985 | 14.90931 | 13.69319 |
| LPI16:0 | 0.002614 | 0.002235 | 0.003861 | 0.003103 | 0.002773 | 0.004579 | 0.003274 |
| LPI18:0 | 0.032017 | 0.031434 | 0.037381 | 0.036145 | 0.044602 | 0.042668 | 0.042564 |
| LPI 20:4 | 0.001634 | 0.002384 | 0.004563 | 0.002556 | 0.003466 | 0.004163 | 0.005239 |
| LPI22:6 | 0.010291 | 0.006406 | 0.009652 | 0.008763 | 0.01063 | 0.009574 | 0.009823 |
| PI 32:2 | 0.00098 | 0.001192 | 0.001053 | 0.002191 | 0.000462 | 0.001665 | 0.000655 |
| PI 32:1 | 0.007351 | 0.006108 | 0.00544 | 0.00785 | 0.007164 | 0.007701 | 0.00502 |
| PI 34:2 | 0.018132 | 0.02041 | 0.02299 | 0.020628 | 0.021954 | 0.021646 | 0.022046 |
| PI 34:1 | 0.049006 | 0.048268 | 0.05458 | 0.047464 | 0.036976 | 0.052658 | 0.055006 |

TABLE 1-continued

Mass spectrometry analysis of free fatty acid uptake in HEK239 cells. Mfsd2a expressing HEK293 cells were incubated with 100 uM of indicated fatty acid/BSA complex overnight. Lipids extraction and phospholipid analysis by MS were performed as described in Methods section. Amount of each lipid species was normalized to internal standard and expressed as mol percent in total phospholipid analysed.

| | | | | | | | |
|---|---|---|---|---|---|---|---|
| PI 36:4 | 0.05554 | 0.061676 | 0.073534 | 0.055313 | 0.055694 | 0.063065 | 0.060245 |
| PI 36:3 | 0.092458 | 0.097132 | 0.098104 | 0.092006 | 0.086893 | 0.099281 | 0.110886 |
| PI 36:2 | 0.122026 | 0.122011 | 0.136187 | 0.118841 | 0.10746 | 0.133415 | 0.132059 |
| PI 36:1 | 0.123169 | 0.114115 | 0.142856 | 0.11519 | 0.106305 | 0.131542 | 0.135551 |
| PI 38:6 | 0.049006 | 0.051546 | 0.057564 | 0.05148 | 0.048993 | 0.048704 | 0.058935 |
| PI 38:5 | 0.713041 | 0.647449 | 0.771667 | 0.63875 | 0.6339 | 0.699751 | 0.739964 |
| PI 38:4 | 0.610128 | 0.586667 | 0.675319 | 0.559887 | 0.579823 | 0.629401 | 0.620566 |
| PI 38:3 | 0.575987 | 0.544953 | 0.619861 | 0.55934 | 0.531062 | 0.650007 | 0.598738 |
| PI 38:2 | 0.136564 | 0.116201 | 0.141101 | 0.130525 | 0.12225 | 0.144446 | 0.150176 |
| PI 40:6 | 0.010945 | 0.011769 | 0.013162 | 0.014787 | 0.009706 | 0.014986 | 0.014188 |
| PI 40:5 | 0.028424 | 0.028305 | 0.038961 | 0.031399 | 0.02958 | 0.03018 | 0.033615 |
| PI 40:4 | 0.012088 | 0.016387 | 0.017901 | 0.012596 | 0.01271 | 0.019357 | 0.016807 |
| PI 40:3 | 0.013395 | 0.009832 | 0.013162 | 0.009128 | 0.009706 | 0.013321 | 0.012005 |
| | | | | | | | |
| Total PI + lysoPI | 2.664797 | 2.52648 | 2.9389 | 2.517942 | 2.462111 | 2.822107 | 2.827362 |
| % DHA in PI and lysoPI | 0.059951 | 0.063315 | 0.070726 | 0.066266 | 0.058699 | 0.063689 | 0.073123 |
| PS:34:2 | 0.020487 | 0.01239 | 0.025138 | 0.020508 | 0.029566 | 0.032943 | 0.016357 |
| PS:34:1 | 0.397319 | 0.322142 | 0.394858 | 0.32943 | 0.441358 | 0.33884 | 0.371238 |
| PS:36:4 | 0.018004 | 0.016679 | 0.023912 | 0.022317 | 0.022175 | 0.01748 | 0.024891 |
| PS:36:3 | 0.102434 | 0.081965 | 0.11343 | 0.100729 | 0.108762 | 0.096139 | 0.113078 |
| PS:36:2 | 0.29116 | 0.238747 | 0.294917 | 0.226791 | 0.321006 | 0.261525 | 0.279495 |
| PS:36:1 | 1.444007 | 1.204219 | 1.419404 | 1.220209 | 1.588133 | 1.403764 | 1.365472 |
| PS:38:5 | 0.116092 | 0.081012 | 0.120787 | 0.088666 | 0.114041 | 0.105551 | 0.108811 |
| PS:38:4 | 0.132233 | 0.095785 | 0.147765 | 0.113999 | 0.130936 | 0.133116 | 0.155038 |
| PS:38:3 | 0.144028 | 0.106269 | 0.137342 | 0.107967 | 0.143608 | 0.129754 | 0.115212 |
| PS:38:2 | 0.183139 | 0.158212 | 0.177196 | 0.165268 | 0.171062 | 0.178832 | 0.163572 |
| PS:40:7 | 0.011175 | 0.012867 | 0.007971 | 0.01146 | 0.010559 | 0.007395 | 0.008534 |
| PS:40:6 | 0.148995 | 0.129619 | 0.16432 | 0.133903 | 0.172118 | 0.160008 | 0.122324 |
| PS:40:5 | 0.277503 | 0.205389 | 0.265487 | 0.201458 | 0.288271 | 0.226565 | 0.245358 |
| PS:40:4 | 0.105538 | 0.091019 | 0.104846 | 0.095904 | 0.11193 | 0.090088 | 0.096721 |
| | | | | | | | |
| PS(sum) | 3.392113 | 2.756312 | 3.397374 | 2.838509 | 3.65355 | 3.182 | 3.186101 |
| % DHA in PS | 0.160169 | 0.142486 | 0.172291 | 0.145363 | 0.182677 | 0.167403 | 0.130858 |
| | | | | Linoleic | | | |
| LysoPC16:0e | 0.004905 | 0.004227 | 0.005291 | 0.006453 | 0.004343 | 0.002849 | 0.00473 |
| LysoPC16:1 | 0.005687 | 0.005997 | 0.006313 | 0.005628 | 0.005242 | 0.005187 | 0.005008 |
| LysoPC16:0 | 0.021755 | 0.019591 | 0.021344 | 0.022586 | 0.020294 | 0.020381 | 0.018501 |
| LysoPC18:0e | 0.00128 | 0.001885 | 0.001443 | 0.001726 | 0.001273 | 0.002045 | 0.001878 |
| LysoPC18:2 | 0.002204 | 0.001656 | 0.002285 | 0.001876 | 0.002396 | 0.002045 | 0.002574 |
| LysoPC18:1 | 0.01429 | 0.012451 | 0.013167 | 0.012531 | 0.01318 | 0.014829 | 0.012937 |
| LysoPC18:0 | 0.006967 | 0.006454 | 0.007395 | 0.006903 | 0.007189 | 0.00599 | 0.008764 |
| LysoPC20:4 | 0.00064 | 0.001142 | 0.001503 | 0.001126 | 0.001123 | 0.001023 | 0.001182 |
| LysoPC22:6 | 0.00064 | 0.000685 | 0.001022 | 0.0006 | 0.000824 | 0.000657 | 0.000278 |
| LysoPC22:5 | 0.00064 | 0.000286 | 0.000661 | 0.000825 | 0.000674 | 0.000511 | 0.000765 |
| PC32:1e | 1.561068 | 1.423604 | 1.485856 | 1.593727 | 1.465913 | 1.449972 | 1.383918 |
| PC32:0e | 1.550404 | 1.375284 | 1.462949 | 1.551481 | 1.458799 | 1.401686 | 1.363539 |
| PC32:2 | 1.402459 | 1.286241 | 1.359835 | 1.510285 | 1.354556 | 1.313296 | 1.306644 |
| PC32:1 | 7.671186 | 6.936164 | 7.393929 | 7.925038 | 7.61406 | 7.339787 | 7.347209 |
| PC32:0 | 3.580404 | 3.244446 | 3.416935 | 3.617871 | 3.500068 | 3.349423 | 3.3523 |
| PC34:3e | 0.236385 | 0.208929 | 0.230036 | 0.232317 | 0.230352 | 0.22178 | 0.214574 |
| PC34:2e | 1.300866 | 1.191886 | 1.237663 | 1.329819 | 1.261247 | 1.219499 | 1.193479 |
| PC34:1e | 4.255435 | 3.897962 | 3.976032 | 4.28188 | 4.028321 | 3.942005 | 3.83271 |
| PC34:3 | 0.94021 | 0.87798 | 0.889421 | 0.97444 | 0.919912 | 0.883249 | 0.863862 |
| PC34:2 | 6.959471 | 6.255805 | 6.498855 | 6.957351 | 6.809624 | 6.584376 | 6.487242 |
| PC34:1 | 18.19706 | 16.32013 | 17.04758 | 18.34306 | 18.1759 | 17.73314 | 17.48597 |
| PC36:5e | 0.540736 | 0.493992 | 0.518574 | 0.530817 | 0.544728 | 0.50032 | 0.509971 |
| PC36:4e | 1.103156 | 1.034019 | 1.066969 | 1.104256 | 1.061298 | 0.957468 | 1.005335 |
| PC36:3e | 0.798094 | 0.731707 | 0.761897 | 0.802979 | 0.746623 | 0.724511 | 0.719676 |
| PC36:2e | 1.333711 | 1.200796 | 1.250469 | 1.356308 | 1.281616 | 1.234475 | 1.194175 |
| PC36:1e | 1.1815 | 1.075142 | 1.103044 | 1.199404 | 1.150414 | 1.147472 | 1.099025 |
| PC36:6 | 0.060856 | 0.054088 | 0.055435 | 0.059205 | 0.060134 | 0.057637 | 0.057799 |
| PC36:5 | 0.158254 | 0.141532 | 0.149109 | 0.157729 | 0.154043 | 0.138868 | 0.148915 |
| PC36:4 | 1.229417 | 1.138027 | 1.162086 | 1.230169 | 1.236759 | 1.126214 | 1.218588 |
| PC36:3 | 1.986348 | 1.808791 | 1.860973 | 1.951207 | 1.95822 | 1.857592 | 1.887212 |
| PC36:2 | 5.49964 | 4.977045 | 5.178522 | 5.576656 | 5.352398 | 5.291899 | 5.248136 |
| PC36:1 | 2.531705 | 2.277995 | 2.37155 | 2.550459 | 2.54466 | 2.474939 | 2.494976 |
| PC38:5e | 0.850987 | 0.802016 | 0.812643 | 0.86436 | 0.805559 | 0.744746 | 0.781719 |
| PC38:4e | 0.822621 | 0.762092 | 0.788713 | 0.839372 | 0.760028 | 0.718521 | 0.736717 |
| PC38:3e | 0.489122 | 0.436191 | 0.455804 | 0.483393 | 0.454115 | 0.427051 | 0.424837 |
| PC38:1e | 0.329233 | 0.29564 | 0.296534 | 0.327765 | 0.316323 | 0.301478 | 0.297274 |
| PC38:7 | 0.142613 | 0.133936 | 0.134017 | 0.145948 | 0.140338 | 0.131198 | 0.129788 |
| PC38:6 | 0.38106 | 0.361084 | 0.367 | 0.372412 | 0.389637 | 0.353855 | 0.372045 |

TABLE 1-continued

Mass spectrometry analysis of free fatty acid uptake in HEK239 cells. Mfsd2a expressing HEK293 cells were incubated with 100 uM of indicated fatty acid/BSA complex overnight. Lipids extraction and phospholipid analysis by MS were performed as described in Methods section. Amount of each lipid species was normalized to internal standard and expressed as mol percent in total phospholipid analysed.

| | | | | | | | |
|---|---|---|---|---|---|---|---|
| PC38:5 | 0.889947 | 0.853763 | 0.868378 | 0.912309 | 0.921185 | 0.82817 | 0.863584 |
| PC38:4 | 1.120076 | 1.050868 | 1.05278 | 1.125266 | 1.128472 | 1.025113 | 1.064665 |
| PC38:3 | 0.740508 | 0.669451 | 0.691732 | 0.746401 | 0.728875 | 0.71633 | 0.687403 |
| PC40:5e | 0.318712 | 0.300085 | 0.310723 | 0.323263 | 0.306138 | 0.275545 | 0.287537 |
| PC40:4e | 0.266387 | 0.245597 | 0.239957 | 0.263232 | 0.251171 | 0.227916 | 0.235371 |
| PC40:3e | 0.17233 | 0.149928 | 0.165102 | 0.189095 | 0.166024 | 0.166043 | 0.159418 |
| PC40:2e | 0.185696 | 0.174317 | 0.172437 | 0.194798 | 0.196878 | 0.179046 | 0.177989 |
| PC40:1e | 0.218114 | 0.19602 | 0.198291 | 0.216409 | 0.217771 | 0.208777 | 0.209567 |
| PC40:7 | 0.259704 | 0.235487 | 0.244947 | 0.260306 | 0.270342 | 0.257283 | 0.251299 |
| PC40:6 | 0.28288 | 0.264559 | 0.266472 | 0.282892 | 0.29835 | 0.267802 | 0.275573 |
| PC40:5 | 0.309469 | 0.283064 | 0.296293 | 0.306829 | 0.316023 | 0.27591 | 0.293518 |
| Total PC + lysoPC | 71.91683 | 65.22003 | 67.89996 | 72.75076 | 70.63341 | 68.10992 | 67.72018 |
| % DHA in PC + lysoPC | 0.067348 | 0.065558 | 0.066668 | 0.064857 | 0.079881 | 0.065066 | 0.071748 |
| Lyso PE16:0p | 1.996581 | 3.121412 | 2.462198 | 2.098055 | 2.124621 | 2.274347 | 2.564282 |
| LysoPE16:1 | 0.052889 | 0.118749 | 0.14205 | 0.099316 | 0.157911 | 0.165681 | 0.158289 |
| LysoPE16:0 | 0.039667 | 0.101785 | 0.063133 | 0.024829 | 0.057422 | 0.090371 | 0.063315 |
| Lyso PE18:1p | 0.158669 | 0.135714 | 0.1894 | 0.086902 | 0.157911 | 0.210867 | 0.205776 |
| Lyso PE18:0p | 0.343782 | 0.305355 | 0.252533 | 0.198632 | 0.473733 | 0.346424 | 0.364065 |
| LysoPE18:2 | 0.013222 | 0 | 0 | 0 | 0 | 0.030124 | 0 |
| LysoPE18:1 | 0.132224 | 0.101785 | 0.205183 | 0.086902 | 0.100489 | 0.07531 | 0.110802 |
| LysoPE18:0 | 0.105779 | 0.101785 | 0.1894 | 0.086902 | 0.172267 | 0.090371 | 0.14246 |
| Lyso PE20:0p | 0.185114 | 0.271427 | 0.299883 | 0.186218 | 0.1292 | 0.256052 | 0.237434 |
| LysoPE20:4 | 0 | 0.016964 | 0 | 0.024829 | 0.014355 | 0.030124 | 0 |
| LysoPE22:6 | 0.013222 | 0.016964 | 0.031567 | 0.012414 | 0 | 0.015062 | 0 |
| PE32:2 | 0.03526 | 0.090476 | 0.126267 | 0.082763 | 0.153126 | 0.070289 | 0.073868 |
| PE32:1 | 0.202743 | 0.305355 | 0.368278 | 0.173804 | 0.229689 | 0.180743 | 0.232157 |
| PE34p:2 | 0.185114 | 0.124404 | 0.168356 | 0.099316 | 0.181837 | 0.170702 | 0.221605 |
| PE34p:1 | 0.493636 | 0.588092 | 0.610288 | 0.562792 | 0.602933 | 0.753095 | 0.580393 |
| PE34:2 | 0.546526 | 0.780353 | 0.820732 | 0.587621 | 0.698637 | 0.903714 | 0.833656 |
| PE34:1 | 0.899123 | 1.345826 | 1.146921 | 0.935228 | 1.081451 | 1.064375 | 1.276865 |
| PE34:0 | 0.176298 | 0.124404 | 0.105222 | 0.132422 | 0.143555 | 0.130537 | 0.221605 |
| PE36p:4 | 1.613132 | 1.877371 | 1.694076 | 1.473191 | 1.445126 | 1.696974 | 1.614548 |
| PE36p:3 | 0.467191 | 0.814281 | 0.599766 | 0.405541 | 0.459378 | 0.602476 | 0.48542 |
| PE36p:2 | 0.449561 | 0.316665 | 0.389322 | 0.355883 | 0.354103 | 0.321321 | 0.379894 |
| PE36p:1 | 0.370227 | 0.531545 | 0.220967 | 0.413818 | 0.449807 | 0.301238 | 0.517078 |
| PE36:4 | 0.290893 | 0.441069 | 0.420889 | 0.322778 | 0.229689 | 0.321321 | 0.306025 |
| PE36:3 | 0.520081 | 0.542854 | 0.694466 | 0.52141 | 0.411526 | 0.652682 | 0.590945 |
| PE36:2 | 1.868765 | 2.420225 | 1.872954 | 1.671823 | 1.770518 | 2.008253 | 2.015547 |
| PE36:1 | 1.048976 | 1.651181 | 1.504677 | 1.017991 | 1.129303 | 1.355571 | 1.656759 |
| PE38p:6 | 0.837418 | 1.153565 | 1.010132 | 0.736595 | 0.679496 | 0.903714 | 0.854761 |
| PE38p:5 | 0.969642 | 1.119637 | 1.104832 | 0.811083 | 0.995318 | 0.913755 | 1.171339 |
| PE38p:4 | 1.392759 | 1.752967 | 1.588854 | 1.191795 | 1.215437 | 1.626685 | 1.58289 |
| PE38p:3 | 0.493636 | 0.712496 | 0.641855 | 0.480028 | 0.478518 | 0.6326 | 0.612051 |
| PE38p:2 | 0.185114 | 0.407141 | 0.242011 | 0.231738 | 0.220118 | 0.251032 | 0.158289 |
| PE38p:1 | 0.123409 | 0.169642 | 0.178878 | 0.18208 | 0.143555 | 0.16066 | 0.116078 |
| PE38p:0 | 0.044075 | 0.079166 | 0.021044 | 0.024829 | 0.00957 | 0.100413 | 0.073868 |
| PE38:7 | 0.123409 | 0.158332 | 0.073656 | 0.124145 | 0.095704 | 0.090371 | 0.137184 |
| PE38:6 | 0.202743 | 0.169642 | 0.147311 | 0.148974 | 0.105274 | 0.110454 | 0.200499 |
| PE38:5 | 0.714009 | 1.006542 | 0.747077 | 0.70349 | 0.918755 | 0.883632 | 0.791445 |
| PE38:4 | 1.313424 | 1.933918 | 1.799256 | 1.282834 | 1.521698 | 1.646768 | 1.857258 |
| PE38:3 | 0.581785 | 0.8369 | 0.526111 | 0.546239 | 0.717778 | 0.753095 | 0.707024 |
| PE38:2 | 0.264448 | 0.305355 | 0.294622 | 0.289672 | 0.287111 | 0.24099 | 0.253262 |
| PE38:1 | 0.414301 | 0.452379 | 0.431411 | 0.355883 | 0.325393 | 0.39161 | 0.306025 |
| PE40p:6 | 0.361412 | 0.610711 | 0.610288 | 0.463476 | 0.52637 | 0.773178 | 0.749235 |
| PE40p:5 | 0.484821 | 0.588092 | 0.536633 | 0.43037 | 0.583793 | 0.461898 | 0.622603 |
| PE40p:4 | 0.334967 | 0.41845 | 0.357755 | 0.347607 | 0.325393 | 0.361486 | 0.369341 |
| PE40:6 | 0.273263 | 0.463688 | 0.462977 | 0.289672 | 0.373244 | 0.251032 | 0.348236 |
| PE40:5 | 0.167484 | 0.339284 | 0.305144 | 0.240014 | 0.24883 | 0.251032 | 0.28492 |
| PE40:4 | 0.132224 | 0.169642 | 0.263056 | 0.132422 | 0.124415 | 0.150619 | 0.274368 |
| PE40:3 | 0.096964 | 0.158332 | 0.105222 | 0.148974 | 0.114845 | 0.100413 | 0.126631 |
| PE42p:7 | 0.158669 | 0.21488 | 0.147311 | 0.157251 | 0.162696 | 0.230949 | 0.24271 |
| PE42p:6 | 0.193928 | 0.124404 | 0.126267 | 0.165527 | 0.200978 | 0.200825 | 0.105526 |
| PE42p:5 | 0.061705 | 0.135714 | 0.0947 | 0.066211 | 0.143555 | 0.130537 | 0.137184 |
| PE42p:4 | 0.105779 | 0.101785 | 0.031567 | 0.09104 | 0.057422 | 0.040165 | 0.105526 |
| PE42:7 | 0.01763 | 0.033929 | 0.031567 | 0.057935 | 0.086133 | 0.08033 | 0.073868 |
| PE42:6 | 0.052889 | 0.033929 | 0.042089 | 0.041382 | 0.038282 | 0.060247 | 0.052763 |

TABLE 1-continued

Mass spectrometry analysis of free fatty acid uptake in HEK239 cells. Mfsd2a expressing HEK293 cells were incubated with 100 uM of indicated fatty acid/BSA complex overnight. Lipids extraction and phospholipid analysis by MS were performed as described in Methods section. Amount of each lipid species was normalized to internal standard and expressed as mol percent in total phospholipid analysed.

| | | | | | | | |
|---|---|---|---|---|---|---|---|
| PE42:5 | 0.052889 | 0.067857 | 0.084178 | 0.074487 | 0.066993 | 0.040165 | 0.063315 |
| PE42:4 | 0.105779 | 0.067857 | 0.073656 | 0.099316 | 0.143555 | 0.170702 | 0.116078 |
| Total PE + lysoPE | 22.25769 | 29.86263 | 26.45811 | 21.36127 | 23.38998 | 25.85627 | 27.11491 |
| % DHA in PE + lysoPE | 10.0396 | 9.97917 | 10.14118 | 10.28671 | 9.697218 | 10.50485 | 10.19654 |
| LPI16:0 | 0.002421 | 0.002583 | 0.004097 | 0.003665 | 0.003029 | 0.004291 | 0.00407 |
| LPI18:0 | 0.032161 | 0.026817 | 0.028093 | 0.04343 | 0.033655 | 0.038107 | 0.026922 |
| LPI20:4 | 0.00536 | 0.002706 | 0.00278 | 0.003482 | 0.002524 | 0.002575 | 0.003757 |
| LPI22:6 | 0.011066 | 0.005905 | 0.007901 | 0.009712 | 0.009928 | 0.007209 | 0.007513 |
| PI 32:2 | 0.002421 | 0.000738 | 0.001024 | 0.001283 | 0.00101 | 0.001545 | 0.001096 |
| PI 32:1 | 0.011412 | 0.006643 | 0.00834 | 0.008246 | 0.011274 | 0.009269 | 0.0108 |
| PI 34:2 | 0.044957 | 0.037027 | 0.038482 | 0.038483 | 0.036684 | 0.04463 | 0.034905 |
| PI 34:1 | 0.078328 | 0.062368 | 0.076086 | 0.066153 | 0.075724 | 0.076042 | 0.06668 |
| PI 36:4 | 0.087838 | 0.078606 | 0.092034 | 0.079897 | 0.085652 | 0.086857 | 0.080611 |
| PI 36:3 | 0.104265 | 0.087832 | 0.100521 | 0.100971 | 0.090532 | 0.099559 | 0.09689 |
| PI 36:2 | 0.269912 | 0.213921 | 0.243182 | 0.247205 | 0.220608 | 0.260742 | 0.225241 |
| PI 36:1 | 0.120172 | 0.094475 | 0.094961 | 0.112699 | 0.101638 | 0.114836 | 0.09642 |
| PI 38:6 | 0.010202 | 0.006766 | 0.006145 | 0.00788 | 0.008077 | 0.007381 | 0.008139 |
| PI 38:5 | 0.139538 | 0.118462 | 0.136515 | 0.123694 | 0.121326 | 0.131143 | 0.124595 |
| PI 38:4 | 0.96864 | 0.800081 | 0.887276 | 0.899026 | 0.862241 | 0.920234 | 0.829276 |
| PI 38:3 | 0.811811 | 0.654556 | 0.771245 | 0.815281 | 0.717019 | 0.815697 | 0.696228 |
| PI 38:2 | 0.189509 | 0.15266 | 0.1848 | 0.199743 | 0.171304 | 0.201006 | 0.169205 |
| PI 40:6 | 0.007262 | 0.008365 | 0.009072 | 0.00733 | 0.007572 | 0.009784 | 0.00767 |
| PI 40:5 | 0.009683 | 0.009718 | 0.009218 | 0.010629 | 0.010096 | 0.008068 | 0.008609 |
| PI 40:4 | 0.02317 | 0.021527 | 0.022972 | 0.021807 | 0.021371 | 0.0218 | 0.021444 |
| PI 40:3 | 0.022132 | 0.018821 | 0.022826 | 0.018142 | 0.017669 | 0.01974 | 0.017531 |
| Total PI + lysoPI | 2.952261 | 2.410577 | 2.747571 | 2.818757 | 2.608934 | 2.880516 | 2.537602 |
| % DHA in PI and lysoPI | 0.017464 | 0.015131 | 0.015217 | 0.01521 | 0.01565 | 0.017165 | 0.015809 |
| PS:34:2 | 0.035187 | 0.027145 | 0.038818 | 0.031528 | 0.026592 | 0.036377 | 0.026278 |
| PS:34:1 | 0.337686 | 0.28325 | 0.323479 | 0.359834 | 0.395476 | 0.355891 | 0.286382 |
| PS:36:4 | 0.012604 | 0.005114 | 0.005354 | 0.007539 | 0.009546 | 0.015763 | 0.005899 |
| PS:36:3 | 0.022582 | 0.027145 | 0.032571 | 0.023989 | 0.035456 | 0.023039 | 0.023061 |
| PS:36:2 | 0.425389 | 0.350522 | 0.38416 | 0.433172 | 0.454115 | 0.418338 | 0.35181 |
| PS:36:1 | 1.201068 | 1.050385 | 1.221191 | 1.346123 | 1.438713 | 1.342927 | 1.092433 |
| PS:38:5 | 0.016806 | 0.014162 | 0.018739 | 0.015079 | 0.017046 | 0.017582 | 0.017161 |
| PS:38:4 | 0.131818 | 0.127462 | 0.144116 | 0.130911 | 0.148644 | 0.147934 | 0.12013 |
| PS:38:3 | 0.160177 | 0.136511 | 0.15884 | 0.169979 | 0.173873 | 0.175217 | 0.151235 |
| PS:38:2 | 0.173307 | 0.170343 | 0.202119 | 0.209047 | 0.220239 | 0.217051 | 0.193066 |
| PS:40:7 | 0.012079 | 0.013376 | 0.012939 | 0.008225 | 0.008864 | 0.01637 | 0.01019 |
| PS:40:6 | 0.110811 | 0.110546 | 0.121361 | 0.106237 | 0.15069 | 0.129139 | 0.132465 |
| PS:40:5 | 0.094006 | 0.074353 | 0.099498 | 0.089102 | 0.118643 | 0.102463 | 0.077763 |
| PS:40:4 | 0.139696 | 0.116447 | 0.131176 | 0.138451 | 0.169782 | 0.15521 | 0.139437 |
| PS(sum) | 2.873216 | 2.506761 | 2.89436 | 3.069215 | 3.367679 | 3.153301 | 2.62731 |
| % DHA in PS | 0.12289 | 0.123922 | 0.1343 | 0.114462 | 0.159554 | 0.145509 | 0.142655 |
| | | | | Oleic | | | |
| LysoPC16:0e | 0.002972 | 0.00261 | 0.002228 | 0.001403 | 0.003153 | 0.001998 | 0.003294 |
| LysoPC16:1 | 0.004272 | 0.005694 | 0.005178 | 0.004647 | 0.005029 | 0.003639 | 0.00532 |
| LysoPC16:0 | 0.017767 | 0.014947 | 0.015954 | 0.019641 | 0.015389 | 0.01577 | 0.016299 |
| LysoPC18:0e | 0.002105 | 0.002254 | 0.001084 | 0.001841 | 0.001802 | 0.00157 | 0.001773 |
| LysoPC18:2 | 0.001052 | 0.001246 | 0.000903 | 0.001403 | 0.001276 | 0.001356 | 0.001351 |
| LysoPC18:1 | 0.015539 | 0.013642 | 0.013546 | 0.015082 | 0.015389 | 0.015627 | 0.015793 |
| LysoPC18:0 | 0.005262 | 0.005101 | 0.005659 | 0.004823 | 0.005105 | 0.004638 | 0.005658 |
| LysoPC20:4 | 0.000371 | 0.000534 | 0.000542 | 0.000263 | 0.000601 | 0.000428 | 0.000676 |
| LysoPC22:6 | 0.000557 | 0.000475 | 0.000482 | 0.000526 | 0.000676 | 0.000143 | 0.000845 |
| LysoPC22:5 | 0.000557 | 0.000119 | 0.000301 | 0.000614 | 0.000601 | 0.000571 | 0.000929 |
| PC32:1e | 1.528972 | 1.476883 | 1.455869 | 1.473518 | 1.337764 | 1.386076 | 1.49168 |
| PC32:0e | 1.27404 | 1.24858 | 1.216676 | 1.255976 | 1.12435 | 1.143325 | 1.258507 |
| PC32:2 | 1.319046 | 1.251071 | 1.261107 | 1.260799 | 1.198365 | 1.205618 | 1.308334 |
| PC32:1 | 6.871767 | 6.654071 | 6.601267 | 6.737268 | 6.380898 | 6.507598 | 7.251152 |
| PC32:0 | 2.719004 | 2.587556 | 2.558939 | 2.655753 | 2.443798 | 2.532897 | 2.751876 |
| PC34:3e | 0.202063 | 0.183224 | 0.184889 | 0.18773 | 0.174605 | 0.17218 | 0.190946 |
| PC34:2e | 1.27274 | 1.225447 | 1.218422 | 1.225462 | 1.13606 | 1.17886 | 1.298537 |
| PC34:1e | 4.739205 | 4.564227 | 4.514868 | 4.594519 | 4.224456 | 4.352099 | 4.768679 |
| PC34:3 | 0.674102 | 0.635263 | 0.6413 | 0.627111 | 0.614271 | 0.60652 | 0.678827 |
| PC34:2 | 6.084005 | 5.850887 | 5.869232 | 5.906086 | 5.622348 | 5.738603 | 6.30799 |
| PC34:1 | 18.97335 | 18.38088 | 18.20396 | 18.67287 | 18.21577 | 18.62936 | 20.71005 |
| PC36:5e | 0.320429 | 0.312175 | 0.30608 | 0.319693 | 0.301018 | 0.309753 | 0.342623 |
| PC36:4e | 0.388217 | 0.380743 | 0.377604 | 0.373268 | 0.350487 | 0.3612 | 0.393041 |

TABLE 1-continued

Mass spectrometry analysis of free fatty acid uptake in HEK239 cells. Mfsd2a expressing HEK293 cells were incubated with 100 uM of indicated fatty acid/BSA complex overnight. Lipids extraction and phospholipid analysis by MS were performed as described in Methods section. Amount of each lipid species was normalized to internal standard and expressed as mol percent in total phospholipid analysed.

| | | | | | | | |
|---|---|---|---|---|---|---|---|
| PC36:3e | 0.706913 | 0.676902 | 0.675135 | 0.678581 | 0.641445 | 0.639557 | 0.699264 |
| PC36:2e | 1.615022 | 1.58626 | 1.566224 | 1.591891 | 1.482343 | 1.515086 | 1.633137 |
| PC36:1e | 1.245563 | 1.228176 | 1.219325 | 1.230811 | 1.173218 | 1.185996 | 1.334683 |
| PC36:6 | 0.047421 | 0.046681 | 0.046297 | 0.050243 | 0.04519 | 0.04581 | 0.053289 |
| PC36:5 | 0.058192 | 0.056231 | 0.059904 | 0.056994 | 0.054724 | 0.055086 | 0.065619 |
| PC36:4 | 0.361226 | 0.353873 | 0.35015 | 0.342842 | 0.351462 | 0.345359 | 0.369394 |
| PC36:3 | 1.197461 | 1.175682 | 1.146598 | 1.182497 | 1.114966 | 1.143468 | 1.25648 |
| PC36:2 | 8.47577 | 8.253796 | 8.16032 | 8.311064 | 7.947766 | 8.068352 | 8.800512 |
| PC36:1 | 3.067786 | 2.994219 | 2.976217 | 3.020691 | 2.948021 | 3.026747 | 3.323955 |
| PC38:5e | 0.378064 | 0.375701 | 0.380433 | 0.379669 | 0.351538 | 0.359488 | 0.376995 |
| PC38:4e | 0.506273 | 0.490238 | 0.469596 | 0.481732 | 0.443494 | 0.453677 | 0.499366 |
| PC38:3e | 0.456995 | 0.447413 | 0.442444 | 0.444204 | 0.395076 | 0.405797 | 0.437462 |
| PC38:1e | 0.324453 | 0.312708 | 0.3059 | 0.315923 | 0.289908 | 0.287205 | 0.332826 |
| PC38:7 | 0.113846 | 0.110207 | 0.105117 | 0.118636 | 0.105394 | 0.105891 | 0.120429 |
| PC38:6 | 0.190611 | 0.190164 | 0.182962 | 0.179663 | 0.190369 | 0.191303 | 0.200912 |
| PC38:5 | 0.31591 | 0.300074 | 0.301385 | 0.309785 | 0.310701 | 0.307684 | 0.325901 |
| PC38:4 | 0.723751 | 0.711068 | 0.7059 | 0.714794 | 0.701949 | 0.694572 | 0.737015 |
| PC38:3 | 0.733966 | 0.731176 | 0.733835 | 0.733296 | 0.719665 | 0.724327 | 0.774089 |
| PC40:5e | 0.136876 | 0.128476 | 0.127814 | 0.122932 | 0.119731 | 0.122303 | 0.13487 |
| PC40:4e | 0.188134 | 0.180792 | 0.180975 | 0.173788 | 0.163345 | 0.163332 | 0.176758 |
| PC40:3e | 0.179591 | 0.175098 | 0.17068 | 0.170281 | 0.162369 | 0.161976 | 0.173803 |
| PC40:2e | 0.199401 | 0.19218 | 0.181096 | 0.185713 | 0.184814 | 0.181885 | 0.204121 |
| PC40:1e | 0.18473 | 0.175098 | 0.184407 | 0.183521 | 0.179259 | 0.171253 | 0.196689 |
| PC40:7 | 0.213021 | 0.206357 | 0.217519 | 0.207371 | 0.205308 | 0.212496 | 0.220505 |
| PC40:6 | 0.149071 | 0.142356 | 0.137447 | 0.14722 | 0.143302 | 0.143139 | 0.16105 |
| PC40:5 | 0.120842 | 0.112224 | 0.107947 | 0.108552 | 0.108922 | 0.111671 | 0.119331 |
| Total PC + lysoPC | 68.30828 | 66.15077 | 65.59207 | 66.78331 | 63.70749 | 64.99328 | 71.53263 |
| % DHA in PC + lysoPC | 0.043043 | 0.040537 | 0.042736 | 0.041389 | 0.044274 | 0.044024 | 0.049113 |
| Lyso PE16:0p | 2.254311 | 2.590888 | 2.663677 | 2.476488 | 3.061623 | 2.456003 | 2.052145 |
| LysoPE16:1 | 0.122684 | 0.085227 | 0.147982 | 0.125619 | 0.130679 | 0.068222 | 0.080476 |
| LysoPE16:0 | 0.046006 | 0.017045 | 0.115097 | 0.089728 | 0.056005 | 0.034111 | 0.067064 |
| Lyso PE18:1p | 0.184025 | 0.25568 | 0.295964 | 0.233292 | 0.261358 | 0.221722 | 0.107302 |
| Lyso PE18:0p | 0.475399 | 0.409087 | 0.460388 | 0.340966 | 0.336032 | 0.562834 | 0.509683 |
| LysoPE18:2 | 0.046006 | 0.017045 | 0.032885 | 0.017945 | 0.018668 | 0.085278 | 0.040238 |
| LysoPE18:1 | 0.122684 | 0.136363 | 0.082212 | 0.089728 | 0.149348 | 0.068222 | 0.120714 |
| LysoPE18:0 | 0.092013 | 0.119317 | 0.147982 | 0.053837 | 0.168016 | 0.102333 | 0.040238 |
| Lyso PE20:0p | 0.184025 | 0.306816 | 0.197309 | 0.287129 | 0.186684 | 0.221722 | 0.228016 |
| LysoPE20:4 | 0.030671 | 0 | 0.032885 | 0.017945 | 0.018668 | 0 | 0 |
| LysoPE22:6 | 0.015335 | 0 | 0 | 0.017945 | 0 | 0.034111 | 0 |
| PE32:2 | 0.122684 | 0.079545 | 0.142501 | 0.09571 | 0.149348 | 0.136445 | 0.035767 |
| PE32:1 | 0.184025 | 0.272725 | 0.339811 | 0.239274 | 0.236467 | 0.181926 | 0.232487 |
| PE34p:2 | 0.204472 | 0.136363 | 0.153643 | 0.167492 | 0.174239 | 0.113704 | 0.223545 |
| PE34p:1 | 0.879232 | 0.954538 | 0.964624 | 0.933169 | 1.244562 | 1.216631 | 0.84053 |
| PE34:2 | 0.70543 | 0.784084 | 0.811161 | 0.921206 | 1.020541 | 0.841408 | 0.688519 |
| PE34:1 | 1.329072 | 1.670441 | 1.414051 | 1.25619 | 1.281899 | 1.239372 | 1.108785 |
| PE34:0 | 0.184025 | 0.238635 | 0.175386 | 0.179745 | 0.112011 | 0.125074 | 0.116244 |
| PE36p:4 | 0.991692 | 1.102264 | 0.986547 | 1.088698 | 1.219671 | 1.159779 | 0.724287 |
| PE36p:3 | 0.89968 | 0.89772 | 0.876931 | 0.83746 | 0.970758 | 1.114298 | 0.679578 |
| PE36p:2 | 0.623642 | 0.613631 | 0.53712 | 0.490512 | 0.672064 | 0.59126 | 0.44709 |
| PE36p:1 | 0.490734 | 0.35227 | 0.580967 | 0.550331 | 0.684509 | 0.568519 | 0.527567 |
| PE36:4 | 0.327156 | 0.284089 | 0.295964 | 0.299093 | 0.448042 | 0.318371 | 0.214603 |
| PE36:3 | 0.388498 | 0.454542 | 0.504235 | 0.263202 | 0.373369 | 0.614001 | 0.259312 |
| PE36:2 | 3.026195 | 2.931794 | 3.332337 | 3.385731 | 3.385209 | 3.365634 | 2.476881 |
| PE36:1 | 1.676675 | 2.056801 | 1.885401 | 2.057758 | 1.854398 | 1.853373 | 1.537991 |
| PE38p:6 | 1.175718 | 1.147712 | 0.887892 | 1.088698 | 1.319236 | 1.341705 | 0.876297 |
| PE38p:5 | 0.756548 | 0.829538 | 0.767315 | 0.873351 | 0.90853 | 0.784556 | 0.858414 |
| PE38p:4 | 0.889456 | 0.954538 | 1.063279 | 0.801569 | 1.257008 | 1.023335 | 0.849472 |
| PE38p:3 | 0.889456 | 0.93181 | 1.052317 | 1.052807 | 1.107661 | 1.046075 | 0.697461 |
| PE38p:2 | 0.204472 | 0.374997 | 0.361734 | 0.358912 | 0.323596 | 0.341112 | 0.277196 |
| PE38p:1 | 0.194249 | 0.238635 | 0.252118 | 0.215347 | 0.286249 | 0.170556 | 0.143069 |
| PE38p:0 | 0.092013 | 0.079545 | 0.087693 | 0.167492 | 0.149348 | 0.079593 | 0.071535 |
| PE38:7 | 0.102236 | 0.079545 | 0.076732 | 0.09571 | 0.08712 | 0.113704 | 0.071535 |
| PE38:6 | 0.194249 | 0.181817 | 0.164604 | 0.251238 | 0.186684 | 0.216037 | 0.134127 |
| PE38:5 | 0.644089 | 0.647722 | 0.570005 | 0.586222 | 0.808965 | 0.682223 | 0.456032 |
| PE38:4 | 1.226836 | 1.215899 | 1.304434 | 1.06477 | 1.319236 | 1.239372 | 1.055133 |
| PE38:3 | 0.725878 | 0.886356 | 0.898854 | 0.885314 | 0.90853 | 0.841408 | 0.777937 |
| PE38:2 | 0.388498 | 0.465285 | 0.438465 | 0.382639 | 0.497825 | 0.397964 | 0.205662 |
| PE38:1 | 0.429392 | 0.488633 | 0.482312 | 0.610149 | 0.560053 | 0.488927 | 0.402381 |
| PE40p:6 | 0.500958 | 0.681812 | 0.679621 | 0.598186 | 0.721846 | 0.807297 | 0.500741 |
| PE40p:5 | 0.265815 | 0.35227 | 0.339811 | 0.382839 | 0.311141 | 0.272889 | 0.250371 |
| PE40p:4 | 0.255591 | 0.306816 | 0.449427 | 0.299093 | 0.410705 | 0.523038 | 0.330847 |
| PE40:6 | 0.296485 | 0.409087 | 0.394619 | 0.358912 | 0.423151 | 0.341112 | 0.250371 |

TABLE 1-continued

Mass spectrometry analysis of free fatty acid uptake in HEK239 cells. Mfsd2a expressing HEK293 cells were incubated with 100 uM of indicated fatty acid/BSA complex overnight. Lipids extraction and phospholipid analysis by MS were performed as described in Methods section. Amount of each lipid species was normalized to internal standard and expressed as mol percent in total phospholipid analysed.

| | | | | | | | |
|---|---|---|---|---|---|---|---|
| PE40:5 | 0.245367 | 0.181817 | 0.186348 | 0.167492 | 0.211576 | 0.159185 | 0.187778 |
| PE40:4 | 0.194249 | 0.136363 | 0.109616 | 0.203383 | 0.174239 | 0.193297 | 0.152011 |
| PE40:3 | 0.11246 | 0.181817 | 0.197309 | 0.131601 | 0.248912 | 0.181926 | 0.116244 |
| PE42p:7 | 0.173802 | 0.15909 | 0.208271 | 0.334984 | 0.211576 | 0.307 | 0.205662 |
| PE42p:6 | 0.122684 | 0.170453 | 0.142501 | 0.287129 | 0.211576 | 0.238778 | 0.19672 |
| PE42p:5 | 0.071566 | 0.090908 | 0.076732 | 0.083746 | 0.124456 | 0.079593 | 0.09836 |
| PE42p:4 | 0.102236 | 0.079545 | 0.032885 | 0.155528 | 0.186684 | 0.034111 | 0.053651 |
| PE42:7 | 0.061342 | 0.034091 | 0.054808 | 0.071782 | 0.037337 | 0.022741 | 0.008942 |
| PE42:6 | 0.051118 | 0.011363 | 0.010962 | 0.071782 | 0.049783 | 0.034111 | 0.035767 |
| PE42:5 | 0.061342 | 0.079545 | 0.043847 | 0.083746 | 0.124456 | 0.045482 | 0.053651 |
| PE42:4 | 0.040895 | 0.056818 | 0.054808 | 0.083746 | 0.074674 | 0.045482 | 0.017883 |
| Total PE + lysoPE | 25.92202 | 28.07363 | 28.4564 | 28.02499 | 31.2074 | 29.22189 | 22.58701 |
| % DHA in PE + lysoPE | 10.39243 | 10.24084 | 9.206471 | 11.33404 | 10.40878 | 11.82879 | 10.09501 |
| LPI16:0 | 0.003305 | 0.002531 | 0.002415 | 0.003238 | 0.003369 | 0.003584 | 0.002627 |
| LPI18:0 | 0.028367 | 0.029305 | 0.027206 | 0.028936 | 0.026492 | 0.031168 | 0.030698 |
| LPI20:4 | 0.002479 | 0.002664 | 0.001017 | 0.002023 | 0.001684 | 0.002338 | 0.002462 |
| LPI22:6 | 0.0084 | 0.008125 | 0.007119 | 0.009713 | 0.005972 | 0.00748 | 0.009521 |
| PI 32:2 | 0.001377 | 0.001465 | 0.001144 | 0.002023 | 0.000459 | 0.001403 | 0.00197 |
| PI 32:1 | 0.0084 | 0.007859 | 0.005339 | 0.006273 | 0.006125 | 0.00561 | 0.011163 |
| PI 34:2 | 0.039245 | 0.032768 | 0.037122 | 0.036018 | 0.03032 | 0.030233 | 0.034474 |
| PI 34:1 | 0.087028 | 0.079522 | 0.078057 | 0.072642 | 0.061252 | 0.083685 | 0.086677 |
| PI 36:4 | 0.023134 | 0.024376 | 0.026951 | 0.018414 | 0.018529 | 0.020259 | 0.02643 |
| PI 36:3 | 0.118286 | 0.105097 | 0.108568 | 0.096722 | 0.087897 | 0.096152 | 0.107033 |
| PI 36:2 | 0.310105 | 0.293845 | 0.302566 | 0.281262 | 0.258945 | 0.280664 | 0.301893 |
| PI 36:1 | 0.186586 | 0.171831 | 0.154593 | 0.154593 | 0.140268 | 0.163785 | 0.186651 |
| PI 38:6 | 0.007574 | 0.00706 | 0.007246 | 0.006475 | 0.006125 | 0.006545 | 0.006074 |
| PI 38:5 | 0.049848 | 0.049818 | 0.048436 | 0.043505 | 0.041039 | 0.044258 | 0.053024 |
| PI 38:4 | 0.416274 | 0.394546 | 0.389522 | 0.359165 | 0.355417 | 0.393334 | 0.441758 |
| PI 38:3 | 1.302938 | 1.210946 | 1.152929 | 1.138402 | 1.056757 | 1.189509 | 1.302292 |
| PI 38:2 | 0.312584 | 0.292247 | 0.279556 | 0.275798 | 0.234444 | 0.277859 | 0.304191 |
| PI 40:6 | 0.006472 | 0.007459 | 0.006992 | 0.006273 | 0.006738 | 0.006389 | 0.006238 |
| PI 40:5 | 0.005646 | 0.005595 | 0.006484 | 0.005868 | 0.005513 | 0.004208 | 0.006402 |
| PI 40:4 | 0.021068 | 0.019714 | 0.019959 | 0.021246 | 0.016998 | 0.017765 | 0.017237 |
| PI 40:3 | 0.043101 | 0.037297 | 0.035977 | 0.03622 | 0.035986 | 0.036154 | 0.039563 |
| Total PI + lysoPI | 2.982215 | 2.784069 | 2.699321 | 2.604808 | 2.400329 | 2.702382 | 2.978379 |
| % DHA in PI and lysoPI | 0.014046 | 0.014519 | 0.014238 | 0.012748 | 0.012863 | 0.012935 | 0.012312 |
| PS:34:2 | 0.032482 | 0.031962 | 0.029317 | 0.028345 | 0.031298 | 0.030728 | 0.030126 |
| PS:34:1 | 0.289775 | 0.344476 | 0.361246 | 0.27678 | 0.283957 | 0.363314 | 0.317147 |
| PS:36:4 | 0.003419 | 0.003995 | 0.004969 | 0.003335 | 0.004552 | 0.001808 | 0.002739 |
| PS:36:3 | 0.018805 | 0.02264 | 0.018882 | 0.012505 | 0.014795 | 0.013255 | 0.019171 |
| PS:36:2 | 0.467145 | 0.483864 | 0.571931 | 0.425174 | 0.446136 | 0.535633 | 0.454632 |
| PS:36:1 | 1.289458 | 1.357927 | 1.479269 | 1.190487 | 1.210372 | 1.397826 | 1.339248 |
| PS:38:5 | 0.008121 | 0.011986 | 0.010932 | 0.010838 | 0.010812 | 0.013858 | 0.011503 |
| PS:38:4 | 0.065392 | 0.083012 | 0.082485 | 0.07253 | 0.076253 | 0.068686 | 0.077233 |
| PS:38:3 | 0.125655 | 0.155369 | 0.14907 | 0.127552 | 0.132589 | 0.165691 | 0.136937 |
| PS:38:2 | 0.232504 | 0.245927 | 0.252922 | 0.198415 | 0.208273 | 0.234979 | 0.23115 |
| PS:40:7 | 0.011112 | 0.011986 | 0.008944 | 0.015006 | 0.008536 | 0.00964 | 0.011503 |
| PS:40:6 | 0.094455 | 0.096773 | 0.122237 | 0.094205 | 0.098446 | 0.100619 | 0.113384 |
| PS:40:5 | 0.050005 | 0.056377 | 0.058634 | 0.054189 | 0.068286 | 0.044586 | 0.061896 |
| PS:40:4 | 0.099156 | 0.085231 | 0.101367 | 0.077532 | 0.090479 | 0.101824 | 0.095308 |
| PS(sum) | 2.787485 | 2.991524 | 3.252206 | 2.586892 | 2.684784 | 3.082448 | 2.901978 |
| % DHA in PS | 0.105567 | 0.108758 | 0.131181 | 0.109211 | 0.106982 | 0.11026 | 0.124887 |

| | Mfsd2a | Mfsd2a | Mfsd2a | mock | mock | mock |
|---|---|---|---|---|---|---|
| | | | Palmitic acid | | | |
| LysoPC16:0e | 0.004306 | 0.004045 | 0.00338 | 0.003391 | 0.004221 | 0.003565 |
| LysoPC16:1 | 0.006002 | 0.005731 | 0.005746 | 0.006406 | 0.00591 | 0.006781 |
| LysoPC16:0 | 0.022312 | 0.022384 | 0.018386 | 0.023834 | 0.021275 | 0.020084 |
| LysoPC18:0e | 0.002349 | 0.002697 | 0.00142 | 0.002449 | 0.002111 | 0.001826 |
| LysoPC18:2 | 0.001631 | 0.001146 | 0.001487 | 0.00179 | 0.001266 | 0.001826 |
| LysoPC18:1 | 0.013113 | 0.012541 | 0.012505 | 0.015638 | 0.015028 | 0.016171 |
| LysoPC18:0 | 0.005806 | 0.006675 | 0.006016 | 0.0065 | 0.007261 | 0.008694 |
| LysoPC20:4 | 0.000587 | 0.000539 | 0.000608 | 0.000565 | 0.000507 | 0.000435 |
| LysoPC22:6 | 0.000652 | 0.000809 | 0.000879 | 0.000659 | 0.000929 | 0.000348 |
| LysoPC22:5 | 0.000457 | 0.000944 | 0.000608 | 0.000565 | 0.000507 | 0.000609 |
| PC32:1e | 2.402963 | 2.511897 | 2.300319 | 2.440081 | 2.388089 | 2.446029 |

TABLE 1-continued

Mass spectrometry analysis of free fatty acid uptake in HEK239 cells. Mfsd2a expressing HEK293 cells were incubated with 100 uM of indicated fatty acid/BSA complex overnight. Lipids extraction and phospholipid analysis by MS were performed as described in Methods section. Amount of each lipid species was normalized to internal standard and expressed as mol percent in total phospholipid analysed.

| | | | | | | |
|---|---|---|---|---|---|---|
| PC32:0e | 1.809138 | 1.851155 | 1.70202 | 1.800622 | 1.766372 | 1.854301 |
| PC32:2 | 1.487629 | 1.518964 | 1.412233 | 1.525828 | 1.443356 | 1.528442 |
| PC32:1 | 9.10408 | 9.243977 | 8.73148 | 9.659338 | 9.461091 | 9.558068 |
| PC32:0 | 2.455808 | 2.44407 | 2.298292 | 2.544554 | 2.525198 | 2.566879 |
| PC34:3e | 0.228344 | 0.231866 | 0.217459 | 0.238243 | 0.226854 | 0.236743 |
| PC34:2e | 1.486259 | 1.536966 | 1.423386 | 1.577735 | 1.538167 | 1.559481 |
| PC34:1e | 4.812907 | 4.891173 | 4.611049 | 4.963251 | 4.846505 | 4.905013 |
| PC34:3 | 0.615029 | 0.629525 | 0.597556 | 0.639082 | 0.601286 | 0.624679 |
| PC34:2 | 6.060122 | 6.220208 | 5.829143 | 6.328461 | 6.182133 | 6.317996 |
| PC34:1 | 18.55544 | 18.94339 | 17.94425 | 19.9344 | 19.95717 | 20.13336 |
| PC36:5e | 0.325292 | 0.334281 | 0.308985 | 0.344976 | 0.329517 | 0.346725 |
| PC36:4e | 0.4287 | 0.444787 | 0.417275 | 0.428818 | 0.411326 | 0.434537 |
| PC36:3e | 0.801162 | 0.822354 | 0.760329 | 0.804788 | 0.784069 | 0.796216 |
| PC36:2e | 1.608652 | 1.633313 | 1.503961 | 1.666664 | 1.628757 | 1.643206 |
| PC36:1e | 1.431718 | 1.425044 | 1.341932 | 1.47232 | 1.428666 | 1.480102 |
| PC36:6 | 0.051084 | 0.048207 | 0.043262 | 0.046914 | 0.052935 | 0.05486 |
| PC36:5 | 0.052323 | 0.056635 | 0.051644 | 0.060479 | 0.055131 | 0.063033 |
| PC36:4 | 0.326793 | 0.319313 | 0.308039 | 0.338005 | 0.334245 | 0.33464 |
| PC36:3 | 1.148571 | 1.164591 | 1.070733 | 1.196301 | 1.137479 | 1.173197 |
| PC36:2 | 5.692292 | 5.815403 | 5.438975 | 5.976042 | 5.823743 | 5.921975 |
| PC36:1 | 2.539708 | 2.547429 | 2.40915 | 2.713651 | 2.676152 | 2.73146 |
| PC38:5e | 0.351324 | 0.362531 | 0.326357 | 0.357788 | 0.344882 | 0.355159 |
| PC38:4e | 0.416761 | 0.414312 | 0.384288 | 0.422412 | 0.398493 | 0.404455 |
| PC38:3e | 0.416434 | 0.406761 | 0.379759 | 0.417702 | 0.384732 | 0.397673 |
| PC38:1e | 0.35165 | 0.355519 | 0.337781 | 0.368433 | 0.349948 | 0.364287 |
| PC38:7 | 0.11763 | 0.11954 | 0.11363 | 0.118132 | 0.114905 | 0.121806 |
| PC38:6 | 0.168257 | 0.172669 | 0.159055 | 0.173995 | 0.178478 | 0.184665 |
| PC38:5 | 0.226778 | 0.245149 | 0.22726 | 0.247663 | 0.242389 | 0.256131 |
| PC38:4 | 0.440704 | 0.445529 | 0.422818 | 0.471587 | 0.439271 | 0.456707 |
| PC38:3 | 0.514557 | 0.531695 | 0.506638 | 0.55119 | 0.534082 | 0.547735 |
| PC40:5e | 0.117238 | 0.116911 | 0.111467 | 0.113893 | 0.115327 | 0.119719 |
| PC40:4e | 0.123697 | 0.127159 | 0.120525 | 0.123408 | 0.119295 | 0.129718 |
| PC40:3e | 0.139681 | 0.143408 | 0.133233 | 0.140082 | 0.138713 | 0.144932 |
| PC40:2e | 0.194353 | 0.199234 | 0.178794 | 0.20009 | 0.200429 | 0.206053 |
| PC40:1e | 0.179283 | 0.187907 | 0.167978 | 0.190293 | 0.187427 | 0.196924 |
| PC40:7 | 0.169431 | 0.16532 | 0.161894 | 0.177764 | 0.171133 | 0.17684 |
| PC40:6 | 0.113128 | 0.120349 | 0.105045 | 0.131509 | 0.124782 | 0.12824 |
| PC40:5 | 0.082334 | 0.087649 | 0.079967 | 0.090436 | 0.083498 | 0.089029 |
| Total PC + lysoPC | 67.60447 | 68.89371 | 64.689 | 71.05873 | 69.78503 | 71.05135 |
| % DHA in PC + lysoPC | 0.038231 | 0.037897 | 0.034213 | 0.040254 | 0.038369 | 0.039393 |
| Lyso PE16:0p | 2.77737 | 2.934341 | 3.346767 | 2.64938 | 2.594178 | 2.175334 |
| LysoPE16:1 | 0.173585 | 0.132709 | 0.12528 | 0.138711 | 0.117917 | 0.135114 |
| LysoPE16:0 | 0.104151 | 0.088473 | 0.035794 | 0.041613 | 0.103177 | 0.040534 |
| Lyso PE18:1p | 0.12151 | 0.176945 | 0.286354 | 0.208066 | 0.132657 | 0.121603 |
| Lyso PE18:0p | 0.433964 | 0.545581 | 0.787475 | 0.416133 | 0.41271 | 0.418853 |
| LysoPE18:2 | 0.034717 | 0.014745 | 0 | 0.013871 | 0 | 0.013511 |
| LysoPE18:1 | 0.12151 | 0.073727 | 0.071588 | 0.069356 | 0.103177 | 0.108091 |
| LysoPE18:0 | 0.104151 | 0.088473 | 0.161074 | 0.12484 | 0.132657 | 0.067557 |
| Lyso PE20:0p | 0.260378 | 0.1622 | 0.322149 | 0.180324 | 0.280053 | 0.18916 |
| LysoPE20:4 | 0.017358 | 0 | 0.017897 | 0 | 0 | 0.027023 |
| LysoPE22:6 | 0 | 0.029491 | 0.017897 | 0.013871 | 0 | 0 |
| PE32:2 | 0.092579 | 0.117964 | 0.119314 | 0.110969 | 0.147396 | 0.081068 |
| PE32:1 | 0.43975 | 0.314569 | 0.369875 | 0.397638 | 0.294793 | 0.360304 |
| PE34p:2 | 0.28931 | 0.245757 | 0.429532 | 0.258927 | 0.265314 | 0.270228 |
| PE34p:1 | 1.041514 | 1.071501 | 1.479498 | 0.970977 | 1.041602 | 0.810684 |
| PE34:2 | 1.087803 | 0.963368 | 1.014172 | 0.739792 | 0.943337 | 0.792669 |
| PE34:1 | 1.562271 | 1.425392 | 1.336321 | 1.13471 | 1.326568 | 1.143964 |
| PE34:0 | 0.185158 | 0.157285 | 0.071588 | 0.166453 | 0.186702 | 0.153129 |
| PE36p:4 | 1.272961 | 1.140314 | 1.431772 | 0.961729 | 0.943337 | 0.945797 |
| PE36p:3 | 0.844783 | 0.806084 | 1.169281 | 0.730545 | 0.727156 | 0.954805 |
| PE36p:2 | 0.786921 | 0.599648 | 0.680092 | 0.453123 | 0.589586 | 0.648547 |
| PE36p:1 | 0.555474 | 0.422703 | 0.560777 | 0.49936 | 0.393057 | 0.360304 |
| PE36:4 | 0.312454 | 0.255588 | 0.346011 | 0.221937 | 0.255487 | 0.171144 |
| PE36:3 | 0.462895 | 0.511175 | 0.477257 | 0.480865 | 0.363578 | 0.414349 |
| PE36:2 | 2.152462 | 2.192155 | 2.266972 | 1.821738 | 1.935807 | 1.702435 |
| PE36:1 | 1.712712 | 1.464713 | 1.861304 | 1.322378 | 1.424833 | 1.179995 |
| PE38p:6 | 1.215099 | 1.297598 | 1.348252 | 0.970977 | 1.23813 | 1.107934 |
| PE38p:5 | 0.948935 | 0.756932 | 0.859063 | 0.63807 | 0.727156 | 0.702592 |
| PE38p:4 | 0.914218 | 0.943708 | 1.08576 | 1.035709 | 0.854899 | 0.999843 |
| PE38p:3 | 0.97208 | 0.865066 | 0.942584 | 0.776782 | 0.835247 | 0.765646 |
| PE38p:2 | 0.393461 | 0.235927 | 0.393737 | 0.231185 | 0.294793 | 0.342288 |
| PE38p:1 | 0.150441 | 0.176945 | 0.274423 | 0.203443 | 0.226008 | 0.243205 |
| PE38p:0 | 0.127296 | 0.117964 | 0.107383 | 0.055484 | 0.088438 | 0.090076 |
| PE38:7 | 0.081007 | 0.078642 | 0.047726 | 0.147959 | 0.108091 | 0.072061 |

TABLE 1-continued

Mass spectrometry analysis of free fatty acid uptake in HEK239 cells. Mfsd2a expressing HEK293 cells were incubated with 100 uM of indicated fatty acid/BSA complex overnight. Lipids extraction and phospholipid analysis by MS were performed as described in Methods section. Amount of each lipid species was normalized to internal standard and expressed as mol percent in total phospholipid analysed.

| | | | | | | |
|---|---|---|---|---|---|---|
| PE38:6 | 0.208303 | 0.108133 | 0.143177 | 0.166453 | 0.13757 | 0.153129 |
| PE38:5 | 0.48604 | 0.422703 | 0.548846 | 0.379143 | 0.540454 | 0.468395 |
| PE38:4 | 0.902645 | 0.973199 | 1.300526 | 0.869256 | 0.923685 | 0.864729 |
| PE38:3 | 0.613336 | 0.66846 | 0.620435 | 0.63807 | 0.795941 | 0.549463 |
| PE38:2 | 0.312454 | 0.33423 | 0.357943 | 0.258927 | 0.255487 | 0.342288 |
| PE38:1 | 0.497612 | 0.33423 | 0.572709 | 0.379143 | 0.304619 | 0.306258 |
| PE40p:6 | 0.601764 | 0.609478 | 0.489189 | 0.527102 | 0.727156 | 0.648547 |
| PE40p:5 | 0.28931 | 0.206436 | 0.33408 | 0.231185 | 0.284966 | 0.315266 |
| PE40p:4 | 0.173585 | 0.176945 | 0.310217 | 0.295917 | 0.216182 | 0.29725 |
| PE40:6 | 0.428178 | 0.35389 | 0.369875 | 0.305164 | 0.383231 | 0.270228 |
| PE40:5 | 0.150441 | 0.186775 | 0.190903 | 0.157206 | 0.13757 | 0.243205 |
| PE40:4 | 0.115724 | 0.117964 | 0.190903 | 0.120216 | 0.157223 | 0.072061 |
| PE40:3 | 0.081007 | 0.098303 | 0.107383 | 0.120216 | 0.117917 | 0.162137 |
| PE42p:7 | 0.092579 | 0.167115 | 0.190903 | 0.194196 | 0.127744 | 0.162137 |
| PE42p:6 | 0.081007 | 0.088473 | 0.16704 | 0.157206 | 0.167049 | 0.144122 |
| PE42p:5 | 0.034717 | 0.098303 | 0.035794 | 0.129464 | 0.088438 | 0.03603 |
| PE42p:4 | 0.092579 | 0.108133 | 0.107383 | 0.073979 | 0.058958 | 0.081068 |
| PE42:7 | 0.069434 | 0.058982 | 0.095452 | 0 | 0.029479 | 0.027023 |
| PE42:6 | 0.034717 | 0.01966 | 0.059657 | 0.03699 | 0.058958 | 0.018015 |
| PE42:5 | 0.011572 | 0.00983 | 0.023863 | 0.083227 | 0.019653 | 0.027023 |
| PE42:4 | 0.069434 | 0.01966 | 0.047726 | 0.03699 | 0.058958 | 0.099083 |
| Total PE + lysoPE | 26.98099 | 25.51943 | 29.97773 | 23.19248 | 24.54151 | 22.75319 |
| % DHA in PE + lysoPE | 10.42248 | 11.01695 | 9.771145 | 10.86523 | 12.13213 | 11.44101 |
| LPI16:0 | 0.004365 | 0.003505 | 0.0022 | 0.004053 | 0.002611 | 0.002621 |
| LPI18:0 | 0.02606 | 0.026498 | 0.025882 | 0.032597 | 0.026109 | 0.032266 |
| LPI20:4 | 0.001669 | 0.001542 | 0.001553 | 0.002114 | 0.002121 | 0.002948 |
| LPI22:6 | 0.007831 | 0.008132 | 0.006212 | 0.009339 | 0.008648 | 0.007698 |
| PI 32:2 | 0.002439 | 0.002103 | 0.001294 | 0.001586 | 0.001469 | 0.001965 |
| PI 32:1 | 0.015148 | 0.015282 | 0.0154 | 0.016739 | 0.018602 | 0.017853 |
| PI 34:2 | 0.062904 | 0.069819 | 0.064577 | 0.065018 | 0.060376 | 0.073049 |
| PI 34:1 | 0.110274 | 0.113981 | 0.102883 | 0.10713 | 0.12271 | 0.129882 |
| PI 36:4 | 0.038641 | 0.042901 | 0.039212 | 0.04176 | 0.039652 | 0.041602 |
| PI 36:3 | 0.168428 | 0.186464 | 0.158012 | 0.169506 | 0.166279 | 0.178527 |
| PI 36:2 | 0.371902 | 0.372087 | 0.340224 | 0.359275 | 0.371884 | 0.38981 |
| PI 36:1 | 0.150327 | 0.153798 | 0.154259 | 0.154352 | 0.164321 | 0.176889 |
| PI 38:6 | 0.006419 | 0.006589 | 0.006082 | 0.0074 | 0.009628 | 0.007698 |
| PI 38:5 | 0.051863 | 0.048228 | 0.049435 | 0.053918 | 0.048301 | 0.048153 |
| PI 38:4 | 0.360734 | 0.381059 | 0.338542 | 0.363503 | 0.396687 | 0.399801 |
| PI 38:3 | 1.005304 | 1.022327 | 0.963603 | 0.929639 | 0.991146 | 1.026282 |
| PI 38:2 | 0.356369 | 0.36003 | 0.319001 | 0.344121 | 0.347407 | 0.363113 |
| PI 40:6 | 0.008088 | 0.005328 | 0.005047 | 0.007048 | 0.006527 | 0.006715 |
| PI 40:5 | 0.006419 | 0.00673 | 0.006341 | 0.004934 | 0.004895 | 0.009172 |
| PI 40:4 | 0.013736 | 0.013599 | 0.014494 | 0.015153 | 0.015991 | 0.011956 |
| PI 40:3 | 0.027215 | 0.026357 | 0.023424 | 0.025549 | 0.026272 | 0.028007 |
| Total PI + lysoPI | 2.796135 | 2.866357 | 2.637678 | 2.714735 | 2.831637 | 2.956008 |
| % DHA in PI and lysoPI | 0.014506 | 0.011917 | 0.011129 | 0.014449 | 0.016155 | 0.014413 |
| PS:34:2 | 0.040423 | 0.038542 | 0.049684 | 0.047385 | 0.044923 | 0.048667 |
| PS:34:1 | 0.403402 | 0.43902 | 0.43147 | 0.496822 | 0.448646 | 0.543445 |
| PS:36:4 | 0.004537 | 0.005316 | 0.006102 | 0.00359 | 0.006418 | 0.006239 |
| PS:36:3 | 0.025986 | 0.021707 | 0.02615 | 0.025846 | 0.02217 | 0.026205 |
| PS:36:2 | 0.398865 | 0.383201 | 0.387015 | 0.459489 | 0.414808 | 0.461086 |
| PS:36:1 | 1.063364 | 1.165994 | 1.106567 | 1.269338 | 1.209419 | 1.374522 |
| PS:38:5 | 0.007425 | 0.010632 | 0.014382 | 0.015077 | 0.007001 | 0.014974 |
| PS:38:4 | 0.056509 | 0.075311 | 0.061016 | 0.074667 | 0.081678 | 0.076744 |
| PS:38:3 | 0.149729 | 0.147078 | 0.146874 | 0.152206 | 0.144687 | 0.156607 |
| PS:38:2 | 0.219437 | 0.208656 | 0.230989 | 0.23118 | 0.214697 | 0.26018 |
| PS:40:7 | 0.017324 | 0.012404 | 0.012639 | 0.010769 | 0.014585 | 0.01435 |
| PS:40:6 | 0.108894 | 0.097462 | 0.101112 | 0.098359 | 0.103848 | 0.124786 |
| PS:40:5 | 0.049085 | 0.056262 | 0.061888 | 0.066052 | 0.065342 | 0.05865 |
| PS:40:4 | 0.073421 | 0.05892 | 0.059708 | 0.083282 | 0.063592 | 0.073 |
| PS(sum) | 2.6184 | 2.720505 | 2.695596 | 3.034062 | 2.841814 | 3.239456 |
| % DHA in PS | 0.126218 | 0.109866 | 0.113751 | 0.109129 | 0.118433 | 0.139137 |

TABLE 2

Lipidomic Analysis. Complete data set for FIG. 2. Lipids extraction and phospholipid analysis by MS were performed as described in Methods section. Amount of each lipid species was normalized to internal standard and expressed as mol percent in total phospholipid analysed.

| lipid species | brain-WT1 | brain-WT2 | brain-WT3 | brain-WT4 | brain-WT5 | brain-KO1 | brain-KO2 | brain-KO3 | brain-KO4 |
|---|---|---|---|---|---|---|---|---|---|
| LysoPC16:0e | 0.00295901 | 0.003426309 | 0.00389749 | 0.00332961 | 0.003526932 | 0.00498458 | 0.00493272 | 0.00432922 | 0.00424764 |
| LysoPC16:1 | 0.00161005 | 0.001361739 | 0.00101497 | 0.00106876 | 0.001376362 | 0.00185377 | 0.00144187 | 0.00159108 | 0.00143766 |
| LysoPC16:0 | 0.06588142 | 0.058115467 | 0.05493027 | 0.05680891 | 0.053291068 | 0.07419197 | 0.06621222 | 0.07611293 | 0.06263628 |
| LysoPC18:0e | 0.00126193 | 0.001317811 | 0.00125857 | 0.00115098 | 0.001118294 | 0.00168899 | 0.00151776 | 0.00155408 | 0.00147034 |
| LysoPC18:2 | 0.00191465 | 0.001801007 | 0.00146156 | 0.00143872 | 0.002408634 | 0.004861 | 0.00295963 | 0.00477325 | 0.00212382 |
| LysoPC18:1 | 0.0311566 | 0.029431115 | 0.02582088 | 0.02569144 | 0.029376754 | 0.03732255 | 0.03441518 | 0.0329687 | 0.02963542 |
| LysoPC18:0 | 0.03098255 | 0.031056412 | 0.02967777 | 0.03033645 | 0.029935903 | 0.04572631 | 0.04052416 | 0.05017459 | 0.03659501 |
| LysoPC20:4 | 0.01105276 | 0.0081265 | 0.00816037 | 0.00768688 | 0.008000112 | 0.0088569 | 0.00770262 | 0.00814042 | 0.00695959 |
| LysoPC22:6 | 0.01427286 | 0.008697553 | 0.00868816 | 0.00994772 | 0.009505508 | 0.00366634 | 0.00235252 | 0.00403321 | 0.00245056 |
| LysoPC22:5 | 0.00161005 | 0.000790687 | 0.00093377 | 0.00061659 | 0.001247328 | 0.00144182 | 0.00151776 | 0.00088805 | 0.00133964 |
| PC32:0p | 0.09129408 | 0.095365591 | 0.0863132 | 0.08554222 | 0.098625038 | 0.10933119 | 0.10074123 | 0.10297631 | 0.09295786 |
| PC32:0e | 0.19133463 | 0.198462344 | 0.18569923 | 0.17836025 | 0.192518824 | 0.23019695 | 0.20740173 | 0.22745074 | 0.21179361 |
| PC32:2 | 0.09551501 | 0.108148359 | 0.09427058 | 0.09162595 | 0.108388614 | 0.11864123 | 0.11144143 | 0.12773059 | 0.11880308 |
| PC32:1 | 1.64716617 | 1.683503621 | 1.59435824 | 1.56105298 | 1.681184824 | 2.12462556 | 2.00939872 | 2.17430622 | 2.03291805 |
| PC32:0 | 10.0774647 | 10.70892798 | 9.85387362 | 9.97481453 | 10.16070136 | 10.4705419 | 9.78275173 | 10.1153601 | 9.32561703 |
| PC34:3e | 0.11044059 | 0.115176686 | 0.11189049 | 0.10893171 | 0.113291908 | 0.11847645 | 0.10996162 | 0.11004368 | 0.10821667 |
| PC34:2e | 0.07036345 | 0.071601068 | 0.0683279 | 0.06877084 | 0.075398906 | 0.06574702 | 0.05896493 | 0.06297725 | 0.05672226 |
| PC34:1e | 0.48505961 | 0.507005838 | 0.47313923 | 0.50120916 | 0.546889372 | 0.47596555 | 0.44796649 | 0.48265291 | 0.41280476 |
| PC34:3 | 0.0229323 | 0.02367667 | 0.02342555 | 0.02503374 | 0.024559485 | 0.03608671 | 0.03096228 | 0.03822297 | 0.03476526 |
| PC34:2 | 0.64924099 | 0.656972736 | 0.61377372 | 0.65256257 | 0.678547138 | 0.77157996 | 0.72066978 | 0.76112929 | 0.73170412 |
| PC34:1 | 19.3544745 | 19.86591364 | 18.5624938 | 18.8420196 | 19.68715727 | 21.5646095 | 20.1494992 | 20.7563692 | 18.7889228 |
| PC36:5e | 0.24951393 | 0.246386737 | 0.23214434 | 0.24075962 | 0.250455118 | 0.28197891 | 0.25373131 | 0.26138149 | 0.23986067 |
| PC36:4e | 0.03951145 | 0.044410232 | 0.0397057 | 0.0404075 | 0.045075901 | 0.0425955 | 0.03942378 | 0.03974005 | 0.03770593 |
| PC36:3e | 0.02806705 | 0.028157228 | 0.0251713 | 0.02515706 | 0.029032664 | 0.0345625 | 0.03058284 | 0.03655789 | 0.0324454 |
| PC36:2e | 0.09085893 | 0.08135287 | 0.07880241 | 0.08546001 | 0.092646458 | 0.07637529 | 0.07095522 | 0.07614993 | 0.0674067 |
| PC36:1e | 0.26565793 | 0.267339933 | 0.25309336 | 0.25966852 | 0.288090052 | 0.22636582 | 0.2239453 | 0.22833879 | 0.1957833 |
| PC36:6 | 0.02123523 | 0.019547532 | 0.01770911 | 0.01705912 | 0.020860506 | 0.01713707 | 0.01494942 | 0.01483776 | 0.01411522 |
| PC36:5 | 0.02663106 | 0.026356221 | 0.02448112 | 0.02454046 | 0.028301473 | 0.03476847 | 0.03202471 | 0.03015656 | 0.03264144 |
| PC36:4 | 2.12730861 | 2.206586746 | 2.02450327 | 1.97700767 | 2.042222131 | 2.36631587 | 2.17092618 | 2.07584415 | 2.04128264 |
| PC36:3 | 0.46469467 | 0.483944145 | 0.44642518 | 0.51654181 | 0.522114836 | 0.84346502 | 0.81651625 | 0.99501836 | 0.77548743 |
| PC36:2 | 1.64890677 | 1.609047293 | 1.53699203 | 1.60368022 | 1.712497085 | 1.95379041 | 1.83633627 | 2.01649307 | 1.76528439 |
| PC36:1 | 6.40324807 | 6.785628678 | 6.46841501 | 6.60549526 | 6.74172874 | 6.6511593 | 6.37242381 | 6.58278774 | 5.55662527 |
| PC38:5e | 0.10587154 | 0.109685808 | 0.10332413 | 0.10662975 | 0.123012476 | 0.11048465 | 0.10271432 | 0.10090421 | 0.0951797 |
| PC38:4e | 0.05334916 | 0.058818301 | 0.05290033 | 0.05051965 | 0.052172775 | 0.05754924 | 0.05038959 | 0.0522467 | 0.04734479 |
| PC38:3e | 0.02445533 | 0.021743882 | 0.02127381 | 0.02030651 | 0.022150846 | 0.03151408 | 0.02967218 | 0.03652088 | 0.02725021 |
| PC38:1e | 0.06562033 | 0.063562421 | 0.06434921 | 0.06186499 | 0.066753624 | 0.05730207 | 0.05699184 | 0.05657592 | 0.04734479 |
| PC38:7 | 0.04203531 | 0.043751327 | 0.043116 | 0.04361379 | 0.047570557 | 0.02793012 | 0.02432208 | 0.02501329 | 0.02287188 |
| PC38:6 | 2.20271976 | 2.26382367 | 2.07232874 | 2.23338767 | 2.364119104 | 0.65454533 | 0.5815672 | 0.51843376 | 0.50706958 |
| PC38:5 | 1.04009103 | 1.056664826 | 0.97441349 | 0.96961549 | 0.992056901 | 1.36173771 | 1.21913969 | 1.18550419 | 1.20276683 |
| PC38:4 | 2.66106126 | 2.84067651 | 2.65545032 | 2.63318761 | 2.632983089 | 2.9502532 | 2.69485649 | 2.71734625 | 2.4905517 |
| PC38:3 | 0.42370372 | 0.454732668 | 0.42563856 | 0.45159385 | 0.46998507 | 0.74678065 | 0.73266008 | 0.88301357 | 0.65733783 |
| PC40:5e | 0.02153983 | 0.021128905 | 0.02021824 | 0.01993656 | 0.030796129 | 0.02718862 | 0.02568807 | 0.02723341 | 0.02238177 |
| PC40:4e | 0.01662266 | 0.017526887 | 0.01774171 | 0.0149627 | 0.016344313 | 0.02133894 | 0.02014825 | 0.02075807 | 0.01702321 |
| PC40:3e | 0.01092222 | 0.010322855 | 0.01063691 | 0.0103999 | 0.009763475 | 0.01466932 | 0.01377366 | 0.01620684 | 0.01238349 |
| PC40:2e | 0.01871137 | 0.017395106 | 0.01648314 | 0.01574371 | 0.018752952 | 0.01709587 | 0.01563292 | 0.01653985 | 0.01414789 |
| PC40:1e | 0.05526381 | 0.057588343 | 0.05574225 | 0.05685002 | 0.051613626 | 0.04350179 | 0.04397706 | 0.04506833 | 0.04123473 |
| PC40:7 | 0.50960196 | 0.52101856 | 0.48211159 | 0.51247229 | 0.518501878 | 0.24152554 | 0.21965763 | 0.21868129 | 0.20192603 |
| PC40:6 | 1.62867237 | 1.708278452 | 1.60873024 | 1.64651299 | 1.70875511 | 0.74814008 | 0.69892789 | 0.65393475 | 0.62387954 |
| PC40:5 | 0.36295704 | 0.386162561 | 0.3558897 | 0.35339089 | 0.361768503 | 0.49112527 | 0.46458594 | 0.45123829 | 0.42077725 |
| Lyso PE16:0p | 2.65992321 | 2.567717144 | 2.77675546 | 2.27457479 | 2.04847383 | 2.28600844 | 2.4123788 | 2.31928956 | 2.81491102 |
| LysoPE16:1 | 0.08269192 | 0.073363347 | 0.08288822 | 0.02644868 | 0.068740865 | 0.06145196 | 0.07222705 | 0.05916567 | 0.06832322 |
| LysoPE16:0 | 0.16538384 | 0.220090041 | 0.1381469 | 0.1322426 | 0.12373331 | 0.23351687 | 0.13000843 | 0.07099866 | 0.13664602 |
| LysoPE18:1p | 0.56506158 | 0.550225102 | 0.67692035 | 0.70088659 | 0.577422115 | 0.71284122 | 0.73671444 | 0.60348864 | 0.87453528 |
| LysoPE18:0p | 0.89582925 | 0.721406368 | 0.89795588 | 0.96537178 | 1.141096221 | 0.60222791 | 0.7222692 | 0.70998664 | 0.65590156 |
| LysoPE18:2 | 0.04134596 | 0 | 0.08288822 | 0.03967282 | 0 | 0.01229025 | 0.02889091 | 0.01183299 | 0.02732937 |
| LysoPE18:1 | 0.11025603 | 0.097817918 | 0.12453323 | 0.10579431 | 0.068740865 | 0.09832307 | 0.13000843 | 0.15383012 | 0.10931706 |
| LysoPE18:0 | 0.38589548 | 0.489088858 | 0.31773832 | 0.31783255 | 0.412444368 | 0.3932919 | 0.49114281 | 0.50882364 | 0.396274 |
| Lyso PE20:0p | 0.04134596 | 0.048908776 | 0.04144411 | 0.05289696 | 0.054992445 | 0.0368711 | 0.04333614 | 0.07099866 | 0.0819877 |
| LysoPE20:4 | 0 | 0 | 0.01381457 | 0 | 0 | 0 | 0.02889091 | 0.03549933 | 0 |
| LysoPE22:6 | 0.05512781 | 0.012227102 | 0.04144411 | 0 | 0.013748008 | 0 | 0.02889091 | 0.01183299 | 0 |
| PE32:2 | 0.03675201 | 0 | 0.00920799 | 0 | 0 | 0.01638699 | 0.00963013 | 0.00788866 | 0 |
| PE32:1 | 0.0091879 | 0.032605973 | 0.02762955 | 0.00881609 | 0.009165339 | 0.03277436 | 0.01926032 | 0.01577732 | 0.02732937 |
| PE34p:2 | 0.02756411 | 0.081514748 | 0.08288822 | 0.09697782 | 0.054992445 | 0.06554871 | 0.09630244 | 0.05522134 | 0.07287804 |
| PE34p:1 | 1.44251461 | 1.214570926 | 1.40909978 | 1.27834628 | 1.438972618 | 1.14710097 | 1.43490781 | 1.35686327 | 1.23892509 |
| PE34:2 | 0.08269192 | 0.10596932 | 0.11972748 | 0.09697782 | 0.14664707 | 0.16387141 | 0.06741197 | 0.13410867 | 0.13664602 |
| PE34:1 | 0.58803132 | 0.464634653 | 0.69994504 | 0.48488992 | 0.559091437 | 0.60632466 | 0.80894149 | 0.75731896 | 0.86542563 |
| PE34:0 | 0.15619594 | 0.10596932 | 0.1381469 | 0.14987518 | 0.082488874 | 0.18845227 | 0.14445367 | 0.14199733 | 0.11842672 |
| PE36p:4 | 0.61559543 | 0.456482885 | 0.71836446 | 0.65239728 | 0.559091437 | 1.00781005 | 1.1941517 | 0.97820397 | 1.19337641 |
| PE36p:3 | 0.20213584 | 0.187484068 | 0.10130764 | 0.23880691 | 0.201639514 | 0.38509803 | 0.58744569 | 0.66265431 | 0.6285722 |
| PE36p:2 | 1.47926662 | 1.353146218 | 1.42751921 | 1.34887583 | 1.457303295 | 1.34374673 | 1.54084085 | 1.29375327 | 1.69441224 |
| PE36p:1 | 1.47926662 | 1.418358164 | 1.46435846 | 1.42822147 | 1.677273899 | 1.12252011 | 1.54084085 | 1.41208461 | 1.36646146 |
| PE36:4 | 0.56965552 | 0.464634653 | 0.5433783 | 0.5025225 | 0.549925686 | 0.4916146 | 0.75115968 | 0.48910198 | 0.71966995 |
| PE36:3 | 0.17457173 | 0.081514748 | 0.11051777 | 0.19395605 | 0.201639514 | 0.27858184 | 0.32742883 | 0.35499332 | 0.30062141 |
| PE36:2 | 0.82691918 | 0.652118721 | 0.78283326 | 0.96977983 | 0.89821227 | 0.92587435 | 1.05932776 | 0.85987262 | 0.992962 |

TABLE 2-continued

Lipidomic Analysis. Complete data set for FIG. 2. Lipids extraction and phospholipid analysis by MS were performed as described in Methods section. Amount of each lipid species was normalized to internal standard and expressed as mol percent in total phospholipid analysed.

| | | | | | | | | | |
|---|---|---|---|---|---|---|---|---|---|
| PE36:1 | 0.92798689 | 0.82329962 | 0.86572148 | 0.93451546 | 0.870715842 | 0.81116429 | 1.10747941 | 0.82831762 | 1.02940102 |
| PE38p:6 | 2.06729794 | 1.972658967 | 1.99852705 | 2.1423322 | 2.0530565 | 1.02419741 | 0.8282018 | 0.8125403 | 1.04762074 |
| PE38p:5 | 0.98311511 | 0.994480885 | 1.12359586 | 0.96977983 | 0.861550503 | 1.17987532 | 1.28082399 | 1.15175594 | 1.44844915 |
| PE38p:4 | 2.3521257 | 2.225354981 | 2.37612891 | 1.72797183 | 1.658942809 | 2.61375163 | 2.8216644 | 2.71372654 | 2.96977635 |
| PE38p:3 | 0.36751968 | 0.268998817 | 0.39602169 | 0.52897078 | 0.439940796 | 0.99142306 | 1.20378186 | 1.23853228 | 1.29358382 |
| PE38p:2 | 0.32157977 | 0.415725511 | 0.6078471 | 0.65239728 | 0.50409858 | 0.50800196 | 0.71263861 | 0.64687663 | 0.66501122 |
| PE38p:1 | 0.5145273 | 0.326059361 | 0.55258801 | 0.51133859 | 0.63241456 | 0.37690454 | 0.34668915 | 0.4417693 | 0.47370687 |
| PE38p:0 | 0.11025603 | 0.097817918 | 0.08288822 | 0.10579431 | 0.155812408 | 0.05735521 | 0.04815122 | 0.04733232 | 0.09109735 |
| PE38:7 | 0.06431612 | 0.065211945 | 0.08288822 | 0.07934564 | 0.073323535 | 0.04916135 | 0.04815122 | 0.031555 | 0.07287804 |
| PE38:6 | 1.55277064 | 1.369449021 | 1.72223325 | 1.41940537 | 1.548957507 | 0.4834211 | 0.51040356 | 0.52854565 | 0.65590156 |
| PE38:5 | 0.80854338 | 0.864057361 | 0.95781942 | 1.07557415 | 0.999031821 | 1.10613312 | 1.07858851 | 1.15175594 | 0.98385235 |
| PE38:4 | 4.38267164 | 3.309502015 | 3.96021527 | 3.76450971 | 3.418705582 | 5.98950582 | 6.50042152 | 6.3109924 | 7.34245358 |
| PE38:3 | 0.50533941 | 0.505392027 | 0.48811963 | 0.60831642 | 0.52242967 | 1.75342599 | 1.71418542 | 2.3429559 | 2.14078974 |
| PE38:2 | 0.33076767 | 0.220090041 | 0.22103512 | 0.22040472 | 0.192474176 | 0.49980846 | 0.49114281 | 0.35499332 | 0.37349946 |
| PE38:1 | 0.83610708 | 0.766239442 | 1.09596632 | 0.89043419 | 0.769896291 | 0.37690454 | 0.70300845 | 0.34710466 | 0.51925554 |
| PE40p:6 | 3.41793274 | 3.024200029 | 3.17738201 | 3.5264728 | 3.537856223 | 1.31916624 | 1.39638675 | 1.47519461 | 1.68530259 |
| PE40p:5 | 0.90961749 | 0.790694014 | 0.90256074 | 0.81108856 | 0.843219413 | 0.97503569 | 1.24230292 | 0.98609263 | 1.16604704 |
| PE40p:4 | 0.59721922 | 0.717330667 | 1.05912747 | 0.67002987 | 0.568256776 | 0.9586487 | 1.00154638 | 0.86776129 | 0.90186465 |
| PE40:6 | 5.46685447 | 5.200646234 | 5.61797972 | 5.80104759 | 5.444265654 | 1.68787728 | 2.00309276 | 1.57774792 | 2.35942387 |
| PE40:5 | 0.9463631 | 1.010784055 | 0.98544896 | 0.99622851 | 1.00819716 | 0.9504552 | 0.95339516 | 0.97031495 | 1.27536411 |
| PE40:4 | 0.66153534 | 0.62766415 | 0.86572148 | 0.51133859 | 0.540760347 | 0.71284122 | 0.85709271 | 0.7809853 | 0.92008396 |
| PE40:3 | 0.08269192 | 0.122272123 | 0.07367851 | 0.1234265 | 0.073323535 | 0.27038797 | 0.30816808 | 0.22088465 | 0.29151176 |
| PE42p:7 | 0.04593991 | 0.008151401 | 0.05525868 | 0.05289696 | 0.027496429 | 0.03277436 | 0.05778138 | 0.06311 | 0.02732937 |
| PE42p:6 | 0.05512781 | 0.057060544 | 0.04604897 | 0.06171345 | 0.064158196 | 0.06554871 | 0.05778138 | 0.06311 | 0.06376839 |
| PE42p:5 | 0.05512781 | 0.032605973 | 0.04604897 | 0.06171345 | 0.045827106 | 0.04096785 | 0.07704213 | 0.04733232 | 0.06376839 |
| PE42p:4 | 0.07350402 | 0.073363347 | 0.0644688 | 0.02644868 | 0.027496429 | 0.02458086 | 0.07704213 | 0.06311 | 0.02732937 |
| PE42:7 | 0.04593991 | 0.024454571 | 0.0644688 | 0.05289696 | 0.045827106 | 0.05735521 | 0.07704213 | 0.14199733 | 0.13664602 |
| PE42:6 | 0.0183758 | 0.016302803 | 0.02762955 | 0.02644868 | 0 | 0.02458086 | 0 | 0.01577732 | 0.05465833 |
| PE42:5 | 0.04593991 | 0.057060544 | 0.04604897 | 0.05289696 | 0.054992445 | 0.01638695 | 0.05778138 | 0.02366634 | 0.03643902 |
| PE42:4 | 0.03675201 | 0.032605973 | 0.01841942 | 0.04408087 | 0.009165339 | 0.06554871 | 0.05778138 | 0.07099866 | 0.05465833 |
| LPI16:0 | 0.00248615 | 0.003247541 | 0.0028475 | 0.00313564 | 0.00323556 | 0.00297901 | 0.00251013 | 0.0028016 | 0.00323795 |
| LPI18:0 | 0.00157658 | 0.00122685 | 0.0004241 | 0.0010209 | 0.00084406 | 0.00057925 | 0.00059062 | 0.00083291 | 0.00080949 |
| LPI20:4 | 0.00030319 | 0.000505175 | 0.00012117 | 0.00021877 | 0.000422029 | 0.00057925 | 0.00022148 | 0.00022716 | 0.00029436 |
| LPI22:6 | 0.00315516 | 0.002958871 | 0.00224165 | 0.00306271 | 0.003376218 | 0.00364101 | 0.00251013 | 0.00348307 | 0.00272282 |
| PI 32:2 | 0.00024255 | 7.21669E−05 | 0.00012117 | 0.00014584 | 7.03376E−05 | 0.00024825 | 0 | 0.00015144 | 0.00014718 |
| PI 32:1 | 0.00200105 | 0.002381529 | 0.00169638 | 0.00182304 | 0.00246184 | 0.001655 | 0.00147655 | 0.00189297 | 0.00301718 |
| PI 34:2 | 0.00103084 | 0.001010346 | 0.00109053 | 0.0010209 | 0.001688117 | 0.00198601 | 0.00110741 | 0.0015901 | 0.00125103 |
| PI 34:1 | 0.0146137 | 0.017969727 | 0.01569156 | 0.01998055 | 0.016810847 | 0.01928081 | 0.01358424 | 0.01544664 | 0.01670486 |
| PI 36:4 | 0.08489286 | 0.114169117 | 0.09493698 | 0.103403 | 0.095167683 | 0.10774085 | 0.09250572 | 0.09548147 | 0.11053172 |
| PI 36:3 | 0.01255202 | 0.015876869 | 0.01090533 | 0.01305299 | 0.012309198 | 0.02134957 | 0.0202287 | 0.02559297 | 0.02325434 |
| PI 36:2 | 0.00648824 | 0.007216758 | 0.00587676 | 0.00780263 | 0.007104164 | 0.00910253 | 0.00812101 | 0.00901054 | 0.00949307 |
| PI 36:1 | 0.01904026 | 0.019485248 | 0.01490396 | 0.01874088 | 0.015826111 | 0.0139848 | 0.01343658 | 0.01211502 | 0.01648409 |
| PI 38:6 | 0.01303712 | 0.015083024 | 0.01569156 | 0.01655323 | 0.01793626 | 0.00786128 | 0.00627533 | 0.0064361 | 0.00838922 |
| PI 38:5 | 0.0836801 | 0.105364672 | 0.08318346 | 0.09326688 | 0.08707878 | 0.12156015 | 0.10033142 | 0.11388115 | 0.1263535 |
| PI 38:4 | 0.53779627 | 0.699520397 | 0.55344565 | 0.63142921 | 0.562495156 | 0.62592305 | 0.53583918 | 0.59053131 | 0.6547275 |
| PI 38:3 | 0.08672199 | 0.114962962 | 0.08784852 | 0.10515312 | 0.091932123 | 0.13819299 | 0.12617011 | 0.1434115 | 0.14077708 |
| PI 38:2 | 0.01400732 | 0.018186231 | 0.01502513 | 0.01706368 | 0.016670171 | 0.02192882 | 0.02177908 | 0.02415431 | 0.02479973 |
| PI 40:6 | 0.00976268 | 0.012124153 | 0.01157177 | 0.01473019 | 0.014560022 | 0.00711652 | 0.00428199 | 0.00484601 | 0.00625512 |
| PI 40:5 | 0.00218296 | 0.003464045 | 0.00266575 | 0.00306271 | 0.00323556 | 0.00504777 | 0.00317458 | 0.00310447 | 0.00382667 |
| PI 40:4 | 0.00333508 | 0.003031037 | 0.00296867 | 0.00357316 | 0.002743194 | 0.00537377 | 0.00420816 | 0.00386166 | 0.00507769 |
| PI 40:3 | 0.00054574 | 0.000721675 | 0.00096936 | 0.00043753 | 0.00077372 | 0.00157225 | 0.00169803 | 0.00166582 | 0.00228128 |
| PS:34:2 | 0.00088533 | 0.003064134 | 0.00135642 | 0.00222939 | 0.005370949 | 0.00356882 | 0.0019471 | 0.00310401 | 0.00324863 |
| PS:34:1 | 0.08809083 | 0.130736704 | 0.08635848 | 0.10032248 | 0.099362656 | 0.11836608 | 0.10222277 | 0.10605391 | 0.10766854 |
| PS:36:4 | 0.00708269 | 0.010724503 | 0.00542567 | 0.0083602 | 0.008056424 | 0.01605972 | 0.00584131 | 0.00362136 | 0.00835359 |
| PS:36:3 | 0.00177067 | 0.010213795 | 0.0058778 | 0.00668817 | 0.005908039 | 0.00951688 | 0.00486775 | 0.0072427 | 0.00510496 |
| PS:36:2 | 0.30809659 | 0.371271791 | 0.30338504 | 0.36673439 | 0.370595854 | 0.39435535 | 0.31981122 | 0.360066 | 0.38240893 |
| PS:36:1 | 0.75209207 | 0.885536866 | 0.81656242 | 0.98761904 | 0.871168813 | 0.83807948 | 0.72480805 | 0.80807913 | 0.70912722 |
| PS:38:5 | 0.02169071 | 0.029620036 | 0.01898982 | 0.02786735 | 0.02578059 | 0.0404467 | 0.02482552 | 0.02224547 | 0.03434254 |
| PS:38:4 | 0.18060835 | 0.229299922 | 0.19306321 | 0.22851231 | 0.218060748 | 0.35450345 | 0.29255182 | 0.37455141 | 0.37034262 |
| PS:38:3 | 0.06462945 | 0.072518024 | 0.06149085 | 0.09196228 | 0.110104579 | 0.27301525 | 0.22196942 | 0.31919643 | 0.29330393 |
| PS:38:2 | 0.06728546 | 0.069964552 | 0.06827295 | 0.07691391 | 0.070359502 | 0.11182324 | 0.08421208 | 0.12985139 | 0.104884 |
| PS:40:7 | 0.05400543 | 0.066900419 | 0.06013445 | 0.06409493 | 0.05370954 | 0.04163632 | 0.0311536 | 0.03673087 | 0.04037569 |
| PS:40:6 | 2.13144402 | 3.085590024 | 2.461895 | 2.93554716 | 2.511995423 | 1.72255373 | 1.34057853 | 1.56701132 | 1.53566888 |
| PS:40:5 | 0.36210202 | 0.48311296 | 0.37979648 | 0.45479522 | 0.384023251 | 0.71554978 | 0.61236302 | 0.70254255 | 0.71840901 |
| PS:40:4 | 0.21690708 | 0.33756625 | 0.27083106 | 0.24133129 | 0.203559171 | 0.60551093 | 0.49651057 | 0.5804512 | 0.55969074 |

| lipid species | liver-WT1 | liver-WT2 | liver-WT3 | liver-WT4 | liver-WT5 | liver-KO1 | liver-KO2 | liver-KO3 | liver-KO4 |
|---|---|---|---|---|---|---|---|---|---|
| LysoPC16:0e | 0.00564517 | 0.00645951 | 0.00588679 | 0.00568193 | 0.00525491 | 0.00791241 | 0.00704598 | 0.00744472 | 0.00626608 |
| LysoPC16:1 | 0.00364657 | 0.0026741 | 0.0020193 | 0.00262789 | 0.0034796 | 0.00130115 | 0.00202839 | 0.00248157 | 0.00119843 |
| LysoPC16:0 | 0.19642376 | 0.17020454 | 0.13002267 | 0.14883114 | 0.16631067 | 0.16538695 | 0.17006445 | 0.18029318 | 0.17942215 |
| LysoPC18:0e | 0.0059958 | 0.00517455 | 0.00475735 | 0.00518476 | 0.00614256 | 0.00699809 | 0.0057649 | 0.00727239 | 0.00592367 |
| LysoPC18:2 | 0.04417957 | 0.03208916 | 0.02306798 | 0.02855171 | 0.04037046 | 0.04142586 | 0.03341505 | 0.04825281 | 0.0258861 |
| LysoPC18:1 | 0.03523846 | 0.02417106 | 0.02022727 | 0.02858723 | 0.04097406 | 0.02560104 | 0.0232731 | 0.02936528 | 0.02092117 |
| LysoPC18:0 | 0.18369583 | 0.16367558 | 0.14213849 | 0.16395929 | 0.15835729 | 0.23955261 | 0.23383417 | 0.27652307 | 0.20414405 |
| LysoPC20:4 | 0.05743344 | 0.04250772 | 0.03467043 | 0.04066133 | 0.0394828 | 0.03896423 | 0.03234748 | 0.04904554 | 0.03400118 |

TABLE 2-continued

Lipidomic Analysis. Complete data set for FIG. 2. Lipids extraction and phospholipid analysis by MS were performed as described in Methods section. Amount of each lipid species was normalized to internal standard and expressed as mol percent in total phospholipid analysed.

| | | | | | | | | | |
|---|---|---|---|---|---|---|---|---|---|
| LysoPC22:6 | 0.02370269 | 0.01944798 | 0.01553838 | 0.01484405 | 0.02325651 | 0.01709081 | 0.01466134 | 0.0210589 | 0.01568232 |
| LysoPC22:5 | 0.00301543 | 0.00256991 | 0.00164282 | 0.00262789 | 0.00284049 | 0.0026023 | 0.00302479 | 0.00268837 | 0.00219142 |
| PC32:0p | 0.02843621 | 0.02618532 | 0.02761998 | 0.03181882 | 0.03241709 | 0.02830885 | 0.03031909 | 0.02736624 | 0.02752966 |
| PC32:0e | 0.05624129 | 0.05969835 | 0.05698545 | 0.06047708 | 0.06884637 | 0.05257357 | 0.04718675 | 0.04363433 | 0.06029817 |
| PC32:2 | 0.07748956 | 0.06660933 | 0.06044223 | 0.06534223 | 0.08482412 | 0.05405055 | 0.05337867 | 0.04752902 | 0.06337985 |
| PC32:1 | 0.42419396 | 0.35982233 | 0.42785295 | 0.38946101 | 0.48693092 | 0.30046059 | 0.35094699 | 0.25966906 | 0.33508114 |
| PC32:0 | 0.91458715 | 0.96291804 | 0.92740831 | 1.02842992 | 1.04185607 | 0.92888178 | 0.78480885 | 0.70938525 | 0.99277974 |
| PC34:3e | 0.01595373 | 0.01750318 | 0.01656514 | 0.01697478 | 0.01700743 | 0.01863812 | 0.01679649 | 0.01650935 | 0.01701771 |
| PC34:2e | 0.07780512 | 0.07675006 | 0.06297492 | 0.07439781 | 0.09771284 | 0.07529098 | 0.05964177 | 0.06448643 | 0.07053619 |
| PC34:1e | 0.18092584 | 0.1579801 | 0.15931969 | 0.18210596 | 0.23370128 | 0.14066507 | 0.13124037 | 0.13307436 | 0.16278109 |
| PC34:3 | 0.7490891 | 0.69849499 | 0.66178422 | 0.68424681 | 0.81369375 | 0.69864823 | 0.59011903 | 0.57968859 | 0.61969123 |
| PC34:2 | 12.7177544 | 14.4228641 | 12.6978649 | 12.7229848 | 12.430444 | 12.7955277 | 11.4627499 | 10.8065617 | 14.450434 |
| PC34:1 | 8.01596159 | 7.90553384 | 7.80789697 | 7.9713262 | 8.90891152 | 6.40258164 | 6.09687613 | 5.67515094 | 6.77123448 |
| PC36:5e | 0.1212133 | 0.11835484 | 0.11729078 | 0.11527222 | 0.12768001 | 0.10876927 | 0.09750505 | 0.09361045 | 0.11138555 |
| PC36:4e | 0.11335916 | 0.1208553 | 0.10928201 | 0.11896548 | 0.13108859 | 0.10971875 | 0.09722036 | 0.10622512 | 0.13569656 |
| PC36:3e | 0.07899727 | 0.06539383 | 0.06643169 | 0.07858824 | 0.10950087 | 0.06783573 | 0.06572694 | 0.06396944 | 0.06813933 |
| PC36:2e | 0.24130458 | 0.22729825 | 0.19847346 | 0.24794536 | 0.31522333 | 0.22875657 | 0.21337235 | 0.23151009 | 0.21013621 |
| PC36:1e | 0.13895526 | 0.13148223 | 0.1237594 | 0.13988209 | 0.18417024 | 0.11882682 | 0.10636591 | 0.11770239 | 0.10905716 |
| PC36:6 | 0.02149371 | 0.02177479 | 0.01991924 | 0.01981574 | 0.02915052 | 0.01909528 | 0.01644063 | 0.01799141 | 0.01859279 |
| PC36:5 | 0.22840134 | 0.19757063 | 0.21363555 | 0.24503337 | 0.33375753 | 0.22977639 | 0.22888775 | 0.23216495 | 0.20613003 |
| PC36:4 | 8.66424414 | 8.54596274 | 8.72431891 | 8.32829363 | 8.29295134 | 8.37294761 | 7.90705412 | 8.23448001 | 9.70536869 |
| PC36:3 | 3.23944918 | 2.77904669 | 2.85786328 | 3.27101793 | 3.98467429 | 3.05524532 | 3.06382911 | 3.0829755 | 3.02788575 |
| PC36:2 | 6.71960688 | 6.51694818 | 6.13615255 | 7.17574898 | 6.97705902 | 8.1228451 | 8.57389614 | 9.05646668 | 6.64286545 |
| PC36:1 | 1.82724583 | 1.7224658 | 1.74639025 | 2.0056514 | 1.95894365 | 1.98622597 | 2.07283624 | 2.14942146 | 1.62620155 |
| PC38:5e | 0.1524195 | 0.15134695 | 0.15021571 | 0.16062115 | 0.17298582 | 0.13799243 | 0.13593769 | 0.14269046 | 0.16825963 |
| PC38:4e | 0.27422888 | 0.26501344 | 0.25186544 | 0.28132672 | 0.29562395 | 0.2670878 | 0.23621842 | 0.29082658 | 0.27485145 |
| PC38:3e | 0.08043486 | 0.07063784 | 0.06739001 | 0.08039935 | 0.10900379 | 0.07511515 | 0.07131391 | 0.08233998 | 0.07183734 |
| PC38:1e | 0.1000001 | 0.09769136 | 0.09500998 | 0.09900769 | 0.1293488 | 0.10022386 | 0.10547626 | 0.09984885 | 0.08995076 |
| PC38:7 | 0.12198469 | 0.11224262 | 0.11564796 | 0.11399378 | 0.18104571 | 0.11668168 | 0.12294888 | 0.11639267 | 0.10981046 |
| PC38:6 | 5.90642236 | 6.49177001 | 5.82565886 | 5.54560234 | 6.99424401 | 6.30548759 | 6.09591574 | 5.94643513 | 6.7194965 |
| PC38:5 | 3.07686135 | 2.7427901 | 2.83544558 | 2.94256666 | 3.50299825 | 2.80384168 | 2.74882376 | 3.00225544 | 2.89379851 |
| PC38:4 | 9.2594761 | 9.26713542 | 9.18181114 | 9.9877377 | 7.85824993 | 11.8557093 | 10.7877944 | 12.9817984 | 10.2459978 |
| PC38:3 | 1.87465121 | 1.7643484 | 1.82661481 | 2.09095142 | 1.9482918 | 2.46547185 | 2.44951176 | 2.75720007 | 1.8947527 |
| PC40:5e | 0.07163401 | 0.07751409 | 0.06749268 | 0.07027841 | 0.08525019 | 0.07996809 | 0.06850263 | 0.08182298 | 0.06872142 |
| PC40:4e | 0.05967748 | 0.06344903 | 0.05671165 | 0.05728099 | 0.07065718 | 0.05922 | 0.05014037 | 0.06224613 | 0.05636047 |
| PC40:3e | 0.02422864 | 0.02687988 | 0.02351292 | 0.02542665 | 0.03149393 | 0.02978583 | 0.02889565 | 0.02908955 | 0.02218808 |
| PC40:2e | 0.01872372 | 0.01830194 | 0.01639401 | 0.01931857 | 0.02396663 | 0.02155692 | 0.02088885 | 0.02295455 | 0.01876399 |
| PC40:1e | 0.2013326 | 0.1649258 | 0.16356365 | 0.18061445 | 0.22642252 | 0.2173627 | 0.21924401 | 0.25050102 | 0.2279757 |
| PC40:7 | 0.85746929 | 0.73398755 | 0.75285827 | 0.79046344 | 1.20127854 | 0.71813035 | 0.69267725 | 0.75246812 | 0.73939731 |
| PC40:6 | 2.40982003 | 2.63565258 | 2.39636665 | 2.41293947 | 2.59585241 | 3.00115961 | 3.03625014 | 3.18530591 | 2.64038184 |
| PC40:5 | 0.5832404 | 0.61789007 | 0.59997297 | 0.54418715 | 0.57306877 | 0.68848518 | 0.72715988 | 0.75912011 | 0.59363393 |
| LysoPE16:0p | 0.36433654 | 0.18997434 | 0.1801 7503 | 0.23183803 | 0.27208576 | 0.18635234 | 0.28445493 | 0.15902601 | 0.26824991 |
| LysoPE16:1 | 0.03835111 | 0.01727049 | 0.02001955 | 0.02675053 | 0.00877687 | 0 | 0.04063633 | 0.02510938 | 0.03725701 |
| LysoPE16:0 | 0.48897786 | 0.44903037 | 0.53051546 | 0.45475904 | 0.53539464 | 0.34029544 | 0.44700086 | 0.46870857 | 0.44708319 |
| Lyso PE18:1p | 0.06711451 | 0.06044632 | 0.0400388 | 0.04458431 | 0.00877687 | 0.07292045 | 0.03047732 | 0.03347909 | 0.01490285 |
| Lyso PE18:0p | 0.0767025 | 0.0690817 | 0.05004872 | 0.05350106 | 0.0438849 | 0.03240901 | 0.03047723 | 0.08369786 | 0.03725701 |
| LysoPE18:2 | 0.00958771 | 0.01727049 | 0.02001955 | 0.00891675 | 0.02633089 | 0.00810219 | 0.01015901 | 0 | 0.03725701 |
| LysoPE18:1 | 0.12464132 | 0.1208929 | 0.16015548 | 0.13375266 | 0.10532355 | 0.05671583 | 0.09143197 | 0.1506563 | 0.09686795 |
| LysoPE18:0 | 0.50815356 | 0.37994894 | 0.39037923 | 0.32100638 | 0.34230155 | 0.41321589 | 0.50795551 | 0.4519689 | 0.4545345 |
| Lyso PE20:0p | 0.03835111 | 0.03454072 | 0.05004872 | 0.04458431 | 0.01755401 | 0.02430682 | 0.03047732 | 0.02510938 | 0.00745131 |
| LysoPE20:4 | 0.0287634 | 0.00863511 | 0.0400388 | 0.06241782 | 0.02633089 | 0.01620463 | 0.01015901 | 0.01673967 | 0.00745131 |
| LysoPE22:6 | 0.00958771 | 0.00863511 | 0.02001955 | 0.00891675 | 0 | 0.01620463 | 0.03047732 | 0.01673967 | 0.00745131 |
| PE32:2 | 0.0255675 | 0.02302723 | 0.02669263 | 0.01783378 | 0.00585125 | 0.01080292 | 0.00677267 | 0 | 0.00993508 |
| PE32:1 | 0.0191757 | 0.01151349 | 0.02001955 | 0.01783378 | 0.02925651 | 0.01080292 | 0.01354534 | 0.00557981 | 0.00496754 |
| PE34p:2 | 0 | 0.00575674 | 0.00667308 | 0.01188901 | 0.00585125 | 0.00540146 | 0.01354534 | 0.00557981 | 0.01490285 |
| PE34p:1 | 0.0191757 | 0.01727049 | 0.02669263 | 0.02972278 | 0.02925651 | 0.01080292 | 0.03386366 | 0.02231948 | 0.03477324 |
| PE34:2 | 0.95878002 | 0.9613857 | 1.05435755 | 0.86196153 | 0.73141362 | 0.60496969 | 0.77209212 | 0.83139955 | 0.84945805 |
| PE34:1 | 0.32598514 | 0.25905604 | 0.3069648 | 0.2853391 | 0.28671415 | 0.16204553 | 0.16254563 | 0.15623611 | 0.18380082 |
| PE34:0 | 0.06391861 | 0.02878398 | 0.0400388 | 0.01188901 | 0.03510776 | 0.01620463 | 0.02790099 | 0.01673967 | 0.00993508 |
| PE36p:4 | 0.26206653 | 0.24754255 | 0.18684811 | 0.2853391 | 0.22820112 | 0.24306817 | 0.21672761 | 0.25667364 | 0.2881203 |
| PE36p:3 | 0.051135 | 0.07483844 | 0.08675097 | 0.04755656 | 0.04681053 | 0.01620463 | 0.05418198 | 0.04463896 | 0.02483793 |
| PE36p:2 | 0 | 0 | 0.02669263 | 0.02377828 | 0.04095928 | 0.02700755 | 0.02709099 | 0.01115961 | 0.0546434 |
| PE36p:1 | 0.0447432 | 0.02302723 | 0.03336571 | 0.03566729 | 0.07021579 | 0.01620463 | 0.02031832 | 0.01673967 | 0.04967586 |
| PE36:4 | 2.28189657 | 2.18182744 | 2.19546606 | 1.95576109 | 2.04795803 | 1.49621973 | 1.82863948 | 1.71859767 | 2.04664735 |
| PE36:3 | 0.80537529 | 0.78868159 | 0.78075846 | 0.78468218 | 0.75481888 | 0.57256069 | 0.7043648 | 0.61936487 | 0.53649982 |
| PE36:2 | 1.08661753 | 1.03622414 | 1.034338 | 0.97490816 | 0.98301974 | 1.17753014 | 1.28004763 | 1.17735111 | 0.84945805 |
| PE36:1 | 0.14701292 | 0.13240639 | 0.21354074 | 0.19617048 | 0.18724184 | 0.18905307 | 0.27090959 | 0.14507649 | 0.10928703 |
| PE38p:6 | 0.10227001 | 0.10362241 | 0.08007789 | 0.09511312 | 0.16968783 | 0.10262873 | 0.05418198 | 0.07253825 | 0.15399534 |
| PE38p:5 | 0.10227001 | 0.10937916 | 0.08675097 | 0.11294663 | 0.12872882 | 0.10262873 | 0.07449999 | 0.10601734 | 0.1490278 |
| PE38p:4 | 0.34516084 | 0.35116496 | 0.28694555 | 0.32100638 | 0.31011941 | 0.35109836 | 0.26413691 | 0.23993422 | 0.32289331 |
| PE38p:3 | 0.10227001 | 0.08635193 | 0.12678977 | 0.1664477 | 0.15798533 | 0.12423487 | 0.11513663 | 0.11717711 | 0.14406004 |
| PE38p:2 | 0.0255675 | 0.00575674 | 0.02001955 | 0.01783378 | 0.01755401 | 0.02160609 | 0.03386366 | 0.00557981 | 0.03477324 |
| PE38p:1 | 0.03195931 | 0.01151349 | 0.00667308 | 0.02972278 | 0.02340526 | 0.01620463 | 0.00677267 | 0.01115961 | 0.01490285 |
| PE38p:0 | 0 | 0.00575674 | 0 | 0 | 0 | 0.00540146 | 0 | 0 | 0.00496754 |
| PE38:7 | 0.051135 | 0.05756795 | 0.14013623 | 0.11889113 | 0.16383658 | 0.06481826 | 0.07449999 | 0.04463896 | 0.06954625 |
| PE38:6 | 4.58936065 | 4.23700523 | 5.03822774 | 4.21469505 | 4.01399751 | 3.65142401 | 4.30068911 | 3.4037165 | 3.92439696 |

TABLE 2-continued

Lipidomic Analysis. Complete data set for FIG. 2. Lipids extraction and phospholipid analysis by MS were performed as described in Methods section. Amount of each lipid species was normalized to internal standard and expressed as mol percent in total phospholipid analysed.

| | | | | | | | | | |
|---|---|---|---|---|---|---|---|---|---|
| PE38:5 | 2.41612588 | 1.94004189 | 2.62254755 | 2.72260976 | 2.31711816 | 1.83651493 | 1.93023046 | 1.84135469 | 1.88271693 |
| PE38:4 | 8.22633337 | 8.22071143 | 9.00875147 | 7.71604223 | 6.76411265 | 8.1346815 | 9.18383372 | 8.34747484 | 7.54577077 |
| PE38:3 | 1.20167114 | 1.13408981 | 1.16780115 | 1.07596578 | 0.84843967 | 0.95066659 | 1.25972932 | 1.14387201 | 0.94880977 |
| PE38:2 | 0.10227001 | 0.07483844 | 0.08675097 | 0.05350106 | 0.08191829 | 0.10803019 | 0.08127297 | 0.05579857 | 0.02483793 |
| PE38:1 | 0.051135 | 0.02878398 | 0.02669263 | 0.05944557 | 0.06436428 | 0.04861363 | 0.06772732 | 0.05579857 | 0.04967586 |
| PE40p:6 | 0.18536403 | 0.08059518 | 0.12011669 | 0.14266941 | 0.11702605 | 0.09182581 | 0.10836396 | 0.06695844 | 0.14406004 |
| PE40p:5 | 0.10227001 | 0.10362241 | 0.10677052 | 0.05944557 | 0.0994723 | 0.04861363 | 0.07449999 | 0.05021877 | 0.06954625 |
| PE40p:4 | 0.05752681 | 0.05181121 | 0.07340451 | 0.07133484 | 0.10532355 | 0.08642435 | 0.08127297 | 0.10601734 | 0.10431948 |
| PE40:6 | 1.33590016 | 1.64644514 | 1.84846247 | 1.42669495 | 1.24632862 | 1.62585601 | 1.9437761 | 1.60700053 | 1.579694 |
| PE40:5 | 0.35794445 | 0.48357135 | 0.38036961 | 0.41017474 | 0.25160638 | 0.47533342 | 0.41990987 | 0.30689241 | 0.40734241 |
| PE40:4 | 0.09587792 | 0.16119036 | 0.13346285 | 0.11889113 | 0.1111748 | 0.1458409 | 0.10836396 | 0.08369786 | 0.10928703 |
| PE40:3 | 0.051135 | 0.00575674 | 0.04671218 | 0.06539007 | 0.03510776 | 0.00540146 | 0.02709099 | 0.02789929 | 0.02980547 |
| PE42p:7 | 0.0063918 | 0.01151349 | 0.02001955 | 0.01188901 | 0.00585125 | 0.01620463 | 0.01354534 | 0.01115961 | 0.00993508 |
| PE42p:6 | 0.0191757 | 0.00575674 | 0.02669263 | 0.02377828 | 0.02340526 | 0.02700755 | 0.03386366 | 0.03347909 | 0.01490285 |
| PE42p:5 | 0.01278361 | 0.01151349 | 0.00667308 | 0 | 0.0117025 | 0.01620463 | 0.00677267 | 0.01673967 | 0.00993508 |
| PE42p:4 | 0.0063918 | 0.00575674 | 0 | 0.0059445 | 0.00585125 | 0.02160609 | 0.01354534 | 0.01115961 | 0 |
| PE42:7 | 0.01278361 | 0.02302723 | 0.01334617 | 0.02972278 | 0.01755401 | 0.02160609 | 0.02031832 | 0.02231948 | 0.01987039 |
| PE42:6 | 0.0191757 | 0.01727049 | 0.01334617 | 0.0059445 | 0.00585125 | 0.01620463 | 0.01354534 | 0.01673967 | 0.00496754 |
| PE42:5 | 0.01278361 | 0.06332469 | 0.02669263 | 0.01188901 | 0.02925651 | 0.04861363 | 0.03386366 | 0.07811805 | 0.02980547 |
| PE42:4 | 0.0191757 | 0.04029772 | 0.06005834 | 0.01783378 | 0.04681053 | 0.03781071 | 0.05418198 | 0.03347909 | 0.03477324 |
| LPI16:0 | 0.00420978 | 0.00474362 | 0.00410316 | 0.00394419 | 0.00386058 | 0.00497629 | 0.00583323 | 0.00373223 | 0.00527537 |
| LPI18:0 | 0.00096224 | 0.00085142 | 0.00095741 | 0.00126214 | 0.00185308 | 0.0017106 | 0.00225803 | 0.00162271 | 0.00228124 |
| LPI20:4 | 0.00072167 | 0.0003649 | 0.00068386 | 0.00031553 | 0.00077211 | 0.00093305 | 0.00056451 | 0.00016227 | 0.00028515 |
| LPI22:6 | 0.00420978 | 0.00328404 | 0.00328252 | 0.00220874 | 0.0020075 | 0.00279916 | 0.00432788 | 0.0038945 | 0.00228124 |
| PI 32:2 | 0 | 0.00012163 | 0.00013677 | 0.0004733 | 0.00061769 | 0.00031101 | 0.00018817 | 0 | 0 |
| PI 32:1 | 0.00048112 | 0.00012163 | 0.00054709 | 0.0004733 | 0.00030884 | 0.00015551 | 0.00037633 | 0 | 0.00014258 |
| PI 34:2 | 0.01082515 | 0.01459575 | 0.01340363 | 0.01151701 | 0.01451575 | 0.00901952 | 0.01185462 | 0.01217032 | 0.00969527 |
| PI 34:1 | 0.00312727 | 0.0035273 | 0.00314575 | 0.00378641 | 0.0060225 | 0.00388773 | 0.00263436 | 0.00551721 | 0.00270897 |
| PI 36:4 | 0.05568938 | 0.06774859 | 0.07262581 | 0.07115305 | 0.08385164 | 0.06127053 | 0.05682692 | 0.0709124 | 0.07770473 |
| PI 36:3 | 0.01491465 | 0.01824468 | 0.02078931 | 0.02066752 | 0.03242881 | 0.01819455 | 0.01956954 | 0.01979705 | 0.01440032 |
| PI 36:2 | 0.01936499 | 0.0249344 | 0.01737001 | 0.02697821 | 0.02995804 | 0.02037167 | 0.01862869 | 0.02255566 | 0.01383002 |
| PI 36:1 | 0.00420978 | 0.00316241 | 0.00492378 | 0.00583739 | 0.00586807 | 0.00404323 | 0.00263436 | 0.00308315 | 0.00256639 |
| PI 38:6 | 0.00276643 | 0.00304078 | 0.00259826 | 0.00394419 | 0.00416942 | 0.00248815 | 0.0030107 | 0.00178498 | 0.00327928 |
| PI 38:5 | 0.02970902 | 0.03052944 | 0.03528711 | 0.04338601 | 0.05620994 | 0.03001323 | 0.03311768 | 0.03602414 | 0.03878107 |
| PI 38:4 | 0.81681762 | 1.08458552 | 1.20837856 | 1.28974769 | 1.12775054 | 1.16693914 | 1.11772165 | 1.24981073 | 1.26494701 |
| PI 38:3 | 0.16887232 | 0.20725959 | 0.22963979 | 0.26315586 | 0.25973933 | 0.21366929 | 0.22486151 | 0.24438002 | 0.22627047 |
| PI 38:2 | 0.01323074 | 0.0136227 | 0.01285655 | 0.01893208 | 0.02084709 | 0.01539539 | 0.01542983 | 0.01525347 | 0.01440032 |
| PI 40:6 | 0.00276643 | 0.00304078 | 0.00273543 | 0.00362865 | 0.00833284 | 0.00311018 | 0.00376337 | 0.00275861 | 0.00228124 |
| PI 40:5 | 0.00144335 | 0.00170284 | 0.00164126 | 0.00220874 | 0.00216192 | 0.00155509 | 0.00319887 | 0.00194725 | 0.00199608 |
| PI 40:4 | 0.00312727 | 0.00231099 | 0.00246189 | 0.00331312 | 0.0054048 | 0.00202162 | 0.0030107 | 0.00275861 | 0.00228124 |
| PI 40:3 | 0.00036084 | 0.00048653 | 0.00109418 | 0.00031553 | 0.00015442 | 0.00046653 | 0.00056451 | 0.00016227 | 0.00071289 |
| PS:34:2 | 0.00078942 | 0.0013024 | 0.00089285 | 0.00103638 | 0.00263138 | 0.00135736 | 0.00047939 | 0.0016555 | 0.00042955 |
| PS:34:1 | 0.00947312 | 0.00651197 | 0.00535719 | 0.00621834 | 0.00657846 | 0.00588187 | 0.00143818 | 0.0049665 | 0.00214776 |
| PS:36:4 | 0.03591894 | 0.04037427 | 0.04910746 | 0.03731 | 0.04341785 | 0.03438631 | 0.02684592 | 0.02690186 | 0.04209605 |
| PS:36:3 | 0.002763 | 0.00651197 | 0.00401788 | 0.00725472 | 0.00701703 | 0.00316717 | 0.00335575 | 0.00413874 | 0.00300687 |
| PS:36:2 | 0.04183966 | 0.04514971 | 0.03125022 | 0.03523722 | 0.03201518 | 0.0298618 | 0.02349019 | 0.016555 | 0.02749129 |
| PS:36:1 | 0.07025904 | 0.05773955 | 0.04821461 | 0.04663749 | 0.0499963 | 0.03755346 | 0.02205201 | 0.02441862 | 0.03994829 |
| PS:38:5 | 0.01184142 | 0.01866768 | 0.01964299 | 0.018655 | 0.01973539 | 0.01493089 | 0.00958782 | 0.01117462 | 0.02190712 |
| PS:38:4 | 0.43142203 | 0.60735049 | 0.60714693 | 0.67935282 | 0.53110116 | 0.53298785 | 0.4487106 | 0.52520721 | 0.64604543 |
| PS:38:3 | 0.07736389 | 0.10809283 | 0.08794702 | 0.12436664 | 0.09209847 | 0.0773692 | 0.07094907 | 0.08360273 | 0.10309235 |
| PS:38:2 | 0.0146044 | 0.00998503 | 0.00714291 | 0.01295487 | 0.00657846 | 0.01040638 | 0.00623209 | 0.00620812 | 0.00773193 |
| PS:40:7 | 0.00473657 | 0.00607784 | 0.00312503 | 0.00829112 | 0.00657846 | 0.00180981 | 0.00335575 | 0.0016555 | 0.00386596 |
| PS:40:6 | 0.26643172 | 0.28782943 | 0.24330519 | 0.28293412 | 0.26182279 | 0.26015961 | 0.2353813 | 0.20238482 | 0.23410556 |
| PS:40:5 | 0.06394361 | 0.06729043 | 0.06160756 | 0.06425611 | 0.05350482 | 0.05022212 | 0.05608882 | 0.04966499 | 0.05627124 |
| PS:40:4 | 0.03828723 | 0.05166168 | 0.05089319 | 0.04301012 | 0.03026092 | 0.04207799 | 0.02636654 | 0.03021286 | 0.04037784 |

| lipid species | heart-WT1 | heart-WT2 | heart-WT3 | heart-WT4 | heart-WT5 | heart-KO1 | heart-KO2 | heart-KO3 | heart-KO4 |
|---|---|---|---|---|---|---|---|---|---|
| LysoPC16:0e | 0.03160403 | 0.02805851 | 0.02752524 | 0.02467689 | 0.02464919 | 0.03161066 | 0.02205302 | 0.02885865 | 0.02450268 |
| LysoPC16:1 | 0.00241225 | 0.00149424 | 0.00122789 | 0.00159325 | 0.00171413 | 0.00122794 | 0.00172137 | 0.00170411 | 0.00201345 |
| LysoPC16:0 | 0.15606237 | 0.12209603 | 0.11088543 | 0.11723377 | 0.11844641 | 0.14998399 | 0.13689759 | 0.19282324 | 0.16793547 |
| LysoPC18:0e | 0.00555867 | 0.00468195 | 0.00405886 | 0.00403871 | 0.00383965 | 0.0061397 | 0.00506667 | 0.00766847 | 0.00607448 |
| LysoPC18:2 | 0.05597129 | 0.0298516 | 0.02404621 | 0.02990128 | 0.02852313 | 0.03066339 | 0.03497913 | 0.07238744 | 0.03641275 |
| LysoPC18:1 | 0.04209209 | 0.02437272 | 0.02790043 | 0.02652951 | 0.02550626 | 0.02547097 | 0.02656755 | 0.04486243 | 0.03235172 |
| LysoPC18:0 | 0.18570863 | 0.15566662 | 0.13561381 | 0.16647641 | 0.13267369 | 0.21271414 | 0.19760023 | 0.29677367 | 0.21926141 |
| LysoPC20:4 | 0.03471549 | 0.02397425 | 0.02240902 | 0.02208323 | 0.01954109 | 0.02413778 | 0.02153336 | 0.03671236 | 0.0256971 |
| LysoPC22:6 | 0.04502875 | 0.03556292 | 0.03768945 | 0.03645956 | 0.04261328 | 0.03347011 | 0.02429405 | 0.04100967 | 0.03211284 |
| LysoPC22:5 | 0.01297024 | 0.00783646 | 0.00920919 | 0.00655827 | 0.00510811 | 0.00775356 | 0.00626838 | 0.0092244 | 0.00709827 |
| PC32:0p | 0.05729978 | 0.05628305 | 0.05576674 | 0.0642859 | 0.05601778 | 0.05076651 | 0.04985476 | 0.05708753 | 0.05327114 |
| PC32:0e | 0.08107273 | 0.08666593 | 0.08155247 | 0.09063016 | 0.08433522 | 0.06771207 | 0.05716246 | 0.07116493 | 0.079446 |
| PC32:2 | 0.05205575 | 0.04034449 | 0.04362426 | 0.05013189 | 0.04816707 | 0.04880181 | 0.05190091 | 0.05412387 | 0.05132594 |
| PC32:1 | 0.28835181 | 0.25963254 | 0.26781681 | 0.30275511 | 0.27439799 | 0.25604285 | 0.25992679 | 0.27980671 | 0.28461325 |
| PC32:0 | 1.5433534 | 1.35082634 | 1.35797993 | 1.63986485 | 1.54761977 | 1.285968 | 1.11963717 | 1.47142097 | 1.29570695 |
| PC34:3e | 0.09107135 | 0.09104904 | 0.09881117 | 0.09566928 | 0.07638165 | 0.08518389 | 0.08532146 | 0.08909508 | 0.0755556 |
| PC34:2e | 0.13840747 | 0.14895915 | 0.14386797 | 0.14806137 | 0.11673228 | 0.11819791 | 0.12228219 | 0.11717577 | 0.11940789 |
| PC34:1e | 0.18123373 | 0.17954126 | 0.18159153 | 0.2026766 | 0.17967515 | 0.14840521 | 0.14378307 | 0.15914863 | 0.18824061 |

TABLE 2-continued

Lipidomic Analysis. Complete data set for FIG. 2. Lipids extraction and phospholipid analysis by MS were performed as described in Methods section. Amount of each lipid species was normalized to internal standard and expressed as mol percent in total phospholipid analysed.

| | | | | | | | | | |
|---|---|---|---|---|---|---|---|---|---|
| PC34:3 | 0.10169925 | 0.08015768 | 0.07981296 | 0.08851817 | 0.08114693 | 0.08992023 | 0.11172662 | 0.10998889 | 0.0807428 |
| PC34:2 | 3.65501996 | 2.97715738 | 3.14691573 | 3.19814035 | 2.85663256 | 3.61894701 | 4.48903927 | 4.32690897 | 3.18463119 |
| PC34:1 | 4.87862728 | 4.27209915 | 4.60892534 | 4.77186669 | 4.13060854 | 4.59379037 | 4.88631834 | 4.93775669 | 4.37963145 |
| PC36:5e | 0.45902755 | 0.47360773 | 0.52304773 | 0.4457403 | 0.34999114 | 0.43816376 | 0.41059534 | 0.46033075 | 0.49278362 |
| PC36:4e | 0.20713924 | 0.2170965 | 0.22443131 | 0.21427399 | 0.18461184 | 0.19759294 | 0.17593695 | 0.21360591 | 0.23809912 |
| PC36:3e | 0.07359124 | 0.07049493 | 0.07196809 | 0.07410479 | 0.06239435 | 0.06623854 | 0.06482742 | 0.07386927 | 0.07135807 |
| PC36:2e | 0.12421363 | 0.11963883 | 0.11337533 | 0.11460305 | 0.10360204 | 0.11283006 | 0.11640355 | 0.12388106 | 0.10043367 |
| PC36:1e | 0.15459405 | 0.14573823 | 0.13946802 | 0.14365213 | 0.14343843 | 0.13510838 | 0.12406852 | 0.1388105 | 0.12459508 |
| PC36:6 | 0.03377156 | 0.02829095 | 0.02827562 | 0.03086464 | 0.03939072 | 0.03494364 | 0.02309233 | 0.02915502 | 0.03074779 |
| PC36:5 | 0.05681034 | 0.04994083 | 0.05511869 | 0.05435586 | 0.05032687 | 0.05518709 | 0.05859152 | 0.05871755 | 0.05624013 |
| PC36:4 | 4.06272593 | 4.1864958 | 4.41089371 | 4.03656193 | 3.22266798 | 4.26824616 | 4.02430198 | 4.32053711 | 4.59227236 |
| PC36:3 | 1.69249365 | 1.50134615 | 1.65717619 | 1.61522502 | 1.24277882 | 1.68852151 | 1.93728767 | 1.89655823 | 1.64386336 |
| PC36:2 | 3.20987163 | 2.6518779 | 2.82128567 | 2.95407622 | 2.30128862 | 3.30596289 | 3.99997549 | 3.95496944 | 2.98608445 |
| PC36:1 | 2.30901695 | 2.00673137 | 2.00490829 | 2.22029061 | 1.68516159 | 2.20569438 | 2.33239069 | 2.41293925 | 2.15156017 |
| PC38:5e | 0.37896867 | 0.36193818 | 0.39388035 | 0.34751441 | 0.32715893 | 0.32740365 | 0.29107383 | 0.32992963 | 0.36706237 |
| PC38:4e | 0.21063526 | 0.20949248 | 0.22054298 | 0.18915247 | 0.16349376 | 0.19422488 | 0.16707027 | 0.20515948 | 0.21014969 |
| PC38:3e | 0.0510419 | 0.05143507 | 0.05054821 | 0.04709359 | 0.03993924 | 0.04785454 | 0.04426843 | 0.05149362 | 0.04924424 |
| PC38:1e | 0.0806532 | 0.07431355 | 0.07456031 | 0.07992201 | 0.07322765 | 0.07279925 | 0.05881887 | 0.06579329 | 0.06323601 |
| PC38:7 | 0.11225723 | 0.1038663 | 0.1119769 | 0.12623751 | 0.13596482 | 0.11072502 | 0.08398984 | 0.09535581 | 0.10265188 |
| PC38:6 | 8.61010528 | 8.18040063 | 8.39523151 | 9.86212458 | 10.9188048 | 8.97367368 | 6.55851514 | 7.74745616 | 8.09304954 |
| PC38:5 | 3.40323654 | 3.153843 | 3.36217766 | 3.06160227 | 2.86667738 | 3.17274904 | 2.73379455 | 3.08583862 | 3.23681028 |
| PC38:4 | 7.58783378 | 7.78977303 | 8.08010679 | 7.4273006 | 5.20989361 | 8.03875593 | 7.11785089 | 8.43835972 | 8.82574097 |
| PC38:3 | 1.28985693 | 1.28946289 | 1.31200221 | 1.26482052 | 0.88517694 | 1.38809744 | 1.26887666 | 1.47834852 | 1.44572611 |
| PC40:5e | 0.10893601 | 0.10310257 | 0.1039956 | 0.09433539 | 0.08827772 | 0.09244627 | 0.07499325 | 0.09568923 | 0.09237987 |
| PC40:4e | 0.07117899 | 0.07311815 | 0.07404869 | 0.06158108 | 0.05560639 | 0.06122153 | 0.05277784 | 0.06390395 | 0.06354315 |
| PC40:3e | 0.02066148 | 0.02058731 | 0.02186329 | 0.01982303 | 0.01830691 | 0.0201382 | 0.01636925 | 0.01911562 | 0.02010039 |
| PC40:2e | 0.02115093 | 0.02078654 | 0.02077183 | 0.02115692 | 0.02063813 | 0.02055921 | 0.01740857 | 0.02007881 | 0.02068053 |
| PC40:1e | 1.14159068 | 1.15504768 | 1.24443406 | 1.3744215 | 1.25906306 | 1.11868761 | 0.89348819 | 1.06373227 | 1.0978086 |
| PC40:7 | 1.12208288 | 1.04892342 | 1.1288076 | 1.18993763 | 1.05998395 | 0.99108719 | 0.77343421 | 0.92655177 | 1.03293453 |
| PC40:6 | 8.76253177 | 8.55698232 | 8.57313936 | 10.5819785 | 10.8156142 | 9.30521727 | 6.78196835 | 8.52886259 | 7.44836977 |
| PC40:5 | 3.30800494 | 2.98017909 | 3.10673638 | 2.67433065 | 2.51085819 | 3.19551854 | 2.38110868 | 3.04101324 | 2.79627402 |
| Lyso PE16:0p | 2.46996369 | 2.86088499 | 2.7294344 | 3.00647254 | 2.55720425 | 2.05902958 | 2.78870858 | 2.33590366 | 3.13045716 |
| LysoPE16:1 | 0.0830241 | 0.18021311 | 0.17736397 | 0.14583625 | 0.07595657 | 0.04159645 | 0.11204632 | 0.12473283 | 0.14638817 |
| LysoPE16:0 | 0.31133997 | 0.27031983 | 0.22663184 | 0.1907092 | 0.2152104 | 0.15598709 | 0.19919334 | 0.20410808 | 0.2477339 |
| Lyso PE18:1p | 0.36323007 | 0.49558647 | 0.37443516 | 0.22436374 | 0.25318868 | 0.33277256 | 0.23654211 | 0.31750134 | 0.34907963 |
| Lyso PE18:0p | 0.44625386 | 0.5181129 | 0.59121325 | 0.4150726 | 0.41776111 | 0.36396998 | 0.47308459 | 0.44223417 | 0.41664345 |
| LysoPE18:2 | 0.10377989 | 0.07884317 | 0.08868199 | 0.06730909 | 0.07595657 | 0.08319322 | 0.03734877 | 0.06803603 | 0.06756382 |
| LysoPE18:1 | 0.16604788 | 0.14642313 | 0.13794986 | 0.12340011 | 0.17723211 | 0.16638612 | 0.12449579 | 0.10205404 | 0.09008521 |
| LysoPE18:0 | 0.59154595 | 0.66453636 | 0.46311714 | 0.40385454 | 0.50637698 | 0.56155352 | 0.61002985 | 0.62366345 | 0.56303195 |
| Lyso PE20:0p | 0.04151189 | 0.1238967 | 0.06897478 | 0.08974556 | 0.11393485 | 0.06239484 | 0.06224808 | 0.0566968 | 0.03378191 |
| LysoPE20:4 | 0 | 0.03378998 | 0.01970721 | 0.01121807 | 0 | 0.01039904 | 0.02489931 | 0.02267879 | 0 |
| LysoPE22:6 | 0.04151189 | 0.02252677 | 0.04926787 | 0.01121807 | 0 | 0.01039904 | 0.04979824 | 0.02267879 | 0.01126052 |
| PE32:2 | 0.0276747 | 0.03003557 | 0 | 0.02243648 | 0.02531898 | 0.02773107 | 0.02489931 | 0.01511897 | 0.03753542 |
| PE32:1 | 0.0069186 | 0 | 0.00656897 | 0 | 0.00843953 | 0.00693269 | 0.00829964 | 0.00755948 | 0.00750702 |
| PE34p:2 | 0.1106988 | 0.03754438 | 0.0853975 | 0.08974556 | 0.06751703 | 0.06932753 | 0.07469755 | 0.07559551 | 0.10509924 |
| PE34p:1 | 0.0553494 | 0.03754438 | 0.0656903 | 0.05235166 | 0.05063758 | 0.04852946 | 0.0414986 | 0.04535724 | 0.03753542 |
| PE34:2 | 0.14529209 | 0.1201423 | 0.09853544 | 0.12713947 | 0.1687922 | 0.11092429 | 0.215793 | 0.20410808 | 0.11260626 |
| PE34:1 | 0.13837318 | 0.11263315 | 0.04598338 | 0.08974556 | 0.07595657 | 0.05546215 | 0.09959685 | 0.07559551 | 0.07507084 |
| PE34:0 | 0.0276747 | 0.02252677 | 0.00656897 | 0.05235166 | 0.0590775 | 0.02079838 | 0.00829964 | 0.03023827 | 0.03753542 |
| PE36p:4 | 0.67111075 | 0.78092392 | 0.61748992 | 0.50107881 | 0.50637698 | 0.63781374 | 0.62247709 | 0.71059853 | 0.83328724 |
| PE36p:3 | 0.1106988 | 0.15768668 | 0.09853544 | 0.08974556 | 0.10971508 | 0.11092429 | 0.1078965 | 0.11339326 | 0.15014167 |
| PE36p:2 | 0.13837318 | 0.1201423 | 0.07225927 | 0.10470299 | 0.10971508 | 0.08319322 | 0.09959685 | 0.12095309 | 0.11260626 |
| PE36p:1 | 0.01383719 | 0.04505319 | 0.01970721 | 0.00747871 | 0.03375852 | 0.02773107 | 0.03319895 | 0.03023827 | 0.02252139 |
| PE36:4 | 0.37360797 | 0.36793536 | 0.36786509 | 0.39637582 | 0.32070533 | 0.4852933 | 0.63907898 | 0.37797788 | 0.54801758 |
| PE36:3 | 0.20756009 | 0.13515992 | 0.21020912 | 0.20192727 | 0.20255072 | 0.18025182 | 0.31538948 | 0.30238237 | 0.32280507 |
| PE36:2 | 0.44971316 | 0.5181129 | 0.34159001 | 0.4562062 | 0.49793744 | 0.53382245 | 0.74697548 | 0.55184769 | 0.54051057 |
| PE36:1 | 0.17988539 | 0.15768668 | 0.17736397 | 0.17201208 | 0.15191313 | 0.20798289 | 0.18259405 | 0.15119102 | 0.14263466 |
| PE38p:6 | 3.12723693 | 3.30390912 | 3.30422522 | 3.47763616 | 4.16073204 | 2.75923815 | 3.36138965 | 2.54757122 | 3.29561286 |
| PE38p:5 | 1.01012511 | 1.0662617 | 1.06418385 | 0.84510297 | 0.85240129 | 0.88046039 | 1.13706251 | 0.84667058 | 1.34376941 |
| PE38p:4 | 0.87175193 | 0.96113703 | 0.9459412 | 0.51603624 | 0.51481689 | 0.79033448 | 0.99576743 | 0.86934937 | 0.87082266 |
| PE38p:3 | 0.12453599 | 0.1727043 | 0.19707118 | 0.09722428 | 0.07595657 | 0.13172236 | 0.1078965 | 0.18142929 | 0.12762063 |
| PE38p:2 | 0.01383719 | 0.03754438 | 0.02627618 | 0.0373939 | 0.02531898 | 0.02079838 | 0.02489931 | 0.00755948 | 0.01501403 |
| PE38p:1 | 0.01383719 | 0.01501762 | 0 | 0 | 0.01687907 | 0.00693269 | 0.00829964 | 0.01511897 | 0.01501403 |
| PE38p:0 | 0.0276747 | 0 | 0.01970721 | 0.00747871 | 0.02531898 | 0.00693269 | 0.02489931 | 0.02267879 | 0.00750702 |
| PE38:7 | 0.20064118 | 0.12765111 | 0.14451883 | 0.09722428 | 0.15191313 | 0.08319322 | 0.18259405 | 0.06803603 | 0.12762063 |
| PE38:6 | 2.4492079 | 2.71821592 | 2.50280285 | 2.57270281 | 3.51088109 | 3.08507802 | 2.95470296 | 2.39637986 | 2.79263805 |
| PE38:5 | 1.27303459 | 1.4642323 | 1.30066915 | 1.27438255 | 1.27438255 | 1.28949317 | 1.80104079 | 1.39095878 | 1.41133323 |
| PE38:4 | 4.7392862 | 5.02344363 | 4.51292769 | 4.28534523 | 4.41392034 | 5.26196458 | 6.5484849 | 4.739843 | 4.97720137 |
| PE38:3 | 0.69186654 | 0.73587073 | 0.68974869 | 0.57586661 | 0.60765253 | 0.68634319 | 0.70547688 | 0.51404993 | 0.74320203 |
| PE38:2 | 0.20756009 | 0.18021311 | 0.19707118 | 0.24679988 | 0.26162821 | 0.18718451 | 0.22409264 | 0.12851257 | 0.18767743 |
| PE38:1 | 1.08623061 | 1.38914354 | 1.49117106 | 1.44340606 | 1.65416538 | 0.99831737 | 1.31135691 | 1.06589762 | 1.41133323 |
| PE40p:6 | 2.30391581 | 2.68067154 | 2.67359785 | 2.20624252 | 3.23237381 | 2.11449172 | 2.27412539 | 1.98060422 | 2.40226916 |
| PE40p:5 | 0.59500525 | 0.69832634 | 0.57807531 | 0.58334533 | 0.69204862 | 0.49222599 | 0.61417967 | 0.4686927 | 0.59306036 |
| PE40p:4 | 0.31825857 | 0.21775749 | 0.28903765 | 0.20192727 | 0.15191313 | 0.18025182 | 0.215793 | 0.17386981 | 0.26274827 |
| PE40:6 | 7.73506855 | 8.53760143 | 8.43464224 | 8.62304213 | 10.9630644 | 8.47876496 | 9.42849069 | 8.27771633 | 7.6722472 |
| PE40:5 | 2.52531309 | 2.8683938 | 2.64075241 | 1.89213321 | 2.21961947 | 2.710709 | 2.90490472 | 2.58536897 | 2.51487541 |

TABLE 2-continued

Lipidomic Analysis. Complete data set for FIG. 2. Lipids extraction and phospholipid analysis by MS were performed as described in Methods section. Amount of each lipid species was normalized to internal standard and expressed as mol percent in total phospholipid analysed.

| | | | | | | | | | |
|---|---|---|---|---|---|---|---|---|---|
| PE40:4 | 0.47738786 | 0.37544417 | 0.3875731 | 0.30663026 | 0.19411118 | 0.37436901 | 0.41498634 | 0.45357339 | 0.41288994 |
| PE40:3 | 0.04151189 | 0.06007115 | 0.05255235 | 0.04487261 | 0.00843953 | 0.04852946 | 0.03319895 | 0.03779775 | 0.0300284 |
| PE42p:7 | 0.0830241 | 0.06007115 | 0.02627618 | 0.0373939 | 0.05063758 | 0.05546215 | 0.0663979 | 0.08315499 | 0.09759222 |
| PE42p:6 | 0.1106988 | 0.27782864 | 0.19050192 | 0.15705465 | 0.33758478 | 0.08319322 | 0.09959685 | 0.09071481 | 0.12011361 |
| PE42p:5 | 0.08994269 | 0.14266872 | 0.12481162 | 0.10470299 | 0.10127555 | 0.05546215 | 0.0663979 | 0.06803603 | 0.07507084 |
| PE42p:4 | 0.04151189 | 0.02252677 | 0.03284515 | 0.05235166 | 0.03375852 | 0.06932753 | 0.0663979 | 0.09071481 | 0.06756382 |
| PE42:7 | 0.0553494 | 0.05256234 | 0.04598338 | 0.05235166 | 0.11815462 | 0.04852946 | 0.03319895 | 0.06803603 | 0.11260626 |
| PE42:6 | 0.0553494 | 0.04505319 | 0.01970721 | 0.0373939 | 0.02531898 | 0.03466376 | 0.05809826 | 0.02267879 | 0.00750702 |
| PE42:5 | 0.0553494 | 0.04505319 | 0.04598338 | 0.02991519 | 0.06751703 | 0.02773107 | 0.03319895 | 0.03023827 | 0.04504243 |
| PE42:4 | 0.04151189 | 0.01501762 | 0.02627618 | 0.0373939 | 0.0590775 | 0.03466376 | 0.01659929 | 0.09071481 | 0.0300284 |
| LPI16:0 | 0.00356935 | 0.00541095 | 0.00494528 | 0.0081386 | 0.00688385 | 0.00558726 | 0.00330475 | 0.00759367 | 0.00484546 |
| LPI18:0 | 0.0005949 | 0.00074634 | 0.00114122 | 0.00095748 | 0.00114731 | 0.00072878 | 0.00110158 | 0.0002712 | 0.00147471 |
| LPI20:4 | 0 | 0.00037317 | 0.0001902 | 0.00047874 | 0.00068839 | 0.00072878 | 0.00088127 | 0.0002712 | 0.00021067 |
| LPI22:6 | 0.00495744 | 0.00317194 | 0.00361386 | 0.00311182 | 0.00435977 | 0.00461556 | 0.00176254 | 0.00406803 | 0.00337076 |
| PI 32:2 | 0.0001983 | 0.00037317 | 0.0003804 | 0.00047874 | 0.00022946 | 0 | 0.00044063 | 0.0005424 | 0 |
| PI 32:1 | 0.0001983 | 0.00018658 | 0.0003804 | 0.00023937 | 0 | 0 | 0.00044063 | 0 | 0 |
| PI 34:2 | 0.00713871 | 0.00764997 | 0.01141218 | 0.00718112 | 0.00573654 | 0.00655896 | 0.00771109 | 0.00976329 | 0.00758419 |
| PI 34:1 | 0.00535403 | 0.00317194 | 0.00456487 | 0.00263307 | 0.00252407 | 0.00534434 | 0.00352507 | 0.00569526 | 0.00316008 |
| PI 36:4 | 0.01883826 | 0.02462918 | 0.02776964 | 0.02106461 | 0.0256997 | 0.02259196 | 0.02886149 | 0.0322731 | 0.03054745 |
| PI 36:3 | 0.0156655 | 0.01697921 | 0.02073213 | 0.01579846 | 0.01193201 | 0.01506131 | 0.01916755 | 0.01735696 | 0.01390436 |
| PI 36:2 | 0.06484326 | 0.0695961 | 0.0814069 | 0.05792768 | 0.05966002 | 0.07336314 | 0.08063592 | 0.09953136 | 0.06762573 |
| PI 36:1 | 0.01011317 | 0.01119508 | 0.01160239 | 0.01029294 | 0.01353823 | 0.01311791 | 0.01410027 | 0.01708576 | 0.0090589 |
| PI 38:6 | 0.00495744 | 0.00578413 | 0.00551588 | 0.00430867 | 0.00688385 | 0.00655896 | 0.00594855 | 0.00569526 | 0.00589882 |
| PI 38:5 | 0.03628843 | 0.03433159 | 0.03747 | 0.03183628 | 0.03579601 | 0.0349811 | 0.04406334 | 0.04285001 | 0.03939568 |
| PI 38:4 | 0.65933897 | 0.74689866 | 0.77526756 | 0.60608642 | 0.54061155 | 0.70982482 | 0.67438948 | 0.76994414 | 0.84079217 |
| PI 38:3 | 0.14436053 | 0.14646901 | 0.16452562 | 0.13883493 | 0.11794327 | 0.15109892 | 0.1410027 | 0.16299276 | 0.15568665 |
| PI 38:2 | 0.01189784 | 0.01287434 | 0.01103178 | 0.01196853 | 0.01239093 | 0.01214621 | 0.01211742 | 0.01383133 | 0.01137629 |
| PI 40:6 | 0.00852679 | 0.01809872 | 0.01711827 | 0.01508035 | 0.02317562 | 0.01967687 | 0.00815172 | 0.01627215 | 0.01242965 |
| PI 40:5 | 0.00694041 | 0.00820973 | 0.00874934 | 0.00550552 | 0.01078469 | 0.01093159 | 0.00594855 | 0.00840728 | 0.00695217 |
| PI 40:4 | 0.00594893 | 0.00876948 | 0.0062767 | 0.00765986 | 0.00849008 | 0.00558726 | 0.00572824 | 0.00732247 | 0.00779486 |
| PI 40:3 | 0.00118978 | 0.00093292 | 0.00095101 | 0.00143622 | 0.00114731 | 0.0009717 | 0.00176254 | 0.00081361 | 0.00042134 |
| PS:34:2 | 0 | 0 | 0.00047758 | 0.00117158 | 0.00104951 | 0 | 0 | 0.00184591 | 0.00053017 |
| PS:34:1 | 0.00215657 | 0.00318873 | 0.00429829 | 0.00468636 | 0.00262379 | 0.0037925 | 0.00303978 | 0.00738361 | 0.00212071 |
| PS:36:4 | 0.00539142 | 0.00501084 | 0.00525345 | 0.00410057 | 0.00262379 | 0.00433428 | 0.00202652 | 0.00123059 | 0.00318106 |
| PS:36:3 | 0.00161743 | 0.0013666 | 0.00047758 | 0.00058579 | 0.00472283 | 0.00162536 | 0.0015199 | 0.0024612 | 0.00318106 |
| PS:36:2 | 0.03019195 | 0.03370931 | 0.01910351 | 0.03690503 | 0.02413891 | 0.03629953 | 0.0379973 | 0.02953441 | 0.03499175 |
| PS:36:1 | 0.05660992 | 0.04783078 | 0.05635533 | 0.05272147 | 0.05719872 | 0.04984411 | 0.03951718 | 0.06891361 | 0.0646817 |
| PS:38:5 | 0.01186113 | 0.00911062 | 0.00477587 | 0.00820112 | 0.00419808 | 0.0037925 | 0.00303978 | 0.01046011 | 0.00583195 |
| PS:38:4 | 0.19247374 | 0.15032533 | 0.14041074 | 0.13004629 | 0.10075373 | 0.12027603 | 0.09575318 | 0.13167423 | 0.14897997 |
| PS:38:3 | 0.05660992 | 0.043731 | 0.04441565 | 0.04334876 | 0.03358457 | 0.0438845 | 0.0349575 | 0.0449169 | 0.04082369 |
| PS:38:2 | 0.00431314 | 0.01002169 | 0.00620864 | 0.00761533 | 0.00892091 | 0.00704319 | 0.00607957 | 0.00922949 | 0.00689231 |
| PS:40:7 | 0.0140177 | 0.01002169 | 0.01002935 | 0.01874541 | 0.00839615 | 0.00812675 | 0.0065862 | 0.0079989 | 0.0095432 |
| PS:40:6 | 0.45180111 | 0.41225584 | 0.4350823 | 0.47742223 | 0.45076797 | 0.44534641 | 0.3890923 | 0.45163024 | 0.48246185 |
| PS:40:5 | 0.15850778 | 0.15715831 | 0.1270383 | 0.12360257 | 0.10075373 | 0.14573989 | 0.11905818 | 0.14890262 | 0.18079066 |
| PS:40:4 | 0.05822735 | 0.05694142 | 0.05301223 | 0.0486209 | 0.03988169 | 0.05309483 | 0.05015643 | 0.0670677 | 0.08217756 |

TABLE 3

Lipidomic Analysis. Complete data set for Extended Data 2d. Lipids extraction and phospholipid analysis by MS were performed as described in Methods section. Amount of each lipid species was normalized to internal standard and expressed as mol percent in total phospholipid analysed.

| Lipid species | Brain-WT1 | Brain-WT2 | Brain-WT3 | Brain-WT4 | Brain-WT5 | Brain-WT6 |
|---|---|---|---|---|---|---|
| lysoPC14:0 | 0.017287 | 0.013954 | 0.017273 | 0.022744 | 0.015918 | 0.015343 |
| lysoPC 16:0e | 0.010842 | 0.006951 | 0.011815 | 0.019767 | 0.009344 | 0.009936 |
| lysoPC 16:1 | 0.075959 | 0.086081 | 0.106707 | 0.167366 | 0.106215 | 0.113897 |
| lysoPC 16:0 | 0.023002 | 0.021915 | 0.030437 | 0.031197 | 0.026859 | 0.022873 |
| lysoPC 18:0e | 0.008894 | 0.008446 | 0.016004 | 0.015494 | 0.014798 | 0.011108 |
| lysoPC 18:2 | 0.055003 | 0.058714 | 0.069538 | 0.103692 | 0.086241 | 0.081722 |
| lysoPC 18:1 | 0.143055 | 0.149941 | 0.214667 | 0.292570 | 0.204935 | 0.192010 |
| lysoPC 18:0 | 0.161327 | 0.154936 | 0.237254 | 0.322620 | 0.209573 | 0.212917 |
| lysoPC 19:1 | 0.021128 | 0.022956 | 0.030681 | 0.034205 | 0.021521 | 0.025196 |
| lysoPC 19:0 | 0.019023 | 0.017780 | 0.022161 | 0.026899 | 0.025964 | 0.022484 |
| lysoPC 20:4 | 0.016096 | 0.020276 | 0.031868 | 0.034887 | 0.022239 | 0.019148 |
| lysoPC 20:3 | 0.017066 | 0.013965 | 0.028465 | 0.022561 | 0.025998 | 0.020913 |
| lysoPC 22:6 | 0.021753 | 0.021314 | 0.027432 | 0.039900 | 0.025437 | 0.022880 |
| lysoPC 22:5 | 0.020086 | 0.022442 | 0.032389 | 0.037267 | 0.022489 | 0.021246 |
| PC 32:1e | 0.222918 | 0.235920 | 0.239880 | 0.212436 | 0.266818 | 0.219049 |
| PC 32:0e | 0.051713 | 0.061169 | 0.064522 | 0.055894 | 0.135398 | 0.064250 |
| PC 32:2 | 13.543890 | 13.669660 | 13.021884 | 12.748357 | 12.630092 | 13.274380 |
| PC 32:1 | 5.964785 | 6.195732 | 6.035134 | 6.025340 | 5.855526 | 6.326796 |
| PC 32:0e | 0.463222 | 0.419218 | 0.474821 | 0.464833 | 0.519122 | 0.481994 |

TABLE 3-continued

Lipidomic Analysis. Complete data set for Extended Data 2d. Lipids extraction and phospholipid analysis by MS were performed as described in Methods section. Amount of each lipid species was normalized to internal standard and expressed as mol percent in total phospholipid analysed.

| | | | | | | |
|---|---|---|---|---|---|---|
| PC 34:3e | 0.806080 | 0.858698 | 0.894594 | 0.849136 | 1.047098 | 0.843429 |
| PC 34:2e | 0.581719 | 0.596244 | 0.609864 | 0.600060 | 0.769343 | 0.612674 |
| PC 34:1e | 0.161144 | 0.149221 | 0.167483 | 0.150568 | 0.230500 | 0.154802 |
| PC 34:0e | 0.170107 | 0.137975 | 0.166581 | 0.153275 | 0.185225 | 0.165622 |
| PC 34:3 | 18.918019 | 18.283564 | 17.853515 | 19.643069 | 19.293971 | 17.838688 |
| PC 34:2 | 14.152231 | 13.477264 | 14.070179 | 13.569759 | 13.790446 | 13.647300 |
| PC 34:1 | 6.341122 | 5.618504 | 7.123699 | 6.574428 | 6.291814 | 5.617526 |
| PC 34:0 | 0.896861 | 0.758365 | 1.013361 | 0.902137 | 0.880896 | 0.899118 |
| PC 36:4p | 0.144023 | 0.172148 | 0.155986 | 0.166400 | 0.209447 | 0.164923 |
| PC 36:3p | 0.179836 | 0.185502 | 0.181306 | 0.197535 | 0.262483 | 0.213432 |
| PC 36:2p | 0.191061 | 0.195875 | 0.217483 | 0.214337 | 0.302135 | 0.210275 |
| PC 36:1p | 0.192164 | 0.198959 | 0.204118 | 0.214397 | 0.410949 | 0.252303 |
| PC 36:0p | 0.551357 | 0.522442 | 0.574333 | 0.575743 | 0.591366 | 0.620098 |
| PC 36:6 | 2.988210 | 2.969732 | 2.768084 | 2.882643 | 2.556706 | 3.001282 |
| PC 36:5 | 3.209418 | 3.382490 | 3.248430 | 3.481586 | 3.459978 | 3.566980 |
| PC 36:4 | 3.712193 | 4.142377 | 3.730120 | 3.957583 | 4.196836 | 3.851645 |
| PC 36:3 | 3.129475 | 3.491056 | 3.337346 | 3.210606 | 3.441481 | 3.398610 |
| PC 36:2 | 1.463473 | 1.505161 | 1.557887 | 1.431405 | 1.603006 | 1.449580 |
| PC 36:1 | 0.505751 | 0.519822 | 0.561462 | 0.527150 | 0.568638 | 0.481540 |
| PC 36:0 | 0.206368 | 0.196712 | 0.217070 | 0.208832 | 0.297292 | 0.224538 |
| PC 38:4e | 0.078796 | 0.083100 | 0.085394 | 0.089930 | 0.158022 | 0.085385 |
| PC 38:3e | 0.085351 | 0.092766 | 0.096137 | 0.095763 | 0.155482 | 0.094612 |
| PC 38:2e | 0.709748 | 0.675832 | 0.694616 | 0.677959 | 0.780662 | 0.805744 |
| PC 38:1e | 1.959342 | 1.838389 | 1.956343 | 1.862074 | 1.766203 | 2.133177 |
| PC 38:8 | 1.112406 | 1.170255 | 1.053816 | 0.981369 | 0.898740 | 1.116433 |
| PC 38:7 | 4.493897 | 4.378617 | 4.269352 | 3.829969 | 4.034989 | 4.615659 |
| PC 38:6 | 3.668786 | 3.847795 | 3.699677 | 3.293358 | 3.244926 | 3.567904 |
| PC 38:5 | 1.884006 | 2.034933 | 1.951957 | 1.779102 | 1.956810 | 1.931683 |
| PC 38:4 | 1.257286 | 1.479759 | 1.231456 | 1.338301 | 1.309897 | 1.151627 |
| PC 38:3 | 1.979771 | 1.854553 | 2.054663 | 1.945182 | 1.905968 | 1.649164 |
| PC 40:6e | 0.026156 | 0.030158 | 0.026883 | 0.027128 | 0.032052 | 0.023101 |
| PC 40:1e | 0.358690 | 0.365204 | 0.361528 | 0.332335 | 0.344339 | 0.371492 |
| PC 40:0e | 0.295439 | 0.288331 | 0.270768 | 0.280610 | 0.266030 | 0.276814 |
| PC 40:6 | 0.145968 | 0.160797 | 0.157685 | 0.146051 | 0.158842 | 0.137519 |
| PC 40:5 | 0.067901 | 0.071325 | 0.067707 | 0.073726 | 0.067433 | 0.070472 |
| PC 40:4 | 0.135022 | 0.146268 | 0.141270 | 0.150462 | 0.137862 | 0.133689 |
| PC 40:1 | 0.041780 | 0.051463 | 0.052471 | 0.052893 | 0.052883 | 0.054672 |
| PC 41:3 | 0.018494 | 0.025801 | 0.023136 | 0.026295 | 0.029697 | 0.026410 |
| PC 42:3 | 0.019438 | 0.026039 | 0.027996 | 0.027093 | 0.033722 | 0.021913 |
| PC 43:5 | 0.015387 | 0.007704 | 0.011856 | 0.012514 | 0.015236 | 0.011142 |
| PC 44:5 | 0.014736 | 0.010112 | 0.013410 | 0.012238 | 0.017274 | 0.010075 |
| lysoPE 16:0p | 0.058685 | 0.078561 | 0.065190 | 0.081087 | 0.069061 | 0.127230 |
| lysoPE 16:3 | 0.141023 | 0.138453 | 0.182267 | 0.174321 | 0.139635 | 0.201382 |
| lysoPE 16:1 | 0.003602 | 0.005177 | 0.005216 | 0.005540 | 0.004707 | 0.012036 |
| lysoPE 16:0 | 0.041221 | 0.066168 | 0.065464 | 0.081533 | 0.065540 | 0.109798 |
| lysoPE 18:1p | 0.023884 | 0.031816 | 0.026830 | 0.029910 | 0.030876 | 0.051902 |
| lysoPE 18:0p | 0.032537 | 0.044734 | 0.041180 | 0.058705 | 0.038534 | 0.059695 |
| lysoPE 18:2 | 0.001883 | 0.004366 | 0.003170 | 0.002036 | 0.003114 | 0.005949 |
| lysoPE 18:1 | 0.010978 | 0.023444 | 0.024359 | 0.041101 | 0.023055 | 0.032303 |
| lysoPE 18:0 | 0.058282 | 0.080564 | 0.102402 | 0.146586 | 0.081901 | 0.183466 |
| lysoPE 20:0p | 0.003213 | 0.005945 | 0.003594 | 0.006311 | 0.003114 | 0.006756 |
| lysoPE 20:4 | 0.003101 | 0.006592 | 0.003868 | 0.006664 | 0.001016 | 0.006894 |
| lysoPE 22:6 | 0.002548 | 0.002391 | 0.003494 | 0.006413 | 0.003625 | 0.005465 |
| PE 32:2 | 0.001499 | 0.000647 | 0.001907 | 0.001572 | 0.001591 | 0.002542 |
| PE 32:1 | 0.006724 | 0.012059 | 0.007022 | 0.010371 | 0.006838 | 0.009333 |
| PE 34:2p | 0.003141 | 0.004091 | 0.002409 | 0.003899 | 0.003269 | 0.002988 |
| PE 34:1p | 0.023717 | 0.030170 | 0.018419 | 0.028958 | 0.023651 | 0.032736 |
| PE 34:2 | 0.011661 | 0.017566 | 0.009663 | 0.015059 | 0.008845 | 0.012675 |
| PE 34:1 | 0.051983 | 0.076293 | 0.059647 | 0.070008 | 0.045984 | 0.078828 |
| PE 34:0 | 0.008820 | 0.009760 | 0.009437 | 0.011098 | 0.009220 | 0.011424 |
| PE 36:4p | 0.068806 | 0.082441 | 0.070046 | 0.073484 | 0.053977 | 0.088085 |
| PE 36:3p | 0.007543 | 0.013405 | 0.007633 | 0.011755 | 0.006835 | 0.011442 |
| PE 36:2p | 0.003531 | 0.007471 | 0.004030 | 0.006346 | 0.004312 | 0.005442 |
| PE 36:1p | 0.003153 | 0.005672 | 0.004552 | 0.006289 | 0.004940 | 0.006267 |
| PE 36:4 | 0.042535 | 0.050091 | 0.043301 | 0.046669 | 0.036453 | 0.055215 |
| PE 36:3 | 0.008976 | 0.012695 | 0.007452 | 0.011189 | 0.010023 | 0.013529 |
| PE 36:2 | 0.019292 | 0.027842 | 0.017846 | 0.030456 | 0.019221 | 0.026514 |
| PE 36:1 | 0.037120 | 0.045412 | 0.040376 | 0.044388 | 0.031751 | 0.054484 |
| PE 38:6p | 0.154794 | 0.171425 | 0.138096 | 0.155596 | 0.099605 | 0.195517 |
| PE 38:5p | 0.069329 | 0.082441 | 0.059202 | 0.068001 | 0.059563 | 0.091640 |
| PE 38:4p | 0.074152 | 0.080327 | 0.066975 | 0.070030 | 0.059022 | 0.095354 |
| PE 38:3p | 0.011140 | 0.017690 | 0.010700 | 0.014939 | 0.009581 | 0.013345 |
| PE 38:2p | 0.002176 | 0.002169 | 0.002276 | 0.001972 | 0.001937 | 0.002900 |
| PE 38:1p | 0.001003 | 0.000961 | 0.001396 | 0.001092 | 0.001050 | 0.001553 |
| PE 38:0p | 0.000743 | 0.000567 | 0.000578 | 0.000880 | 0.000314 | 0.000908 |
| PE 38:7 | 0.007271 | 0.008857 | 0.006188 | 0.009090 | 0.006854 | 0.010178 |

TABLE 3-continued

Lipidomic Analysis. Complete data set for Extended Data 2d. Lipids extraction and phospholipid analysis by MS were performed as described in Methods section. Amount of each lipid species was normalized to internal standard and expressed as mol percent in total phospholipid analysed.

| | | | | | | |
|---|---|---|---|---|---|---|
| PE 38:6 | 0.108010 | 0.114412 | 0.107838 | 0.123634 | 0.077869 | 0.148085 |
| PE 38:5 | 0.071282 | 0.103265 | 0.072531 | 0.087503 | 0.068517 | 0.102475 |
| PE 38:4 | 0.294805 | 0.379644 | 0.274548 | 0.324190 | 0.252788 | 0.399669 |
| PE 38:3 | 0.036950 | 0.054459 | 0.029872 | 0.047911 | 0.038588 | 0.040451 |
| PE 38:2 | 0.004430 | 0.007508 | 0.005452 | 0.006055 | 0.004408 | 0.007356 |
| PE 38:1 | 0.041237 | 0.038155 | 0.031998 | 0.038192 | 0.029484 | 0.042752 |
| PE 40:6p | 0.092170 | 0.101520 | 0.083268 | 0.090677 | 0.063597 | 0.113002 |
| PE 40:5p | 0.036832 | 0.050751 | 0.037743 | 0.042748 | 0.037241 | 0.054078 |
| PE 40:4p | 0.026474 | 0.028352 | 0.022101 | 0.027471 | 0.021337 | 0.032462 |
| PE 40:7 | 0.046648 | 0.056779 | 0.045937 | 0.050249 | 0.036175 | 0.060439 |
| PE 40:6 | 0.109737 | 0.125776 | 0.101558 | 0.118245 | 0.081022 | 0.150156 |
| PE 40:5 | 0.038533 | 0.050791 | 0.039901 | 0.048174 | 0.031069 | 0.057667 |
| PE 40:4 | 0.042891 | 0.051345 | 0.044325 | 0.051341 | 0.029289 | 0.064308 |
| PE 40:3 | 0.007114 | 0.014723 | 0.007636 | 0.013796 | 0.010212 | 0.016427 |
| PE 42:7p | 0.003867 | 0.004205 | 0.002757 | 0.003471 | 0.002852 | 0.005359 |
| PE 42:6p | 0.006947 | 0.011253 | 0.008173 | 0.009834 | 0.006585 | 0.009230 |
| PE 42:5p | 0.008363 | 0.012203 | 0.009974 | 0.011320 | 0.008797 | 0.014432 |
| PE 42:4p | 0.004807 | 0.007415 | 0.004986 | 0.005020 | 0.005096 | 0.006881 |
| PE 42:3p | 0.002776 | 0.003952 | 0.002214 | 0.002973 | 0.001959 | 0.004256 |
| PE 42:2p | 0.002997 | 0.003894 | 0.003386 | 0.003985 | 0.002712 | 0.005630 |
| PE 42:1p | 0.004313 | 0.005704 | 0.003182 | 0.003339 | 0.003291 | 0.005812 |
| PE 42:0p | 0.010189 | 0.012229 | 0.010817 | 0.011772 | 0.008845 | 0.015423 |
| PE 42:7 | 0.004546 | 0.007538 | 0.007079 | 0.006815 | 0.006780 | 0.007802 |
| PE 42:6 | 0.003062 | 0.007585 | 0.004558 | 0.008433 | 0.005573 | 0.006890 |
| PE 42:5 | 0.011336 | 0.015292 | 0.013213 | 0.012801 | 0.009524 | 0.015114 |
| PE 42:4 | 0.005236 | 0.007820 | 0.004869 | 0.007015 | 0.004712 | 0.009165 |
| PE 44:3p | 0.002306 | 0.002731 | 0.002015 | 0.002121 | 0.001450 | 0.003427 |
| PE 46:4 | 0.000560 | 0.001466 | 0.000593 | 0.001675 | 0.001287 | 0.000809 |
| lysoPI 16:0 | 0.000144 | 0.000306 | 0.000250 | 0.000289 | 0.000169 | 0.000145 |
| lysoPI 18:0 | 0.000168 | 0.000272 | 0.000163 | 0.000336 | 0.000192 | 0.000118 |
| lysoPI 20:4 | 0.000156 | 0.000151 | 0.000210 | 0.000288 | 0.000135 | 0.000184 |
| lysoPI 22:6 | 0.000000 | 0.000034 | 0.000066 | 0.000069 | 0.000079 | 0.000000 |
| PI 32:2 | 0.000018 | 0.000042 | 0.000068 | 0.000047 | 0.000056 | 0.000026 |
| PI 32:1 | 0.000205 | 0.000168 | 0.000071 | 0.000150 | 0.000158 | 0.000145 |
| PI 34:2 | 0.000018 | 0.000042 | 0.000018 | 0.000035 | 0.000023 | 0.000027 |
| PI 34:1 | 0.000030 | 0.000017 | 0.000084 | 0.000023 | 0.000000 | 0.000039 |
| PI 36:4 | 0.000066 | 0.000055 | 0.000060 | 0.000058 | 0.000079 | 0.000053 |
| PI 36:3 | 0.000012 | 0.000013 | 0.000029 | 0.000081 | 0.000000 | 0.000039 |
| PI 36:2 | 0.000000 | 0.000025 | 0.000011 | 0.000023 | 0.000000 | 0.000000 |
| PI 36:1 | 0.000000 | 0.000025 | 0.000055 | 0.000058 | 0.000000 | 0.000000 |
| PI 38:7 | 0.000018 | 0.000021 | 0.000011 | 0.000023 | 0.000000 | 0.000000 |
| PI 38:6 | 0.000042 | 0.000021 | 0.000047 | 0.000046 | 0.000000 | 0.000000 |
| PI 38:5 | 0.000091 | 0.000075 | 0.000113 | 0.000196 | 0.000034 | 0.000078 |
| PI 38:4 | 0.133967 | 0.141163 | 0.171221 | 0.159331 | 0.100248 | 0.161657 |
| PI 38:3 | 0.020207 | 0.026813 | 0.024273 | 0.028275 | 0.019937 | 0.024025 |
| PI 38:2 | 0.000855 | 0.001939 | 0.001535 | 0.002196 | 0.001567 | 0.001396 |
| PI 40:7 | 0.000569 | 0.000947 | 0.000686 | 0.000565 | 0.000710 | 0.000645 |
| PI 40:6 | 0.000564 | 0.000562 | 0.000888 | 0.000819 | 0.000428 | 0.000574 |
| PI 40:5 | 0.001512 | 0.002110 | 0.002281 | 0.002126 | 0.001882 | 0.001743 |
| PI 40:4 | 0.001592 | 0.001710 | 0.002250 | 0.002222 | 0.001262 | 0.002025 |
| PI 40:3 | 0.000000 | 0.000000 | 0.000000 | 0.000000 | 0.000000 | 0.000000 |
| lysoPS 16:1 | 0.000026 | 0.000024 | 0.000020 | 0.000043 | 0.000036 | 0.000058 |
| lysoPS 18:1 | 0.000295 | 0.000514 | 0.000352 | 0.000539 | 0.000384 | 0.000491 |
| lysoPS 18:0 | 0.001465 | 0.002024 | 0.001612 | 0.001975 | 0.001824 | 0.001893 |
| PS 34:2 | 0.001344 | 0.001420 | 0.000836 | 0.001318 | 0.001332 | 0.001961 |
| PS 34:1 | 0.008532 | 0.009385 | 0.007121 | 0.009112 | 0.007551 | 0.011223 |
| PS 36:4 | 0.000873 | 0.000973 | 0.000952 | 0.000843 | 0.000623 | 0.001347 |
| PS 36:3 | 0.000584 | 0.000571 | 0.000506 | 0.000782 | 0.000507 | 0.000867 |
| PS 36:2 | 0.002116 | 0.002534 | 0.001875 | 0.002527 | 0.002494 | 0.003350 |
| PS 36:1 | 0.007833 | 0.008548 | 0.008734 | 0.008737 | 0.007747 | 0.012638 |
| PS 38:5 | 0.001438 | 0.001712 | 0.001415 | 0.001410 | 0.001272 | 0.002004 |
| PS 38:4 | 0.010779 | 0.011851 | 0.010349 | 0.012150 | 0.009238 | 0.015814 |
| PS 38:3 | 0.002341 | 0.002810 | 0.002168 | 0.003205 | 0.002621 | 0.003997 |
| PS 38:2 | 0.000484 | 0.000525 | 0.000290 | 0.000496 | 0.000362 | 0.000669 |
| PS 40:7 | 0.001437 | 0.001892 | 0.001573 | 0.001924 | 0.001468 | 0.002411 |
| PS 40:6 | 0.032236 | 0.032578 | 0.031351 | 0.027453 | 0.022705 | 0.043342 |
| PS 40:5 | 0.008391 | 0.008893 | 0.008020 | 0.007933 | 0.006747 | 0.010979 |
| PS 40:4 | 0.004237 | 0.004514 | 0.004699 | 0.004200 | 0.003921 | 0.006026 |
| PS 40:3 | 0.000721 | 0.000888 | 0.000963 | 0.000854 | 0.000807 | 0.001308 |
| PS 40:2 | 0.000090 | 0.000123 | 0.000104 | 0.000144 | 0.000164 | 0.000170 |

| Lipid species | Brain-KO1 | Brain-KO2 | Brain-KO3 | Brain-KO4 | Brain-KO5 |
|---|---|---|---|---|---|
| lysoPC14:0 | 0.016850 | 0.026906 | 0.016491 | 0.015512 | 0.015801 |
| lysoPC 16:0e | 0.012752 | 0.015233 | 0.010997 | 0.011861 | 0.011326 |
| lysoPC 16:1 | 0.232653 | 0.242093 | 0.203363 | 0.242736 | 0.161363 |

TABLE 3-continued

Lipidomic Analysis. Complete data set for Extended Data 2d. Lipids extraction and phospholipid analysis by MS were performed as described in Methods section. Amount of each lipid species was normalized to internal standard and expressed as mol percent in total phospholipid analysed.

| | | | | | |
|---|---|---|---|---|---|
| lysoPC 16:0 | 0.032199 | 0.036078 | 0.022238 | 0.033035 | 0.028181 |
| lysoPC 18:0e | 0.016905 | 0.015192 | 0.013752 | 0.012023 | 0.015103 |
| lysoPC 18:2 | 0.158072 | 0.199441 | 0.156238 | 0.191524 | 0.130843 |
| lysoPC 18:1 | 0.266843 | 0.270052 | 0.261458 | 0.299970 | 0.210166 |
| lysoPC 18:0 | 0.222657 | 0.232402 | 0.240917 | 0.274271 | 0.204028 |
| lysoPC 19:1 | 0.029720 | 0.031097 | 0.036061 | 0.037011 | 0.035899 |
| lysoPC 19:0 | 0.028917 | 0.022956 | 0.025304 | 0.025420 | 0.026239 |
| lysoPC 20:4 | 0.024542 | 0.038750 | 0.023697 | 0.026744 | 0.025022 |
| lysoPC 20:3 | 0.025337 | 0.023781 | 0.024244 | 0.023577 | 0.023927 |
| lysoPC 22:6 | 0.025573 | 0.034261 | 0.024892 | 0.031693 | 0.025387 |
| lysoPC 22:5 | 0.024636 | 0.029933 | 0.024145 | 0.029028 | 0.024811 |
| PC 32:1e | 0.272079 | 0.221710 | 0.261266 | 0.251258 | 0.262836 |
| PC 32:0e | 0.071653 | 0.067611 | 0.069146 | 0.060410 | 0.072811 |
| PC 32:2 | 11.648075 | 11.407448 | 11.874247 | 11.494647 | 11.292689 |
| PC 32:1 | 4.441459 | 4.336431 | 4.282044 | 4.479932 | 3.964024 |
| PC 32:0e | 0.393521 | 0.291020 | 0.319989 | 0.318336 | 0.338193 |
| PC 34:3e | 0.997252 | 0.885807 | 0.974498 | 1.003044 | 0.888915 |
| PC 34:2e | 0.669123 | 0.637436 | 0.675026 | 0.644597 | 0.610442 |
| PC 34:1e | 0.165244 | 0.157704 | 0.161938 | 0.141065 | 0.144303 |
| PC 34:0e | 0.118333 | 0.118651 | 0.116805 | 0.110757 | 0.121440 |
| PC 34:3 | 21.004563 | 20.001272 | 21.211758 | 22.239744 | 20.942768 |
| PC 34:2 | 14.630698 | 14.900753 | 14.925071 | 15.024047 | 15.374772 |
| PC 34:1 | 6.085548 | 7.092939 | 7.566023 | 5.619687 | 7.748593 |
| PC 34:0 | 0.754076 | 0.927276 | 0.998392 | 0.820839 | 0.919507 |
| PC 36:4p | 0.201138 | 0.205211 | 0.187062 | 0.197358 | 0.198702 |
| PC 36:3p | 0.292018 | 0.231246 | 0.255063 | 0.260927 | 0.238441 |
| PC 36:2p | 0.272617 | 0.196581 | 0.246427 | 0.247259 | 0.259699 |
| PC 36:1p | 0.221511 | 0.153588 | 0.185559 | 0.204166 | 0.214307 |
| PC 36:0p | 0.281916 | 0.253332 | 0.256926 | 0.232029 | 0.275678 |
| PC 36:6 | 2.044017 | 2.026676 | 2.134438 | 2.243780 | 2.079348 |
| PC 36:5 | 5.012724 | 4.864533 | 4.910354 | 5.066043 | 5.068319 |
| PC 36:4 | 6.660434 | 6.619847 | 6.500981 | 6.921370 | 6.605280 |
| PC 36:3 | 5.037816 | 4.848753 | 4.605831 | 4.932657 | 4.613846 |
| PC 36:2 | 1.810741 | 1.742305 | 1.715544 | 1.731377 | 1.759829 |
| PC 36:1 | 0.456185 | 0.415070 | 0.402173 | 0.418811 | 0.437844 |
| PC 36:0 | 0.171868 | 0.154651 | 0.147708 | 0.144841 | 0.173150 |
| PC 38:4e | 0.094992 | 0.094231 | 0.091002 | 0.084681 | 0.094043 |
| PC 38:3e | 0.106972 | 0.095294 | 0.090094 | 0.099527 | 0.108494 |
| PC 38:2e | 0.285967 | 0.252477 | 0.255069 | 0.238544 | 0.271488 |
| PC 38:1e | 0.573896 | 0.605022 | 0.520003 | 0.518154 | 0.601495 |
| PC 38:8 | 0.357936 | 0.340611 | 0.314183 | 0.303108 | 0.323102 |
| PC 38:7 | 1.869319 | 1.992126 | 1.742780 | 1.719901 | 1.655098 |
| PC 38:6 | 2.127313 | 2.149497 | 1.992112 | 2.057956 | 1.945190 |
| PC 38:5 | 1.940276 | 1.946183 | 1.658400 | 1.889980 | 1.634050 |
| PC 38:4 | 1.886558 | 2.004267 | 1.742788 | 2.041694 | 1.940854 |
| PC 38:3 | 1.806042 | 2.082174 | 1.891983 | 1.923038 | 2.192828 |
| PC 40:6e | 0.024079 | 0.013633 | 0.017202 | 0.021129 | 0.021630 |
| PC 40:1e | 0.128903 | 0.116587 | 0.113466 | 0.116424 | 0.124936 |
| PC 40:0e | 0.115896 | 0.124456 | 0.108798 | 0.117165 | 0.115651 |
| PC 40:6 | 0.083490 | 0.081328 | 0.069669 | 0.081323 | 0.081147 |
| PC 40:5 | 0.070219 | 0.065954 | 0.067016 | 0.058100 | 0.070112 |
| PC 40:4 | 0.162595 | 0.171097 | 0.143270 | 0.145362 | 0.180082 |
| PC 40:1 | 0.049877 | 0.057366 | 0.055408 | 0.043474 | 0.062913 |
| PC 41:3 | 0.014818 | 0.009797 | 0.016024 | 0.010385 | 0.022469 |
| PC 42:3 | 0.036781 | 0.035864 | 0.037262 | 0.026067 | 0.050358 |
| PC 43:5 | 0.008221 | 0.007431 | 0.011093 | 0.010139 | 0.011336 |
| PC 44:5 | 0.010490 | 0.009662 | 0.011823 | 0.007495 | 0.013988 |
| lysoPE 16:0p | 0.179950 | 0.208145 | 0.147687 | 0.088673 | 0.136899 |
| lysoPE 16:3 | 0.203294 | 0.196940 | 0.190870 | 0.162630 | 0.156526 |
| lysoPE 16:1 | 0.013572 | 0.014005 | 0.009991 | 0.008698 | 0.013400 |
| lysoPE 16:0 | 0.137846 | 0.194864 | 0.114638 | 0.102126 | 0.133862 |
| lysoPE 18:1p | 0.128593 | 0.210570 | 0.106512 | 0.094284 | 0.127623 |
| lysoPE 18:0p | 0.102944 | 0.149266 | 0.095173 | 0.063288 | 0.089616 |
| lysoPE 18:2 | 0.007468 | 0.009713 | 0.006416 | 0.005724 | 0.007192 |
| lysoPE 18:1 | 0.106726 | 0.181848 | 0.084250 | 0.057763 | 0.097462 |
| lysoPE 18:0 | 0.279245 | 0.386105 | 0.231620 | 0.192398 | 0.268640 |
| lysoPE 20:0p | 0.009060 | 0.006982 | 0.007158 | 0.004185 | 0.004314 |
| lysoPE 20:4 | 0.008329 | 0.005853 | 0.007258 | 0.006415 | 0.005426 |
| lysoPE 22:6 | 0.001460 | 0.003331 | 0.003991 | 0.002092 | 0.003116 |
| PE 32:2 | 0.006151 | 0.006449 | 0.003671 | 0.003745 | 0.005618 |
| PE 32:1 | 0.020512 | 0.021688 | 0.016037 | 0.015058 | 0.019099 |
| PE 34:2p | 0.024782 | 0.022861 | 0.021041 | 0.014269 | 0.019218 |
| PE 34:1p | 0.095149 | 0.102893 | 0.086977 | 0.065936 | 0.072887 |
| PE 34:2 | 0.054714 | 0.052405 | 0.041509 | 0.036455 | 0.040818 |
| PE 34:1 | 0.117629 | 0.112238 | 0.101454 | 0.081153 | 0.094444 |
| PE 34:0 | 0.011903 | 0.014069 | 0.012420 | 0.011420 | 0.010211 |

TABLE 3-continued

Lipidomic Analysis. Complete data set for Extended Data 2d. Lipids extraction and phospholipid analysis by MS were performed as described in Methods section. Amount of each lipid species was normalized to internal standard and expressed as mol percent in total phospholipid analysed.

| | | | | | |
|---|---|---|---|---|---|
| PE 36:4p | 0.063885 | 0.077769 | 0.070213 | 0.050799 | 0.062769 |
| PE 36:3p | 0.043823 | 0.041971 | 0.035595 | 0.026479 | 0.032571 |
| PE 36:2p | 0.043085 | 0.036814 | 0.035237 | 0.024023 | 0.035534 |
| PE 36:1p | 0.035178 | 0.034234 | 0.027926 | 0.023884 | 0.027636 |
| PE 36:4 | 0.040138 | 0.035325 | 0.038886 | 0.029854 | 0.038317 |
| PE 36:3 | 0.045102 | 0.043693 | 0.034925 | 0.032214 | 0.037617 |
| PE 36:2 | 0.092078 | 0.089727 | 0.074970 | 0.061089 | 0.076779 |
| PE 36:1 | 0.075803 | 0.075305 | 0.074248 | 0.054123 | 0.068063 |
| PE 38:6p | 0.051810 | 0.049162 | 0.048826 | 0.033052 | 0.039341 |
| PE 38:5p | 0.070023 | 0.072025 | 0.065412 | 0.046947 | 0.054701 |
| PE 38:4p | 0.088216 | 0.081873 | 0.074986 | 0.053794 | 0.060601 |
| PE 38:3p | 0.043952 | 0.042907 | 0.042697 | 0.028640 | 0.038591 |
| PE 38:2p | 0.015637 | 0.015671 | 0.015018 | 0.008556 | 0.013439 |
| PE 38:1p | 0.006121 | 0.004416 | 0.005401 | 0.005343 | 0.005319 |
| PE 38:0p | 0.002422 | 0.001211 | 0.001012 | 0.001781 | 0.001229 |
| PE 38:7 | 0.002135 | 0.002735 | 0.002602 | 0.002535 | 0.004892 |
| PE 38:6 | 0.015196 | 0.016609 | 0.014939 | 0.014546 | 0.017571 |
| PE 38:5 | 0.081731 | 0.076633 | 0.065194 | 0.066246 | 0.074065 |
| PE 38:4 | 0.294907 | 0.299901 | 0.273943 | 0.243012 | 0.253205 |
| PE 38:3 | 0.122161 | 0.112976 | 0.100285 | 0.094014 | 0.094291 |
| PE 38:2 | 0.021186 | 0.020985 | 0.020176 | 0.016236 | 0.018852 |
| PE 38:1 | 0.023601 | 0.022705 | 0.022476 | 0.020223 | 0.020064 |
| PE 40:6p | 0.038531 | 0.038182 | 0.031847 | 0.027740 | 0.030677 |
| PE 40:5p | 0.038241 | 0.035484 | 0.033426 | 0.025780 | 0.031308 |
| PE 40:4p | 0.029578 | 0.029230 | 0.028454 | 0.024916 | 0.026100 |
| PE 40:7 | 0.018223 | 0.019501 | 0.015698 | 0.018513 | 0.016341 |
| PE 40:6 | 0.026246 | 0.032514 | 0.023751 | 0.023059 | 0.025400 |
| PE 40:5 | 0.017698 | 0.017937 | 0.016482 | 0.015717 | 0.017323 |
| PE 40:4 | 0.022171 | 0.025206 | 0.023316 | 0.021131 | 0.023043 |
| PE 40:3 | 0.011767 | 0.015593 | 0.013330 | 0.012071 | 0.014779 |
| PE 42:7p | 0.006659 | 0.007034 | 0.005039 | 0.004903 | 0.004713 |
| PE 42:6p | 0.014338 | 0.011685 | 0.012580 | 0.009437 | 0.009059 |
| PE 42:5p | 0.011985 | 0.014577 | 0.012183 | 0.011131 | 0.010672 |
| PE 42:4p | 0.008120 | 0.007933 | 0.006455 | 0.006295 | 0.006139 |
| PE 42:3p | 0.006848 | 0.002736 | 0.002717 | 0.003523 | 0.002049 |
| PE 42:2p | 0.002573 | 0.003283 | 0.002319 | 0.002186 | 0.002732 |
| PE 42:1p | 0.003050 | 0.003791 | 0.003466 | 0.005149 | 0.002331 |
| PE 42:0p | 0.008486 | 0.006486 | 0.008441 | 0.006514 | 0.005737 |
| PE 42:7 | 0.007156 | 0.006956 | 0.007573 | 0.007097 | 0.006455 |
| PE 42:6 | 0.006151 | 0.006018 | 0.006052 | 0.005224 | 0.004431 |
| PE 42:5 | 0.008771 | 0.009145 | 0.009847 | 0.008211 | 0.005396 |
| PE 42:4 | 0.007420 | 0.004611 | 0.005683 | 0.004701 | 0.005208 |
| PE 44:3p | 0.001948 | 0.001133 | 0.002230 | 0.001008 | 0.001835 |
| PE 46:4 | 0.002125 | 0.001290 | 0.001483 | 0.000722 | 0.000777 |
| lysoPI 16:0 | 0.000296 | 0.000214 | 0.000266 | 0.000099 | 0.000280 |
| lysoPI 18:0 | 0.000244 | 0.000061 | 0.000291 | 0.000044 | 0.000196 |
| lysoPI 20:4 | 0.000195 | 0.000187 | 0.000149 | 0.000125 | 0.000142 |
| lysoPI 22:6 | 0.000041 | 0.000080 | 0.000059 | 0.000066 | 0.000052 |
| PI 32:2 | 0.000045 | 0.000060 | 0.000119 | 0.000048 | 0.000091 |
| PI 32:1 | 0.000098 | 0.000107 | 0.000118 | 0.000114 | 0.000145 |
| PI 34:2 | 0.000016 | 0.000053 | 0.000044 | 0.000074 | 0.000081 |
| PI 34:1 | 0.000126 | 0.000134 | 0.000089 | 0.000140 | 0.000052 |
| PI 36:4 | 0.000195 | 0.000127 | 0.000107 | 0.000077 | 0.000069 |
| PI 36:3 | 0.000102 | 0.000100 | 0.000059 | 0.000048 | 0.000081 |
| PI 36:2 | 0.000155 | 0.000020 | 0.000058 | 0.000015 | 0.000027 |
| PI 36:1 | 0.000049 | 0.000000 | 0.000046 | 0.000030 | 0.000042 |
| PI 38:7 | 0.000016 | 0.000026 | 0.000014 | 0.000102 | 0.000029 |
| PI 38:6 | 0.000016 | 0.000013 | 0.000000 | 0.000015 | 0.000012 |
| PI 38:5 | 0.000110 | 0.000074 | 0.000092 | 0.000139 | 0.000223 |
| PI 38:4 | 0.112574 | 0.120282 | 0.098932 | 0.078338 | 0.113350 |
| PI 38:3 | 0.062685 | 0.069623 | 0.051817 | 0.047100 | 0.055882 |
| PI 38:2 | 0.010134 | 0.010667 | 0.008684 | 0.007165 | 0.009297 |
| PI 40:7 | 0.000236 | 0.000246 | 0.000132 | 0.000269 | 0.000425 |
| PI 40:6 | 0.000443 | 0.000241 | 0.000318 | 0.000170 | 0.000554 |
| PI 40:5 | 0.001668 | 0.001967 | 0.001023 | 0.000996 | 0.001570 |
| PI 40:4 | 0.001481 | 0.001857 | 0.001587 | 0.001358 | 0.001711 |
| PI 40:3 | 0.000024 | 0.000000 | 0.000000 | 0.000015 | 0.000015 |
| lysoPS 16:1 | 0.000046 | 0.000057 | 0.000090 | 0.000072 | 0.000046 |
| lysoPS 18:1 | 0.000621 | 0.000556 | 0.000530 | 0.000573 | 0.000519 |
| lysoPS 18:0 | 0.001809 | 0.001542 | 0.001729 | 0.001695 | 0.001722 |
| PS 34:2 | 0.006870 | 0.005766 | 0.005497 | 0.004632 | 0.005505 |
| PS 34:1 | 0.024957 | 0.018819 | 0.019304 | 0.014424 | 0.018775 |
| PS 36:4 | 0.001473 | 0.001253 | 0.001300 | 0.001033 | 0.001370 |
| PS 36:3 | 0.003412 | 0.002882 | 0.002822 | 0.002231 | 0.002702 |
| PS 36:2 | 0.009450 | 0.007654 | 0.007567 | 0.005985 | 0.007762 |
| PS 36:1 | 0.023052 | 0.017191 | 0.019388 | 0.013267 | 0.019688 |

TABLE 3-continued

Lipidomic Analysis. Complete data set for Extended Data 2d. Lipids extraction and phospholipid analysis by MS were performed as described in Methods section. Amount of each lipid species was normalized to internal standard and expressed as mol percent in total phospholipid analysed.

| | | | | | |
|---|---|---|---|---|---|
| PS 38:5 | 0.002337 | 0.001426 | 0.001405 | 0.001594 | 0.001711 |
| PS 38:4 | 0.018208 | 0.014888 | 0.014474 | 0.011757 | 0.016236 |
| PS 38:3 | 0.011045 | 0.008462 | 0.008152 | 0.006778 | 0.008947 |
| PS 38:2 | 0.002347 | 0.001916 | 0.002072 | 0.001603 | 0.001957 |
| PS 40:7 | 0.001970 | 0.001816 | 0.001331 | 0.001407 | 0.001786 |
| PS 40:6 | 0.016417 | 0.013534 | 0.015271 | 0.012300 | 0.016195 |
| PS 40:5 | 0.006021 | 0.004534 | 0.005757 | 0.004248 | 0.005639 |
| PS 40:4 | 0.004318 | 0.003335 | 0.003683 | 0.002694 | 0.003807 |
| PS 40:3 | 0.001806 | 0.001644 | 0.001802 | 0.001225 | 0.001547 |
| PS 40:2 | 0.000388 | 0.000300 | 0.000299 | 0.000174 | 0.000336 |

What is claimed:

1. A method for screening one or more compound or fatty acid to determine transport of the one or more compound or fatty acid via Major Facilitator Superfamily Domain Containing 2A (Mfsd2a) protein, wherein the compound or fatty acid comprises a zwitterionic head group and an acyl or alkyl chain, the method comprising:
   (a) contacting a biological mixture comprising said one or more compound or fatty acid with (i) a cell line comprising a human wild type Mfsd2a cDNA and (ii) a cell line comprising a mutant human Mfsd2a cDNA, or a mock transfected cell;
   (b) measuring the amount of said one or more compound or fatty acid in cells comprising the human wild type Mfsd2a cDNA and a cell comprising mutant human Mfsd2a cDNA or a mock transfected cell; and
   (c) comparing the amount of said one or more compound or fatty acid in the cells comprising wild type Mfsd2a cDNA and cells comprising mutant human Mfsd2a cDNA or mock transfected cells, wherein higher amounts of said one or more compound or fatty acid in the cells comprising wild-type Mfsd2a cDNA as compared to cells comprising mutant human Mfsd2a cDNA or mock transfected cells is an indication of transport of the compound or fatty acid via Mfsd2a protein.

2. The method of claim 1, wherein the cell is HEK 293 and/or the mutant human Mfsd2a cDNA comprises a mutation at a position encoding D93 or D97 of the human Mfsd2a protein sequence of SEQ ID NO: 2.

3. A method of screening for compounds that modulate transport through Mfsd2a protein comprising:
   (a) contacting cell lines comprising (i) a human wild type Mfsd2a cDNA and (ii) a mutant human Mfsd2a cDNA, or a mock transfected cell with LPC-palmitate, -oleate, -stearate, -linoleate, -linolenate, -arachidonate, or -docosahexaenoate;
   (b) measuring uptake of the LPC-palmitate, -oleate, -stearate, -linoleate, -linolenate, -arachidonate, or -docosahexaenoate in the presence and absence of a test compound in the cells comprising the human wild type Mfsd2a cDNA and the cells comprising mutant human Mfsd2a cDNA or mock transfected cells;
   wherein an increased or decreased level of uptake of LPC-palmitate, -oleate, -stearate, -linoleate, -linolenate, -arachidonate, -docosahexaenoate into cells comprising the human wild type Mfsd2a cDNA compared to the level of uptake in cells comprising mutant human Mfsd2a cDNA or mock transfected cells in the presence of the test compound as compared to in the absence of the test compound identifies the compound as a modulator of transport through the Mfsd2a protein.

4. The method of claim 3, wherein the cell is HEK 293, and/or the mutant human Mfsd2a cDNA comprises a mutation at a position encoding D93 or D97 of the human Mfsd2a protein sequence of SEQ ID NO: 2, and/or the test compound is directly transported through the Mfsd2a protein.

5. A method for evaluating transport function of a Mfsd2a protein from a subject comprising:
   (a) expressing a test Mfsd2a cDNA in a first cell and a wild type Mfsd2a cDNA in a second cell;
   (b) contacting the first cell expressing the test Mfsd2a cDNA and the second cell expressing the wild type Mfsd2a cDNA with lysophosphatidylcholine (LPC)-docosahexaenoic (DHA) or LPC-omega 3 fatty acids; and
   (c) measuring uptake of LPC-DHA or LPC-omega 3 fatty acids into the first cell expressing the test Mfsd2a cDNA and the second cell expressing the wild type Mfsd2a cDNA,
   wherein a decreased level of uptake of LPC-DHA or LPC-omega 3 fatty acids into the first cell expressing the test Mfsd2a cDNA as compared to the second cell expressing the wild type Mfsd2a cDNA indicates that the test Mfsd2a cDNA encodes a protein deficient for transport.

6. The method of claim 5, wherein the test Mfsd2a cDNA encodes a human Mfsd2a protein comprising one or more substitution mutations selected from the group consisting of T159M, S166L, R114H, Y147C, L168F, S173G, S223L, V264M, Q274R, A281T, R283W, G284A, R286W, M337V, T358A, V374M, L181F, S186G, T223M, S236L, V277M, Q287R, A293T, R296W, G297A, R299W, K309R, M350V, T371A, V387M, A399V, and R513W, wherein the amino acid positions are numbered relative to the human Mfsd2a sequence of SEQ ID NO: 2.

* * * * *